US006033865A

United States Patent [19]

Daggett et al.

[11] Patent Number: 6,033,865

[45] Date of Patent: Mar. 7, 2000

[54] HUMAN N-METHYL-D-ASPARTATE RECEPTOR TYPE 1 SUBUNITS, DNA ENCODING SAME AND USES THEREFOR

[75] Inventors: Lorrie P. Daggett; Steven B. Ellis; Chen Wang Liaw, all of San Diego, Calif.

[73] Assignee: Sibia Neurosciences, Inc., La Jolla, Calif.

[21] Appl. No.: 08/480,474

[22] Filed: Jun. 6, 1995

Related U.S. Application Data

[63] Continuation of application No. 08/052,449, Apr. 20, 1993, abandoned.

[51] Int. Cl.[7] .......................... C12N 15/10; C12N 15/12; C07K 1/00; G01N 33/566

[52] U.S. Cl. ...................... 435/7.21; 536/23.1; 536/23.5; 435/6; 435/325; 435/254.11; 435/69.1; 530/350

[58] Field of Search .............................. 536/29.5, 24.31, 536/23.1; 530/530; 435/6, 7.2, 240.2, 7.21, 325, 259.11, 69.1

[56] References Cited

U.S. PATENT DOCUMENTS

| | | | |
|---|---|---|---|
| 4,837,148 | 6/1989 | Cregg | 435/172.3 |
| 4,855,231 | 8/1989 | Stroman et al. | 435/68 |
| 4,882,279 | 11/1989 | Cregg | 435/68 |
| 4,929,555 | 5/1990 | Cregg et al. | 435/172.3 |
| 5,024,939 | 6/1991 | Gorman | 435/69.1 |
| 5,028,707 | 7/1991 | Nichols et al. | 546/156 |
| 5,202,257 | 4/1993 | Heinemann et al. | 435/252.3 |
| 5,401,629 | 3/1995 | Harpold et al. | 435/6 |
| 5,403,484 | 4/1995 | Ladner et al. | 435/235.1 |
| 5,436,128 | 7/1995 | Harpold et al. | 435/6 |
| 5,502,166 | 3/1996 | Mishina | 530/350 |

FOREIGN PATENT DOCUMENTS

| | | |
|---|---|---|
| 0600278 | 6/1994 | European Pat. Off. . |
| 0606734 | 7/1994 | European Pat. Off. . |
| 0674003 | 9/1995 | European Pat. Off. . |
| 6014783 | 1/1994 | Japan . |
| 9223769 | 11/1992 | United Kingdom . |
| 9307026 | 4/1993 | United Kingdom . |
| 2291647 | 1/1996 | United Kingdom . |
| 9106648 | 5/1991 | WIPO . |
| 9313423 | 7/1993 | WIPO . |
| 9323536 | 11/1993 | WIPO . |
| 9324629 | 12/1993 | WIPO . |
| 9325679 | 12/1993 | WIPO . |
| 9401094 | 1/1994 | WIPO . |
| 9404698 | 3/1994 | WIPO . |
| 9406428 | 3/1994 | WIPO . |
| 9411501 | 5/1994 | WIPO . |
| 9526401 | 10/1995 | WIPO . |

OTHER PUBLICATIONS

Bledsoe et al., Molecular homology and DNA hybridization, J. Mol. Evol., 30: 425–433, 1990.

Sun et al., Molecular cloning, chromosomal mapping, and functional expression of human brain glutamate receptors, Proc. Natl. Acad. Sci, USA, 89: 1443–1447, Feb. 1992.

Anantharam et al., Combinatorial RNA splicing alters the surface charge on the NMDA receptor, FEBS Lett., 305(1):27–30, Jun. 1992.

Jansen et al., Autoradiographic visualisation of [3H]DTG binding to sigma receptors, [3H]TCP binding sites, and L–[3H]glutamate binding to NMDA receptors in human cerebellum, Neurosci. Lett., 125(2): 143–146, Apr. 1991.

Masayuki, Human mRNA for key subunit of the N–methyl–D–aspartate receptor, DDBJ database, Oct. 1992.

Nakanishi et al., Alternative splicing generates functionally distinct N–methyl–D–aspartate receptors, Proc. Natl. Acad. Sci. USA, 89: 8552–8556, Sep. 1992.

Puckett et al., Molecular cloning and chromosomal localization of one of the human glutamate receptor genes, Proc. Natl. Acad. Sci. USA, 88: 7557–7561, Sep. 1991.

Reeck et al., "Homology" in proteins and nucleic acids: a terminology muddled and a way out of it, Cell, 50(667): 667, Aug. 1987.

Ikeda et al., Cloning and expression of the epsilon4 subunit of the NMDA receptor channel, *FEBS Lett. 313*(*1*): 34–38 (1992).

Shepherd, *Neurobiology*, Second Edition, Oxford University Press, New York, pp. 31, 76, 155, 157, 161 (1988).

Gilbert, *Developmental Biology*, Second Edition, Sinauer Assoiciates, Sunderland MA, pp. 54–55 (1988).

(List continued on next page.)

*Primary Examiner*—Paula K. Hutzell
*Assistant Examiner*—Claire M. Kaufman
*Attorney, Agent, or Firm*—Stephanie L. Seidman; Heller Ehrman White & McAuliffe

[57] ABSTRACT

In accordance with the present invention, there are provided nucleic acids encoding human NMDA receptor protein subunits and the proteins encoded thereby. The NMDA receptor subunits of the invention comprise components of NMDA receptors that have cation-selective channels and bind glutamate and NMDA. In one aspect of the invention, the nucleic acids encode NMDAR1 and NMDAR2 subunits of human NMDA receptors. In a preferred embodiment, the invention nucleic acids encode NMDAR1, NMDAR2A and NMDAR2C subunits of human NMDA receptors. In addition to being useful for the production of NMDA receptor subunit proteins, these nucleic acids are also useful as probes, thus enabling those skilled in the art, without undue experimentation, to identify and isolate related human receptor subunits. Functional glutamate receptors can be assembled, in accordance with the present invention, from a plurality of one type of NMDA receptor subunit protein (homomeric) or from a mixture of two or more types of subunit proteins (heteromeric). In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

37 Claims, 10 Drawing Sheets

OTHER PUBLICATIONS

George et al., Current Methods in Sequence Comparison, *Macromolecular Sequencing and Synthesis Selected Methods and Applications*, Alan R. Liss, Inc., pp. 127–149 (1988).

Grenningloh et al., Alpha subunit variants of the human glycine receptor: primary structures, functional expression and chromosomal localization of the corresponding genes, *The EMBO J. 9*(*3*): 771–776 (1990).

Schofield et al., Sequence and expression of human $GABA_A$ $\alpha1$ and $\Delta1$ subunits, *FEBS Lett. 244*(2): 361–364 (1989).

Abbott, NMDA receptor cloned, *Trends Pharmacol. Sci. 12*:449 (1991).

Abbott, NMDA receptor subunit cloned, *Trends Pharmacol. Sci. 12*:334 (1991).

Abe et al., Molecular characterization of a novel metabotropic glutamate receptor mGluR5 coupled to inositol phosphate/$Ca^{2+}$ signal transduction, *J. Biol. Chem. 267*:13361–13368 (1992).

Albin et al., Abnormalities of striatal projection neurons and N–methyl–D–asparate receptors in presymptomatic Huntington's Disease, *N. Engl. J. Med. 322*(*18*):1293–1298 (1990).

Bahouth et al., Immunological approaches for probing receptor structure and function, *Trends Pharmacol. Sci. 12*:338–343 (1991).

Barnard, Will the real NMDA receptor please stand up? *Trends Pharmacol. Sci. 13*:11–12 (1992).

Beal, Mechanisms of excitotoxicity in neurologic diseases, *FASEB J. 6*:3338–3344 (1992).

Ben–Ari et al., Protein kinase C modulation of NMDA currents: an important link for LTP induction, *Trends Neurosci. 15*:333–339 (1992).

Black et al., N–methyl–D–aspartate– or glutamate–mediated toxicity in cultured rat cortical rat cortical neurons is antagonized by FPL 15896AR, *J. Neurochem. 65*:2170–2177 (1995).

Bottaro et al, Identification of the hepatocyte growth factor receptor as the c–met proto–oncogene product, *Science 251*:802–804 (1991).

Bradford, A rapid and sensitive method for the quantitation of microgram quantities of protein utilizing the principle of protein–dye binding, *Anal. Biochem. 72*:248–254 (1976).

Bristow et al., The glycine/NMDA receptor antagonist R–(+)–HA–966, blocks actvation of the mesolimbic dopaminergic system induced by phencyclidine and dizcilpine (MK–801) in rodents, *Br. J. Pharmacol. 108*:1156–1163 (1993).

Choi, Calcium–mediated neurotoxicity: Relationship to specific channel types and role in ischemic damage, *Trends Neurosci. 11*(*10*):465–469 (1988).

Choi, Glutamate neurotoxicity and diseases of the nervous system, *Neuron 1*:623–634 (1988).

Ciba–Geigy Unveils Research Agreement with SIBIA of U.S., *The Wall Street Journal* (Sep. 17, 1992).

Coyle et al., Oxidative stress, glutamate, and neurodegenerative disorders, *Science 262*:689–695 (1993).

Daggett et al., Cloning and functional characterization of three splice variants of the human NMDAR1 receptor, *Biophys J., 36*(*2*):447 (1994).

Dascal, The use of *Xenopus oocytes* for the study of ion channels, *CRC Critical Reviews in Biochemistry 22*(*4*):317–387 (1987).

Donnelly and Pallotta, Single–channel currents from diethylpyrocarbonate–modified NMDA receptors and cultured rat brain cortical neurons, *J. Gen. Physol. 105*:837–859 (1995).

Durand et al., Cloning of an apparent splice variant of the rat N–methyl–D–asparate receptor NMDAR1 with altered sensitivity to polyamines and activators of protein kinase *C. Proc. Natl. Acad. Sci. USA 89*:9359–9363 (1992).

Egebjerg et al., Intron sequence directs RNA editing of the glutamate receptor subunit GluR2 coding sequence, *Proc. Natl. Acad. Sci. USA 91*:10270–10274 (1994).

Felder et al., A transfected m1 muscarinic acetylcholine receptor stimulates adenylate cyclase via phosphatidylinisitol hydrolysis, *J. Biol. Chem. 264*:20356–20362 (1989).

Fisher and Aronson, Characterization of the cDNA and genomic sequence of a G protein $\gamma$ subunit ($\gamma_5$), *Mol. Cell. Bio. 12*:1585–1591 (1992).

Foldes et al., Cloning and sequence analysis of cDNAs encoding human hippocampus N–methyl–D–aspartate receptor subunits: Evidence for alternative splicing, *Gene 131*:293–298 (1993).

Gautum et al., A G protein gamma subunit shares homology with ras proteins, *Science 244*:971–974 (1989).

Gautum et al., G protein diversity is increased by associations with a variety of $\gamma$ subunits, *Proc. Natl. Acad. Sci. USA 87*:7973–7977 (1990).

Gereau and Conn, Multiple presynaptic metabotropic glutamate receptors modulate excitory and inhibitory synaptic transmission in hippocampal area CA1, *J. Neurosci 15*(*10*):6879–6889 (1995).

Greenamyre et al., Synaptic localization of striatal NMDA, quisqualate and kainate receptors, *Neurosci. Lttrs. 101*:133–137 (1989).

Grimwood et al., Interactions between the glutamate and glycine recognition sites of the N–methyl–D–aspartate receptor from rat brain, as revealed from radioligand binding studies, *J. Neurochem. 60*:1729–1738 (1993).

Gubler et al., A simple and very efficient method for generating cDNA libraries, *Gene 25*:263–269 (1983).

Gunasekar et al., NMDA recepetor activation produces concurrent generation of nitric oxide and reactive oxygen species: Implication for cell death, *J. Neurochem. 65*:2016–2021 (1995).

Gundersen et al., Glutamate and kainate receptors induced by rat brain messenger RNA in *Xenopus oocytes, Proc. R. Soc. London Ser. 221*:127–143 (1984).

Hess et al., Cloning, functional expression, and pharmacological characterization of human NMDAR1/NMDAR2 heteromeric receptors, *Biophys J., 36*(*2*):446 (1994).

Hess et al., Biophysical properties of human NMDA receptors stably expressed in mammalian cells, *Soc. Neurosci. Abstr. 21*:1–3 (1995).

Hoffman, NMDA receptor cloned—twice! *Science 254*:801–802 (1991).

Hollman et al., Zinc potentiates agonist–induced currents at certain splice variants of the NMDA receptor, *Neuron 10*:943–954 (1993).

Hollman et al., Cloned glutamate receptors, *Annu. Rev. Neurosci. 17*:31–108 (1994).

Hurley et al., Isolation and characterization of a cDNA clone for the $\gamma$ subunit of bovine retinal transducin, *Proc. Natl. Acad. Sci. USA 81*:6948–6952 (1984).

Ishii et al., Molecular characterization of the family of the N–methyl–D–aspartate receptor subunits, *J. Biol. Chem.* 268(4):2836–2843 (1993).

Ito et al., Chacterization of prostaglandin $E_2$–induced $Ca^{2+}$ mobilization in single bovine adrenal chromaffin cells by digital image microscopy, *J. Neurochem. 56*:531–540 (1991).

Jones et al., Chacterization of the binding of radioligands to the N–methyl–D–aspartate, phenyclidine, and glycine receptors in buffy coat membranes, *J. Pharmacol. Meth. 21*:161–168 (1989).

Kantak et al., Effects of N–methyl–D–aspartate antagonists in rats discriminating different doses of cocaine: Comparisons with direct and indirect dopamine agonists, *J. Pharmacol. Exper. Therap. 274*:657–665 (1995).

Karp et al., Molecular cloning and chromosomal localization of the key subunit of the human N–methyl–D–aspartate receptor, *J. Biol. Chem. 268*:3728–3733 (1993).

Kemp et al., Protein kinase recognition sequence motifs, *Trends Biochem. Sci. 15*:342–346 (1990).

Kishimoto et al. Studies on the phosphorylation of myelin basic protein by protein kinase C and adenosine 3':5'–monophosphate–dependent protein kinase, *J. Biol. Chem. 260*:12492–12499 (1985).

Kisselev et al., Receptor–G protein coupling is established by a conformational switch in the βγ complex, *Proc. Natl. Acad. Sci. USA 92*:9102–9106 (1995).

Kleuss et al., Selectivity in signal transduction determined by γ subunits of heterotrimeric G proteins, *Science 259*:832–834 (1993).

Köhr et al., NMDA receptor Channels: Subunit–specific potentiation by reducing agents, *Neuron 12*:1031–1040 (1994).

Kozak, Structural features in eukaryotic mRNAs that modulate the initiation of translation, *J. Biol. Chem. 266*:19867–19870 (1991).

Krieg and Melton, Functional messenger RNAs are produced by SP6 in vitro transcription of cloned cDNAs, *Nucleic Acids Research 12*:7057–7070 (1984).

Kumar et al., Cloning of cDNA for the glutamate–binding subunit of an NMDA receptor complex, *Nature 354*:70–73 (1991).

Kutsuwada et al., Molecular diversity of the NMDA receptor channel, *Nature 358*:36–41 (1992).

Kyte and Doolittle, A simple method for displaying the hydropathic chacter of a protein, *J. Mol. Biol. 157*:105–132 (1982).

Landwehrmeyer et al., NMDA receptor subunit mRNA expression by projection neurons and interneurons in rat striatum, *J. Neurosci. 15*(*7*):5297–5307 (1995).

Le Bourdellès et al., Cloning, functional coexpression, and pharmacological characterisation of human cDNAs encoding NMDA receptor NR1 and NR2A subunits, *J. Neurochem. 62*:2091–2098 (1994).

Linder and Gilman, G proteins, *Scientific American 267*:56–65 (1992).

Liu et al., Mutational analysis of the relative orientation of transmembrane helices I and VII in G protein–coupled receptors, *J. Biol. Chem. 270*(*3*):19532–19539 (1995).

Lynch et al., Pharmacological chacterization of heterodimeric NMDA receptors of NR1a and 2B subunits: Differences with receptors formed from NR 1a and 2A, *J. Neurochem. 64*:1462–1468 (1995).

Masu et al., Sequence and expression of a metabotropic glutamate receptor, *Nature 349*:760–765 (1991).

Mayer, NMDA receptors cloned at last, *Nature 354*:16–17 (1991).

Meguro et al., Functional characterization of a heteromeric NMDA receptor channel expressed from cloned cDNAs, *Nature 357*:70–74 (1992).

Meldrum, Possible therapeutic applications of antagonists of excitatory amino acid neurotransmitters, *Clin. Sci. 68*:113–122 (1985).

Meldrum et al., Excitatory amino acid neurotoxicity and neurodegenerative disease, *Trends Pharmacol. Sci. 11*:379–387 (1990).

Minakami et al., The expression of two splice variants of metabotropic glutamate receptor subtype 5 in the rat brain and neuronal cells during development, *J. Neurochem. 65*:1536–1542 (1995).

Monaghan et al., The excitatory amino acid receptors: Their classes, pharmacology, and distinct properties in the function of the central nervous system, *Ann. Rev. Pharmacol. Toxicol. 29*: 365–402 (1980).

Monyer et al., Heteromeric NMDA receptors: Molecular and functional distinction of subtypes, *Science 256*:1217–1221 (1992).

Monyer et al., Developmental and regional expression in the rat brain and functional properties of four NMDA receptors, *Neuron 12*:529–540 (1994).

Moriyoshi et al., Molecular cloning and characterization of the rat NMDA receptor, *Nature 354*:31–37 (1991).

Nakajima et al., Direct linkage of three tachykinin receptors to stimulation of both phosphatidylinositol hydrolysis and cyclic AMP cascades in transfected Chinese hamster ovary cells, *J. Biol. Chem. 267*:2437–2442 (1992).

Nakanishi, Molecular diversity of glutamate receptors and implications for brain function, *Science 258*:597–603 (1992).

Nicoletti et al., The activation of inositol phospholipid metabolism as a signal–transducing system for excitory amino acids in primary cultures of cerebellar granule cells, *J. Neurosci. 6*:1905–1911 (1986).

SIBIA/Ciba–Geigy agreement, *UCSD Connect* (Sep. 16, 1992).

Ogita et al., A possible role of glutathione as an endogenous agonist at the N–methyl–D–aspartate recognition domain in rat brain, *J. Neurochem. 64*:1088–1096 (1995).

Other News to Note, *BioWorld Today*, 6 (Apr. 15, 1994).

O'Connor et al., Tetanically induced LTP involves a similar increase in the AMPA and NMDA receptor components of the excitory postsynaptic current: Investigations of the involvement of mGlu receptors, *J. Neurosci. 15*(*3*):2013–2020 (1995).

Paoletti and Ascher, Mechanosensitivity of NMDA receptors in cultured mouse central neurons, *Neuron 13*:645–655 (1995).

Pin et al., Alternative splicing generates metabotropic glutamate receptors inducing different patterns of calcium release in *Xenopus oocytes, Neurobiology 89*:10331–10335 (1992).

Planells–Cases et al., Molecular cloning, functional expression, and pharmacological characterization of an N–methyl–D–aspartate receptor subunit from human brain, *Proc. Natl. Acad. Sci. USA 90*:5057–5061 (1993).

Potter, Sibia to collaborate with Ciba–Geigy, *BioWorld Today 3*:1 (Sep. 17, 1992).

Rueter et al., Glutamate receptor RNA editing in vitro by enzymatic conversion of adenosine to inosine, *Science 267*:1491–1494 (1995).

Sakurada et al., Alteration of $Ca^{2+}$ permeability and sensitivity to $Mg^{2+}$ and channel blockers by a single amino acid substitution in the N–methy–D–aspartate, *J. Biol. Chem. 268*(*1*):410–415 (1993).

Sambrook et al., *Molecular Cloning. A Labortatory Manual*, 2d Ed., Cold Spring Harbor Laboratory Press (1989).

Sanes et al., Use of a recombinant retrovirus to study post–implantation cell lineage in mouse embryos, *EMBO J. 5*(*12*):3133–3142 (1986).

Sanner et al., NMDA receptor blockade rescues Clarke's and red nucleus nuerons after spinal hemisection, *J. Neurosci. 14*(*11*):6472–6480 (1995).

Schoepp et al., 1S,3R–ACPD–sensitive (metabotropic [$^3$H] glutamate receptor binding in membranes, *Neurosci. Lett. 145*:100–104 (1992).

Sills et al., [$^3$H]CGP 39653: a new N–methyl–D–aspartate antagonist radioligand with low nanomolar affinity in rat grain, *Eur. J. Pharmacol. 192*:19–24 (1991)

Simon et al., Diversity of G proteins in signal transduction, *Science 252*:802–808 (1991).

Singaram et al., Dopaminergic defect of enteric nervous system in Parkinson's disease patients with chronic constipation, *Lancet 346*:861–864 (1995).

Sladeczek et al., Glutamate stimulates inositol phosphate formation in striatial neurones, *Nature 317*:717–719 (1985).

Smirnova et al., Isolation and Study of cDNA coding for the synthesis of glutamate receptors ofhuman brain, *Dol. Akad. Nauk SSSR* 303(3):756–759 (1988).

Smirnova et al., Cloning a complementary DNA fragment of human brain kainate receptor, *Dol. Akad. Nauk SSSR* 309(3):745–748 (1989).

Smirnova et al., Characterization of a presynaptic glutamate receptor, *Science 262*:430–433 (1993).

Smirnova et al., Transsynaptic expression of a presynaptic glutamate receptor during hippocampal long–term potentiation, *Science* 262:433–436 (1993).

Sommer et al., Glutamate receptor channels: novel properties and new clones, *Trends Pharmacol. Sci 13*:291–296 (1992).

Steiner et al., Radioimmunoassay for cyclic nucleotides, *J. Biol. Chem. 247*:1106–1113 (1972).

Stillman et al., Replication and supercoiling of simian virus 40DNA in cell extracts from human cells, *Mol. Cell. Biol. 5*:2051–2060 (1985).

Stümer, Electrophysiological recording from *Xenopus oocytes, Meth. Enzymol. 207*:319–339 (1992).

Sugihara et al., Structures and properties of seven isoforms of the NMDA receptor generated by alternative splicing, *Biochem. Biophys. Res. Commun. 183*(*3*):826–832 (1992).

Sugiyama et al., A new type of glutamate receptor linked to inositol phospholipid metabolism, *Nature 325*:531–533 (1987).

Sullivan et al., Identifiction of two cysteine residues that are required for redox modulation of the NMDA subtype of glutamate receptor, *Neuron 13*:929–936 (1994).

Takano et al., Chromosomal localization of the $\epsilon1$, $\epsilon3$ and $\zeta1$ subunit genes of the human NMDA receptor channel, *Biochem. Biophys. Res. Commun. 197*(*2*):922–926 (1993).

Tamir et al., G–protein $\beta\gamma$ forms: Identity of $\beta$ and diversity of $\gamma$ subunits, *Biochemistry 30*:3929–3936 (1991).

Tanabe et al., A family of metabotropic glutamate receptors, *Neuron 8*:169–179 (1992).

Tingley et al., Regulation of NMDA receptor phosphorylation by alternative splicing of the C–terminal domain, Nature 364:70–73 (1993).

Ulas et al., Selective increase of NMDA–sensitive glutamate binding in the striatum of Parkinson's disease, Alzheimer's disease, and mixed Parkinson's disease/Alzheimer's disease patients: An autoradiographic study, *J. Neurosci. 14*(*11*):6317–6324 (1994).

Urlaub et al., Effect of gamma rays at the dihydrofolate reductase locus: Deletions and Inversions, *Somatic Cell and Mol. Genetics 12*(*6*):555–566 (1986.

Varney et al., Stable expression and characterization of recombinant human dimeric NMDA receptor subtypes 1A/2A and 1A/2B in mammalian cells, *Soc. Neurosci. Abstr.* (1995).

Vornov et al., Enhancement of NMDA receptor–mediated neurotoxicity in the hippocampal slice by depolarization and ischemia, *Brain Res. 555*:99–106 (1991).

Waechter and Baserga, Effect of methylation on expression of microinjected genes, *Proc. Natl. Acad. Sci. USA 79*:1106–1110 (1982).

Wafford et al., Preferential co–assembly of recombinant NMDA receptors composed of three different subunits, *NeuroReport 4*(*12*):1347–1349 (1993).

Wahlestedt et al., Antisense oligodeoxynucleotides to NMDA–R1 receptor channel protect cortical neurons from excitotoxicity and reduce focal ischaemic infarctions, *Nature 363*:260–263 (1993).

Wenzel et al., Distribution of NMDA receptor subunit proteins NR2A, 2B, 2C, and 2D in rat brain, *NeuroReport 7*:45–48 (1995).

Wigler et al., DNA–mediated transfer of the adenine phosphoribosyltransferase locus into mammalian cells, *Proc. Natl. Acad. Sci. USA 76*:1373–1376 (1979).

Wong et al., The anticonvulsant MK–801 is a potent N–methyl–D–aspartate antagonist, *Proc. Natl. Acad. Sci. USA 83*:7104–7108 (1986).

Yakel et al., Identification of a $Ca^{2+}$/calmodulin–dependent protein kinase II regulatory phosphorylation site in N–methyl–D–aspartate glutamate receptors, *Proc. Natl. Acad. Sci. USA 92*:1376–1380 (1995).

Young et al., NMDA receptor losses in putamen from patients with Huntington's Disease, *Science 241*:981–983 (1988).

Younkin et al., Inducible expression of neuronal glutamate receptor channels in the NT2 human cell line, *Proc. Natl. Acad. Sci. USA 90*:2174–2178 (1993).

Zeevalk et al., Chemically induced hypoglycemia and anoxia: Relationship to glutamate receptor–mediated toxicity in retina, *J. Pharmacol. Exp. Thera. 253*(*3*):1285–1292 (1990).

Zeevalk et al., Mechanisms underlying initiation of excitotoxicity associated with metabolic inhibition, *J. Pharmacol. Exp. Thera. 257*(*2*):870–878 (1991).

Zhang et al., Spermine potentiation of recombinant N–methyl–D–aspartate receptors is affected by subunit composition, *Proc. Natl. Acad. Sci. USA 91*:10883–10887 (1994).

Zipser et al., Mapping function domains in the promoter region of the herpes thomidine kinase gene, *Proc. Natl. Acad. Sci. USA 78*(*10*):6276–6280 (1981).

1 CAAGCCGGGC GTTCGGAGCT GTGCCCGGCC CCGCTTCAGC ACCGCGGACA GCGCCGGCCG CGTGGGGCTG AGCGCCGAGC CCCCGCGCAC GCTTCAGCCC

101 CCCTTCCCTC GGCCGACGTC CCGGGACCGC CGCTCCGGGG GAGACGTGGC GTCCGCAGCC CGCGGGGCCG GGCGAGCGCA GGACGGCCCG GAAGCCCCGC

-START

201 GGGGGATGCG CCGAGGGCCC CGCGTTCGCG CCGCGCAGAG CCAGGCCCGC GGCCCGAGCC CATGAGCACC ATGCGCCTGC TGACGCTCGC CCTGCTGTTC

301 TCCTGCTCCG TCGCCCGTGC CGCGTGCGAC CCCAAGATCG TCAACATTGG CGCGGTGCTG AGCACGCGGA AGCACGAGCA GATGTTCCGC GAGGCCGTGA

401 ACCAGGCCAA CAAGCGGCAC GGCTCCTGGA AGATTCAGCT CAATGCCACC TCCGTCACGC ACAAGCCCAA CGCCATCCAG ATGGCTCTGT CGGTGTGCGA

501 GGACCTCATC TCCAGCCAGG TCTACGCCAT CCTAGTTAGC CATCCACCTA CCCCCAACGA CCACTTCACT CCCACCCCTG TCTCCTACAC AGCCGGCTTC

601 TACCGCATAC CCGTGCTGGG GCTGACCACC CGCATGTCCA TCTACTCGGA CAAGAGCATC CACCTGAGCT TCCTGCGCAC CGTGCCGCCC TACTCCCACC

Pvu II

701 AGTCCAGCGT GTGGTTTGAG ATGATGCGTG TCTACAGCTG GAACCACATC ATCCTGCTGG TCAGCGACGA CCACGAGGGC CGGGCGGCTC AGAAACGCCT 63 bp INSERT

801 GGAGACGCTG CTGGAGGAGC GTGAGTCCAA GGCAGAGAAG GTGCTGCAGT TTGACCCAGG GACCAAGAAC GTGACGGCCC TGCTGATGGA GGCGAAAGAG

Sma I

901 CTGGAGGCCC GGGTCATCAT CCTTTCTGCC AGCGAGGACG ATGCTGCCAC TGTATACCGC GCAGCCGCGA TGCTGAACAT GACGGGCTCC GGGTACGTGT

Bgl II

1001 GGCTGGTCGG CGAGCGCGAG ATCTCGGGGA ACGCCCTGCG CTACGCCCCA GACGGCATCC TCGGGCTGCA GCTCATCAAC GGCAAGAACG AGTCGGCCCA 204 bp DELETION

1101 CATCAGCGAC GCCGTGGGCG TGGTGGCCCA GGCCGTGCAC GAGCTCCTCG AGAAGGAGAA CATCACCGAC CCGCCGCGGG GCTGCGTGGG CAACACCAAC

1201 ATCTGGAAGA CCGGGCCGCT CTTCAAGAGA GTGCTGATGT CTTCCAAGTA TGCGGATGGG GTGACTGGTC GCGTGGAGTT CAATGAGGAT GGGGACCGGA

1301 AGTTCGCCAA CTACAGCATC ATGAACCTGC AGAACCGCAA GCTGGTGCAA GTGGGCATCT ACAATGGCAC CCACGTCATC CCTAATGACA GGAAGATCAT

Kpn I

1401 CTGGCCAGGC GGAGAGACAG AGAAGCCTCG AGGGTACCAG ATGTCCACCA GACTGAAGAT TGTGACGATC CACCAGGAGC CCTTCGTGTA CGTCAAGCCC

1501 ACGCTGAGTG ATGGGACATG CAAGGAGGAG TTCACAGTCA ACGGCGACCC AGTCAAGAAG GTGATCTGCA CCGGGCCCAA CGACACGTCG CCGGGCAGCC

1601 CCCGCCACAC GGTGCCTCAG TGTTGCTACG GCTTTTGCAT CGACCTGCTC ATCAAGCTGG CACGGACCAT GAACTTCACC TACGAGGTGC ACCTGGTGGC

FIG. 3A

```
                                         ┌Hind III┐
1701 AGATGGCAAG TTCGGCACAC AGGAGCGGGT GAACAACAGC AACAAGAAGG AGTGGAATGG GATGATGGGC GAGCTGCTCA GCGGGCAGGC AGACATGATC
1801 GTGGCGCCGC TAACCATAAA CAACGAGCGC GCGCAGTACA TCGAGTTTTC CAAGCCCTTC AAGTACCAGG GCCTGACTAT TCTGGTCAAG AAGGAGATTC
1901 CCCGGAGCAC GCTGGACTCG TTCATGCAGC CGTTCCAGAG CACACTGTGG CTGCTGGTGG GGCTGTCGGT GCACGTGGTG GCCGTGATGC TGTACCTGCT
2001 GGACCGCTTC AGCCCCTTCG GCCGGTTCAA GGTGAACAGC GAGGAGGAGG AGGAGGACGC ACTGACCCTG TCCTCGGCCA TGTGGTTCTC CTGGGGCGTC

2101 CTGCTCAACT CCGGCATCGG GGAAGGCGCC CCCAGAAGCT TCTCAGCGCG CATCCTGGGC ATGGTGTGGG CCGGCTTTGC CATGATCATC GTGGCCTCCT
2201 ACACCGCCAA CCTGGCGGCC TTCCTGGTGC TGGACCGGCC GGAGGAGCGC ATCACGGGCA TCAACGACCC TCGGCTGAGG AACCCCTCGG ACAAGTTTAT
2301 CTACGCCACG GTGAAGCAGA GCTCCGTGGA TATCTACTTC CGGCGCCAGG TGGAGCTGAG CACCATGTAC CGGCATATGG AGAAGCACAA CTACGAGAGT
2401 GCGGCGGAGG CCATCCAGGC CGTGAGAGAC AACAAGCTGC ATGCCTTCAT CTGGGACTCG GCGGTGCTGG AGTTCGAGGC CTCGCAGAAG TGCGACCTGG
2501 TGACGACTGG AGAGCTGTTT TTCCGCTCGG GCTTCGGCAT AGGCATGCGC AAAGACAGCC CCTGGAAGCA GAACGTCTCC CTGTCCATCC TCAAGTCCCA
2601 CGAGAATGGC TTCATGGAAG ACCTGGACAA GACGTGGGTT CGGTATCAGG AATGTGACTC GCGCAGCAAC GCCCCTGCGA CCCTTACTTT TGAGAACATG
2701 GCCGGGGTCT TCATGCTGGT AGCTGGGGGC ATCGTGGCCG GGATCTTCCT GATTTTCATC GAGATTGCCT ACAAGCGGCA CAAGGATGCT CGCCGGAAGC

                                            ┌Pst I┐
2801 AGATGCAGCT GGCCTTTGCC GCCGTTAACG TGTGGCGGAA GAACCTGCAG GATAGAAAGA GTGGTAGAGC AGAGCCTGAC CCTAAAAAGA AAGCCACATT
2901 TAGGGCTATC ACCTCCACCC TGGCTTCCAG CTTCAAGAGG CGTAGGTCCT CCAAAGACAC GAGCACCGGG GGTGGACGCG GTGCTTTGCA AAACCAAAAA
3001 GACACAGTGC TGCCGCGACG CGCTATTGAG AGGGAGGAGG GCCAGCTGCA GCTGTGTTCC CGTCATAGGG AGAGCTGAGA CTCCCCGCCC GCCCTCCTCT
3101 GCCCCCTCCC CCGCAGACAG ACAGACAGAC GGACGGGACA GCGGCCCGGC CCACGCAGAG CCCCGGAGCA CCACGGGGTC GGGGGAGGAG CACCCCCAGC
3201 CTCCCCCAGG CTGCGCCTGC CCGCCCGCCG GTTGGCCGGC TGGCCGGTCC ACCCCGTCCC GGCCCCGCGC GTGCCCCCAG CGTGGGGCTA ACGGGCGCCT
3301 TGTCTGTGTA TTTCTATTTT GCAGCAGTAC CATCCCACTG ATATCACGGG CCCGCTCAAC CTCTCAGATC CCTCGGTCAG CACCGTGGTG TGAGGCCCCC
```

363 bp DELETION

FIG. 3B

```
3401 GGAGGCGCCC ACCTGCCCAG TTAGCCCGGC CAAGGACACT GATGGGTCCT GCTGCTCGGG AAGGCCTGAG GGAAGCCCAC CCGCCCCAGA GACTGCCCAC
3501 CCTGGGCCTC CCGTCCGTCC GCCCGCCCAC CCCGCTGCCT GGCGGGCAGC CCCTGCTGGA CCAAGGTGCG GACCGGAGCG GCTGAGGACG GGGCAGAGCT
3601 GAGTCGGCTG GGCAGGGCCG CAGGGCGCTC CGGCAGAGGC AGGCCCCTGG GGTCTCTGAG CAGTGGGGAG CGGGGGCTAA CTGCCCCCAG GCGGAGGGGC
3701 TTGGAGCAGA GACGGCAGCC CCATCCTTCC CGCAGCACCA GCCTGAGCCA CAGTGGGGCC CATGGCCCCA GCTGGCTGGG TCGCCCCTCC TCGGGCGCCT
3801 GCGCTCCTCT GCAGCCTGAG CTCCACCCTC CCCTCTTCTT GCGGCACCGC CCACCAAACA CCCCGTCTGC CCCTTGACGC CACACGCCGG GGCTGGCGCT
3901 GCCCTCCCCC ACGGCCGTCC CTGACTTCCC AGCTGGCAGC GCCTCCCGCC GCCTCGGGCC GCCTCCTCCA GAATCGAGAG GGCTGAGCCC CTCCTCTCCT
4001 CGTCCGGCCT GCAGCACAGA AGGGGGCCTC CCCGGGGGTC CCCGGACGCT GGCTCGGGAC TGTCTTCAAC CCTGCCCTGC ACCTTGGGCA CGGGAGAGCG
4101 CCACCCGCCC GCCCCCGCCC TCGCTCCGGG TGCGTGACCG GCCCGCCACC TTGTACAGAA CCAGCACTCC CAGGGCCCGA GCGCGTGCCT TCCCCGTGCG
4201 CAGCCGCGCT CTGCCCCTCC GTCCCCAGGG TGCAGGCGCG CACCGCCCAA CCCCCACCTC CCGGTGTATG CAGTGGTGAT GCCTAAAGGA ATGTCACG
```

1087 bp DELETION

FIG. 3C

HUMAN N-METHYL-D-ASPARTATE RECEPTOR TYPE 1 SUBUNITS, DNA ENCODING SAME AND USES THEREFOR

This application is a continuation of application Ser. No. 08/052,449, filed Apr. 20, 1993, now abandoned. The entire contents of which are hereby incorporated by reference herein.

The present invention relates to DNA and receptor proteins encoded thereby. Invention DNAs encode novel human N-methyl-D-aspartate (NMDA) receptor subunits. The invention also relates to methods for making such receptor subunits and for using the receptor proteins in assays designed to identify and characterize compounds which affect the function of such receptors, e.g., agonists and antagonists of NMDA receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria which serve to define five receptor subtypes or classes: those activated by N-methyl-D-aspartic acid (NMDA), kainic acid (KA), α-amino-3-hydroxy-5-methyl-isoxazole-4-propionic-acid (AMPA, formally called the quisqualic acid or QUIS receptor), 2-amino-4-phosphonobutyric acid (AP4 or APB), and 1-amino-cyclopentyl-1,3-dicarboxylic acid (ACPD). The effects of glutamate are mediated primarily through interactions with cation-selective, ionotropic receptors [Foster and Fagg, Brain Res. 7:103–164 (1984); Strange, Biochem. J. 249:309–318 (1988)]. An exception is the ACPD receptor, which is a subtype of the metabotropic receptors. This class of glutamate receptors alters synaptic physiology via GTP-binding proteins and second messengers such as cyclic AMP, cyclic GMP, diacylglycerol and inositol 1,4,5-triphosphate [Gundersen et al., Proc. R. Soc. London Ser. 221:127 (1984); Sladeczek et al., Nature 317:717 (1985); Nicoletti et al., J. Neurosci. 6:1905 (1986); Sugiyama et al., Nature 325:531 (1987)].

The electrophysiological and pharmacological properties of the glutamate receptors have been studied using animal tissues and cell lines as a source of receptors. See, for example, Foster and Fagg, supra; Cotman et al., Trends Neurosci. 10:263 (1987); Mayer and Westbrook, Prog. Neurobiol. 28:197 (1987); Watkins and Olvermann, Trends Neurosci. 10:265 (1987); and Blair et al., Science 242:577 (1988). The value of such studies for application to the development of human therapeutics has been limited by the availability of only non-human receptor subunits. Moreover, it is only recently that the characteristics and structure of glutamate receptors have been investigated at the molecular level. The majority of such investigation has, however, been carried out in non-human species. Because of the potential physiological and pathological significance of glutamate receptors, it would be desirable (for example, for drug screening assays) to have available human sequences (i.e., DNA, RNA, proteins) which encode representative members of the various glutamate receptor subtypes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding NMDA receptor protein subunits and the proteins encoded thereby. In a particular embodiment the novel nucleic acids encode NMDAR1 and NMDAR2 subunits of human NMDA receptors. More specifically, the invention nucleic acids encode NMDAR1, NMDAR2A and NMDAR2C subunits that contribute to the formation of NMDA-activated cation-selective ion channels. In addition to being useful for the production of NMDA receptor subunit proteins, these nucleic acids are also useful as probes, thus enabling those skilled in the art, without undue experimentation, to identify and isolate nucleic acids encoding related receptor subunits.

Functional glutamate receptors can be assembled, in accordance with the present invention, from a plurality of NMDA subunit proteins of one type (homomeric) or from combinations of subunit proteins of different types (heteromeric).

In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

BRIEF DESCRIPTION OF THE FIGURES

FIGS. 3A–3C presents the entire nucleotide sequence of construct NMDAR1 (see Sequence ID No. 1) with the following information added for ease of comparison of the splice variations of the NMDAR1 subunit transcript: the translation initiation codon is identified by the word "START" whereas the three different translation termination codons (TGA) used in the different splice variants are identified by small boxes; significant restriction enzyme sites used in preparing full-length variant constructs are identified by name above the sites; the location of a 63-bp insertion (see Sequence ID No. 3) that exists in some of the variants is marked as "63 bp INSERT"; the nucleotide sequences that are deleted from some of the variants are boxed and labeled as "204 bp DELETION," 363 bp DELETION," and "1087 bp DELETION."

DETAILED DESCRIPTION OF THE INVENTION

Figure 1:
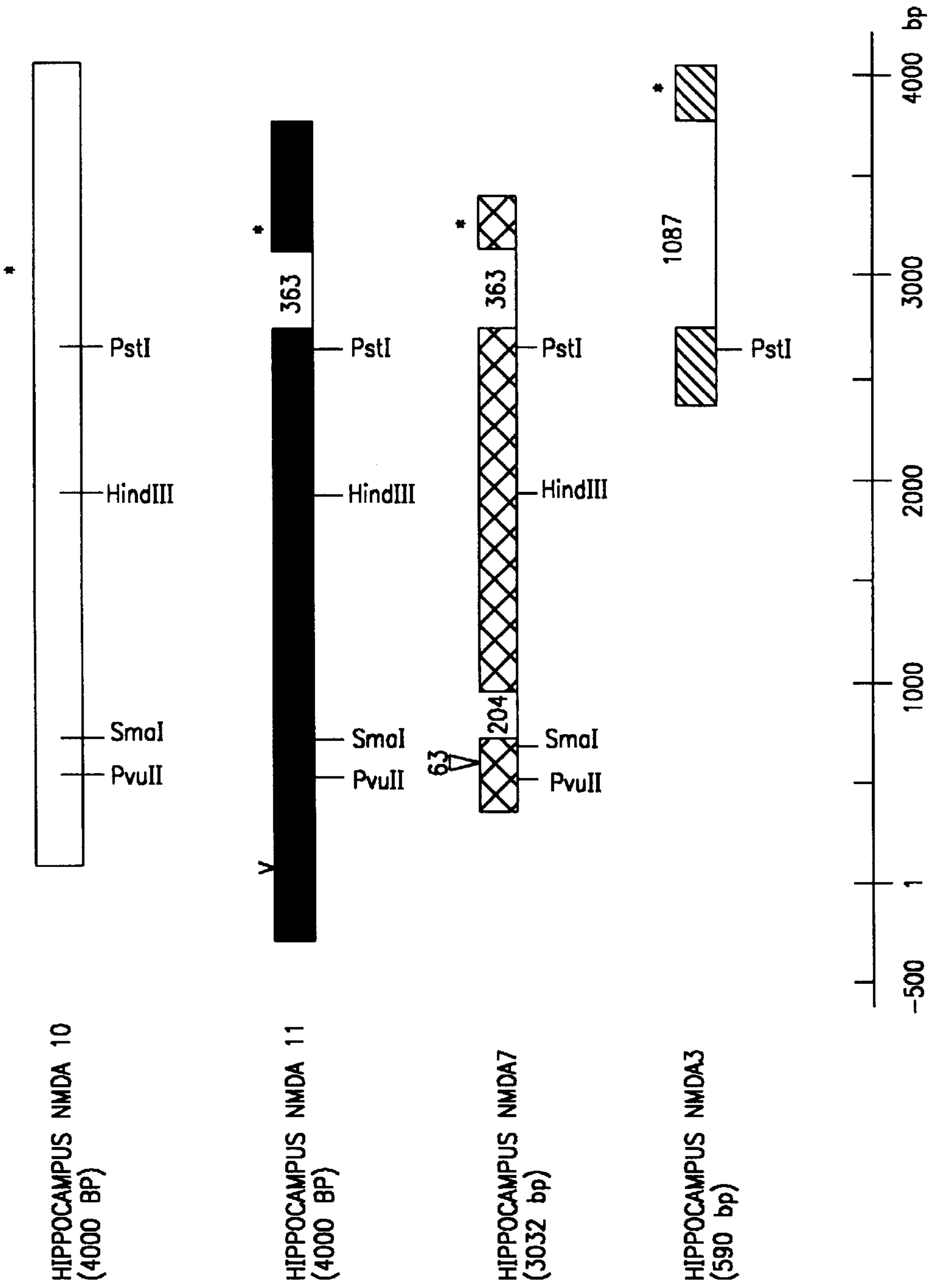
FIG. 1 is a schematic representation of various human NMDAR1 clones of the invention, with partial restriction maps of each clone. The clones are aligned and the differences in the DNAs (i.e., deletions and insertions), relative to clone NMDA10, are indicated. Translation initiation and termination sites are represented by a "V" and a "*", respectively. Insertions are marked as inverted triangles, deletions are indicated by spaces in the boxes. The numbers above the insertions and deletions refer to the number of nucleotides inserted or deleted relative to NMDA10.

In accordance with the present invention, there are provided isolated nucleic acids encoding human N-methyl-D-aspartate (NMDA) receptor subunit(s). In one aspect of the present invention, nucleic acids encoding NMDA receptor subunit(s) of the NMDAR1 subtype are provided. In another aspect, nucleic acids encoding NMDA receptor subunit(s) of the NMDAR2 subtype are provided. In a further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising at least NMDA receptor subunit-selective portions of the above-described nucleic acids.

As employed herein, the phrase "human N-methyl-D-aspartate (NMDA) receptor subunit(s)" refers to recombinantly produced (i.e., isolated or substantially pure) proteins which participate in the formation of a voltage-sensitive cation-selective channel activated by exposure to NMDA, and having at least one transmembrane domain, a large N-terminal extracellular domain, and the like, including variants thereof encoded by mRNA generated by alternative splicing of a primary transcript, and further including fragments thereof which retain one or more of the above properties.

Use of the phrase "recombinantly produced", "isolated" or "substantially pure" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of NMDA (or NMDA-like) ligand to receptors comprising the protein(s) causes the receptor "ion channels" to open. This allows cations, particularly $Ca^{2+}$, as well as $Na^+$ and $K^+$, to move across the membrane. Stated another way, "functional" means that a signal is generated as a consequence of agonist activation of receptor protein(s).

As used herein, a splice variant refers to variant NMDA receptor subunit-encoding nucleic acid(s) produced by differential processing of primary transcript(s) of genomic DNA, resulting in the production of more than one type of mRNA. cDNA derived from differentially processed primary transcript will encode NMDA receptor subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are DNAs that encode NMDA receptor subunits as defined above, but that by virtue of degeneracy of the genetic code do not necessarily hybridize to the disclosed DNA under specified hybridization conditions. Such subunits also contribute to the formation of functional receptor, as assessed by methods described herein or known to those of skill in the art, with one or more additional NMDA receptor subunits of the same or different type (the presence of additional subunits of a different type is optional when said subunit is an NMDAR1 subunit). Typically, unless an NMDA receptor subunit is encoded by RNA that arises from alternative splicing (i.e., a splice variant), NMDA receptor subunit-encoding DNA and the NMDA receptor subunit encoded thereby share substantial sequence homology with at least one of the NMDA receptor subunit DNAs (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional NMDA receptor subunit.

As employed herein, the phrase "NMDA receptor subunit (s) of the NMDAR1 subtype" refers to proteins which, by hydrophobicity analysis of deduced amino acid sequences, are believed to contain 4 putative transmembrane domains, preceded by a large extracellular N-terminal domain. The amino acid sequence typically contains possible phosphorylation sites for $Ca^{2+}$/calmodulin-dependent protein kinase type II and protein kinase C [see Kemp et al. (1990) Trends in Biological Science Vol. 15:342–346; Kishimoto et al. (1985) J. Biol. Chem. Vol. 260:12492–124993. (These protein kinases reportedly play a crucial role in induction and maintenance of long term potentiation.)

The putative TMII segment (i.e., second transmembrane domain) is typically flanked by a glutamic acid residue at the extracellular side and a stretch of glutamic acid residues at the cytoplasmic side. This segment contains an asparagine residue believed to be responsible for high $Ca^{2+}$ permeability of the NMDAR channel. For a summary of NMDAR properties, see Ben-Ari et al., in TINS 15:333–339 (1992), especially at p. 334.

Exemplary DNA sequences encoding human NMDAR1 subunits are represented by nucleotides which encode substantially the same amino acid sequence as set forth in Sequence ID Nos. 2, 20, 22, 24, 26, 28, 30, 32, 34, 36, 38 or 40. Presently preferred sequences encode substantially the same amino acid sequence as set forth in Sequence ID Nos. 2, 20, 22, 24, 26 or 28.

Exemplary DNA can alternatively be characterized as those nucleotide sequences which encode a human NMDAR1 subunit and hybridize under high stringency conditions to any one of Sequence ID Nos. 1, nucleotides 320–3402 of Nos. 1, 13, 15, 17, 19, 21, 23, 25, 27, 29, 31, 33, 35, 37 or 39; preferably to any one of Sequence ID Nos. 1, 29, 21, 23, 25 or 27.

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C.-16.6(\log_{10}[Na^+])+0.41(\% G+C)-600/l,$$

where l is the length of the hybrids in nucleotides. $T_m$ decreases approximately 1–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.;

(2) MODERATE STRINGENCY refers to conditions equivalent to hybridization in 50% formamide, 5× Denhart's solution, 5× SSPE, 0.2% SDS at 42° C., followed by washing in 0.2× SSPE, 0.2% SDS, at 65° C.; and (3) LOW STRINGENCY refers to conditions equivalent to hybridization in 10% formamide, 5× Denhart's solution, 6× SSPE, 0.2% SDS at 42° C., followed by washing in 1× SSPE, 0.2% SDS, at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual,* Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50× stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences are those which have substantially the same nucleotide sequence as the coding sequences in any one of Sequence ID Nos. 1, 19, 21, 23, 25, 27, 29, 31, 33, 35, 37 or 39; with those having substantially the same sequence as the coding sequence in Sequence ID Nos. 1, 19, 21, 23, 25, or 27 being most preferred.

As used herein, nucleotide sequences which are substantially the same share at least about 90% identity, and amino acid sequences which are substantially the same typically share more than 95% amino acid identity (>99% amino acid identity when dealing with NMDAR1 subunits). It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The phrase "substantial sequence homology" is used herein in reference to the nucleotide sequence of DNA, the ribonucleotide sequence of RNA, or the amino acid sequence of protein, that have slight and non-consequential sequence variations from the actual sequences disclosed herein. Species having substantial sequence homology are considered to be equivalent to the disclosed sequences and as such are within the scope of the appended claims. In this regard, "slight and non-consequential sequence variations" mean that "homologous" sequences, i.e., sequences that have substantial homology with the DNA, RNA, or proteins disclosed and claimed herein, are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

As employed herein, the phrase "NMDA subunit(s) of the NMDAR2 subtype" refers to proteins which have large extensions of the putative extracellular domains at both the amino- and carboxyl-terminal regions. Otherwise, the deduced primary structure of NMDAR2 subunits displays the same general characteristics as the NMDAR1 subunit primary structure. A notable typical exception is that the negatively charged glutamic acid residues that are generally present in the putative TMII segment of NMDAR1 subunits are generally absent from the TMII segment of NMDAR2. Instead, NMDAR2 subunits may contain a positively charged lysine residue in TMII. Unlike NMDAR1 subunits, NMDAR2 subunits generally do not form homomeric NMDA receptors. Moreover, the amino acid sequences of NMDAR1 and NMDAR2 subunits are generally less than 50% identical, with identities of less than 30% typically observed.

Reference to NMDAR2 subunits contemplates both NMDAR2A and NMDAR2C types of subunits. Exemplary DNA sequences encoding human NMDAR2C subunits are represented by nucleotides which encode substantially the same amino acid sequence as set forth in Sequence ID Nos. 6, 46, 48, 50, 52, or 54. Preferred sequences are those which have the same sequence as any one of Sequence ID Nos. 6, 46, 48, 50, 52, or 54.

Exemplary DNAs can alternatively be characterized as those nucleotide sequences which encode a human NMDAR2C subunit and hybridize under high stringency conditions to any one of Sequence ID Nos. 5, 41, 43, 44, nucleotides 1–3025 of No. 5, 45, 47, 49, 51 or 53. Especially preferred sequences are those which have substantially the same nucleotide sequence as any one of the sequences set forth in Sequence ID Nos. 5, 45, 47, or 49.

Especially preferred NMDAR2C-encoding sequences are those which have substantially the same nucleotide sequence as the coding sequences in any one of Sequence ID Nos. 5, 45, 47, 49, 51 or 53; with those having substantially the same sequence as the coding sequences in Sequence ID Nos. 5, 45, 47 or 49 being most preferred.

Exemplary DNA sequences encoding human NMDAR2A subunits or portions thereof are represented by nucleotides which encode substantially the same amino acid sequence as set forth in Sequence ID No. 11, or substantially the same amino acid sequence as that encoded by the NMDAR2A-encoding portion of clone NMDA57, deposited with the ATCC under accession number 75442.

The deposited clone has been deposited at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Exemplary human NMDAR2A subunit-encoding DNAs can alternatively be characterized as those nucleotide sequences which hybridize under high stringency conditions to Sequence ID No. 10, or the NMDAR2A-encoding portion of clone NMDA57 (ATCC accession No. 75442). Especially preferred sequences encoding portions of a human NMDAR2A subunit are those which have substantially the same nucleotide sequence as coding sequence of Sequence ID No. 10, or the nucleotide sequence of the coding sequence in NMDAR2A-encoding portion of clone NMDA57.

DNA encoding human NMDA receptor subunits may be isolated by screening suitable human cDNA or human genomic libraries under suitable hybridization conditions with DNA disclosed herein (including nucleotides derived from any of SEQ ID Nos. 1, nucleotides 320–3402 of No. 1, 5, 11, 13, 15, 17, 19, 21, 23, 25, 27, 29, 31, 33, 35, 37, 39, 41, 43, 44, nucleotides 1–3025 of No. 5, 45, 47, 49, 51 or 53). Suitable libraries can be prepared from neuronal tissue samples, e.g., hippocampus and cerebellum tissue, cell lines, and the like. For example, the library can be screened with a portion of DNA including substantially the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 or more contiguous bases set forth in any of SEQ ID Nos. 1, nucleotides 320–3402 of No. 1, 5, 11, 13, 15, 17, 19, 21, 23, 25, 27, 29, 31, 33, 35, 37, 39, 41, 43, 44, nucleotides 1–3025 of No. 5, 45, 47, 49, 51 or 53. Preferred regions from which to construct probes include 5' and/or 3' coding sequences, sequences predicted to encode transmembrane domains, sequences predicted to encode cytoplasmic loops, signal sequences, NMDA binding sites, and the like.

Either the full-length cDNA clones or fragments thereof can be used as probes, preferably labeled with suitable label means for ready detection. When fragments are used as probes, preferably the DNA sequences will be from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol. Vol.* 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human N-methyl-D-aspartate (NMDA) receptor protein subunit(s), said method comprising:

contacting human DNA with a nucleic acid probe as described above, wherein said contacting is carried out under high stringency hybridization conditions, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete NMDA receptor subunit (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and encoded proteins provided herein.

Complementary DNA clones encoding various human NMDA receptor subunits (e.g., NMDAR1, NMDAR2A, NMDAR2C) have been isolated. Each type of subunit appears to be encoded by a different gene. The DNA clones provided herein may be used to isolate genomic clones encoding each type of subunit and to isolate any splice variants by screening libraries prepared from different neural tissues. Nucleic acid amplification techniques, which are well known in the art, can be used to locate DNA encoding splice variants of human NMDA receptor subunits. This is accomplished by employing oligonucleotides based on DNA sequences surrounding divergent sequencers) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human NMDA receptor subunits.

It has been found that not all subunits (and variants thereof) are expressed in all neural tissues or in all portions of the brain. Thus, in order to isolate cDNA encoding a particular subunit or splice variants thereof, it is preferable to screen libraries prepared from different neuronal or neural tissues. Preferred libraries for obtaining DNA encoding each subunit include: hippocampus to isolate human NMDAR1-encoding DNAS; hippocampus and cerebellum to isolate NMDAR2-encoding DNAs; and the like.

Once DNA encoding a subunit has been isolated, ribonuclease (RNase) protection assays can be employed to determine which tissues express mRNA encoding a particular NMDAR subunit subtype or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualed by gel electrophorsis and autoradiography.

It appears that the distribution of expression of some human NMDA receptor subunits differs from the distribution of such receptors in rat. For example, RNA encoding the rat NMDAR2C subunit is abundant in rat cerebellum, but is not abundant in rat hippocampus (see, e.g., Monyer et al., Science 256:1217–1221 (1992)]. Numerous human NMDAR2C clones were ultimately obtained, however, from a human hippocampus library. Thus, the distribution of some NMDA receptor subunits in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention NMDA receptor subunits in eukaryotic host cells, particularly mammalian cells, include cytomegalovirus (CMV) promoter-containing vectors such as pCMV-T7-2, pCMV-T7-3, pcDNA1, and the like (See FIG. 6).

As used herein, a promoter region refers to a segment of DNA that controls transcription of DNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV-T7-2 (described herein) or pCDNA1 (Invitrogen, San Diego, Calif.), and MMTV promoter-based vectors such as pMSG (Catalog No. 27-4506-01 from Pharmacia, Piscataway, N.J.).

Full-length DNAs encoding human NMDA receptor subunits have been inserted into vectors pcDNA1 and PCMV-T7-2. pCMV-T7-2 is a pUC19-based mammalian cell expression vector containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of NMDA receptor subunit DNA between the CMV promoter and SV40 polyadenylation signal should provide for constitutive expression of the foreign DNA in a mammalian host cell transfected with the construct. For inducible expression of human NMDA receptor subunit-encoding DNA in a mammalian cell, the DNA can be inserted into a plasmid such as pMSG. This plasmid contains the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). For synthesis of in vitro transcripts, full-length human DNA clones encoding human NMDAR1, NMDAR2A and NMDAR2C can also be subcloned into pIBI24 (International Biotechnologies, Inc., New Haven, Conn.), pCMV-T7-2 or pGEM7Z (Promega, Madison, Wis.).

In accordance with another embodiment of the present invention, there are provided cells containing the above-described polynucleic acids (i.e., DNA or mRNA). Such host cells as bacterial, yeast and mammalian cells can be used for replicating DNA and producing NMDA receptor subunit(s). Methods for constructing expression vectors, preparing in vitro transcripts, transfecting DNA into mammalian cells, injecting oocytes, and performing electrophysiological and other analyses for assessing receptor expression and function as described herein are also described in PCT Application Nos. PCT/US91/05625 and PCT/US92/11090, and in co-pending U.S. application Ser. Nos. 07/563,751 and 07/812,254. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual,* Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376). Recombinant cells can then be cultured under conditions whereby the subunit(s) encoded by the DNA is (are) expressed. Preferred cells include mammalian cells (e.g., HEK293, CHO and $Ltk^-$ cells), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929, 555 and 4,855,231), *Saccharomyces cerevisiae, Candida tropicalis, Hansenula polymorpha,* and the like), mammalian expression systems, including commercially available systems and other such systems known to those of skill in the art, for expression of DNA encoding the human NMDA receptor subunits provided herein are presently preferred. *Xenopus oocytes* are preferred for expression of in vitro RNA transcripts of the DNA.

In preferred embodiments, human NMDAR subunit-encoding DNA is ligated into a vector, and introduced into suitable host cells to produce transformed cell lines that express a specific human NMDA receptor subtype, or specific combinations of subunits. The resulting cell lines can then be produced in quantity for reproducible quantitative analysis of the effects of known or potential drugs on receptor function. In other embodiments, nRNA may be produced by in vitro transcription of DNA encoding each subunit. This mRNA, either from a single subunit clone or from a combination of clones, can then be injected into *Xenopus oocytes* where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human NMDA receptors comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells, African green monkey cells and other such cells known to those of skill in the art), amphibian cells (e.g., *Xenopus laevis oöcytes*), yeast cells (e.g., *Saccharomyces cerevisiae, Pichia pastoris*), and the like. Exemplary cells for expressing injected RNA transcripts include *Xenopus laevis oöcytes.* Cells that are preferred for transfection of DNA are known to those of skill in the art or may be empirically identified, and include HEK293 (which are available from ATCC under accession #CRL 1573); $Ltk^-$ cells (which are available from ATCC under accession #CCL1.3); COS-7 cells (which are available from ATCC under accession #CRL 1651); and DG44 cells ($dhfr^-$ CHO cells; see, e.g., Urlaub et al. (1986) Cell. Molec. Genet. 12: 555). Presently preferred cells include DG44 cells and HEK293 cells, particularly HEK293 cells that can be frozen in liquid nitrogen and then thawed and regrown; for example, those described in U.S. Pat. No. 5,024,939 to Gorman (see, also, Stillman et al. (1985) Mol. Cell. Biol. 5:2051–2060).

DNA may be stably incorporated into cells or may be transiently expressed using methods known in the art. Stably transfected mammalian cells may be prepared by transfecting cells. with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are not included in the transient transfections because the transfectants are typically not grown under selective conditions, and are usually analyzed within a few days after transfection.

To produce such stably or transiently transfected cells, the cells should be transfected with a sufficient concentration of subunit-encoding nucleic acids to form human NMDA receptors that contain the human subunits encoded by heterologous DNA. The precise amounts and ratios of DNA encoding the subunits may be empirically determined and optimized for a particular combination of subunits, cells and assay conditions. Recombinant cells that express NMDA receptors containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human NMDA receptor subunits may be purified using protein purification methods known to those of skill in the art. For example, antibodies or other ligands that specifically bind to one or more of the subunits may be used for affinity purification of the subunit or human NMDA receptors containing the subunits.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human NMDA receptor subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human NMDA receptor subunits, or may contain a mixture of subunits encoded by the host cell and subunits encoded by heterologous DNA or mRNA. Recombinant receptors may be homomeric or may be a heterogeneous combination of multiple subunits. Mixtures of DNA or mRNA encoding receptors from various species, such as rats and humans, may also be introduced into the cells. Thus, a cell can be prepared that expresses recombinant receptors containing only NNDAR1 subunits, or a combination of NMDAR1 and NMDAR2 subunits provided herein. For example, NMDAR1 subunits of the present invention can be co-expressed with NMDAR2A and/or NMDAR2C receptor subunits.

The DNA, mRNA, vectors, receptor subunits, receptor subunit combinations and cells provided herein permit production of selected NMDA receptor subunits and specific combinations thereof, as well as antibodies to said receptor subunits. This provides a means to prepare synthetic or recombinant receptors and receptor subunits that are substantially free of contamination from many other receptor proteins whose presence can interfere with analysis of a single NMDA receptor subtype. The availability of desired receptor subtypes makes it possible to observe the effect of a drug substance on a particular receptor subtype or combination of NMDA receptor subunits, and to thereby perform initial in vitro screening of the drug substance in a test system that is specific for humans and specific for a human NMDA receptor subtype or combination of NMDA receptor subunits. The availability of specific antibodies makes it possible to identify the subunit combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subunits or specific combinations of various types of receptor subunits with a variety of potential agonists or antagonists provides additional information with respect to the function and activity of the individual subunits and should lead to the identification and design of compounds that are capable of very specific interaction with one or more types of receptor subunits or receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human NMDA receptor subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAS. The modified (e.g., deleted or digested) DNAs are expressed, for example, by transcribing the DNA and then introducing the resulting mRNA into *Xenopus oocytes,* where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel(s). If ion channel(s) are detected, the fragments are functional as glutamate receptors.

The above-described method can be carried out in the presence of NMDAR1-like receptor subunits alone, or in the presence of combinations of NMDAR1-like and NMDAR2-like receptor subunits. Thus, for example, when the protein being tested is an NMDAR2-like receptor subunit, the additional subunit is preferably an NMDAR1-like subunit.

In accordance with still another embodiment of the present invention, there is provided a method for identifying compounds which bind to human N-methyl-D-aspartate (NMDA) receptor subunit(s), said method comprising employing receptor proteins of the invention in a competitive binding assay. Such an assay can accommodate the rapid screening of a large number of compounds to determine which compounds, if any, are capable of binding to NMDA receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor(s).

The binding assays contemplated by the present invention can be carried out in a variety of ways, as can readily be identified by those of skill in the art. For example, competitive binding assays can be employed, as well as radioreceptor assays, and the like.

In accordance with a further embodiment of the present invention, there is provided a bioassay for identifying compounds which modulate the activity of human NMDA receptors of the invention, said bioassay comprising:

(a) exposing cells containing DNA encoding human NMDA receptor subunit(s), wherein said cells express functional NMDA receptors, to at least one compound whose ability to modulate the ion channel activity of said receptors is sought to be determined; and thereafter (b) monitoring said cells for changes in ion channel activity.

The above-described bioassay enables the identification of agonists and antagonists for human NMDA receptors. According to this method, recombinant NMDA receptors are contacted with an "unknown" or test substance (in the further presence of a known NMDA agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for human NMDA receptors.

In accordance with a particular embodiment of the present invention, recombinant human NMDA receptor-expressing mammalian cells or oocytes can be contacted with a test compound, and the modulating effect(s) thereof can then be evaluated by comparing the NMDA receptor-mediated response in the presence and absence of test compound, or by comparing the NMDA receptor-mediated response of test cells, or control cells (i.e., cells that do not express NMDA receptors), to the presence of the compound.

As used herein, a compound or signal that "modulates the activity of an NMDA receptor" refers to a compound or signal that alters the activity of NMDA receptors so that activity of the NMDA receptor is different in the presence of the compound or signal than in the absence of the compound or signal. In particular, such compounds or signals include agonists and antagonists. The term agonist refers to a substance or signal, such as NMDA, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter) for the same or closely situated site. A non-competitive antagonist or blocker inactivates the functioning of the receptor by interacting with a site other than the site that interacts with the agonist.

As understood by those of skill in the art, assay methods for identifying compounds that modulate human NMDA receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which are identical to the transfected cells, except the cells employed for the control culture do not express functional human NMDA receptor subunits. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the ion channel activity of human N-methyl-D-aspartate (NMDA) receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subunit composition, structure of functional domains, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the NMDAR subunits for use as immunogen (as either a synthetic peptide or a recombinantly produced bacterial fusion protein) include antigenicity, accessibility (i.e., extracellular and cytoplasmic domains), uniqueness to the particular subunit, etc.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptorts) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

The invention will now be described in greater detail by reference to the following non-limiting examples.

EXAMPLE 1

Isolation of DNA Encoding Human NMDA Receptor NMDAR1 Subunits

A. cDNA Library Screening

RNA isolated from human hippocampus tissue was used as a template for the synthesis of oligo dT-primed and randomly primed, single-stranded cDNA according to standard procedures [see, for example, Maniatis et al. (1982) *Molecular Cloning: A Laboratory Manual,* Cold Spring Harbor Laboratory Press, Cold Spring Harbor, N.Y.). The single-stranded cDNA was converted to double-stranded cDNA, and EcoRI/SnaBI/XhoI adaptors were added to the ends thereof. The cDNAs were separated by size using agarose gel electrophoresis, and those that were >2.0 kb were ligated into EcoRI-digested λgt10 bacteriophage vectors. The resulting cDNA library was amplified by replication of each clone through limited infection of a bacterial host, and stored at −70° C.

The amplified hippocampus oligo dT-primed cDNA library was later retrieved from storage and $1\times10^6$ recombinants were screened for hybridization to oligonucleotides corresponding to nucleotides 96–128 (SE7) and nucleotides 2576–2609 (SE8) of the rat NMDAR1A receptor cDNA (see Moriyoshi et al. (1991) *Nature* 354:31). Hybridization was performed at 42° C. in 6× SSPE, 5× Denhart's solution, 10% formamide, 0.2% SDS and 200 μg/ml herring sperm DNA. Washes were performed in 1× SSPE and 0.2% SDS at 50° C. Hybridizing clones (e.g. NMDA1–3) were identified. These clones hybridized to SE8 but not to SE7.

A randomly primed primary human hippocampus cDNA library (~$2\times10^5$ recombinants prepared by selecting only cDNAs >2.0 kb for inclusion in the library) was screened under the same conditions for hybridization to oligonucleotide SE8 and an oligonucleotide corresponding to nucleotides 129–141 of the rat NMDAR1A receptor cDNA (SE11). Five hybridizing clones, which hybridized to SE8 and not to SE11, were identified: NMDA5–7 and NMDA10–11.

B. Characterization of Clones

The clones were plaque purified and characterized by restriction enzyme mapping and DNA sequence analysis of the inserts. One of the clones, NMDA11 (see Sequence ID No. 13 for a description of a portion of NMDA11),is a full-length cDNA (i.e., it contains translation initiation and termination codons) encoding a complete NMDAR1 subunit. The remaining clones are partial cDNAs. Clones NMDA2, NMDA3 (see Sequence ID No. 17), NMDA5, NMDA6, NMDA7 (see Sequence ID No. 15), and NMDA10 (see Sequence ID No. 1, nucleotides 320–3402, for a description of a portion of NMDA10) contain a translation termination codon but lack nucleotides at the 5' end of the coding sequence.

Characterization of the clones revealed that the isolated cDNAs correspond to different alternatively spliced forms of the human NMDAR1 subunit transcript. The four types of alternate splicing represented by the clones are depicted schematically in FIG. 1. Clone NMDA10 (which lacks 5' untranslated sequences as well as 57 nucleotides of the 5' end of the coding sequence) is used as a reference to which the other variants are compared. Clone NMDA11 lacks 363 nucleotides (in the 3' portion of the clone) that are present in NMDA10. This 363-nucleotide deletion does not disrupt the reading frame of the transcript; however, it results in a different termination codon. The last 69 nucleotides of the coding sequence of NMDA11 correspond to 3' untranslated sequence of clone NMDA10 (i.e., nucleotides 3325–3393 of Sequence ID No. 1). Clone NMDA7 lacks the same 363-nucleotide sequence that is missing from NMDA11; however, NMDA7 further lacks 204 nucleotides at the 5' end that are present in NMDA10 and NMDA11. This 204-nucleotide deletion also does not disrupt the reading frame of the transcript. Additionally, NMDA7 contains a 63-nucleotide in-frame insertion at the 5' end relative to NMDA10 and NMDA11. The last 69 base pairs of the coding sequence of NMDA7 correspond to 3' untranslated sequence of NMDA10 i.e., nucleotides 3325–3393 of Sequence ID No. 1). Clone NMDA3 lacks 1087 base pairs at the 3' end that are present in NMDA10. This 1087-base pair deletion does not disrupt the reading frame of the transcript; however it results in a different termination codon. The last 231 base pairs of the coding sequence of NMDA3 correspond to 3' untranslated sequence of clone NMDA10 (i.e., nucleotides 4049–4279 in Sequence ID No. 1).

EXAMPLE 2

Preparation of Full-Length NMDAR1 Subunit cDNA Constructs

Portions of clones NMDA10, NMDA11, NMDA7 and NMDA3 were ligated together to construct full-length cDNAs encoding variants of the NMDA receptor NMDAR1 subunit. The full-length NMDAR1 subunit cDNAs were incorporated into vector pcDNA1 (Invitrogen, San Diego, Calif.) for use in expressing the receptor subunits in mammalian host cells and for use in generating in vitro transcripts of the DNAs to be expressed in *Xenopus oocytes.*

Vector pcDNA1 is a pUC19-based plasmid that contains the following elements in the 5'-to-3' order: the cytomegalovirus (CMV) immediate early gene promoter/enhancer, the bacteriophage T7 RNA polymerase promoter, a polylinker, the bacteriophage SP6 RNA polymerase promoter, SV40 RNA processing (i.e., splice donor/acceptor) signals, SV40 polyadenylation signal, and the ColE1 origin and supF suppressor tRNA to permit maintenance of the vector in *Escherichia coli* strains with the P3 episome. This vector thus contains all the regulatory elements required for expression of heterologous DNA in a mammalian host cell, wherein the heterologous DNA has been incorporated into the vector at the polylinker. In addition, because the T7 and SP6 promoters are located on either side of the polylinker, this plasmid can be used for synthesis of in vitro transcripts of heterologous DNA that has been sublconed into the vector at the polylinker.

A. NMDAR1

Figure 2A:
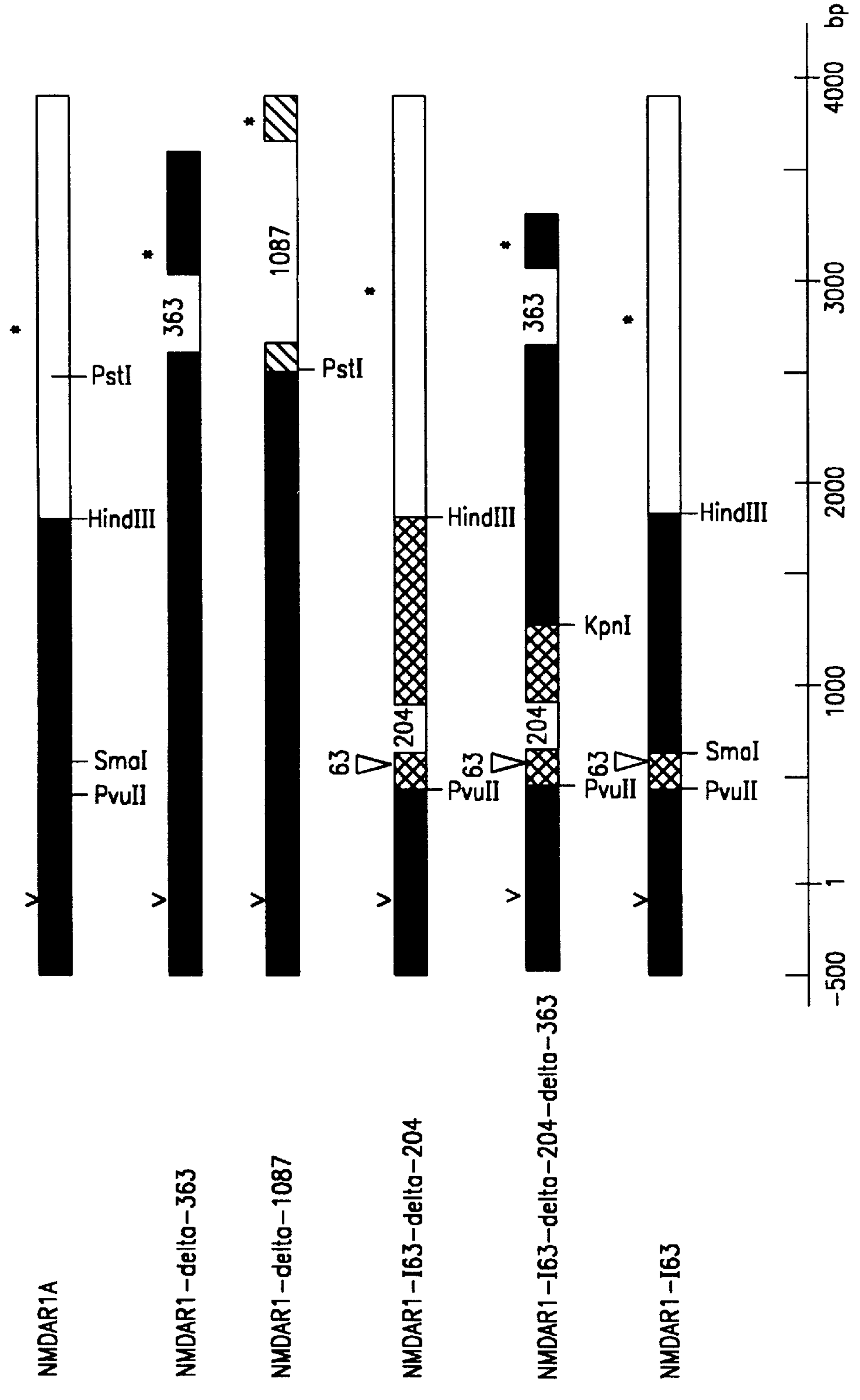
FIGS. 2A–2B is a schematic representation of cDNAs encoding full-length human NMDAR1 subunit subtypes of the invention, with partial restriction maps of each DNA. The full-length cDNAs are constructed by ligation of appropriate portions of the clones shown in FIG. 1. Regions of each full-length cDNA composed of nucleotide sequences corresponding to a particular clone are distinguished as solid, striped, cross-hatched or open boxes.

Full-length construct NMDAR1 was prepared by ligation of a 5' portion of NMDA11 (beginning 5' of the translation initiation codon and extending to the HindIII site in the middle of the clone) and a 3' portion of NMDA10 (beginning at the HindIII site in the middle of the clone and extending 3' of the translation termination codon) as depicted in FIG. 2A. The two DNA fragments were joined in mammalian expression vector pcDNA1.

Initially, the strategy for generating the NMDAR1 construct involved a first step of separately subcloning the entire 4.0 kb EcoRI insert fragment of NMDA10 and the entire 4.0 kb SnaBI insert fragment of NMDA11 into pcDNA1; however, two attempts employing this cloning strategy were unsuccessful. It appeared that there may have been selection against *E. coli* hosts retaining the complete insert fragments since the surviving recombinant *E. coli* that were analyzed contained incomplete insert cDNAs from which nucleotides had been deleted. Therefore, it was necessary to prepare the full-length NMDAR1 construct in several steps by subcloning and combining various fragments of NMDA10 and NMDA11 in pcDNA1 as follows (see FIG. 3 for locations of restriction enzyme sites).

Clone NMDA10 was digested with BglII and EcoRI and the ~3.3 kb fragment containing nucleotides 1020–4298 of Sequence ID No. 1 was isolated and subcloned into BamHI/EcoRI-digested pcDNA1. The resulting plasmid was digested with HindIII and NheI and the fragment containing nucleotides 2137–4298 of Sequence ID No. 1 plus a portion of pcDNA1 was isolated.

Clone NMDA11 was digested with EcoRI and HindIII and the ~2.1 kb fragment containing nucleotides 1–2136 of Sequence ID No. 1 was isolated and subcloned into EcoRI/HindIII-digested modified pcDNA1 (modified by deletion of the HindIII site located 5' of the EcoRI site in the polylinker and addition of a HindIII site into the polylinker at a position 3' of the EcoRI site). The resulting plasmid was digested with NheI and HindIII and the fragment containing nucleotides 1–2136 of Sequence ID No. 1 plus a portion of modified pcDNA1 was isolated. This NheI/HindIII fragment was then ligated to the HindIII/NheI fragment containing nucleotides 2137–4298 of Sequence ID No. 1 to generate the full-length construct NMDAR1A (see FIG. 2). The ligation mix was used to transform *E. coli* strain MC1061/P3. Because the NheI site in pcDNA1 occurs within the supF selection gene, only *E. coli* containing the correctly ligated, complete NMDAR1A plasmid (which has the complete, functional selection gene) were able to survive the selection process. This fragment subcloning strategy enabled selection of the desired correct NMDAR1A-containing *E. coli* host cells, even though the total number of such recombinant host cells was small.

In summary, construct NMDAR1A contains 261 base pairs of 5' untranslated sequence from NMDAR11 (nucleotides 1–261 of Sequence ID No. 1) and a complete coding sequence (nucleotides 262–3078 of Sequence ID No. 1) for the NMDAR1A variant of the NMDAR1 subunit as well as 1220 base pairs of 3' untranslated sequence (nucleotides 3079–4298 of Sequence ID No. 1). The NMDAR1A-encoding sequence is operatively linked to the regulatory elements in pcDNA1 for expression in mammalian cells.

B. NMDAR1-Δ363

Full-length construct NMDAR1-Δ363 was prepared by ligation of a 5' portion of NMDA11 (beginning 5' of the translation initiation codon and extending to the HindIII site in the middle of the clone, i.e., nucleotides 1–2136 in Sequence ID No. 1) and a 3' portion of NMDA11 (beginning at the HindIII site in the middle of the clone and extending 3' of the translation termination codon, i.e., nucleotides 2137–2961 and 3325–4298 of Sequence ID No. 1) as depicted in FIG. 2A. As described above, due to the difficulty in directly subcloning the entire 4.0 kb SnaBI NMDA11 insert into pcDNA1, it was necessary to generate the construct by ligating two fragments of the NMDA11 insert into pcDNA1 as follows (see FIGS. 3A–3C for locations of restriction enzyme sites).

To obtain the 5' NMDA11 fragment, clone NMDA11 was digested with EcoRI and HindIII and the ~2.2 kb fragment containing nucleotides 1–2136 of Sequence ID No. 1 was isolated and subcloned into EcoRI/HindIII-digested modified pcDNA1 (modified as described above). The resulting plasmid was digested with NheI and HindIII and the fragment containing nucleotides 1–2136 of Sequence ID No. 1 plus a portion of modified pcDNA1 was isolated.

To obtain the 3' NMDA11 fragment, clone NMDA11 was digested with BglII and EcoRI and the 3.0 kb fragment containing nucleotides 1020–2961 and 3325–4298 of Sequence ID No. 1 was isolated and subcloned into BamHI/EcoRI-digested pcDNA1. The resulting plasmid was digested with HindIII and NheI and the fragment containing nucleotides 2137–2961 and 3325–4298 of Sequence ID No. 1 plus a portion of pcDNA1 was isolated. This HindIII/NheI fragment was then ligated to the NheI/HindIII fragment containing nucleotides 1–2136 of Sequence ID No. 1 to generate NMDAR1-Δ363.

In summary, construct NMDAR1-Δ363 contains 261 base pairs of 5' untranslated sequence (nucleotides 1–261 of Sequence ID No. 1) and a complete coding sequence for the NMDAR1-Δ363 variant NMDAR1 subunit (nucleotides 262–2961 and 3325–3393 of Sequence ID No. 1) as well as 905 base pairs of 3' untranslated sequence (nucleotides 3394–4298 of Sequence ID No. 1). Thus, NMDAR1-Δ363 differs from NMDAR1 in that it lacks 363 nucleotides (nucleotides 2962–3324 of Sequence ID No. 1) that comprise the last 117 nucleotides of the coding sequence and the first 246 nucleotides of the 3' untranslated sequence of NMDAR1. The NMDAR1-Δ363 subunit variant-encoding sequence is operatively linked to the regulatory elements in pcDNA1 for expression in mammalian cells.

C. NMDAR1-Δ1087

Full-length construct NMDAR1-Δ1087 was prepared by replacing the 3' end of the NMDAR1 variant-encoding insert of NMDAR1-Δ363 with a fragment from the 3' end of clone NMDA3 (see FIG. 2A). Plasmid NMDAR1-Δ363 was partially digested with PstI and completely digested with XbaI. There is a PstI site ~112 nucleotides upstream of the location of the 363-nucleotide deletion in NMDAR1-Δ363 and an XbaI site in the polylinker located downstream of the 3' untranslated sequence of NMDAR1-Δ363 (see FIG. 3). Thus, PstI/XbaI digestion of NMDAR1-Δ363 results in removal of a fragment containing nucleotides 2850–2961 and 3325–4298 of Sequence ID No. 1 from the vector. The larger fragment was isolated from the digest.

The insert of clone NMDA3 was cloned into the EcoRI restriction site(s) of pGEM (Promega, Madison, Wis.); and the resulting plasmid was digested with PstI and XbaI. The smaller fragment containing nucleotides 2850–2961 and 4049–4298 of Sequence ID No. 1 was isolated and ligated to the larger fragment from the PstI/XbaI digest of NMDAR1-Δ363. The resulting construct was designated NMDAR1-Δ1087.

In summary, NMDAR1-Δ1087 contains 261 base pairs of 5' untranslated sequence (nucleotides 1–261 in Sequence ID No. 1), the complete coding sequence for the NMDAR1-Δ1087 variant NMDAR1 subunit (nucleotides 262–2961 and 4049–4279 of Sequence ID No. 1) and 19 base pairs of 3' untranslated sequence (nucleotides 4280–4298 of Sequence ID No. 1). Thus, NMDAR1-Δ1087 differs from NMDAR1 in that it lacks 1087 nucleotides (nucleotides 2962–4048 of Sequence ID No. 1) that comprise the last 117 nucleotides of the coding sequence and the first 970 nucleotides of the 3' untranslated sequence of NMDAR1. The NMDAR1-Δ1087 subunit variant-encoding sequence is operatively linked to the regulatory elements in pcDNA1 for expression in mammalian cells.

D. NMDAR1-I63-Δ204

Full-length construct NMDAR1-I63-Δ204 was prepared by replacing a 1399-nucleotide fragment of construct NMDAR1 (i.e., nucleotides 738–2136 of Sequence ID No. 1) with the PvuII-HindIII fragment of NMDA7 (i.e., nucleotides 738–831 of sequence ID No. 1, plus nucleotides 1–63 of Sequence ID No. 3 and nucleotides 832–984 and 1189–2136 of Sequence ID No. 1), as depicted in FIG. 2A. Because there are multiple PvuII sites in the NMDAR1 construct, a several-step process was required for construction of NMDAR1-I63-Δ204 as follows (see FIGS. 3A–3C for the location of restriction enzyme sites).

The ~2.2-kb EcoRI-HindIII fragment isolated from construct NMDAR1A and containing nucleotides 1–2136 of Sequence ID No. 1 was ligated with modified pcDNA1 (modified as described in Example 2A) that had been digested with EcoRI and HindIII. The resulting plasmid was digested with AvrII and self-ligated to remove two PvuII sites from a portion of the plasmid contributed by pcDNA1.

The plasmid was then partially digested with PvuII and completely digested with HindIII. The digest was ligated with a 1258-nucleotide PvuII-HindIII fragment isolated from clone NMDA7. The resulting plasmid, designated NMDAR1-I63-Δ204-5', was digested with BamHI and HindIII and the ~2-kb fragment containing nucleotides 1–831 of Sequence ID No. 1, plus nucleotides 1–63 of Sequence ID No. 3 and nucleotides 832–984 and 1189–2136 of Sequence ID No. 1 was isolated and ligated to BamHI/HindIII-digested NMDAR1 to generate NMDAR1-I63-Δ204.

NMDAR1-I63-Δ204 contains 261 base pairs of 5' untranslated sequence (nucleotides 1–261 in Sequence ID No. 1), the complete coding sequence for the NMDAR1-I63-Δ204 variant NMDAR1 subunit (nucleotides 262–831 of Sequence ID No. 1 plus nucleotides 1–63 of Sequence ID No. 3 and nucleotides 832–984 and 1189–3078 of Sequence ID No. 1) and 1220 base pairs of 3' untranslated sequence (nucleotides 3079–4298 of Sequence ID No. 1). Thus NMDAR1-I63-Δ204 differs from NMDAR1 in that it contains 63 nucleotides that are not present in NMDAR1 (nucleotides 1–63 of Sequence ID No. 3) located between nt 831 and 832 of Sequence ID No. 1. Further, NMDAR1-I63-Δ204 lacks 204 nucleotides that are present in NMDAR1 (nucleotides 985–1188 of Sequence ID No. 1). The NMDAR1-I63-Δ204 subunit variant-encoding sequence is operatively linked to the regulatory elements in pcDNA1 for expression in mammalian cells.

E. NMDAR1-I63

Full-length construct NMDAR1-I63 can be described as NMDAR1 in which a 173-bp fragment (nucleotides 738–910 of Sequence ID No. 1) is replaced with the 236-bp PvuII-SmaI fragment of NMDA7 (nucleotides 738–831 of Sequence ID No. 1, plus nucleotides 1–63 of Sequence ID No. 3 and nucleotides 832–910 of Sequence ID No. 1). Because there are multiple PvuII sites in the NMDAR1 construct, a several-step process was required for construction of NMDAR1-I63 as follows. Plasmid NMDAR1-I63-Δ204-5' was partially digested with SmaI and completely digested with HindIII. The larger vector fragment was ligated with the 1226-bp SmaI/HindIII fragment isolated from NMDA11 (nucleotides 911–2136 of Sequence ID No. 1). The resulting vector was digested with BamHI and HindIII and the ~2.2-kb fragment containing nucleotides 1–831 of Sequence ID No. 1, plus nucleotides 1–63 of Sequence ID No. 3 and nucleotides 832–2136 of Sequence ID No. 1 was isolated and ligated to BamHI/HindIII-digested NMDAR1 to generate NMDAR1-I63.

NMDAR1-I63 contains 261 base pairs of 5' untranslated sequence (nucleotides 1–261 in Sequence ID No. 1), the complete coding sequence for the NMDAR1-I63 variant NMDAR1 subunit (nucleotides 262–831 of Sequence ID No. 1, plus nucleotides 1–63 of Sequence ID No. 3 and nucleotides 832–3078 of Sequence ID No. 1) and 1220 nucleotides of 3' untranslated sequence (nucleotides 3079–4298 of Sequence ID No. 1). Thus, NMDAR1-I63 differs from NMDAR1 in that it contains 63 nucleotides that are not present in NMDAR1 (nucleotides 1–63 of Sequence ID No. 3), located between nucleotides 831 and 832 of Sequence ID No. 1. The NMDAR1-I63 subunit variant-encoding sequence is operatively linked to the regulatory elements in pcDNA1 for expression in mammalian cells.

Figure 2B:
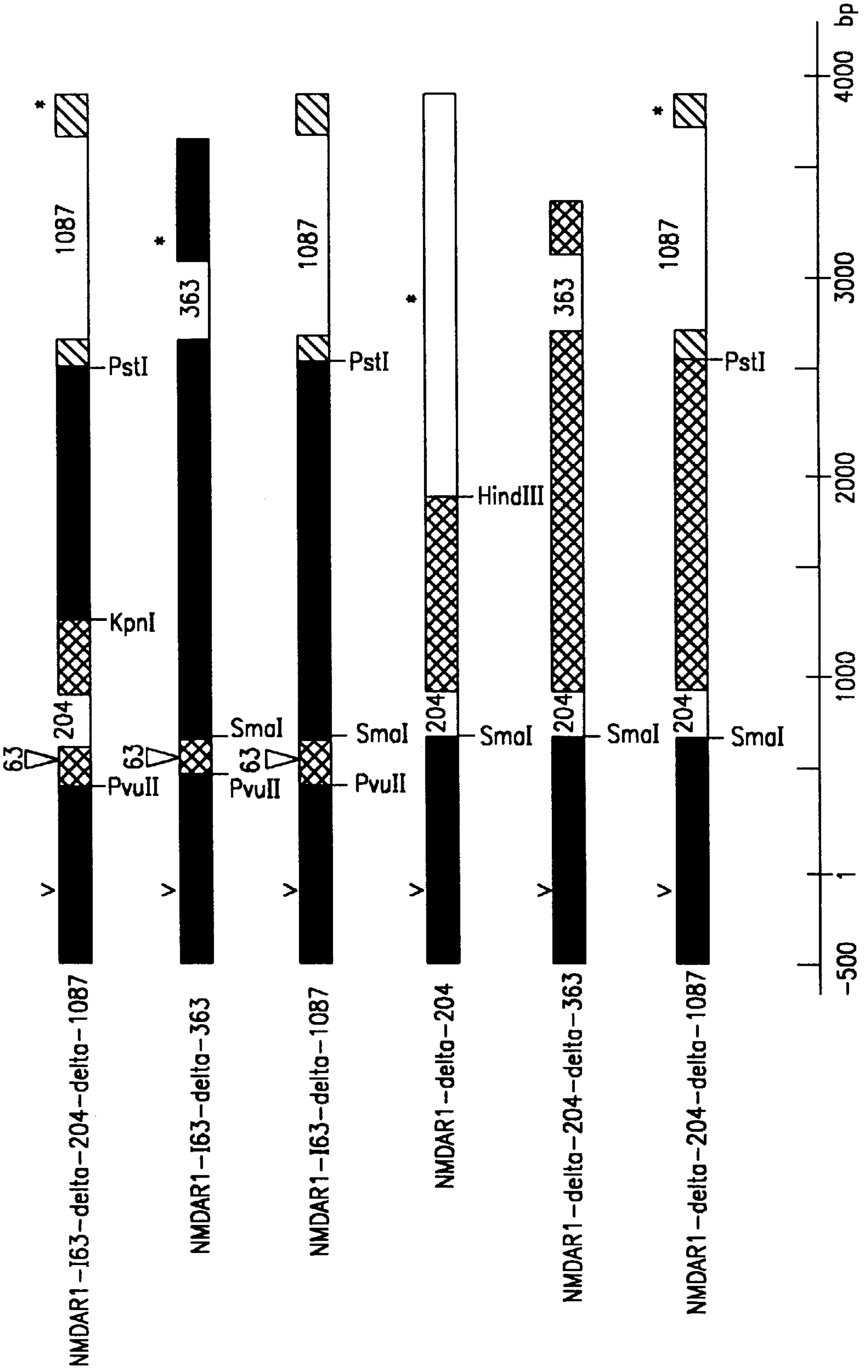

F. Additional Constructs Containing Full-Length cDNAs Encoding Variants of the NMDAR1 Subunit Additional full-length cDNAs encoding further possible NMDAR1 variants can be constructed using methods similar to those described in Examples 2A–E above. Specifically, the following constructs can be prepared by ligating portions of clones NMDA11, NMDA10, NMDA7 and NMDA3 as depicted in FIGS. 2A–2B:

| | |
|---|---|
| NMDAR1-I63-Δ204-Δ363 | (Sequence ID No. 27) |
| NMDAR1-Δ204 | (Sequence ID No. 29) |
| NMDAR1-Δ204-Δ363 | (Sequence ID No. 31) |
| NMDAR1-I63-Δ204-Δ1087 | (Sequence ID No. 39) |
| NMDAR1-I63-Δ363 | (Sequence ID No. 35) |
| NMDAR1-I63-Δ1087 | (Sequence ID No. 37) |
| NMDAR1-Δ204-Δ1087 | (Sequence ID No. 33). |

The full-length cDNAs can also be incorporated into mammalian expression vectors such as pcDNA1, as described in Examples 2A–E.

Several methods can be employed to determine which NMDAR1 subunit variants are actually expressed in various human tissues. For example, oligonucleotides specific for the nucleotide sequences located 5' and 3' of the insertions and deletions of the NMDAR1 transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues. These assays are a sensitive method for detecting and quantitating an RNA species in a complex mixture of total cellular RNA. A portion of the NMDAR1 subunit variant DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualed by gel electrophoresis and autoradiography.

Further information on possible splice variants of the NMDAR1 primary transcript can be obtained by isolation of genomic clones containing NMDAR1 subunit-encoding sequences (for example, by hybridization to the human NMDAR1 subunit cDNAs disclosed herein) and subsequent characterization of the resulting clones.

EXAMPLE 3

Isolation of DNA Encoding Human NMDA Receptor NMDAR2 Subunits

Degenerate oligonucleotides were synthesized based on two conserved regions of rat NMDAR2A, NMDAR2B and NMDAR2C DNAs that encode the putative first and fourth transmembrane domains. In rat NMDAR2A DNA, these regions are encoded by nucleotides 1669–1692 (oligo SE74) and 2437–2465 (olig SE75), respectively. [see Monyer et al. (1992) *Science* 256:1217–1221]. These oligonucleotides were used to prime nucleic acid amplification of cDNAs prepared from RNA isolated from human hippocampus, cerebellum, and orbitofrontal tissue. Two products, a 795-bp and a 640-bp fragment, were detected when the reaction mixture was analyzed by gel electrophoresis and ethidium bromide staining. The 795-bp fragment amplified from the cerebellum cDNA was subcloned into PCR1000 (Invitrogen, San Diego, Calif.) and characterized by DNA sequence analysis, which revealed that it is ~86% similar to the rat NMDAR2A DNA sequence, ~78% similar to the rat NMDAR2B DNA sequence, and ~74% similar to the rat NMDAR2C DNA sequence. Thus, this plasmid was named pcrNMDAR2A.

The 795-bp insert from pcrNMDAR2A was used to screen $1\times10^6$ recombinants of a human hippocampus cDNA library (prepared by using random primers to synthesize cDNAs from hippocampus tissue and selecting fragments >2.0 kb for insertion into λgt10 vectors) and a human cerebellum cDNA library (random-primed library size-selected for fragments >2.8 kb in λgt10). Hybridization was performed in 5× SSPE, 5× Denhart's solution, 50% deionized formamide, 0.2% SDS, 200 μg/ml sonicated, denatured herring sperm DNA at 42° C. Washes were performed in 1× SSPE, 0.2% SDS at 55° C. The probe hybridized to 11 plaques from the hippocampus library and 8 plaques from the cerebellum library.

DNA sequence analysis and/or restriction enzyme mapping of 15 of the hybridizing plaques that were purified surprisingly revealed that they were more similar to rat NMDAR2C DNA than to rat NMDAR2A DNA. All of the clones were partial cDNAs (i.e., they lacked a translation initiation and/or termination codon) and were designated as NMDAR2C cDNAs. Comparison of the clones revealed that the human NMDAR2C subunit transcript is differentially processed.

Figure 4:
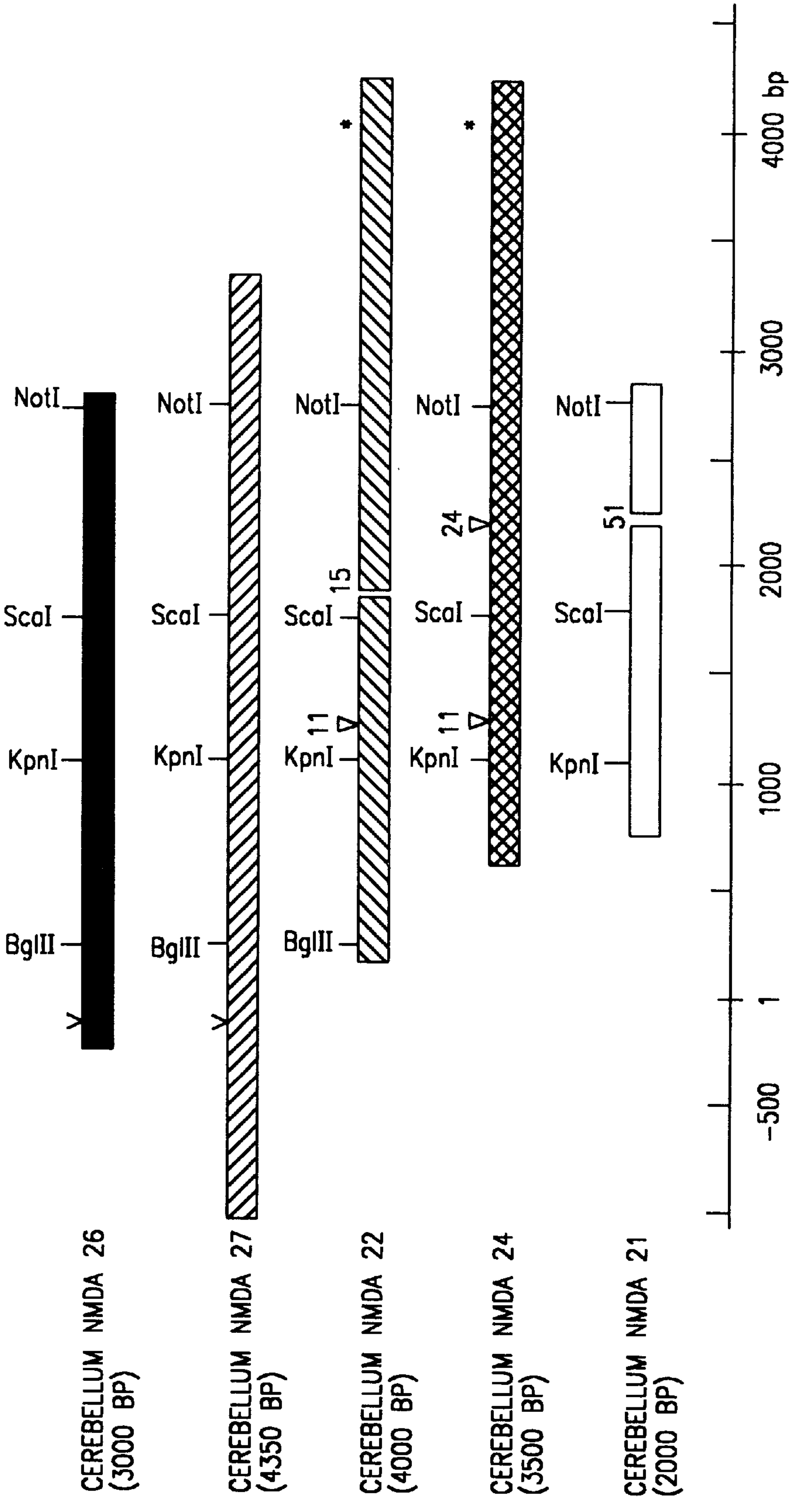
FIG. 4 is a schematic representation of various human NMDAR2C clones of the invention, with partial restriction maps of each clone. The clones are aligned and the differences in the DNAs relative to clone NMDA26 are indicated in the same manner as done in FIG. 1.

Clones NMDA26, NMDA24, NMDA22 and NMDA21 (see FIG. 4) represent four basic clones that were identified, all of which are believed to be splice variants. Clone NMDA26 (Sequence ID No. 5' nucleotides 1–3025) is used as a reference to which the other variants can be compared. Clone NMDA24 (Sequence ID No. 44) contains a 24-bp sequence (see Sequence ID No. 7) that is not present in NMDA26. Clone NMDA22 (Sequence ID No. 43) lacks 15 bp that are present in NMDA26, and clone NMDA21 (Sequence ID No. 41) lacks 51 bp that are present in NMDA26. Clones NMDA22 and NMDA24 both contain an 11-bp sequence (Sequence ID No. 9) that is not present in NMDA26 (between nucleotides 1116–1117 of Sequence ID No. 5). Introduction of this sequence into these clones (between nucleotides 1116–1117 of Sequence ID No. 5) disrupts the reading frame of the transcript and introduces a premature translation termination (i.e., STOP) codon into the transcript.

Clones NMDA26 and NMDA27 (see FIG. 4) are partial NMDAR2C cDNAs that contain 5' untranslated sequence, a translation initiation codon and some of the coding sequence. Clone NMDA26 contains 188 base pairs of 5' untranslated sequence whereas clone NMDA27 contains ~1.1 kb of 5' untranslated sequence. The sequences of the 5' untranslated regions of these two clones are identical for the first 15 nucleotides proceeding 5' of the translation initiation codon. However, beginning with the 16th nucleotide 5' of the translation initiation codon, the sequences of the two clones diverge (compare nucleotides 116–191 of Sequence ID No. 5 to nucleotides 1–74 of Sequence ID No. 12).

EXAMPLE 4

Preparation of Full-Length NMDAR2C Subunit cDNA Constructs

Figure 5:
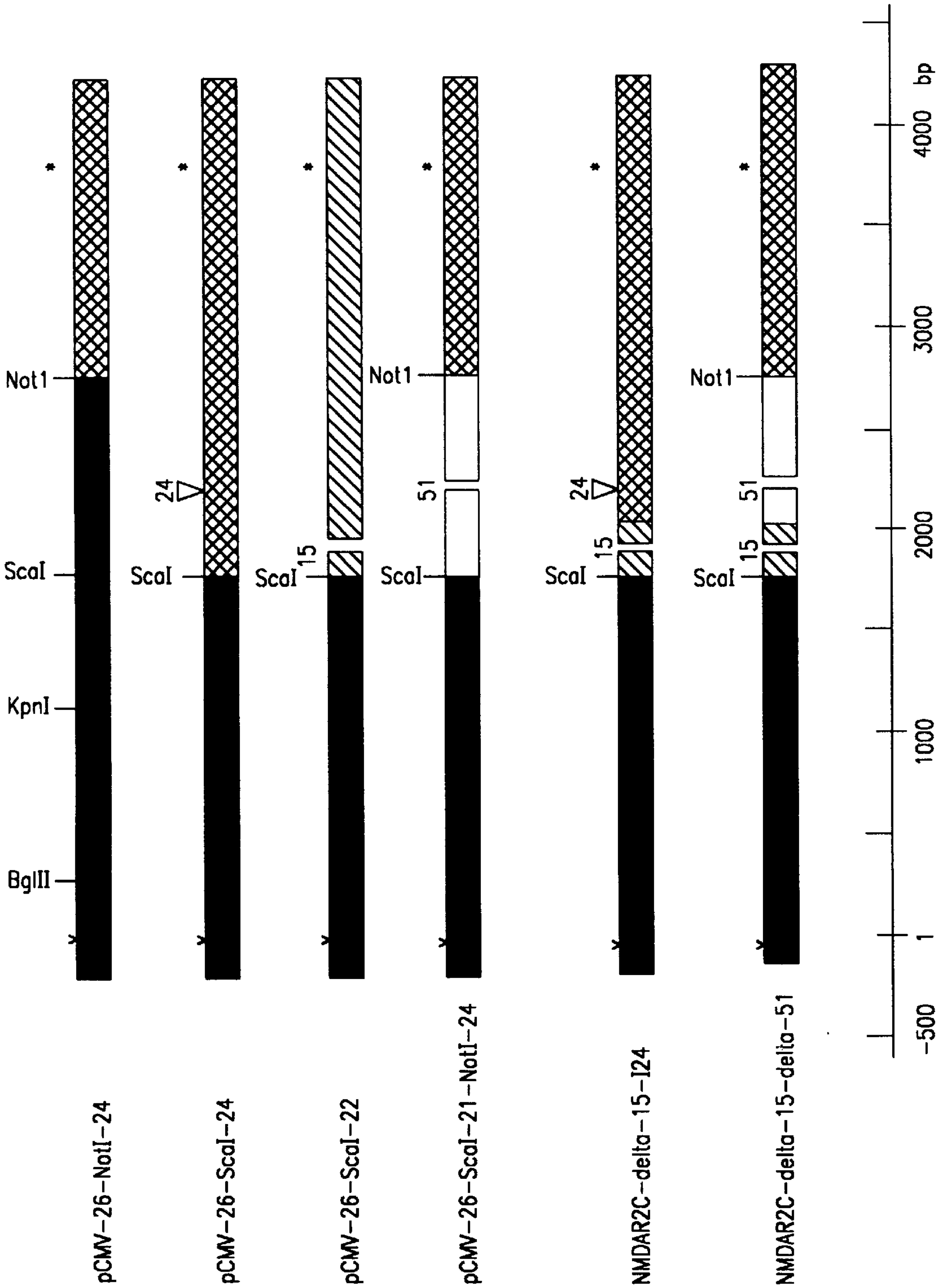
FIG. 5 is a schematic representation of full-length human NMDAR2C subunit subtypes of the invention, with partial restriction maps of each DNA. The full-length cDNAs are constructed by ligation of appropriate portions of the clones shown in FIG. 4. Regions of each full-length cDNA composed of nucleotide sequences corresponding to a particular clone are distinguished as solid, striped, cross-hatched or open boxes.

Portions of the partial NMDAR2C clones can be ligated in a variety of ways to generate constructs encoding full-length NMDAR2C subunit variants. The 5' end of each NMDAR2C cDNA can be contributed by NMDA26, whereas the 3' ends of the constructs are contributed by various combinations of clones NMDA21, NMDA22, and NMDA24. FIG. 5 depicts full-length NMDAR2C constructs and indicates the portions of the different clones that contribute to each construct.

For example, full-length constructs can be prepared using methods such as those described in Example 2 for preparing NMDAR1 constructs. Thus, clone inserts are transferred into a vector (e.g., pcDNA1) for ease of manipulation and then desired portions of the cDNAs are isolated by restriction enzyme digestion of the vectors. This can require several steps and/or partial digests if, for example, there are no unique restriction enzyme sites surrounding the desired portions of the cDNAs. The desired cDNA fragments are then ligated and incorporated into an expression plasmid such as pcDNA1 or pCMV-T7-2.

Figure 6A:
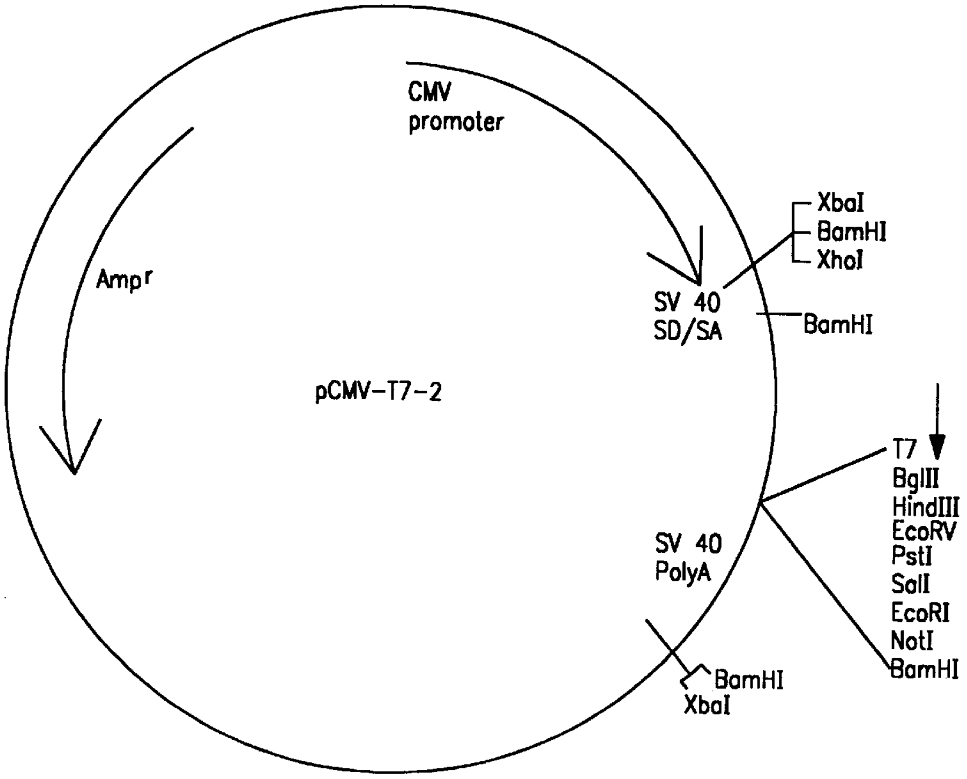
FIG. 6 presents restriction maps of CMV promoter-based vectors pCMV-T7-2 and pCMV-T7-3.
Figure 6B:
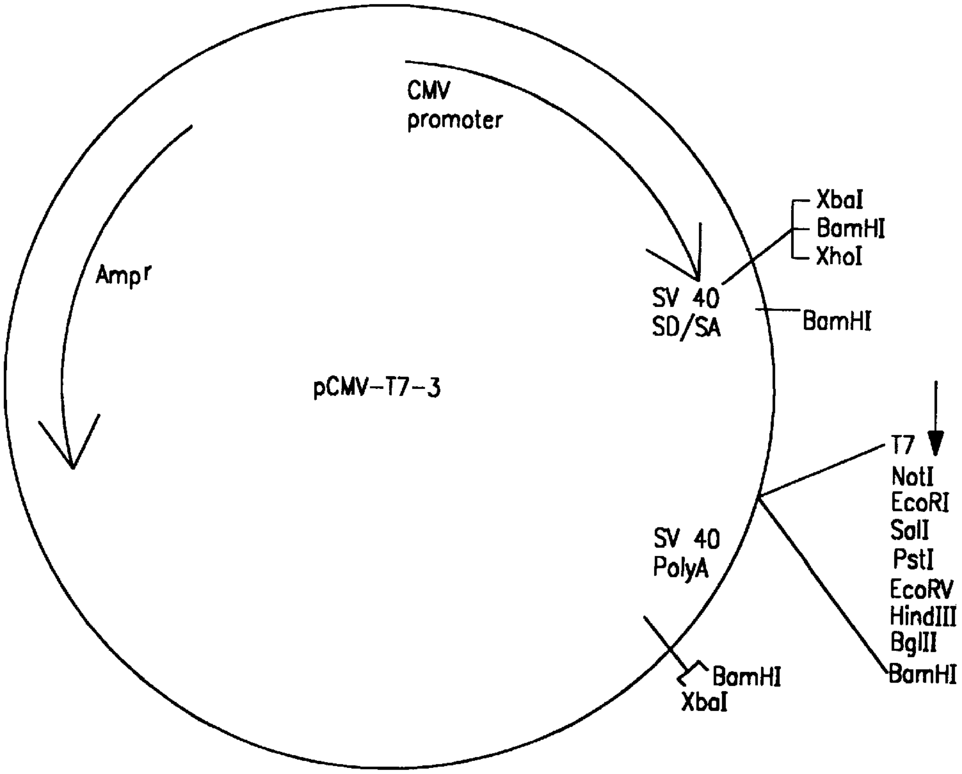

Plasmid pCMV-T7-2 (see FIG. 6) is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. Plasmid pCMV-T7-3, also depicted in FIG. 6, is identical to pCMV-T7-2 except that the order of the restriction enzyme sites in the polylinker is reversed. This plasmid can also be used for heterologous expression of NMDAR subunit DNA.

Construct pcDNA1-26-NotI-24-5'UT contains 188 base pairs of 5' untranslated sequence (nucleotides 1–188 of Sequence ID No. 5), the complete coding sequence of the first variant of the human NMDAR2C subunit (nucleotides 189–3899 of Sequence ID No. 5) and ~370 base pairs of 3' untranslated sequence (nucleotides 3900–4068 of Sequence ID No. 5 followed by ~200 additional base pairs). The NMDAR2C cDNA is contained within the polylinker of expression vector pcDNA1 for expression.

Construct pCMV-26-NotI-24 (Sequence ID No. 5) contains 49 base pairs of 5' untranslated sequence (nucleotides 140–188 of Sequence ID No. 5), the complete coding sequence of a first variant of the human NMDAR2C subunit (nucleotides 189–3899 of Sequence ID No. 5) and ~370 base pairs of 3' untranslated sequence (nucleotides 3900–4068 of Sequence ID No. 5 followed by ~200 additional base pairs). The NMDAR2C cDNA is contained within the polylinker of expression vector pCMV-T7-2 for expression.

Construct pCMV-26-ScaI-24 (Sequence ID No. 45) is identical to pCMV-26-NotI-24, except it contains 24-base pairs (Sequence ID No. 7) inserted between nucleotides 2350 and 2351 of Sequence ID No. 5.

Construct pCMV-26-ScaI-22 (Sequence ID No. 47) is identical to pCMV-26-NotI-24, except that it lacks 15-base pairs (nucleotides 1960–1974 of Sequence ID No. 5).

Construct pCMV-26-ScaI-21-NotI-24 (Sequence ID No. 49) is identical to pCMV-26-NotI-24, except that it lacks 51-base pairs (nucleotides 2351–2401 of Sequence ID No. 5).

Construct NMDAR2C-Δ15-I24 (Sequence ID No. 51) is identical to pCMV-26-NotI-24, except that it lacks 15-base pairs (i.e., nucleotides 1960–1974 of Sequence ID No. 5) and includes a 24-base pair sequence (i.e., Sequence ID No. 7; inserted between nucleotides 2350 and 2351 of Sequence ID No. 5).

Construct NMDAR2C-Δ15-Δ51 (Sequence ID No. 53) is identical to pCMV-26-NotI-24, except that it lacks 15-base pairs (i.e., nucleotides 1960–1974 of Sequence ID No. 5) and 51-base pairs (i.e., nucleotides 2351–2401 of Sequence ID No. 5).

Additional full-length NMDAR2C constructs can readily be prepared as described herein. For example, 5' untranslated sequence obtained from NMDA27 (instead of NMDA26) can be employed, and the 3' ends of the constructs can be contributed by various combinations of clones NMDA21, NMDA22, and NMDA24.

Several methods (e.g., nucleic acid amplification, RNase protection assays, etc.), as described in Example 2, can be employed to determine which NMDAR2C subunit variants are actually expressed in various human tissues.

EXAMPLE 5

Isolation of DNA Encoding Human NMDA Receptor NMDAR2A Subunits

Two human cDNA libraries were prepared using different oligonucleotides (random and specific primers) to prime cDNA synthesis from RNA isolated from cerebellum tissue. The specific primer used for first-strand synthesis was SE162, nucleotides 904 to 929 of Sequence ID No. 10. cDNAs synthesized by random priming that ranged in size from 1.0–2.8 kb, and cDNAs synthesized by specific priming that ranged in size from 0.6–1.1 kb, were isolated and inserted into the λgt10 phage vector to generate the two libraries.

The random-primed library ($3\times10^6$ recombinants) was screened for hybridization to the 795-base pair insert from pcrNMDAR2A (see Example 3) in 5× SSPE, 5× Denhart's solution, 50% deionized formamide, 0.2% SDS, 200 μg/ml sonicated, denatured herring sperm DNA at 42° C. Washes were performed in 1× SSPE, 0.2% SDS at 55° C. The probe hybridized to 11 plaques.

The specifically-primed library ($6\times10^5$ recombinants) was screened for hybridization to oligonucleotide SE177 (nucleotides 859 to 884 of Sequence ID No. 10) in 6× SSPE, 5× Denhart's solution, 10% deionized formamide, 0.2% SDS, 200 μg/ml sonicated, denatured herring sperm DNA at 42° C. Washes were performed in 1× SSPE, 0.2% SDS at 50° C. The probe hybridized to 2 plaques.

Figure 7:
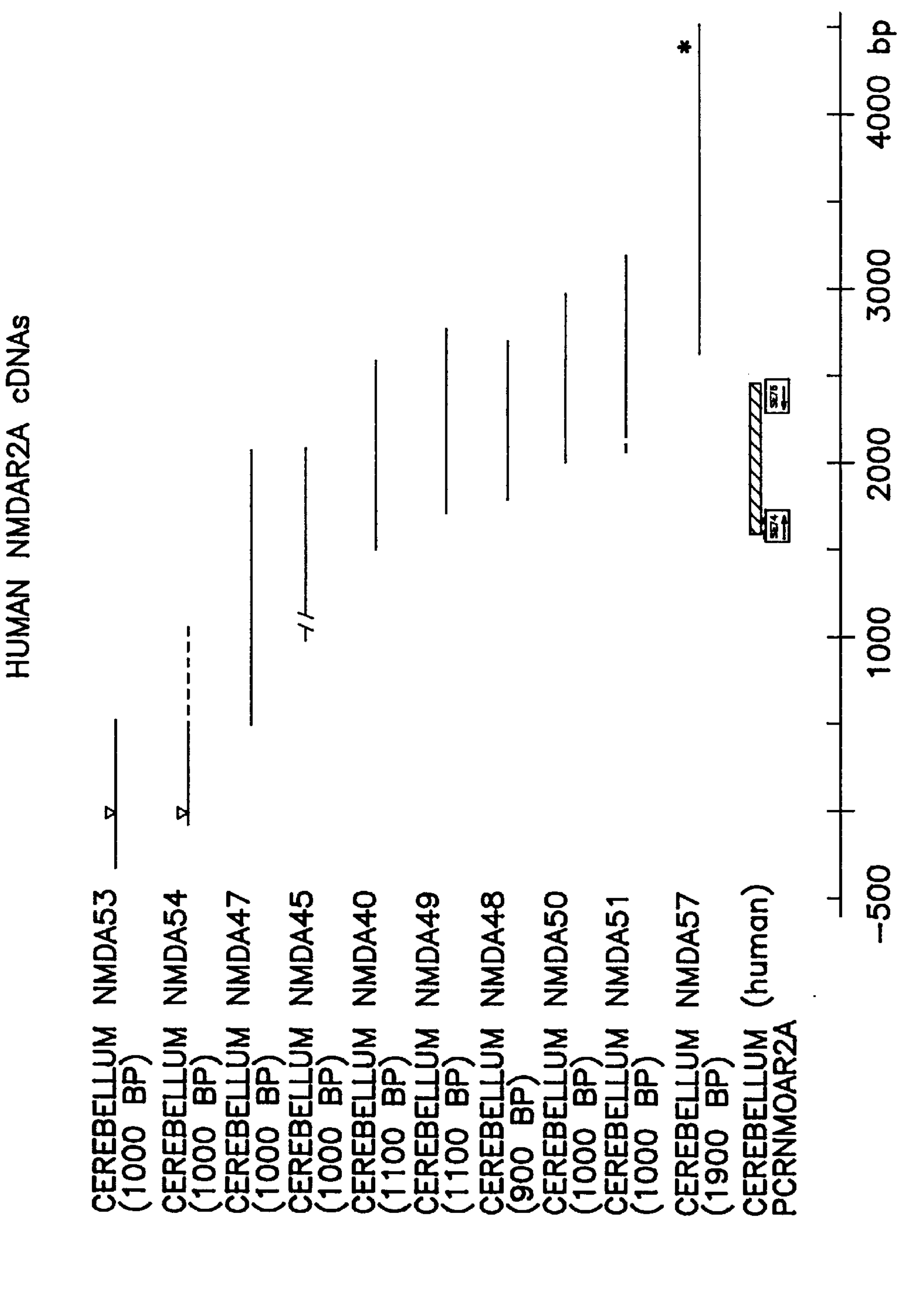
FIG. 7 is a schematic representation of various human NMDAR2A clones of the invention. These partial clones are aligned to illustrate their relative location within a full-length human NMDAR2A cDNA. Inverted triangles identify the position of the translation initiation codon and an asterisk identifies the position of the translation termination codon. The dashed line in clone NMDA54 represents putative intron sequence of this incompletely spliced cDNA. The break in clone NMDA45 represents a deletion of a portion of the NMDAR2A sequence relative to clone 47. The striped box represents the DNA fragment pcrNMDAR2A obtained by nucleic acid amplification of cDNAs prepared from RNA isolated from human cerebellum tissue. The oligonucleotides used to prime the amplification, SE74 and SE75, are designated as small boxes placed below the ends of pcrNMDAR2A.

Nine of the hybridizing plaques were purified and the inserts were characterized by restriction enzyme mapping and DNA sequence analysis. All clones contained partial cDNAs (see FIG. 7). Two of the clones, NMDA53 and NMDA54, contain the translation initiation codon and 320 base pairs and 88 base pairs, respectively, of 5' untranslated sequence. The sequences of three other clones, NMDA47, NMDA49 and NMDA51, along with those of NMDA53 and NMDA54, overlap to comprise ~70% of the human NMDAR2A subunit coding sequence (see Sequence ID No. 10).

To obtain clones containing the remaining ~1300 base pairs of 3' sequence needed to complete the NMDAR2A coding sequence, an additional human cDNA library (an amplified randomly primed cerebellum cDNA library with inserts ranging from 1.0–2.8 kb in length) was screened for hybridization to an oligonucleotide corresponding to the 3' end of clone NMDA51 (oligo SE171; nucleotide 3454 to 3479 of Sequence ID No. 10) using the same conditions as used for screening the specifically primed cerebellum cDNA library as described above. Four hybridizing plaques were purified and the inserts were characterized by DNA sequence analysis to determine if they contain the 3' end of the coding sequence and a translation termination codon. One of the clones, NMDA57, contains a translation termination codon, as determined by DNA sequence analysis. Phage lysate containing clone NMDA57 were deposited under the provisions of the Budapest Treaty with the American Type Culture Collection (ATCC) on Apr. 13, 1993, and assigned Accession No. 75442.

EXAMPLE 6

Preparation of Full-length NMDAR2A Subunit cDNA Constructs

Portions of the partial NMDAR2A clones can be ligated to generate a construct encoding a full-length NMDAR2A subunit. The construct is prepared using methods such as those described in Example 2 for preparing NMDAR1 constructs. The clone inserts are transferred into a vector (e.g., pcDNA1 or pGEM-72) for ease of manipulation and then desired portions of the cDNAs are isolated by restriction enzyme digests of the vectors. This can require several steps and/or partial digests if, for example, there are no unique restriction enzyme sites surrounding the desired portions of the cDNAs. The desired cDNA fragments are then ligated and incorporated into an expression plasmid such as pcDNA1 or pCMV-T7-2.

EXAMPLE 7

Expression of Recombinant Human NMDA Receptor Subunits on Oocytes

*Xenopus oocytes* were injected with in vitro transcripts prepared from constructs containing DNA encoding human NMDA receptor NMDAR1 and NMDAR2 subunits. Electrophysiological measurements of the oocyte transmembrane currents were made using the two-electrode voltage clamp technique (see e.g., Stuhmer (1992) *Meth. Enzymol.* 207:319–339).

A. Preparation of In Vitro Transcripts

Recombinant capped transcripts of NMDA receptor subunit cDNAs contained in constructs NMDAR1, NMDAR1-I63, NMDAR1-I63-Δ204, NMDAR1-Δ1087, NMDAR1-Δ363, and pCMV-26-NotI-24 were synthesized from linearized plasmids using the mCAP RNA Capping Kit (Cat. #200350, Stratagene, Inc., La Jolla, Calif.). The mass of each synthesized transcript was determined by UV absorbance and the integrity of each transcript was determined by electrophoresis through an agarose gel.

B. Electrophysiology

*Xenopus oocytes* were injected with 12.5–50 ng of one or more NMDA receptor subunit transcripts per oocyte. The preparation and injection of oocytes were carried out as described by Dascal [(1987) *Crit. Rev. Biochem.* 22:317–387]. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3), and the membrane potential was clamped at −80 to −100 mV. Drugs were applied by pipetting 6.0 μl aliquots of drug-containing solution directly into the bath. The data were sampled at 2–5 Hz with a Labmaster data acquisition board in a PC-386 using AXOTAPE version 1.2 (Axon Instruments, Foster City, Calif.) software. The data were exported to a laser printer or plotted using Sigmaplot version 5.0.

NMDA agonists, i.e., 10–20 $\mu$M glycine (gly) and 10–100 $\mu$M glutamate (glu) or 100–1000 $\mu$M NMDA, were applied to the bath. If a current response was observed, the agonists were washed from the bath and 100 $\mu$M $MgCl_2$ or 1 $\mu$M MK801 (Research Biochemicals, Inc., Natick, Mass.) (NMDA receptor antagonists) were applied before a second agonist application in order to determine whether the current was blocked by antagonists. The results of multiple recordings are summarized in Table 1.

TABLE 1

Electrophysiological Analysis of Oocytes Injected with NMDA Receptor Subunit Transcripts

| Transcript (ng injected) | No. Oocytes Responding | Agonists | Peak Current Amplitude |
|---|---|---|---|
| NMDAR1 (12.5) | 6 of 8[a] | 10 $\mu$M gly + 10 $\mu$M glu | 3–40 nA* |
| NMDAR1 (12.5) | 2 of 2[a] | 10 $\mu$M gly + 100 $\mu$M NMDA | 3–8 nA |
| NMDAR1 (12.5) | 0 of 9[a] | 10 $\mu$M gly + 10 $\mu$M glu | |
| NMDAR1 (50) | 0 of 1[a] | 20 $\mu$M gly + 20 $\mu$M glu | |
| NMDAR1 (40) | 4 of 10 | 10 $\mu$M gly + 10 $\mu$M glu | 21.3 ± 20.9 nA* |
| NMDAR1 (40) | 1 of 5 | 10 $\mu$M gly + 100 $\mu$M NMDA | 24 nA* |
| NMDAR1 (40) | 1 of 1 | 10 $\mu$M gly + 100 $\mu$M NMDA | 15.4 nA |
| NMDAR1 (30) | 4 of 9 | 10 $\mu$M gly + 50 $\mu$M glu | 10.6 ± 11.7 nA* |
| NMDAR1 (30) | 0 of 8 | 10–20 $\mu$M gly + 10–100 $\mu$M glu | |
| NMDAR1 (30) | 1 of 4 | 20 $\mu$M gly + 100 $\mu$M NMDA | 10.5 nA |
| NMDAR1-I63 (12.5) | 1 of 5[a] | 10 $\mu$M gly + 10 $\mu$M glu | ~30 nA* |
| NMDAR1-I63 (50) | 0 of 4[a] | 10 $\mu$M gly + 10 $\mu$M glu | |
| NMDAR1-I63 (40) | 4 of 5 | 10 $\mu$M gly + 10 $\mu$M glu | 13.4 ± 7.1 nA⁺ |
| NMDAR1-I63 (40) | 3 of 3 | 10 $\mu$M gly + 20 $\mu$M glu | 17.4 + 3.7 nA* |
| NMDAR1-I63 (40) | 1 of 1 | 10 $\mu$M gly + 100 $\mu$M glu | 28 nA |
| NMDAR1-I63 (40) | 1 of 1 | 10 $\mu$M gly + 10 $\mu$M NMDA | 1.4 nA⁺ |
| NMDAR1-I63 (40) | 7 of 10 | 10 $\mu$M gly + 100 $\mu$M NMDA | 8.1 ± 3.0 nA⁺ |
| NMDAR1-I63 (40) | 1 of 2 | 10 $\mu$M gly + 1000 $\mu$M NMDA | 16.4 nA⁺ |
| NMDAR1-I63-Δ204 (12.5) | 0 of 8[a] | 10 $\mu$M gly + 10 $\mu$M glu | |
| NMDAR1-I63-Δ204 (50) | 1 of 5[a] | 20 $\mu$M gly + 20 $\mu$M glu | ~50 nA |
| NMDAR1-Δ1087 (50) | 3 of 13 | 10 $\mu$M gly + 10 $\mu$M glu | 4–11 nA* |
| NMDAR1 (39) + pCMV-26-NotI-24 (39) | 1 of 5 | 10 $\mu$M gly + 50 $\mu$M glu | 10 nA |
| NMDAR1 (30) + pCMV-26-NotI-24 (30) | 0 of 7 | 10 $\mu$M gly + 20 $\mu$M glu | |
| NMDAR1 (32) + pcDNA1-26-NotI-24-5'UT (50) | 4 of 5 | 10 $\mu$M gly + 10 $\mu$M glu | 15.8 ± 2.6 nA |

[a]Oocytes were unhealthy (i.e., the holding current was large)
*The agonist-induced currents in at least 1 cell were blocked by 100 $\mu$M $MgCl_2$.
⁺The agonist-induced currents in at least 1 cell were blocked by 1.0 $\mu$M MK801.

Analysis of the results shown in Table 1 indicates that, on average, the magnitude of the inward current generated in oocytes injected with transcripts of he NMDAR1 cDNA in response to glycine and glutamate is larger than that generated in oocytes injected with transcripts of the NMDAR1-I63 cDNA. In general, the NMDA agonist-induced currents were blocked by either $MgCl_2$ or MK801. The magnitude of the inward current generated in oocytes co-injected with transcripts of NMDAR1 and pCMV-26-NotI-24 cDNAs was comparable to that generated in oocytes injected with transcripts of NMDAR1 cDNA only.

Oocytes injected with transcripts (12.5 to 65 ng) of the NMDAR-1 subunit-encoding inserts of constructs NMDAR1, NMDAR1-I63 or NMDAR1-Δ363 were further analyzed to evaluate human NMDA receptor sensitivity to glutamate and NMDA. The two-electrode voltage clamp methods described above were used to measure current in the cells.

To determine agonist sensitivity of the recombinant human NMDA receptors, various concentrations of glutamate (0.1–100 $\mu$M) or NMDA (3–1000 $\mu$M) were applied to the bath (in the presence of 10 $\mu$M glycine) and the current response was recorded. The bath was flushed between agonist applications. Intermediate test applications of 10 $\mu$M glycine plus 10 $\mu$M glutamate were included in the experiments to monitor the receptors for run-down (i.e., inactivation of receptors that have been repeatedly activated during prolonged electrophysiological recording). The data were used to generate dose-response curves from which $EC_{50}$ values for the two agonists were calculated.

The $EC_{50}$ values determined for glutamate stimulation of NMDA receptors expressed in oocytes injected with NMDAR1, NMDAR1-I63 or NMDAR1-Δ363 transcripts were 0.4, 0.6 and 0.5 $\mu$M, respectively. The $EC_{50}$ values determined for NMDA stimulation of NMDA receptors expressed in oocytes injected with NMDAR1, NMDAR1-I63 or NMDAR1-Δ363 transcripts were 6.3, 10.9 and 11.9 $\mu$M, respectively.

EXAMPLE 8

Recombinant Expression of Human NMDA Receptor Subunits in Mammalian Cells

Mammalian cells, such as human embryonic kidney (HEK293) cells can be transiently and/or stably transfected with DNA encoding human NMDA receptor subunits (e.g., DNA encoding an NMDAR1 subunit or DNA encoding an NMDAR1 subunit and DNA encoding an NMDAR2 subunit such as pCMV-26-NotI-24). Transfectants are analyzed for expression of NMDA receptors using various assays, e.g., northern blot hybridization, electrophysiological recording of cell currents, $Ca^{2+}$-sensitive fluorescent indicator-based assays and [3H]-MK801 binding assays.

A. Transient Transfection of HEK Cells

Two transient transfections were performed. In one transfection, HEK 293 cells were transiently transfected with DNA encoding an NMDAR1 (construct NMDAR1A) subunit. In another transfection, HEK 293 cells were transiently co-transfected with DNA encoding NMDAR1 (construct NMDAR1A) and NMDAR2C (pCMV-26-NotI-24) subunits. In both transfections, ~$2\times10^6$ HEK cells were transiently transfected with 19 $\mu$g of the indicated plasmid(s) according to standard $CaPO_4$ transfection procedures [Wigler et al. (1979) *Proc. Natl. Acad. Sci. USA* 76:1373–1376]. In addition, 1 $\mu$g of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the X-gal substrate [Jones (1986) *EMBO* 5:3133–3142]. Transfectants can also be analyzed for β-galactosidase expression by measurement of β-galactosidase activity [Miller (1972) in *Experiments in Molecular Genetics, pp.*352–355, Cold Spring Harbor Press).

The efficiency of these transfections of HEK cells was typical of standard efficiencies (i.e., ~50%).

B. Stable Transfection of Mammalian Cells

Mammalian cells, such as HEK 293 cells, can be stably transfected using the calcium phosphate transfection procedure [*Current Protocols in Molecular Biology,* Vol. 1, Wiley Inter-Science, Supplement 14, Unit 9.1.1–9.1.9 (1990)]. Ten-cm plates, each containing 1–$2\times10^6$ cells, are transfected with 10 ml of DNA/calcium phosphate precipitate in media containing approximately 19 $\mu$g of NMDA receptor subunit-encoding DNA and 1 $\mu$g of DNA encoding a selectable marker, for example, neomycin-resistance gene (i.e., pSV2neo). After ~14 days of growth in media containing typically 1 $\mu$g/ml G418, colonies form and are individually isolated using cloning cylinders. The isolates are then subjected to limiting dilution and screened to identify those that express NMDA receptors using, for example, methods described below.

C. Analysis of Transfectants

1. Northern Blot Hybridization Analysis

Total RNA was isolated from ~$1\times10^7$ HEK cells co-transfected with NMDAR1 and pCMV-26-NotI-24, and 5–10 $\mu$g of RNA was used for northern hybridization analysis. Fragments from human neuronal NMDAR subunit-encoding plasmids were randomly primed and labeled with $^{32}$P-dCTP Klenow incorporation and used as probes. The northern blot hybridization and wash conditions were as follows:

hybridization in 5× SSPE, 5× Denhart's solution, 50% formamide, at 42° C. followed by washing in 0.2× SSPE, 0.1% SDS, at 65° C.

Results of these studies revealed the transfectants expressed detectable levels of NMDAR1 and NMDAR2C mRNA of the appropriate size (based on the size of the cDNAs).

2. Fluorescent indicator-based assays

Activation of ligand-gated NMDA receptors by agonists leads to an influx of cations (both monovalent and divalent), including $Ca^{2+}$, through the receptor channel. Calcium entry into the cell through the channel can in turn induce release of calcium contained in intracellular stores. Monovalent cation entry into the cell through the channel can also result in an increase in cytoplasmic calcium levels through depolarization of the membrane and subsequent activation of voltage-dependent calcium channels. Therefore, methods of detecting transient increases in intracellular calcium concentration can be applied to the analysis of functional NMDA receptor expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying NMDA receptors has been described in commonly assigned pending U.S. patent application Ser. No. 07/812,254 and corresponding PCT patent application Ser. No. US92/11090, incorporated by reference herein in their entirety.

Mammalian cells that have been transfected with DNA encoding NMDAR1 or NMDAR1 and NMDAR2C subunits can be analyzed for expression of functional recombinant NMDA receptors using the automated fluorescent indicator-based assay. The assay procedure is as follows.

Untransfected mammalian host cells (or host cells transiently transfected with pCMV-T7-2) and mammalian cells that have been transfected with NMDAR1±NMDAR2 subunit DNA are plated in the wells of a 96-well microtiter dish (Nunc Catalog No. 1-6708, available through Alameda Industries, Escondido, Calif.) that has been precoated with poly-L-lysine at a density of $2.5\times10^5$ cells/well and loaded with fluo-3 by incubation for 2 hours at 20° C. in a medium containing 20 $\mu$M fluo-3, 0.2% Pluronic F-127 in HBS (125 mM NaCl, 5 mM KCl, 1.8 mM $CaCl_2$, 0.62 mM $MgCl_2$, 20 mM glucose, 20 mM HEPES, pH 7.4). The cells are then washed with assay buffer (i.e. HBS). The microtiter dish is then placed into a fluorescence plate reader (e.g., Fluoroskan II, Lab Products International, Ltd., Raleigh, N.C.) and the basal fluorescence of each well is measured and recorded before addition of 10 $\mu$M glycine and 10 AM glutamate to the wells. The fluorescence of the wells is monitored repeatedly (75 readings at 0.63-sec intervals) following addition of agonist.

The fluorescence of the untransfected host cells preferably will not change after addition of glycine and glutamate, i.e., the host cells should not express endogenous excitatory amino acid receptors. The fluorescence of mammalian cells transfected with NMDAR1±NMDAR2 subunit DNA will increase after addition of glycine and glutamate if a sufficient number of functional NMDA receptors are expressed at the cell surface, and fluorescence readings are taken rapidly.

The resting potential of the membrane of some mammalian host cells may be relatively positive (e.g., –35 mV). Because activation of some NMDA receptors may be significantly reduced at relatively positive potentials, it may be necessary to lower the resting potential of the membrane of cells transfected with human NMDA receptor subunit-encoding DNAs prior to assaying the cells for NMDA receptor activity using the fluorescent indicator-based assay. This may be accomplished by adding valinomycin (~10 $\mu$M) to the transfected cells prior to adding NMDA receptor agonists to initiate the assay.

3. NMDA Receptor Ligand Binding Assays

Mammalian cells transfected with NMDAR1±NMDAR2 subunit DNAs can be analyzed for [$^3$H]-MK801 binding. An additional ligand-binding assay for NMDA receptors using $^3$H-CGP39653 is also described below. Rat brain membranes are included in the binding assays as a positive control.

a. Preparation of Membranes i. Buffy coat Homogenate from Rat Cerebral Cortex

Buffy coat membranes are prepared from rat brain cortices as described by Jones et al. ((1989) *J. Pharmacol. Meth.* 21:161]. Briefly, cortices from ten freshly thawed frozen rat brains are dissected and weighed. The tissue is homogenized in 20 volumes of 0.32 M ice-cold sucrose in a glass homogenizing tube using a Teflon pestle. The suspension is centrifuged at 1,000×g for 10 minutes at 4° C. The supernatant is decanted and centrifuged at 20,000×g for 20 minutes at 4° C. The pellet is resuspended in 20 volumes of ice-cold distilled water with a Polytron for 30 sec at setting 6. The suspension is centrifuged at 8,000×g for 20 minutes at 4° C. The buffy coat pellet is rinsed gently with supernatant and then recentrifuged at 48,000×g for 20 minutes at 4° C. The pellet is resuspended in 20 volumes of ice-cold distilled water with a Polytron and centrifuged again at 48,000×g for 20 minutes. The wash step is repeated once more. The final suspension is divided into aliquots, centrifuged. Each pellet can be stored frozen at −20° C. for 12 hrs or more before use.

ii. Membranes from Transfected and Untransfected Mammalian Cells

In order to prepare membranes from transfected and untransfected mammalian cells, the cells are scraped from the tissue culture plates, and the plates are rinsed with 5 ml of PBS (phosphate-buffered saline: 137 mM NaCl, 2.7 mM KCl, 10 mM $Na_2HPO_4$, 1.7 mM $KH_2PO_4$). The cells are centrifuged at low speed in a table-top centrifuge, and the cell pellet is rinsed with PBS. The cell pellet is resuspended in 20 ml of 10 mM Hepes buffer, pH 7.4, using a Polytron at setting 3–6 for 30 seconds. The cell suspension is centrifuged at 48,000×g for 20 minutes at 4° C. The supernatant is discarded, and the pellet is kept frozen for 12 hrs or more at −20° C.

b. [$^3$H]-MK801 Binding to NMDA Receptors

The binding of [$^3$H]-MK801 to NMDA receptors is carried out as described by Wong et al. ((1986) *Proc. Natl. Acad. Sci. USA* 83:7104], with a few minor changes. Thus, on the day of the assay, the rat brain and mammalian cell (transfected and untransfected) membrane pellets are resuspended in 50 volumes of 10 mM Hepes buffer, pH 7.4, using a 10-ml syringe and a 21-gauge needle, and incubated for 20 minutes at 37° C. The supernatant is centrifuged at 48,000×g for 20 minutes at 4° C. The pellet is resuspended in 2 ml of 10 mM Hepes, pH 7.4 and centrifuged as described above. The wash step is repeated once more, and the pellet is resuspended in 10 ml of 10 mM Hepes, pH 7.4. The protein concentration is determined using the Biorad Bradford reagent. The pellet is finally resuspended in the assay buffer (10 mM Hepes, pH 7.4) at 1 mg/ml.

For binding studies, the membrane suspension is incubated in duplicate with 2.5 nM [$^3$H]-MK801 (New England Nuclear, Boston, Mass.) in a total volume of 0.5 ml assay buffer (10 mM Hepes, pH 7.4) in the presence and absence of 10 $\mu$M glutamate and 10 $\mu$M glycine for 60 or 120 min at 23° C. Bound radioactivity is separated from free radioactivity by rapid filtration through Whatman GF/C filters which are presoaked for 2–3 hrs in 0.05% polyethylenimine. The filters are washed twice with 3 ml ice-cold assay buffer. The filters are dried and transferred to scintillation vials, each containing 10 ml of scintillation fluid. The vials are vortexed, and the radioactivity is measured in a Beckman scintillation counter. The nonspecific binding observed in the presence of 10 $\mu$M MK801 is subtracted from the total binding in order to determine the specific binding.

Rat brain cortical buffy coat membranes displayed specific saturable binding of [$^3$H]-MK801. In the presence of glycine and glutamate, the ratio of total-to-nonspecific binding (S:N ratio) was 28:1, whereas in the absence of glutamate and glycine the S:N ratio was 5:1. Thus, the binding of MK801 to rat NMDA receptors is potentiated by glutamatergic agonists. Scatchard analysis of [$^3$H]-MK801 binding to rat brain membranes indicated that the sensitivity of the assay was 90 fmoles of receptor.

c. [$^3$H]-CGP39653 Binding to NMDA Receptors

The binding of [$^3$H]-CGP39653 to rat brain membranes is carried out as described by Sills et al. [(1991) *Eur. J. Pharmacol.* 192:19]. The buffy coat membrane pellet is resuspended in 50 volumes of 5 mM Tris-HCl containing 10 mM EDTA, pH 7.7, and incubated for 10 min. at 37° C. The supernatant is centrifuged at 48,000×g for 10 min. at 4° C. The wash step is repeated once and the pellet is resuspended in 10 ml of 5 mM Tris-HCl containing 10 mM EDTA, pH 7.7. This rat brain membrane suspension is incubated in duplicate or triplicate with 2.0 nM [$^3$H]-CGP39653 (New England Nuclear) in a total volume of 0.5 ml assay buffer (5 mM Tris-HCl, pH 7.7) for 60 min at 0° C. Nonspecific binding is determined in the presence of 100 $\mu$M glutamate. Bound radioactivity is separated from the free by vacuum filtration through GF/C filters which are presoaked for 2–3 hrs in 0.05% polyethylenimine, using the filtration manifold. Unbound radioactivity is removed with two washes of 3 ml each of ice-cold buffer. The filters are dried and transferred to scintillation vials, each containing 10 ml of scintillation fluid. The vials are vortexed, and the radioactivity is measured in a Beckman scintillation counter. The nonspecific binding observed in the presence of 100 $\mu$M glutamate is subtracted from the total binding to determine the specific binding.

[$^3$H]-CGP39653 binding was first measured as a function of membrane concentration. Specific binding increased linearly with increasing membrane concentration up to 200 $\mu$g of protein in the presence of 2 nM [$^3$H]-CGP39653.

Saturation analysis of [$^3$H]-CGP39653 binding was carried out by incubating 150 $\mu$g of rat buffy coat homogenate with increasing concentrations of [$^3$H]-CGP39653 for 60 min at 4° C. Scatchard analysis indicated a single class of binding sites with a $B_{max}$ value of 0.69±0.09 pmoles/mg and a $K_d$ value of 12.3±0.12 nM.

While the invention has been described in detail with reference to certain preferred embodiments thereof, it will be understood that modifications and variations are within the spirit and scope of that which is described and claimed.

SUMMARY OF SEQUENCES

Sequence ID No. 1 is a nucleotide sequence encoding a human N-methyl-D-aspartate (NMDA) receptor subunit, NMDAR1, and the deduced amino acid sequence thereof.

Sequence ID No. 2 is the amino acid sequence of the NMDA receptor subunit set forth in Sequence ID No. 1.

Sequence ID No. 1, nucleotides 320–3402, is a 3083 nucleotide sequence encoded by clone NMDA10. Thus, Sequence ID No. 1, nucleotides 320–3402, differs from Sequence ID No. 1 in that it does not contain the 319 5' nucleotides, nor the 896 3' nucleotides thereof.

Sequence ID No. 2, residues 20–938 is the amino acid sequence of a portion of an NMDA receptor subunit as encoded by the nucleotide sequence of Sequence ID No. 1, nucleotides 320–3402.

Sequence ID No. 3 is a nucleotide sequence encoding the 63 nucleotide insert present in Sequence ID Nos. 15, 23, 25, 27, 35, 37 and 39.

Sequence ID No. 4 is the 21 amino acid sequence encoded by the insert set forth in Sequence ID No. 3.

Sequence ID No. 5 is a nucleotide sequence of a clone (pCMV-26-Notl-24) encoding a human N-methyl-D-aspartate (NMDA) receptor subunit, NMDAR16, and the deduced amino acid sequence thereof.

Sequence ID No. 6 is the amino acid sequence of the NMDA receptor subunit set forth in Sequence ID No. 5.

Sequence ID No. 5, nucleotides 1–3025, is a 3025 nucleotide sequence encoded by clone NMDA26. Thus, Sequence ID No. 5, nucleotides 1–3025, differs from Sequence ID No. 5 in that it does not contain the 1043 3'-terminal nucleotides thereof.

Sequence ID No. 6, residues 1–945, is the amino acid sequence of a portion of an NMDA receptor subunit as encoded by the nucleotide sequence of Sequence ID No. 5 nucleotides 1–3025.

Sequence ID No. 7 is a nucleotide sequence encoding the 24 nucleotide insert present in Sequence ID Nos. 44, 45 and 51.

Sequence ID No. 8 is the 7 amino acid sequence encoded by nucleotides 2–22 of the insert set forth in Sequence ID No. 7. Because the insert is introduced within a codon, the insert itself only encodes 7 amino acids. The terminal residues of the nucleotide insert participate in forming codons with adjacent sequence at the site of insertion.

Sequence ID No. 9 is a nucleotide sequence encoding the 11 nucleotide insert present in Sequence ID Nos. 43 and 44.

Sequence ID No. 10 is a nucleotide sequence encoding a portion of a human N-methyl-D-aspartate (NMDA) receptor subunit, NMDAR2A.

Sequence ID No. 11 is the amino acid sequence of a portion of an NMDA receptor subunit as encoded by the nucleotide sequence set forth in Sequence ID No. 10.

Sequence ID No. 12 is the nucleotide sequence of 71 nucleotides of 5' untranslated sequence of clone NMDA27, plus the initiation codon (nucleotides 72–74) of said clone.

Sequence ID No. 13 is a 3155 nucleotide sequence encoded by clone NMDA11, comprising nucleotides 1–2961, plus nucleotides 3325–3518 of Sequence ID No. 1. Thus, Sequence ID No. 13 differs from Sequence ID No. 1 by the deletion of 363 nucleotides from the 3' portion thereof (i.e., by the deletion of nucleotides 2962–3324 of Sequence ID No. 1), and further by the lack of the 781 terminal 3' nucleotides of Sequence ID No. 1.

Sequence ID No. 14 is the amino acid sequence of an NMDA receptor subunit encoded by the nucleotide sequence of Sequence ID No. 13.

Sequence ID No. 15 is a 2542 nucleotide sequence encoded by clone NMDA7, comprising nucleotides 556–831 of Sequence ID No. 1, plus an additional 63 nucleotides (set forth in Sequence ID No. 3) and nucleotides 832–984, 1189–2961 and 3325–3599 of Sequence ID No. 1. Thus, Sequence ID No. 15 differs from Sequence ID No. 1 in that it does not contain the 555 5'-most nucleotides thereof, it does not contain the 204 nucleotides set forth as nucleotides 985–1188 of Sequence ID No. 1, it does not contain the 363 3' nucleotides set forth as nucleotides 2962–3324 of Sequence ID No. 1, and it does not contain the 700 3'-most nucleotides of Sequence ID No. 1, while it does contain an additional 63 nucleotides (Sequence ID No. 3) inserted between nucleotides 831 and 832 of Sequence ID No. 1.

Sequence ID No. 16 is the amino acid sequence of a portion of an NMDA receptor subunit as encoded by the nucleotide sequence of Sequence ID No. 15.

Sequence ID No. 17 is a 593 nucleotide sequence encoded by clone NMDA3, comprising nucleotides 2617–2961, plus nucleotides 4049–4298 of Sequence ID No. 1. Thus, Sequence ID No. 17 differs from Sequence ID No. 1 in that it does not contain the 2616 5' nucleotides thereof, and by the deletion of 1087 nucleotides from the 3' portion thereof (i.e., by the deletion of nucleotides 2962–4048 of Sequence ID No. 1).

Sequence ID No. 18 is the amino acid sequence of a portion of an NMDA receptor subunit as encoded by the nucleotide sequence of Sequence ID No. 17.

Sequence ID No. 19 is a nucleotide sequence encoding human NMDA receptor subunit NMDAR1-Δ363, comprising nucleotides 1–2961, plus nucleotides 3325–4298 of Sequence ID No. 1. Thus, Sequence ID No. 19 differs from sequence ID No. 1 in that it does not contain the 363 nucleotides set forth as nucleotides 2962–3324 of Sequence ID No. 1.

Sequence ID No. 20 is the amino acid sequence of an NMDA receptor subunit encoded by the nucleotide sequence of Sequence ID No. 19.

Sequence ID No. 21 is a nucleotide sequence encoding human NMDA receptor subunit NMDAR1-Δ1087, comprising nucleotides 1–2961, plus nucleotides 4049–4298 of Sequence ID No. 1. Thus, Sequence ID No. 21 differs from Sequence ID No. 1 in that it does not contain the 1087 nucleotides set forth as nucleotides 2962–4048 of Sequence ID No. 1.

Sequence ID No. 22 is the amino acid sequence of an NMDA receptor subunit encoded by the nucleotide sequence of Sequence ID No. 21.

Sequence ID No. 23 is a nucleotide sequence encoding human NMDA receptor subunit NMDAR1-I63. Sequence ID No. 23 is the same as Sequence ID No. 1, further comprising an additional 63 nucleotides (set forth in Sequence ID No. 3) inserted between nucleotides 831 and 832 of Sequence ID No. 1.

Sequence ID No. 24 is the amino acid sequence of an NMDA receptor subunit encoded by the nucleotide sequence of Sequence ID No. 23.

Sequence ID No. 25 is a nucleotide sequence encoding human NMDA receptor subunit NMDAR1-I63-Δ204. Sequence ID No. 25 is the same as Sequence ID No. 23, except Sequence ID No. 25 does not contain the 204 nucleotides set forth as nucleotides 985–1188 of Sequence ID No. 1.

Sequence ID No. 26 is the amino acid sequence of an NMDA receptor subunit encoded by the nucleotide sequence of Sequence ID No. 25.

Sequence ID No. 27 is a nucleotide sequence encoding human NMDA receptor subunit NMDAR1-I63-Δ204-Δ363. Sequence ID No. 27 is the same as Sequence ID No. 25, except Sequence ID No. 27 does not contain the 363 nucleotides 2962–3324 of Sequence ID No. 1.

Sequence ID No. 28 is the amino acid sequence of an NMDA receptor subunit encoded by the nucleotide sequence of Sequence ID No. 27.

Sequence ID No. 29 is a nucleotide sequence encoding human NMDA receptor subunit NMDAR1-Δ204. Sequence ID No. 29 is the same as Sequence ID No. 1, except Sequence ID No. 29 does not contain the 204 nucleotides set forth as nucleotides 985–1188 of Sequence ID No. 1.

Sequence ID No. 30 is the amino acid sequence of an NMDA receptor subunit encoded by the nucleotide sequence of Sequence ID No. 29.

Sequence ID No. 31 is a nucleotide sequence encoding human NMDA receptor subunit NMDAR1-Δ204-Δ363. Sequence ID No. 31 differs from Sequence ID No. 1 in that Sequence ID No. 31 does not contain the 204 nucleotides set forth as nucleotides 985–1188 of Sequence ID No. 1, nor the 363 nucleotides set forth as nucleotides 2962–3324 of Sequence ID No. 1.

Sequence ID No. 32 is the amino acid sequence of an NMDA receptor subunit encoded by the nucleotide sequence of Sequence ID No. 31.

Sequence ID No. 33 is a nucleotide sequence encoding human NMDA receptor subunit NMDAR1-Δ204-Δ1087. Sequence ID No. 33 differs from Sequence ID No. 1 in that Sequence ID No. 33 does not contain the 204 nucleotides set forth as nucleotides 985–1188 of Sequence ID No. 1, nor the 1087 nucleotides set forth as nucleotides 2962–4048 of Sequence ID No. 1.

Sequence ID No. 34 is the amino acid sequence of an NMDA receptor subunit encoded by the nucleotide sequence of Sequence ID No. 33.

Sequence ID No. 35 is a nucleotide sequence encoding human NMDA receptor subunit NMDAR1-I63-Δ363. Sequence ID No. 35 is the same as Sequence ID No. 23 except Sequence ID No. 35 does not contain the 363 nucleotides set forth as nucleotides 2962–3324 of Sequence ID No. 1.

Sequence ID No. 36 is the amino acid sequence of an NMDA receptor subunit encoded by the nucleotide sequence of Sequence ID No. 35.

Sequence ID No. 37 is a nucleotide sequence encoding human NMDA receptor subunit NMDAR1-I63-Δ1087. Sequence No. 37 is the same as Sequence ID No. 23 except Sequence ID No. 37 does not contain the 1087 nucleotides set forth as nucleotides 2962 –4048 of Sequence ID No. 1.

Sequence ID No. 38 is the amino acid sequence of an NMDA receptor subunit encoded by the nucleotide sequence of Sequence ID No. 37.

Sequence ID No. 39 is a nucleotide sequence encoding human NMDA receptor subunit NMDAR1-I63-Δ204-Δ1087. Sequence ID No. 39 is the same as Sequence ID No. 25, except Sequence ID No. 39 does not contain the 1087 nucleotides set forth as nucleotides 2962–4048 of Sequence ID No. 1.

Sequence ID No. 40 is the amino acid sequence of an NMDA receptor subunit encoded by the nucleotide sequence of Sequence ID No. 39.

Sequence ID No. 41 is a 2026 nucleotide sequence encoded by clone NMDA21, comprising nucleotides 931–2350 and 2402–3307 of Sequence ID No. 5. Thus, Sequence ID No. 41 differs from Sequence ID No. 5 in that it does not contain the 930 5' nucleotides thereof, nor the 51 nucleotides located at position 2351–2401 of Sequence ID No. 5, nor the 1061 3' nucleotides of Sequence ID No. 5.

Sequence ID No. 42 is the amino acid sequence of a portion of an NMDA receptor subunit as encoded by the nucleotide sequence of Sequence ID No. 41.

Sequence ID No. 43 is a 3698 nucleotide sequence encoded by clone NMDA22, comprising nucleotides 367–1300 of Sequence ID No. 5, plus an additional 11 nucleotides (set forth as Sequence ID No. 9), and nucleotides 1301–1959 and 1975–4068 of Sequence ID No. 5. Thus, Sequence ID No. 43 differs from Sequence ID No. 5 by the lack of the 366 5'-most nucleotides, by the insertion of 11 nucleotides between nucleotides 1300 and 1301 of sequence ID No. 5, and further by the lack of the 15 nucleotides of Sequence ID No. 5 from residue 1960 to residue 1974.

Sequence ID No. 43, amino acid residues 1 to 1232, correspond to the nucleotide sequence of Sequence ID No. 43.

Sequence ID No. 44 is a 3243 nucleotide sequence encoded by clone NMDA24, comprising nucleotides 861–1300 of Sequence ID No. 5, plus an additional 11 nucleotides (Sequence ID No. 9), nucleotides 1301–2350 of Sequence ID No. 5, an additional 24 nucleotides (set forth as Sequence ID No. 7) and nucleotides 2351–4068 of Sequence ID No. 5. Thus, Sequence ID No. 44 differs from Sequence ID No. 5 in that it does not contain the 860 5'-most nucleotides thereof, while it does contain an additional 11 nucleotides (Sequence ID No. 9) inserted between nucleotides 1300 and 1301, plus an additional 24 nucleotides (Sequence ID No. 7) inserted between nucleotides 2350 and 2351 of Sequence ID No. 5.

Sequence ID No. 44, amino acid residues 1–1081, is the amino acid sequence corresponding to the nucleotide sequence of Sequence ID No. 44.

Sequence ID No. 45 is a nucleotide sequence encoding human NMDA receptor subunit pCMV-26-ScaI-24, which differs from Sequence ID No. 5 only in the insertion of 24 nucleotides (Sequence ID No. 7) between nucleotides 2350 and 2351 of Sequence ID No. 5.

Sequence ID No. 46 is the amino acid sequence of an NMDA receptor subunit encoded by the nucleotide sequence of Sequence ID No. 45.

Sequence ID No. 47 is a nucleotide sequence encoding human NMDA receptor subunit pCMV-26-ScaI-22, which differs from Sequence ID No. 5 only in the deletion of nucleotides 1960–1974 of Sequence ID No. 5.

Sequence ID No. 48 is the amino acid sequence of an NMDA receptor subunit encoded by the nucleotide sequence of Sequence ID No. 47.

Sequence ID No. 49 is a nucleotide sequence encoding human NMDA receptor subunit pCMV-26-ScaI-21 -NotI-24, which differs from Sequence ID No. 5 only in the deletion of nucleotides 2351–2401 of Sequence ID No. 5.

Sequence ID No. 50 is the amino acid sequence of an NMDA receptor subunit encoded by the nucleotide sequence of Sequence ID No. 49.

Sequence ID No. 51 is a nucleotide sequence encoding human NMDA receptor subunit NMDAR16-Δ15-124. Sequence ID No. 51 is the same as Sequence ID No. 47, except Sequence ID No. 51 further contains the 24 nucleotide insert set forth in Sequence ID No. 7, positioned between nucleotides 2350 and 2351 of Sequence ID No. 5.

Sequence ID No. 52 is the amino acid sequence of an NMDA receptor subunit encoded by the nucleotide sequence of Sequence ID No. 51.

Sequence ID No. 53 is a nucleotide sequence encoding human NMDA receptor subunit NMDAR16-Δ15-Δ51. Sequence ID No. 53 is the same as Sequence ID No. 49, except Sequence ID No. 53 does not contain the 15 nucleotides set forth as nucleotides 1960–1974 of Sequence ID No. 5.

Sequence ID No. 54 is the amino acid sequence of an NMDA receptor subunit encoded by the nucleotide sequence of Sequence ID No. 53.

That which is claimed is:

1. An isolated nucleic acid molecule, that is complementary to a nucleic acid native to a human cell, encoding a human N-methyl-D-aspartate receptor type 1 (NMDAR1) subunit selected from the group consisting of:

(a) a nucleic acid molecule that encodes a NMDAR1 subunit and that comprises the coding portion of the sequence of nucleotides that comprises the sequence set forth in any of Sequence ID Nos. 1, 13, 15, 17, 19, 21, 23, 25, 27, 29, 31, 33, 35, 37, 39, or nucleotides 320–3402 of Sequence ID No. 1;

(b) a nucleic acid molecule that encodes a NMDAR1 subunit and that comprises a sequence of nucleotides, wherein the NMDAR1 subunit is encoded by the sequence of nucleotides comprising any of those set forth in Sequence ID Nos. 1, 13, 15, 17, 19, 21, 23, 25, 27, 29, 31, 33, 35, 37, 39, or nucleotides 320–3402 of Sequence ID No. 1; and, (c) a nucleic acid molecule that is degenerate with respect to the codons in the coding portion of the nucleic acid molecule of (a).

2. The nucleic acid molecule of claim 1, comprising the coding portion of the sequence of nucleotides set forth in any of Sequence ID Nos. 1, 13, 15, 17, 19, 21, 23, 25, 27, 29, 31, 33, 35, 37 or 39.

3. The nucleic acid molecule of claim 1, comprising the coding portion of the sequence of nucleotides set forth in any of Sequence ID Nos. 1, 13, 19, 21, 23, 25 or 27.

4. The nucleic acid molecule of claim 1, comprising the coding portion of the any of the sequences of nucleotides set forth in any of Sequence ID Nos. 1, 13, 19, 21, 23 or 25.

5. The nucleic acid molecule of claim 1, comprising the coding portion of the sequence of nucleotides as set forth in Sequence ID No. 13.

6. The nucleic acid molecule of claim 1, comprising the coding portion of the sequence of nucleotides as set forth in Sequence ID No. 21.

7. The nucleic acid molecule of claim 1, comprising the coding portion of the sequence of nucleotides as set forth in Sequence ID No. 23.

8. The nucleic acid molecule of claim 1, comprising the coding portion of the sequence of nucleotides as set forth in Sequence ID No. 25.

9. The nucleic acid molecule of claim 1, comprising the coding portion of the sequence of nucleotides as set forth in Sequence ID No. 27.

10. The nucleic acid molecule of claim 1, wherein the nucleic acid molecule is mRNA that encodes a NMDAR1 receptor subunit.

11. An amphibian of oöcyte, comprising the mRNA of claim 10.

12. An isolated eukaryotic cell, transfected with the nucleic acid molecule of claim 1.

13. The eukaryotic cell of claim 12, which expresses said nucleic acid molecule.

14. The cell of claim 12, wherein the nucleic acid is mRNA.

15. The cell of claim 12, wherein the nucleic acid is DNA.

16. The cell of claim 13, wherein the nucleic acid is mRNA.

17. The cell of claim 13, wherein the nucleic acid is DNA.

18. The cell of claim 12, comprising a heterologous NMDA receptor.

19. A method for identifying compounds that interact with human N-methyl-D-aspartate (NMDA) receptors, said method comprising employing the cell of claim 18 in a competitive binding assay, wherein the cell is contacted with a test compound and a compound known to interact with NMDA receptors, and selecting the test compound that decreases the interaction of the known compound with NMDA receptors.

20. An isolated protein encoded by the nucleic acid molecule of claim 1.

21. An isolated nucleic acid molecule encoding a human N-methyl-D-aspartate receptor type 1 (NMDAR1) subunit, wherein the NMDAR1 subunit comprises the sequence of amino acids set forth in any of Sequence ID Nos. 2, 14, 16, 18, 20, 22, 24, 26, 28, 30, 32, 34, 36, 38 or 40.

22. An isolated nucleic acid molecule encoding a human N-methyl-D-aspartate receptor type 1 (NMDAR1) subunit, wherein the NMDAR1 subunit comprises the sequence of amino acids set forth in any of Sequence ID Nos. 2, 14, 20, 22, 24, 26 or 28.

23. An isolated nucleic acid molecule, comprising the sequence of nucleotides set forth as nucleotides 262–2961 of Sequence ID No. 1.

24. An isolated nucleic acid molecule, comprising the sequence of nucleotides set forth as nucleotides 320–3402 of Sequence ID No. 1.

25. An isolated nucleic acid molecule, comprising the sequence of nucleotides as set forth in Sequence ID No. 13.

26. An isolated nucleic acid molecule, comprising the sequence of nucleotides as set forth in Sequence ID No. 15.

27. An isolated nucleic acid molecule, comprising the sequence of nucleotides as set forth in Sequence ID No. 17.

28. An isolated nucleic acid molecule that encodes a human N-methyl-D-aspartate receptor type 1 (NMDAR1) subunit, comprising the sequence of amino acids encoded by the nucleotides as set forth in Sequence ID No. 21.

29. An isolated nucleic acid molecule, comprising the sequence of nucleotides as set forth in Sequence ID No. 31.

30. An isolated nucleic acid molecule, comprising the sequence of nucleotides as set forth in Sequence ID No. 33.

31. An isolated nucleic acid molecule, comprising the sequence of nucleotides as set forth in Sequence ID No. 35.

32. An isolated nucleic acid molecule, comprising the sequence of nucleotides as set forth in Sequence ID No. 37.

33. An isolated nucleic acid molecule, comprising the sequence of nucleotides as set forth in Sequence ID No. 39.

34. An isolated nucleic acid molecule that encodes a NMDAR1 receptor subunit, which is encoded by the sequence of nucleotides comprising any of Sequence ID Nos. 19, 21, 29, 25, 27, 31, 33, 35, 37 or 39.

35. An isolated nucleic acid molecule, comprising a sequence of nucleotides that encodes a splice variant of a human N-methyl-D-aspartate receptor type 1 (NMDAR1) subunit, wherein the NMDAR1 subunit is encoded by DNA comprising the coding portion of the sequence of nucleotides set forth in any of Sequence ID Nos. 1, 13, 15, 17, 19, 21, 23, 25, 27, 29, 31, 33, 35, 37 or 39.

36. An isolated nucleic acid molecule of claim 35, that encodes an NMDAR1 receptor subunit and that is encoded by the sequence of nucleotides comprising any of those set forth in Sequence ID Nos. 1, 13, 15, 17, 19, 21, 23, 25, 27, 29, 31, 33, 35, 37 or 39.

37. A method for identifying DNA encoding a human N-methyl-D-aspartate receptor type 1 (NMDAR1) subunit (s), said method comprising:

contacting a human DNA library with a probe comprising the sequence of nucleotides set forth in any of Sequence ID Nos. 1, 13, 15, 17, 19, 21, 23, 25, 27, 29, 31, 33, 35, 37 or 39, wherein said contacting is carried out under high stringency hybridization conditions, and identifying clones that hybridize to the probe, and that encode a human NMDAR1 receptor subunit, wherein high stringency conditions are conditions that permit hybridization of only those nucleic acid sequences that form stable hybrids in 0.018M NaCl at 65° C.

* * * * *

SEQUENCE LISTING (1) GENERAL INFORMATION:

(iii) NUMBER OF SEQUENCES: 54

(2) INFORMATION FOR SEQ ID NO:1:

(i) SEQUENCE CHARACTERISTICS:
(A) LENGTH: 4298 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3078

(xi) SEQUENCE DESCRIPTION: SEQ ID NO:1:

```
CAAGCCGGGC GTTCGGAGCT GTGCCCGGCC CCGCTTCAGC ACCGCGGACA GCGCCGGCCG     60

CGTGGGGCTG AGCGCCGAGC CCCCGCGCAC GCTTCAGCCC CCCTTCCCTC GGCCGACGTC    120

CCGGGACCGC CGCTCCGGGG GAGACGTGGC GTCCGCAGCC CGCGGGGCCG GGCGAGCGCA    180

GGACGGCCCG GAAGCCCCGC GGGGGATGCG CCGAGGGCCC CGCGTTCGCG CCGCGCAGAG    240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185
```

-continued

```
CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG     1155
Asp Ala Val Gly Val Val Ala Gln Ala Val His Glu Leu Leu Glu Lys
        285                 290                 295

GAG AAC ATC ACC GAC CCG CCG CGG GGC TGC GTG GGC AAC ACC AAC ATC     1203
Glu Asn Ile Thr Asp Pro Pro Arg Gly Cys Val Gly Asn Thr Asn Ile
    300                 305                 310

TGG AAG ACC GGG CCG CTC TTC AAG AGA GTG CTG ATG TCT TCC AAG TAT     1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG     1299
Ala Asp Gly Val Thr Gly Arg Val Glu Phe Asn Glu Asp Gly Asp Arg
                335                 340                 345

AAG TTC GCC AAC TAC AGC ATC ATG AAC CTG CAG AAC CGC AAG CTG GTG     1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG     1395
Gln Val Gly Ile Tyr Asn Gly Thr His Val Ile Pro Asn Asp Arg Lys
        365                 370                 375

ATC ATC TGG CCA GGC GGA GAG ACA GAG AAG CCT CGA GGG TAC CAG ATG     1443
Ile Ile Trp Pro Gly Gly Glu Thr Glu Lys Pro Arg Gly Tyr Gln Met
    380                 385                 390

TCC ACC AGA CTG AAG ATT GTG ACG ATC CAC CAG GAG CCC TTC GTG TAC     1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC     1539
Val Lys Pro Thr Leu Ser Asp Gly Thr Cys Lys Glu Glu Phe Thr Val
                415                 420                 425

AAC GGC GAC CCA GTC AAG AAG GTG ATC TGC ACC GGG CCC AAC GAC ACG     1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT     1635
Ser Pro Gly Ser Pro Arg His Thr Val Pro Gln Cys Cys Tyr Gly Phe
        445                 450                 455

TGC ATC GAC CTG CTC ATC AAG CTG GCA CGG ACC ATG AAC TTC ACC TAC     1683
Cys Ile Asp Leu Leu Ile Lys Leu Ala Arg Thr Met Asn Phe Thr Tyr
    460                 465                 470

GAG GTG CAC CTG GTG GCA GAT GGC AAG TTC GGC ACA CAG GAG CGG GTG     1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC     1779
Asn Asn Ser Asn Lys Lys Glu Trp Asn Gly Met Met Gly Glu Leu Leu
```

-continued

```
                495                 500                 505

AGC GGG CAG GCA GAC ATG ATC GTG GCG CCG CTA ACC ATA AAC AAC GAG         1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG         1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC         1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG         1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC         2019
His Val Val Ala Val Met Leu Tyr Leu Leu Asp Arg Phe Ser Pro Phe
                575                 580                 585

GGC CGG TTC AAG GTG AAC AGC GAG GAG GAG GAG GAG GAC GCA CTG ACC         2067
Gly Arg Phe Lys Val Asn Ser Glu Glu Glu Glu Glu Asp Ala Leu Thr
            590                 595                 600

CTG TCC TCG GCC ATG TGG TTC TCC TGG GGC GTC CTG CTC AAC TCC GGC         2115
Leu Ser Ser Ala Met Trp Phe Ser Trp Gly Val Leu Leu Asn Ser Gly
        605                 610                 615

ATC GGG GAA GGC GCC CCC AGA AGC TTC TCA GCG CGC ATC CTG GGC ATG         2163
Ile Gly Glu Gly Ala Pro Arg Ser Phe Ser Ala Arg Ile Leu Gly Met
    620                 625                 630

GTG TGG GCC GGC TTT GCC ATG ATC ATC GTG GCC TCC TAC ACC GCC AAC         2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC         2259
Leu Ala Ala Phe Leu Val Leu Asp Arg Pro Glu Glu Arg Ile Thr Gly
                655                 660                 665

ATC AAC GAC CCT CGG CTG AGG AAC CCC TCG GAC AAG TTT ATC TAC GCC         2307
Ile Asn Asp Pro Arg Leu Arg Asn Pro Ser Asp Lys Phe Ile Tyr Ala
            670                 675                 680

ACG GTG AAG CAG AGC TCC GTG GAT ATC TAC TTC CGG CGC CAG GTG GAG         2355
Thr Val Lys Gln Ser Ser Val Asp Ile Tyr Phe Arg Arg Gln Val Glu
        685                 690                 695

CTG AGC ACC ATG TAC CGG CAT ATG GAG AAG CAC AAC TAC GAG AGT GCG         2403
Leu Ser Thr Met Tyr Arg His Met Glu Lys His Asn Tyr Glu Ser Ala
    700                 705                 710

GCG GAG GCC ATC CAG GCC GTG AGA GAC AAC AAG CTG CAT GCC TTC ATC         2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG         2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG         2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG         2595
Arg Lys Asp Ser Pro Trp Lys Gln Asn Val Ser Leu Ser Ile Leu Lys
        765                 770                 775

TCC CAC GAG AAT GGC TTC ATG GAA GAC CTG GAC AAG ACG TGG GTT CGG         2643
Ser His Glu Asn Gly Phe Met Glu Asp Leu Asp Lys Thr Trp Val Arg
    780                 785                 790

TAT CAG GAA TGT GAC TCG CGC AGC AAC GCC CCT GCG ACC CTT ACT TTT         2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC         2739
```

-continued

```
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT     2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG     2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT     2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC     2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG AGC ACC GGG GGT GGA CGC     2979
Phe Lys Arg Arg Arg Ser Ser Lys Asp Thr Ser Thr Gly Gly Gly Arg
                895                 900                 905

GGT GCT TTG CAA AAC CAA AAA GAC ACA GTG CTG CCG CGA CGC GCT ATT     3027
Gly Ala Leu Gln Asn Gln Lys Asp Thr Val Leu Pro Arg Arg Ala Ile
            910                 915                 920

GAG AGG GAG GAG GGC CAG CTG CAG CTG TGT TCC CGT CAT AGG GAG AGC     3075
Glu Arg Glu Glu Gly Gln Leu Gln Leu Cys Ser Arg His Arg Glu Ser
        925                 930                 935

TGAGACTCCC CGCCCGCCCT CCTCTGCCCC CTCCCCCGCA GACAGACAGA CAGACGGACG   3135

GGACAGCGGC CCGGCCCACG CAGAGCCCCG GAGCACCACG GGGTCGGGGG AGGAGCACCC   3195

CCAGCCTCCC CCAGGCTGCG CCTGCCCGCC CGCCGGTTGG CCGGCTGGCC GGTCCACCCC   3255

GTCCCGGCCC CGCGCGTGCC CCCAGCGTGG GGCTAACGGG CGCCTTGTCT GTGTATTTCT   3315

ATTTTGCAGC AGTACCATCC CACTGATATC ACGGGCCCGC TCAACCTCTC AGATCCCTCG   3375

GTCAGCACCG TGGTGTGAGG CCCCCGGAGG CGCCCACCTG CCCAGTTAGC CCGGCCAAGG   3435

ACACTGATGG GTCCTGCTGC TCGGGAAGGC CTGAGGGAAG CCCACCCGCC CCAGAGACTG   3495

CCCACCCTGG GCCTCCCGTC CGTCCGCCCG CCCACCCCGC TGCCTGGCGG GCAGCCCCTG   3555

CTGGACCAAG GTGCGGACCG GAGCGGCTGA GGACGGGGCA GAGCTGAGTC GGCTGGGCAG   3615

GGCCGCAGGG CGCTCCGGCA GAGGCAGGCC CCTGGGGTCT CTGAGCAGTG GGGAGCGGGG   3675

GCTAACTGCC CCCAGGCGGA GGGGCTTGGA GCAGAGACGG CAGCCCCATC CTTCCCGCAG   3735

CACCAGCCTG AGCCACAGTG GGGCCCATGG CCCCAGCTGG CTGGGTCGCC CCTCCTCGGG   3795

CGCCTGCGCT CCTCTGCAGC CTGAGCTCCA CCCTCCCCTC TTCTTGCGGC ACCGCCCACC   3855

AAACACCCCG TCTGCCCCTT GACGCCACAC GCCGGGGCTG GCGCTGCCCT CCCCCACGGC   3915

CGTCCCTGAC TTCCCAGCTG GCAGCGCCTC CCGCCGCCTC GGGCCGCCTC CTCCAGAATC   3975

GAGAGGGCTG AGCCCCTCCT CTCCTCGTCC GGCCTGCAGC ACAGAAGGGG GCCTCCCCGG   4035

GGGTCCCCGG ACGCTGGCTC GGGACTGTCT TCAACCCTGC CCTGCACCTT GGGCACGGGA   4095

GAGCGCCACC CGCCCGCCCC CGCCCTCGCT CCGGGTGCGT GACCGGCCCG CCACCTTGTA   4155

CAGAACCAGC ACTCCCAGGG CCCGAGCGCG TGCCTTCCCC GTGCGCAGCC GCGCTCTGCC   4215

CCTCCGTCCC CAGGGTGCAG GCGCGCACCG CCCAACCCCC ACCTCCCGGT GTATGCAGTG   4275

GTGATGCCTA AAGGAATGTC ACG                                           4298
```

(2) INFORMATION FOR SEQ ID NO:2:

(i) SEQUENCE CHARACTERISTICS:
(A) LENGTH: 938 amino acids
(B) TYPE: amino acid

-continued (D) TOPOLOGY: linear (ii) MOLECULE TYPE: protein (xi) SEQUENCE DESCRIPTION: SEQ ID NO:2:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
```

-continued

```
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815
```

-continued

```
Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Ser Thr Gly Gly Gly Arg Gly Ala Leu Gln Asn Gln
            900                 905                 910

Lys Asp Thr Val Leu Pro Arg Arg Ala Ile Glu Arg Glu Glu Gly Gln
        915                 920                 925

Leu Gln Leu Cys Ser Arg His Arg Glu Ser
    930                 935
```

(2) INFORMATION FOR SEQ ID NO:3:

(i) SEQUENCE CHARACTERISTICS:
(A) LENGTH: 63 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 1..63

(xi) SEQUENCE DESCRIPTION: SEQ ID NO:3:

```
AGT AAA AAA AGG AAC TAT GAA AAC CTC GAC CAA CTG TCC TAT GAC AAC       48
Ser Lys Lys Arg Asn Tyr Glu Asn Leu Asp Gln Leu Ser Tyr Asp Asn
  1               5                  10                  15

AAG CGC GGA CCC AAG                                                   63
Lys Arg Gly Pro Lys
             20
```

(2) INFORMATION FOR SEQ ID NO:4:

(i) SEQUENCE CHARACTERISTICS:
(A) LENGTH: 21 amino acids
(B) TYPE: amino acid
(D) TOPOLOGY: linear (ii) MOLECULE TYPE: protein (xi) SEQUENCE DESCRIPTION: SEQ ID NO:4:

```
Ser Lys Lys Arg Asn Tyr Glu Asn Leu Asp Gln Leu Ser Tyr Asp Asn
  1               5                  10                  15

Lys Arg Gly Pro Lys
             20
```

(2) INFORMATION FOR SEQ ID NO:5:

(i) SEQUENCE CHARACTERISTICS:
(A) LENGTH: 4068 base pairs
(B) TYPE: nucleic acid
(C) STRANDEDNESS: both
(D) TOPOLOGY: both (ii) MOLECULE TYPE: cDNA -continued (ix) FEATURE:
(A) NAME/KEY: CDS
(B) LOCATION: 189..3899

(xi) SEQUENCE DESCRIPTION: SEQ ID NO:5:

```
CCCTTAATAA GATTTGCTAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC     230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG      278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC      326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC      374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC      422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC      758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA      806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC      854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC      902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG      950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC      998
Pro Asn Leu Ala Leu Gly Ser Thr Asp Ala Pro Pro Ala Thr Phe Pro
255                 260                 265                 270
```

-continued

GTG GGC CTC ATC AGC GTC GTC ACC GAG AGC TGG CGC CTC AGC CTG CGC 1046
Val Gly Leu Ile Ser Val Val Thr Glu Ser Trp Arg Leu Ser Leu Arg
275 280 285

CAG AAG GTG CGC GAC GGC GTG GCC ATT CTG GCC CTG GGC GCC CAC AGC 1094
Gln Lys Val Arg Asp Gly Val Ala Ile Leu Ala Leu Gly Ala His Ser
290 295 300

TAC TGG CGC CAG CAT GGA ACC CTG CCA GCC CCG GCC GGG GAC TGC CGT 1142
Tyr Trp Arg Gln His Gly Thr Leu Pro Ala Pro Ala Gly Asp Cys Arg
305 310 315

GTT CAC CCT GGG CCC GTC AGC CCT GCC CGG GAG GCC TTC TAC AGG CAC 1190
Val His Pro Gly Pro Val Ser Pro Ala Arg Glu Ala Phe Tyr Arg His
320 325 330

CTA CTG AAT GTC ACC TGG GAG GGC CGA GAC TTC TCC TTC AGC CCT GGT 1238
Leu Leu Asn Val Thr Trp Glu Gly Arg Asp Phe Ser Phe Ser Pro Gly
335 340 345 350

GGG TAC CTG GTC CAG CCC ACC ATG GTG GTG ATC GCC CTC AAC CGG CAC 1286
Gly Tyr Leu Val Gln Pro Thr Met Val Val Ile Ala Leu Asn Arg His
355 360 365

CGC CTC TGG GAG ATG GTG GGG CGC TGG GAG CAT GGC GTC CTA TAC ATG 1334
Arg Leu Trp Glu Met Val Gly Arg Trp Glu His Gly Val Leu Tyr Met
370 375 380

AAG TAC CCC GTG TGG CCT CGC TAC AGT GCC TCT CTG CAG CCT GTG GTG 1382
Lys Tyr Pro Val Trp Pro Arg Tyr Ser Ala Ser Leu Gln Pro Val Val
385 390 395

GAC AGT CGG CAC CTG ACG GTG GCC ACG CTG GAA GAG CGG CCC TTT GTC 1430
Asp Ser Arg His Leu Thr Val Ala Thr Leu Glu Glu Arg Pro Phe Val
400 405 410

ATC GTG GAG AGC CCT GAC CCT GGC ACA GGA GGC TGT GTC CCC AAC ACC 1478
Ile Val Glu Ser Pro Asp Pro Gly Thr Gly Gly Cys Val Pro Asn Thr
415 420 425 430

GTG CCC TGC CGC AGG CAG AGC AAC CAC ACC TTC AGC AGC GGG GAC GTG 1526
Val Pro Cys Arg Arg Gln Ser Asn His Thr Phe Ser Ser Gly Asp Val
435 440 445

GCC CCC TAC ACC AAG CTC TGC TGT AAG GGA TTC TGC ATC GAC ATC CTC 1574
Ala Pro Tyr Thr Lys Leu Cys Cys Lys Gly Phe Cys Ile Asp Ile Leu
450 455 460

AAG AAG CTG GCC AGA GTG GTC AAA TTC TCC TAC GAC CTG TAC CTG GTG 1622
Lys Lys Leu Ala Arg Val Val Lys Phe Ser Tyr Asp Leu Tyr Leu Val
465 470 475

ACC AAC GGC AAG CAT GGC AAG CGG GTG CGC GGC GTA TGG AAC GGC ATG 1670
Thr Asn Gly Lys His Gly Lys Arg Val Arg Gly Val Trp Asn Gly Met
480 485 490

ATT GGG GAG GTG TAC TAC AAG CGG GCA GAC ATG GCC ATC GGC TCC CTC 1718
Ile Gly Glu Val Tyr Tyr Lys Arg Ala Asp Met Ala Ile Gly Ser Leu
495 500 505 510

ACC ATC AAT GAG GAA CGC TCC GAG ATC GTA GAC TTC TCT GTA CCC TTT 1766
Thr Ile Asn Glu Glu Arg Ser Glu Ile Val Asp Phe Ser Val Pro Phe
515 520 525

GTG GAG ACG GGC ATC AGT GTG ATG GTG GCT CGC AGC AAT GGC ACC GTC 1814
Val Glu Thr Gly Ile Ser Val Met Val Ala Arg Ser Asn Gly Thr Val
530 535 540

TCC CCC TCG GCC TTC TTG GAG CCA TAT AGC CCT GCA GTG TGG GTG ATG 1862
Ser Pro Ser Ala Phe Leu Glu Pro Tyr Ser Pro Ala Val Trp Val Met
545 550 555

ATG TTT GTC ATG TGC CTC ACT GTG GTG GCC ATC ACC GTC TTC ATG TTC 1910
Met Phe Val Met Cys Leu Thr Val Val Ala Ile Thr Val Phe Met Phe
560 565 570

GAG TAC TTC AGC CCT GTC AGC TAC AAC CAG AAC CTC ACC AGA GGC AAG 1958
Glu Tyr Phe Ser Pro Val Ser Tyr Asn Gln Asn Leu Thr Arg Gly Lys

-continued

```
575                 580                 585                 590

AAG TCC GGG GGC CCA GCT TTC ACT ATC GGC AAG TCC GTG TGG CTG CTG      2006
Lys Ser Gly Gly Pro Ala Phe Thr Ile Gly Lys Ser Val Trp Leu Leu
                595                 600                 605

TGG GCG CTG GTC TTC AAC AAC TCA GTG CCC ATC GAG AAC CCG CGG GGC      2054
Trp Ala Leu Val Phe Asn Asn Ser Val Pro Ile Glu Asn Pro Arg Gly
            610                 615                 620

ACC ACC AGC AAG ATC ATG GTT CTG GTC TGG GCC TTC TTT GCT GTC ATC      2102
Thr Thr Ser Lys Ile Met Val Leu Val Trp Ala Phe Phe Ala Val Ile
        625                 630                 635

TTC CTC GCC AGA TAC ACG GCC AAC CTG GCC GCC TTC ATG ATC CAA GAG      2150
Phe Leu Ala Arg Tyr Thr Ala Asn Leu Ala Ala Phe Met Ile Gln Glu
    640                 645                 650

CAA TAC ATC GAC ACT GTG TCG GGC CTC AGT GAC AAG AAG TTT CAG CGG      2198
Gln Tyr Ile Asp Thr Val Ser Gly Leu Ser Asp Lys Lys Phe Gln Arg
655                 660                 665                 670

CCT CAA GAT CAG TAC CCA CCT TTC CGC TTC GGC ACG GTG CCC AAC GGC      2246
Pro Gln Asp Gln Tyr Pro Pro Phe Arg Phe Gly Thr Val Pro Asn Gly
                675                 680                 685

AGC ACG GAG CGG AAC ATC CGC AGT AAC TAC CGT GAC ATG CAC ACC CAC      2294
Ser Thr Glu Arg Asn Ile Arg Ser Asn Tyr Arg Asp Met His Thr His
            690                 695                 700

ATG GTC AAG TTC AAC CAG CGC TCG GTG GAG GAC GCG CTC ACC AGC CTC      2342
Met Val Lys Phe Asn Gln Arg Ser Val Glu Asp Ala Leu Thr Ser Leu
        705                 710                 715

AAG ATG GGG AAG CTG GAT GCC TTC ATC TAT GAT GCT GCT GTC CTC AAC      2390
Lys Met Gly Lys Leu Asp Ala Phe Ile Tyr Asp Ala Ala Val Leu Asn
    720                 725                 730

TAC ATG GCA GGC AAG GAC GAG GGC TGC AAG CTG GTC ACC ATT GGG TCT      2438
Tyr Met Ala Gly Lys Asp Glu Gly Cys Lys Leu Val Thr Ile Gly Ser
735                 740                 745                 750

GGC AAG GTC TTT GCT ACC ACT GGC TAC GGC ATC GCC ATG CAG AAG GAC      2486
Gly Lys Val Phe Ala Thr Thr Gly Tyr Gly Ile Ala Met Gln Lys Asp
                755                 760                 765

TCC CAC TGG AAG CGG GCC ATA GAC CTG GCG CTC TTG CAG TTC CTG GGG      2534
Ser His Trp Lys Arg Ala Ile Asp Leu Ala Leu Leu Gln Phe Leu Gly
            770                 775                 780

GAC GGA GAG ACA CAG AAA CTG GAG ACA GTG TGG CTC TCA GGG ATC TGC      2582
Asp Gly Glu Thr Gln Lys Leu Glu Thr Val Trp Leu Ser Gly Ile Cys
        785                 790                 795

CAG AAT GAG AAG AAC GAG GTG ATG AGC AGC AAG CTG GAC ATC GAC AAC      2630
Gln Asn Glu Lys Asn Glu Val Met Ser Ser Lys Leu Asp Ile Asp Asn
    800                 805                 810

ATG GGA GGC GTC TTC TAC ATG CTG CTG GTG GCC ATG GGG CTG GCC CTG      2678
Met Gly Gly Val Phe Tyr Met Leu Leu Val Ala Met Gly Leu Ala Leu
815                 820                 825                 830

CTG GTC TTC GCC TGG GAG CAC CTG GTC TAC TGG AAG CTG CGC CAC TCG      2726
Leu Val Phe Ala Trp Glu His Leu Val Tyr Trp Lys Leu Arg His Ser
                835                 840                 845

GTG CCC AAC TCA TCC CAG CTG GAC TTC CTG CTG GCT TTC AGC AGG GGC      2774
Val Pro Asn Ser Ser Gln Leu Asp Phe Leu Leu Ala Phe Ser Arg Gly
            850                 855                 860

ATC TAC AGC TGC TTC AGC GGG GTG CAG AGC CTC GCC AGC CCA CCG CGG      2822
Ile Tyr Ser Cys Phe Ser Gly Val Gln Ser Leu Ala Ser Pro Pro Arg
        865                 870                 875

CAG GCC AGC CCG GAC CTC ACG GCC AGC TCG GCC CAG GCC AGC GTG CTC      2870
Gln Ala Ser Pro Asp Leu Thr Ala Ser Ser Ala Gln Ala Ser Val Leu
    880                 885                 890

AAG ATT CTG CAG GCA GCC CGC GAC ATG GTG ACC ACG GCG GGC GTA AGC      2918
```

-continued

```
Lys Ile Leu Gln Ala Ala Arg Asp Met Val Thr Thr Ala Gly Val Ser
895                 900                 905                 910

AAC TCC CTG GAC CGC GCC ACT CGC ACC ATC GAG AAT TGG GGT GGC GGC      2966
Asn Ser Leu Asp Arg Ala Thr Arg Thr Ile Glu Asn Trp Gly Gly Gly
                915                 920                 925

CGC CGT GCG CCC CCA CCG TCC CCC TGC CCG ACC CCG CGG TCT GGC CCC      3014
Arg Arg Ala Pro Pro Pro Ser Pro Cys Pro Thr Pro Arg Ser Gly Pro
            930                 935                 940

AGC CCA TGC CTG CCC ACC CCC GAC CCG CCC CCA GAG CCG AGC CCC ACG      3062
Ser Pro Cys Leu Pro Thr Pro Asp Pro Pro Pro Glu Pro Ser Pro Thr
        945                 950                 955

GGC TGG GGA CCG CCA GAC GGG GGT CGC GCG GCG CTT GTG CGC AGG GCT      3110
Gly Trp Gly Pro Pro Asp Gly Gly Arg Ala Ala Leu Val Arg Arg Ala
    960                 965                 970

CCG CAG CCC CCG GGC CGC CCC CCG ACG CCG GGG CCG CCC CTG TCC GAC      3158
Pro Gln Pro Pro Gly Arg Pro Pro Thr Pro Gly Pro Pro Leu Ser Asp
975                 980                 985                 990

GTC TCC CGA GTG TCG CGC CGC CCA GCC TGG GAG GCG CGG TGG CCG GTG      3206
Val Ser Arg Val Ser Arg Arg Pro Ala Trp Glu Ala Arg Trp Pro Val
                995                 1000                1005

CGG ACC GGG CAC TGC GGG AGG CAC CTC TCG GCC TCC GAG CGG CCC CTG      3254
Arg Thr Gly His Cys Gly Arg His Leu Ser Ala Ser Glu Arg Pro Leu
            1010                1015                1020

TCG CCC GCG CGC TGT CAC TAC AGC TCC TTT CCT CGA GCC GAC CGA TCC      3302
Ser Pro Ala Arg Cys His Tyr Ser Ser Phe Pro Arg Ala Asp Arg Ser
        1025                1030                1035

GGC CGC CCC TTC CTC CCG CTC TTC CCG GAG CCC CCG GAG CTG GAG GAC      3350
Gly Arg Pro Phe Leu Pro Leu Phe Pro Glu Pro Pro Glu Leu Glu Asp
    1040                1045                1050

CTG CCG CTG CTC GGT CCG GAG CAG CTG GCC CGG CGG GAG GCC CTG CTG      3398
Leu Pro Leu Leu Gly Pro Glu Gln Leu Ala Arg Arg Glu Ala Leu Leu
1055                1060                1065                1070

AAC GCG GCC TGG GCC CGG GGC TCG CGC CCG AGT CAC GCT TCC CTG CCC      3446
Asn Ala Ala Trp Ala Arg Gly Ser Arg Pro Ser His Ala Ser Leu Pro
                1075                1080                1085

AGC TCC GTG GCC GAG GCC TTC GCT CGG CCC AGC TCG CTG CCC GCT GGG      3494
Ser Ser Val Ala Glu Ala Phe Ala Arg Pro Ser Ser Leu Pro Ala Gly
            1090                1095                1100

TGC ACC GGC CCC GCC TGC GCC CGC CCC GAC GGC CAC TCG GCC TGC AGG      3542
Cys Thr Gly Pro Ala Cys Ala Arg Pro Asp Gly His Ser Ala Cys Arg
        1105                1110                1115

CGC TTG GCG CAG GCG CAG TCG ATG TGC TTG CCG ATC TAC CGG GAG GCC      3590
Arg Leu Ala Gln Ala Gln Ser Met Cys Leu Pro Ile Tyr Arg Glu Ala
    1120                1125                1130

TGC CAG GAG GGC GAG CAG GCA GGG GCC CCC GCC TGG CAG CAC AGA CAG      3638
Cys Gln Glu Gly Glu Gln Ala Gly Ala Pro Ala Trp Gln His Arg Gln
1135                1140                1145                1150

CAC GTC TGC CTG CAC GCC CAC GCC CAC CTG CCA TTG TGC TGG GGG GCT      3686
His Val Cys Leu His Ala His Ala His Leu Pro Leu Cys Trp Gly Ala
                1155                1160                1165

GTC TGT CCT CAC CTT CCA CCC TGT GAC AGC CAC GGC TCC TGG CTC TCC      3734
Val Cys Pro His Leu Pro Pro Cys Asp Ser His Gly Ser Trp Leu Ser
            1170                1175                1180

GGC GCC TGG GGG CCT CTG GGG CAC AGC GGC AGG ACT CTG GGG CTG GGC      3782
Gly Ala Trp Gly Pro Leu Gly His Ser Gly Arg Thr Leu Gly Leu Gly
        1185                1190                1195

ACA GGC TAC AGA GAC AGT GGG GGA CTG GAC GAG ATC AGC AGT GTA GCC      3830
Thr Gly Tyr Arg Asp Ser Gly Gly Leu Asp Glu Ile Ser Ser Val Ala
    1200                1205                1210
```

-continued

```
CGT GGG ACG CAA GGC TTC CCG GGA CCC TGC ACC TGG AGA CGG ATC TCC      3878
Arg Gly Thr Gln Gly Phe Pro Gly Pro Cys Thr Trp Arg Arg Ile Ser
1215                1220                1225                1230

AGT CTG GAG TCA GAA GTG TGAGTTATCA GCCACTCAGG CTCCGAGCCA             3926
Ser Leu Glu Ser Glu Val
               1235

GCTGGATTCT CTGCCTGCCA CTGTCAGGGT TAAGCGGCAG GCAGGATTGG CCCTTCTCTG   3986

GCTTCTACCA TGAAATCCTG GCCATGGCAC CCCAGTGACA GATGATGTCT TCCATGGTCA   4046

TCAGTGACCT CAGCTAGCCT CA                                             4068
```

(2) INFORMATION FOR SEQ ID NO:6:

(i) SEQUENCE CHARACTERISTICS:
(A) LENGTH: 1236 amino acids
(B) TYPE: amino acid
(D) TOPOLOGY: linear (ii) MOLECULE TYPE: protein (xi) SEQUENCE DESCRIPTION: SEQ ID NO:6:

```
Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
             20                  25                  30

Ala Val Val Phe Ser Ser Ser Gly Pro Pro Gln Ala Gln Phe Arg Val
         35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285
```

-continued

```
Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
    370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
    450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Lys Ser
            580                 585                 590

Gly Gly Pro Ala Phe Thr Ile Gly Lys Ser Val Trp Leu Leu Trp Ala
        595                 600                 605

Leu Val Phe Asn Asn Ser Val Pro Ile Glu Asn Pro Arg Gly Thr Thr
    610                 615                 620

Ser Lys Ile Met Val Leu Val Trp Ala Phe Phe Ala Val Ile Phe Leu
625                 630                 635                 640

Ala Arg Tyr Thr Ala Asn Leu Ala Ala Phe Met Ile Gln Glu Gln Tyr
                645                 650                 655

Ile Asp Thr Val Ser Gly Leu Ser Asp Lys Lys Phe Gln Arg Pro Gln
            660                 665                 670

Asp Gln Tyr Pro Pro Phe Arg Phe Gly Thr Val Pro Asn Gly Ser Thr
        675                 680                 685

Glu Arg Asn Ile Arg Ser Asn Tyr Arg Asp Met His Thr His Met Val
    690                 695                 700
```

-continued

```
Lys Phe Asn Gln Arg Ser Val Glu Asp Ala Leu Thr Ser Leu Lys Met
705                 710                 715                 720

Gly Lys Leu Asp Ala Phe Ile Tyr Asp Ala Ala Val Leu Asn Tyr Met
                725                 730                 735

Ala Gly Lys Asp Glu Gly Cys Lys Leu Val Thr Ile Gly Ser Gly Lys
            740                 745                 750

Val Phe Ala Thr Thr Gly Tyr Gly Ile Ala Met Gln Lys Asp Ser His
        755                 760                 765

Trp Lys Arg Ala Ile Asp Leu Ala Leu Leu Gln Phe Leu Gly Asp Gly
    770                 775                 780

Glu Thr Gln Lys Leu Glu Thr Val Trp Leu Ser Gly Ile Cys Gln Asn
785                 790                 795                 800

Glu Lys Asn Glu Val Met Ser Ser Lys Leu Asp Ile Asp Asn Met Gly
                805                 810                 815

Gly Val Phe Tyr Met Leu Leu Val Ala Met Gly Leu Ala Leu Leu Val
            820                 825                 830

Phe Ala Trp Glu His Leu Val Tyr Trp Lys Leu Arg His Ser Val Pro
        835                 840                 845

Asn Ser Ser Gln Leu Asp Phe Leu Leu Ala Phe Ser Arg Gly Ile Tyr
    850                 855                 860

Ser Cys Phe Ser Gly Val Gln Ser Leu Ala Ser Pro Pro Arg Gln Ala
865                 870                 875                 880

Ser Pro Asp Leu Thr Ala Ser Ser Ala Gln Ala Ser Val Leu Lys Ile
                885                 890                 895

Leu Gln Ala Ala Arg Asp Met Val Thr Thr Ala Gly Val Ser Asn Ser
            900                 905                 910

Leu Asp Arg Ala Thr Arg Thr Ile Glu Asn Trp Gly Gly Gly Arg Arg
        915                 920                 925

Ala Pro Pro Pro Ser Pro Cys Pro Thr Pro Arg Ser Gly Pro Ser Pro
    930                 935                 940

Cys Leu Pro Thr Pro Asp Pro Pro Pro Glu Pro Ser Pro Thr Gly Trp
945                 950                 955                 960

Gly Pro Pro Asp Gly Gly Arg Ala Ala Leu Val Arg Arg Ala Pro Gln
                965                 970                 975

Pro Pro Gly Arg Pro Pro Thr Pro Gly Pro Pro Leu Ser Asp Val Ser
            980                 985                 990

Arg Val Ser Arg Arg Pro Ala Trp Glu Ala Arg Trp Pro Val Arg Thr
        995                 1000                1005

Gly His Cys Gly Arg His Leu Ser Ala Ser Glu Arg Pro Leu Ser Pro
    1010                1015                1020

Ala Arg Cys His Tyr Ser Ser Phe Pro Arg Ala Asp Arg Ser Gly Arg
1025                1030                1035                1040

Pro Phe Leu Pro Leu Phe Pro Glu Pro Pro Glu Leu Glu Asp Leu Pro
                1045                1050                1055

Leu Leu Gly Pro Glu Gln Leu Ala Arg Arg Glu Ala Leu Leu Asn Ala
            1060                1065                1070

Ala Trp Ala Arg Gly Ser Arg Pro Ser His Ala Ser Leu Pro Ser Ser
        1075                1080                1085

Val Ala Glu Ala Phe Ala Arg Pro Ser Ser Leu Pro Ala Gly Cys Thr
    1090                1095                1100

Gly Pro Ala Cys Ala Arg Pro Asp Gly His Ser Ala Cys Arg Arg Leu
1105                1110                1115                1120

Ala Gln Ala Gln Ser Met Cys Leu Pro Ile Tyr Arg Glu Ala Cys Gln
```

-continued

```
                1125                1130                1135

Glu Gly Glu Gln Ala Gly Ala Pro Ala Trp Gln His Arg Gln His Val
            1140                1145                1150

Cys Leu His Ala His Ala His Leu Pro Leu Cys Trp Gly Ala Val Cys
        1155                1160                1165

Pro His Leu Pro Pro Cys Asp Ser His Gly Ser Trp Leu Ser Gly Ala
    1170                1175                1180

Trp Gly Pro Leu Gly His Ser Gly Arg Thr Leu Gly Leu Gly Thr Gly
1185                1190                1195                1200

Tyr Arg Asp Ser Gly Gly Leu Asp Glu Ile Ser Ser Val Ala Arg Gly
                1205                1210                1215

Thr Gln Gly Phe Pro Gly Pro Cys Thr Trp Arg Arg Ile Ser Ser Leu
            1220                1225                1230

Glu Ser Glu Val
        1235
```

(2) INFORMATION FOR SEQ ID NO:7:

(i) SEQUENCE CHARACTERISTICS:
(A) LENGTH: 24 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 2..22

(xi) SEQUENCE DESCRIPTION: SEQ ID NO:7:

```
C TCT GAG GCT CAG CCT GTC CCC AG                                  24
  Ser Glu Ala Gln Pro Val Pro
    1               5
```

(2) INFORMATION FOR SEQ ID NO:8:

(i) SEQUENCE CHARACTERISTICS:
(A) LENGTH: 7 amino acids
(B) TYPE: amino acid
(D) TOPOLOGY: linear (ii) MOLECULE TYPE: protein (xi) SEQUENCE DESCRIPTION: SEQ ID NO:8:

```
Ser Glu Ala Gln Pro Val Pro
  1               5
```

(2) INFORMATION FOR SEQ ID NO:9:

(i) SEQUENCE CHARACTERISTICS:
(A) LENGTH: 11 base pairs
(B) TYPE: nucleic acid
(C) STRANDEDNESS: unknown
(D) TOPOLOGY: unknown (ii) MOLECULE TYPE: cDNA (xi) SEQUENCE DESCRIPTION: SEQ ID NO:9:

```
AGAAGGGGGT G                                                      11
```

(2) INFORMATION FOR SEQ ID NO:10:

(i) SEQUENCE CHARACTERISTICS:
(A) LENGTH: 3545 base pairs

-continued (B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:10:

ATCATGGGAC CGGGTGAGCG CTGAGAATCG CGGCCGCAGC CATCAGCCCT GGAGATGACC 60

AGGAGCGGCC ACTGCTGAGA ACTATGTGGA GAGAGGCTGC GAGCCCTGCT GMAGAGCCTC 120

CGGTTGGGAT AGCCGCCCCC CGTGGGGGGG ATGCGGACAG CGCGGRACAG CCAGGGGAGC 180

GCGCTGGGGC CGCAGAATGC GGGAACCCGC TAAACCCGGT GGCTGCTGAG GCGGCCGAGA 240

TGCTCGTGCG CGCAGCGCGC CCCACTGCAT CCTCGACCTT CTCGGGTTAC AGVGACCGCC 300

AGTGGCGACT ATGGGCAGAG TGGGCTATTG GACCCTGCTG GTGCTGCCGG CCCTTCTGGT 360

CTGGCGCGGT CCGGCGCCGA GCGCGGCGGC GGAGAAGGGT CCCCCCGCGC TAAATATTGC 420

GGTGATGCTG GGTCACAGCC ACGACGTGAC AGAGCGCGAA CTTCGAACAC TGTGGGGCCC 480

CGAGAAGGCG GCGGGGCTGC CCCTGGACGT GAACGTGGTA GCTCTGCTGA TGAACCGCAC 540

CGACCCCAAG AGCCTCATCA CGCACGTGTG CGACCTCATG TCCGGGGGAC GCATCCACGG 600

CCTCGTGCTT GGGGACGACA CGGACCAGGA GCCCGTAACC CAGATGCTGG ATTTTATCTC 660

CTCCCACACC TTCGTCCCCA TCTTGGGCAW TCATGGGGGC GCATCTATGA TCATGGCTGA 720

CAAGGAACCG ACGTCTACCT TCTTCCAGTT TGGAGCGTCC ATCCAGCAGC AAACCACGGT 780

CATGCTGAAG ATCATGCAGG ATTATGACTG GCATGTCTTC TCCCTGGTGA CCACTATCTT 840

CCCTGGCTAC AGGGAATTCA TCAGCTTCGT CAAGACCACA GTGGACAACA GCTTTGTGGG 900

CTGGGACATG CAGAATGTGA TCACACTGGA CACTTCCTTG GAGGATGCAA AGACACAAGT 960

CCAGCTGAAG AAGATCCACT CTTCTGTCAT CTTGCTCTAC TGTCCCAAAG ACGAGGCTGT 1020

TCTCATTCTG AGTGAGGCCC GCTCCCTGGG CCTCACCGGG TATGATTTCT TCTGGATTGC 1080

CCCCAGCTTG GTCTCTGGGA ACACGGAGCT CATCCCAAAA GAGTTTCCAT CGGGACTCAT 1140

TTCTGTCTCC TACGATGACT GGGACTACAG CCTGGAGGCG AAAGTGAGGG ACGGCATTGG 1200

CATCCTAACC ACCGCTGCAT CTTCTATGCT GGAGAAGTTC TCCTACATCC CCGAGGCCAA 1260

GGCCAGCTGC TACGGGCAGA TGGAGAGGCC AGAGGTCCCG ATGCACACCT TGCACCCATT 1320

TATGGTCAAT GTTACATGGG ATGGCAAAGA CTTATCCTTC ACTGAGGAAG GCTACCAGGT 1380

GCACCCCAGG CTGGTGGTGA TTGTGCTGAA CAAAGACCGG GAATGGGAAA AGGTGGGCAA 1440

GTGGGAGAAC CATACGCTGA GCCTGAGGCA CGCCGTGTGG CCCAGGTACA AGTCCTTCTC 1500

CGACTGTGAG CCGGATGACA ACCATCTCAG CATCGTCACC CTGGGGGAGG CCCCATTCGT 1560

CATCGCGGAA GACATAGACC CCCTGACCGA GACGTGTGTG AGGAACACCG TGCCATGTCG 1620

GAAGTTCGTC AAAATCAACA ATTCACCCAA TGAGGGGATG AATGTGAAGA AATGCTGCAA 1680

GGGGTTCTGC ATTGATATTC TGAAGAAGCT TTCCAGAACT GTGAAGTTTA CTTACGACCT 1740

CTATCTGGTG ACCAATGGGA AGCATGGCAA GAAAGTTAAC AATGTGTGGA ATGGAATGAT 1800

CGGTGAAGTG GTCTATCAAC GGGCAGTCAT GGCAGTTGGC TCGCTCACCA TCAATGAGGA 1860

ACGTTCTGAA GTGGTGGACT TCTCTGTGCC CTTTGTGGAA ACGGGAATCA GTGTCATGGT 1920

TTCAAGAAGT AATGGCACCG TCTCACCTTC TGCTTTTCTA GAACCATTCA GCGCCTCTGT 1980

CTGGGTGATG ATGTTTGTGA TGCTGCTCAT TGTTTCTGCC ATAGCTGTTT GGGTCTTGGA 2040

TTACTCCAGC CCTGTTGGAT ACRACAGAAA CTTAGCCAAA GGGAAAGCAC CCCATGGGCC 2100

TTCTTTTACA ATTGGAAAAG CTATATGGCT TCTTTGGGGC CTGGTGTTCA ATAACTCCGT 2160

-continued

```
GCCTGTCCAG AATCCTAAAG GGACCACCAG CAAGATCATG GTATCTGTAT GGGCCTCCTC   2220
CGCTGTCATA TTCCTGGCTA GCTACACAGC CAATCTGGCT GCCTYCATGA TCCAAGAGGA   2280
ATTTGTGGAC CAAGTGACCG GCCTCAGTGA CYMMAAGTTT CAGAGACCTC ATGACTATTC   2340
CCCACCTTTT CGATTTGGGA CAGTGCCTAA TGGAAGCACG GAGAGAAACA TTCGGAATAA   2400
CTATCCCTAC ATGCATCAGT ACATGACCAA ATTTAATCAG AAAGGAGTGG AGGACGCCTT   2460
GGTCAGCCTG AAAACGGGGA AGCTGGACGC TTTCATCTAC GATGCCGCAG TCTTGAATTA   2520
CAAGGCTGGG AGGGATGAAG GCTGCAAGCT GGTGACCATC GGGAGTGGGT ACATCTTTGC   2580
CACCACCGGT TATGGAATTG CCCTCCAGAA AGGCTCTCCT TGGAAGAGGC AGATCGACCT   2640
GGCCTTGCTT CAGTTTGTGG GTGATGGTGA GATGGAGGAG CTGGAGACCC TGTGGCTCAC   2700
TGGGATCTGC CACAACGAGA AGAACGAGGT GATGAGCAGC CAGCTGGACA TTGACAACAT   2760
GGCGGGCGTA TTCTACATGC TGGCTGCCGC CATGGCCCTT AGCCTCATCA CCTTCATCTG   2820
GGAGCACCTC TTCTACTGGA AGCTGCGCTT CTGTTTCACG GGCGTGTGCT CCGACCGGCC   2880
TGGGTTGCTC TTCTCCATCA GCAGGGGCAT CTACAGCTGC ATTCATGGAG TGCACATTGG   2940
AGAAAAGGAG AAGTCTCCAG ACTTCAATCT GACGGGATCC CAGAGCAACA TGTTAAAACT   3000
CCTCCGGTCA GCCCAAAACA TTTCCAGCAT GTCCAACATG GACTCCTCAA GAATGGACTC   3060
ACCCCAAAGA GCTGCTGACT TCATCCCAAG AGGTTCCCTC ATCATGGACA TGGTTTCAGA   3120
TAAGGGGAAT TTGATGTACT CAGACAACAG GTCCTTTCAG GGGAAAGAGA GCATTTTTGG   3180
AGACAACATG GGCGGACTCC AAACATTTGT GGCCAACCGG CAGGAGGATA ACCTCAATAA   3240
CTATGTATTC CAGGGACAAC ATCCTCTTAC TCTCAATGAG TCCAACCCTA ACACGGTGGA   3300
GGTGGCCGTG AGCACAGAAT CCMAAGCGAA CTCTAGACCC CGGCAGCTGT GGGAGGAATC   3360
CGTGGATTCC AWACCCCAGG ATTCACTATC CCAGRATCCA GTCTCCCAGA GGGATGAGGC   3420
GWCAGCAGAG AATAGGACCC ACTCCCTMMA GAGCCCTAGG TATCTTCCAG AAGAGATGGC   3480
CCACTCTGAC ATTTCAGAWA CSTCCAATCG GGCCACGTTC CACAGGGAAC CTGACMACAG   3540
TAAGA                                                               3545
```

(2) INFORMATION FOR SEQ ID NO:11:

(i) SEQUENCE CHARACTERISTICS:
(A) LENGTH: 1078 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:11:

```
Met Gly Arg Val Gly Tyr Trp Thr Leu Leu Val Leu Pro Ala Leu Leu
1               5                   10                  15

Val Trp Arg Gly Pro Ala Pro Ser Ala Ala Ala Glu Lys Gly Pro Pro
            20                  25                  30

Ala Leu Asn Ile Ala Val Met Leu Gly His Ser His Asp Val Thr Glu
        35                  40                  45

Arg Glu Leu Arg Thr Leu Trp Gly Pro Glu Lys Ala Ala Gly Leu Pro
    50                  55                  60

Leu Asp Val Asn Val Val Ala Leu Leu Met Asn Arg Thr Asp Pro Lys
65                  70                  75                  80

Ser Leu Ile Thr His Val Cys Asp Leu Met Ser Gly Gly Arg Ile His
                85                  90                  95
```

-continued

```
Gly Leu Val Leu Gly Asp Asp Thr Asp Gln Glu Pro Val Thr Gln Met
            100                 105                 110

Leu Asp Phe Ile Ser Ser His Thr Phe Val Pro Ile Leu Gly Xaa His
        115                 120                 125

Gly Gly Ala Ser Met Ile Met Ala Asp Lys Glu Pro Thr Ser Thr Phe
    130                 135                 140

Phe Gln Phe Gly Ala Ser Ile Gln Gln Gln Thr Thr Val Met Leu Lys
145                 150                 155                 160

Ile Met Gln Asp Tyr Asp Trp His Val Phe Ser Leu Val Thr Thr Ile
                165                 170                 175

Phe Pro Gly Tyr Arg Glu Phe Ile Ser Phe Val Lys Thr Thr Val Asp
            180                 185                 190

Asn Ser Phe Val Gly Trp Asp Met Gln Asn Val Ile Thr Leu Asp Thr
        195                 200                 205

Ser Leu Glu Asp Ala Lys Thr Gln Val Gln Leu Lys Lys Ile His Ser
    210                 215                 220

Ser Val Ile Leu Leu Tyr Cys Pro Lys Asp Glu Ala Val Leu Ile Leu
225                 230                 235                 240

Ser Glu Ala Arg Ser Leu Gly Leu Thr Gly Tyr Asp Phe Phe Trp Ile
                245                 250                 255

Ala Pro Ser Leu Val Ser Gly Asn Thr Glu Leu Ile Pro Lys Glu Phe
            260                 265                 270

Pro Ser Gly Leu Ile Ser Val Ser Tyr Asp Asp Trp Asp Tyr Ser Leu
        275                 280                 285

Glu Ala Lys Val Arg Asp Gly Ile Gly Ile Leu Thr Thr Ala Ala Ser
    290                 295                 300

Ser Met Leu Glu Lys Phe Ser Tyr Ile Pro Glu Ala Lys Ala Ser Cys
305                 310                 315                 320

Tyr Gly Gln Met Glu Arg Pro Glu Val Pro Met His Thr Leu His Pro
                325                 330                 335

Phe Met Val Asn Val Thr Trp Asp Gly Lys Asp Leu Ser Phe Thr Glu
            340                 345                 350

Glu Gly Tyr Gln Val His Pro Arg Leu Val Val Ile Val Leu Asn Lys
        355                 360                 365

Asp Arg Glu Trp Glu Lys Val Gly Lys Trp Glu Asn His Thr Leu Ser
    370                 375                 380

Leu Arg His Ala Val Trp Pro Arg Tyr Lys Ser Phe Ser Asp Cys Glu
385                 390                 395                 400

Pro Asp Asp Asn His Leu Ser Ile Val Thr Leu Gly Glu Ala Pro Phe
                405                 410                 415

Val Ile Ala Glu Asp Ile Asp Pro Leu Thr Glu Thr Cys Val Arg Asn
            420                 425                 430

Thr Val Pro Cys Arg Lys Phe Val Lys Ile Asn Asn Ser Pro Asn Glu
        435                 440                 445

Gly Met Asn Val Lys Lys Cys Cys Lys Gly Phe Cys Ile Asp Ile Leu
    450                 455                 460

Lys Lys Leu Ser Arg Thr Val Lys Phe Thr Tyr Asp Leu Tyr Leu Val
465                 470                 475                 480

Thr Asn Gly Lys His Gly Lys Lys Val Asn Asn Val Trp Asn Gly Met
                485                 490                 495

Ile Gly Glu Val Val Tyr Gln Arg Ala Val Met Ala Val Gly Ser Leu
            500                 505                 510
```

-continued

```
Thr Ile Asn Glu Glu Arg Ser Glu Val Val Asp Phe Ser Val Pro Phe
        515                 520                 525

Val Glu Thr Gly Ile Ser Val Met Val Ser Arg Ser Asn Gly Thr Val
    530                 535                 540

Ser Pro Ser Ala Phe Leu Glu Pro Phe Ser Ala Ser Val Trp Val Met
545                 550                 555                 560

Met Phe Val Met Leu Leu Ile Val Ser Ala Ile Ala Val Trp Val Leu
                565                 570                 575

Asp Tyr Ser Ser Pro Val Gly Tyr Xaa Arg Asn Leu Ala Lys Gly Lys
            580                 585                 590

Ala Pro His Gly Pro Ser Phe Thr Ile Gly Lys Ala Ile Trp Leu Leu
        595                 600                 605

Trp Gly Leu Val Phe Asn Asn Ser Val Pro Val Gln Asn Pro Lys Gly
    610                 615                 620

Thr Thr Ser Lys Ile Met Val Ser Val Trp Ala Ser Ser Ala Val Ile
625                 630                 635                 640

Phe Leu Ala Ser Tyr Thr Ala Asn Leu Ala Ala Xaa Met Ile Gln Glu
                645                 650                 655

Glu Phe Val Asp Gln Val Thr Gly Leu Ser Asp Xaa Lys Phe Gln Arg
            660                 665                 670

Pro His Asp Tyr Ser Pro Pro Phe Arg Phe Gly Thr Val Pro Asn Gly
        675                 680                 685

Ser Thr Glu Arg Asn Ile Arg Asn Asn Tyr Pro Tyr Met His Gln Tyr
    690                 695                 700

Met Thr Lys Phe Asn Gln Lys Gly Val Glu Asp Ala Leu Val Ser Leu
705                 710                 715                 720

Lys Thr Gly Lys Leu Asp Ala Phe Ile Tyr Asp Ala Ala Val Leu Asn
                725                 730                 735

Tyr Lys Ala Gly Arg Asp Glu Gly Cys Lys Leu Val Thr Ile Gly Ser
            740                 745                 750

Gly Tyr Ile Phe Ala Thr Thr Gly Tyr Gly Ile Ala Leu Gln Lys Gly
        755                 760                 765

Ser Pro Trp Lys Arg Gln Ile Asp Leu Ala Leu Leu Gln Phe Val Gly
    770                 775                 780

Asp Gly Glu Met Glu Glu Leu Glu Thr Leu Trp Leu Thr Gly Ile Cys
785                 790                 795                 800

His Asn Glu Lys Asn Glu Val Met Ser Ser Gln Leu Asp Ile Asp Asn
                805                 810                 815

Met Ala Gly Val Phe Tyr Met Leu Ala Ala Ala Met Ala Leu Ser Leu
            820                 825                 830

Ile Thr Phe Ile Trp Glu His Leu Phe Tyr Trp Lys Leu Arg Phe Cys
        835                 840                 845

Phe Thr Gly Val Cys Ser Asp Arg Pro Gly Leu Leu Phe Ser Ile Ser
    850                 855                 860

Arg Gly Ile Tyr Ser Cys Ile His Gly Val His Ile Gly Glu Lys Glu
865                 870                 875                 880

Lys Ser Pro Asp Phe Asn Leu Thr Gly Ser Gln Ser Asn Met Leu Lys
                885                 890                 895

Leu Leu Arg Ser Ala Gln Asn Ile Ser Ser Met Ser Asn Met Asp Ser
            900                 905                 910

Ser Arg Met Asp Ser Pro Gln Arg Ala Ala Asp Phe Ile Pro Arg Gly
        915                 920                 925

Ser Leu Ile Met Asp Met Val Ser Asp Lys Gly Asn Leu Met Tyr Ser
```

-continued

```
    930                 935                 940

Asp Asn Arg Ser Phe Gln Gly Lys Glu Ser Ile Phe Gly Asp Asn Met
945                 950                 955                 960

Gly Gly Leu Gln Thr Phe Val Ala Asn Arg Gln Glu Asp Asn Leu Asn
                965                 970                 975

Asn Tyr Val Phe Gln Gly Gln His Pro Leu Thr Leu Asn Glu Ser Asn
            980                 985                 990

Pro Asn Thr Val Glu Val Ala Val Ser Thr Glu Ser Xaa Ala Asn Ser
        995                 1000                1005

Arg Pro Arg Gln Leu Trp Glu Glu Ser Val Asp Ser Xaa Pro Gln Asp
    1010                1015                1020

Ser Leu Ser Gln Xaa Pro Val Ser Gln Arg Asp Glu Ala Xaa Ala Glu
1025                1030                1035                1040

Asn Arg Thr His Ser Leu Xaa Ser Pro Arg Tyr Leu Pro Glu Glu Met
                1045                1050                1055

Ala His Ser Asp Ile Ser Xaa Thr Ser Asn Arg Ala Thr Phe His Arg
            1060                1065                1070

Glu Pro Asp Xaa Ser Lys
        1075
```

(2) INFORMATION FOR SEQ ID NO:12:

(i) SEQUENCE CHARACTERISTICS:
(A) LENGTH: 74 base pairs
(B) TYPE: nucleic acid
(C) STRANDEDNESS: both
(D) TOPOLOGY: both (ii) MOLECULE TYPE: cDNA (xi) SEQUENCE DESCRIPTION: SEQ ID NO:12:

```
CGAGGGAGGC GGCCGGCGCG GACTCTCTTC GCGGGCGCAG CGCCCCTTCC CCCTCGGACC     60

CTCCGGTGGA CATG                                                      74
```

(2) INFORMATION FOR SEQ ID NO:13:

(i) SEQUENCE CHARACTERISTICS:
(A) LENGTH: 3155 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3030

(xi) SEQUENCE DESCRIPTION: SEQ ID NO:13:

```
CAAGCCGGGC GTTCGGAGCT GTGCCCGGCC CCGCTTCAGC ACCGCGGACA GCGCCGGCCG     60

CGTGGGGCTG AGCGCCGAGC CCCCGCGCAC GCTTCAGCCC CCCTTCCCTC GGCCGACGTC    120

CCGGGACCGC CGCTCCGGGG GAGACGTGGC GTCCGCAGCC CGCGGGGCCG GGCGAGCGCA    180

GGACGGCCCG GAAGCCCCGC GGGGGATGCG CCGAGGGCCC CGCGTTCGCG CCGCGCAGAG    240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25
```

-continued

```
GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG     1155
Asp Ala Val Gly Val Val Ala Gln Ala Val His Glu Leu Leu Glu Lys
        285                 290                 295

GAG AAC ATC ACC GAC CCG CCG CGG GGC TGC GTG GGC AAC ACC AAC ATC     1203
Glu Asn Ile Thr Asp Pro Pro Arg Gly Cys Val Gly Asn Thr Asn Ile
    300                 305                 310

TGG AAG ACC GGG CCG CTC TTC AAG AGA GTG CTG ATG TCT TCC AAG TAT     1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG     1299
Ala Asp Gly Val Thr Gly Arg Val Glu Phe Asn Glu Asp Gly Asp Arg
                335                 340                 345
```

-continued

```
AAG TTC GCC AAC TAC AGC ATC ATG AAC CTG CAG AAC CGC AAG CTG GTG         1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG         1395
Gln Val Gly Ile Tyr Asn Gly Thr His Val Ile Pro Asn Asp Arg Lys
        365                 370                 375

ATC ATC TGG CCA GGC GGA GAG ACA GAG AAG CCT CGA GGG TAC CAG ATG         1443
Ile Ile Trp Pro Gly Gly Glu Thr Glu Lys Pro Arg Gly Tyr Gln Met
    380                 385                 390

TCC ACC AGA CTG AAG ATT GTG ACG ATC CAC CAG GAG CCC TTC GTG TAC         1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC         1539
Val Lys Pro Thr Leu Ser Asp Gly Thr Cys Lys Glu Glu Phe Thr Val
                415                 420                 425

AAC GGC GAC CCA GTC AAG AAG GTG ATC TGC ACC GGG CCC AAC GAC ACG         1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT         1635
Ser Pro Gly Ser Pro Arg His Thr Val Pro Gln Cys Cys Tyr Gly Phe
        445                 450                 455

TGC ATC GAC CTG CTC ATC AAG CTG GCA CGG ACC ATG AAC TTC ACC TAC         1683
Cys Ile Asp Leu Leu Ile Lys Leu Ala Arg Thr Met Asn Phe Thr Tyr
    460                 465                 470

GAG GTG CAC CTG GTG GCA GAT GGC AAG TTC GGC ACA CAG GAG CGG GTG         1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC         1779
Asn Asn Ser Asn Lys Lys Glu Trp Asn Gly Met Met Gly Glu Leu Leu
                495                 500                 505

AGC GGG CAG GCA GAC ATG ATC GTG GCG CCG CTA ACC ATA AAC AAC GAG         1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG         1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC         1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG         1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC         2019
His Val Val Ala Val Met Leu Tyr Leu Leu Asp Arg Phe Ser Pro Phe
                575                 580                 585

GGC CGG TTC AAG GTG AAC AGC GAG GAG GAG GAG GAG GAC GCA CTG ACC         2067
Gly Arg Phe Lys Val Asn Ser Glu Glu Glu Glu Glu Asp Ala Leu Thr
            590                 595                 600

CTG TCC TCG GCC ATG TGG TTC TCC TGG GGC GTC CTG CTC AAC TCC GGC         2115
Leu Ser Ser Ala Met Trp Phe Ser Trp Gly Val Leu Leu Asn Ser Gly
        605                 610                 615

ATC GGG GAA GGC GCC CCC AGA AGC TTC TCA GCG CGC ATC CTG GGC ATG         2163
Ile Gly Glu Gly Ala Pro Arg Ser Phe Ser Ala Arg Ile Leu Gly Met
    620                 625                 630

GTG TGG GCC GGC TTT GCC ATG ATC ATC GTG GCC TCC TAC ACC GCC AAC         2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC         2259
Leu Ala Ala Phe Leu Val Leu Asp Arg Pro Glu Glu Arg Ile Thr Gly
```

-continued

```
                655                 660                 665

ATC AAC GAC CCT CGG CTG AGG AAC CCC TCG GAC AAG TTT ATC TAC GCC      2307
Ile Asn Asp Pro Arg Leu Arg Asn Pro Ser Asp Lys Phe Ile Tyr Ala
            670                 675                 680

ACG GTG AAG CAG AGC TCC GTG GAT ATC TAC TTC CGG CGC CAG GTG GAG      2355
Thr Val Lys Gln Ser Ser Val Asp Ile Tyr Phe Arg Arg Gln Val Glu
        685                 690                 695

CTG AGC ACC ATG TAC CGG CAT ATG GAG AAG CAC AAC TAC GAG AGT GCG      2403
Leu Ser Thr Met Tyr Arg His Met Glu Lys His Asn Tyr Glu Ser Ala
    700                 705                 710

GCG GAG GCC ATC CAG GCC GTG AGA GAC AAC AAG CTG CAT GCC TTC ATC      2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG      2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG      2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG      2595
Arg Lys Asp Ser Pro Trp Lys Gln Asn Val Ser Leu Ser Ile Leu Lys
        765                 770                 775

TCC CAC GAG AAT GGC TTC ATG GAA GAC CTG GAC AAG ACG TGG GTT CGG      2643
Ser His Glu Asn Gly Phe Met Glu Asp Leu Asp Lys Thr Trp Val Arg
    780                 785                 790

TAT CAG GAA TGT GAC TCG CGC AGC AAC GCC CCT GCG ACC CTT ACT TTT      2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC      2739
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT      2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG      2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT      2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC      2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG CAG TAC CAT CCC ACT GAT      2979
Phe Lys Arg Arg Arg Ser Ser Lys Asp Thr Gln Tyr His Pro Thr Asp
                895                 900                 905

ATC ACG GGC CCG CTC AAC CTC TCA GAT CCC TCG GTC AGC ACC GTG GTG      3027
Ile Thr Gly Pro Leu Asn Leu Ser Asp Pro Ser Val Ser Thr Val Val
            910                 915                 920

TGAGGCCCCC GGAGGCGCCC ACCTGCCCAG TTAGCCCGGC CAAGGACACT GATGGGTCCT    3087

GCTGCTCGGG AAGGCCTGAG GGAAGCCCAC CCGCCCCAGA GACTGCCCAC CCTGGGCCTC    3147

CCGTCCGT                                                             3155
```

(2) INFORMATION FOR SEQ ID NO:14:

(i) SEQUENCE CHARACTERISTICS:
(A) LENGTH: 922 amino acids
(B) TYPE: amino acid
(D) TOPOLOGY: linear -continued (ii) MOLECULE TYPE: protein (xi) SEQUENCE DESCRIPTION: SEQ ID NO:14:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400
```

-continued

```
Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815
```

-continued

```
Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
            900                 905                 910

Leu Ser Asp Pro Ser Val Ser Thr Val Val
        915                 920
```

(2) INFORMATION FOR SEQ ID NO:15:

(i) SEQUENCE CHARACTERISTICS:
(A) LENGTH: 2540 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 1..2334

(xi) SEQUENCE DESCRIPTION: SEQ ID NO:15:

```
AAC GAC CAC TTC ACT CCC ACC CCT GTC TCC TAC ACA GCC GGC TTC TAC       48
Asn Asp His Phe Thr Pro Thr Pro Val Ser Tyr Thr Ala Gly Phe Tyr
  1               5                  10                  15

CGC ATA CCC GTG CTG GGG CTG ACC ACC CGC ATG TCC ATC TAC TCG GAC       96
Arg Ile Pro Val Leu Gly Leu Thr Thr Arg Met Ser Ile Tyr Ser Asp
             20                  25                  30

AAG AGC ATC CAC CTG AGC TTC CTG CGC ACC GTG CCG CCC TAC TCC CAC      144
Lys Ser Ile His Leu Ser Phe Leu Arg Thr Val Pro Pro Tyr Ser His
         35                  40                  45

CAG TCC AGC GTG TGG TTT GAG ATG ATG CGT GTC TAC AGC TGG AAC CAC      192
Gln Ser Ser Val Trp Phe Glu Met Met Arg Val Tyr Ser Trp Asn His
     50                  55                  60

ATC ATC CTG CTG GTC AGC GAC GAC CAC GAG GGC CGG GCG GCT CAG AAA      240
Ile Ile Leu Leu Val Ser Asp Asp His Glu Gly Arg Ala Ala Gln Lys
 65                  70                  75                  80

CGC CTG GAG ACG CTG CTG GAG GAG CGT GAG TCC AAG AGT AAA AAA AGG      288
Arg Leu Glu Thr Leu Leu Glu Glu Arg Glu Ser Lys Ser Lys Lys Arg
                 85                  90                  95

AAC TAT GAA AAC CTC GAC CAA CTG TCC TAT GAC AAC AAG CGC GGA CCC      336
Asn Tyr Glu Asn Leu Asp Gln Leu Ser Tyr Asp Asn Lys Arg Gly Pro
            100                 105                 110

AAG GCA GAG AAG GTG CTG CAG TTT GAC CCA GGG ACC AAG AAC GTG ACG      384
Lys Ala Glu Lys Val Leu Gln Phe Asp Pro Gly Thr Lys Asn Val Thr
        115                 120                 125

GCC CTG CTG ATG GAG GCG AAA GAG CTG GAG GCC CGG GTC ATC ATC CTT      432
Ala Leu Leu Met Glu Ala Lys Glu Leu Glu Ala Arg Val Ile Ile Leu
    130                 135                 140

TCT GCC AGC GAG GAC GAT GCT GCC ACT GTA TAC CGC GCA GCC GCG ATG      480
Ser Ala Ser Glu Asp Asp Ala Ala Thr Val Tyr Arg Ala Ala Ala Met
145                 150                 155                 160

CTG AAC ATG ACG GGC AAC ACC AAC ATC TGG AAG ACC GGG CCG CTC TTC      528
```

-continued

```
Leu Asn Met Thr Gly Asn Thr Asn Ile Trp Lys Thr Gly Pro Leu Phe
                165                 170                 175

AAG AGA GTG CTG ATG TCT TCC AAG TAT GCG GAT GGG GTG ACT GGT CGC      576
Lys Arg Val Leu Met Ser Ser Lys Tyr Ala Asp Gly Val Thr Gly Arg
            180                 185                 190

GTG GAG TTC AAT GAG GAT GGG GAC CGG AAG TTC GCC AAC TAC AGC ATC      624
Val Glu Phe Asn Glu Asp Gly Asp Arg Lys Phe Ala Asn Tyr Ser Ile
        195                 200                 205

ATG AAC CTG CAG AAC CGC AAG CTG GTG CAA GTG GGC ATC TAC AAT GGC      672
Met Asn Leu Gln Asn Arg Lys Leu Val Gln Val Gly Ile Tyr Asn Gly
    210                 215                 220

ACC CAC GTC ATC CCT AAT GAC AGG AAG ATC ATC TGG CCA GGC GGA GAG      720
Thr His Val Ile Pro Asn Asp Arg Lys Ile Ile Trp Pro Gly Gly Glu
225                 230                 235                 240

ACA GAG AAG CCT CGA GGG TAC CAG ATG TCC ACC AGA CTG AAG ATT GTG      768
Thr Glu Lys Pro Arg Gly Tyr Gln Met Ser Thr Arg Leu Lys Ile Val
                245                 250                 255

ACG ATC CAC CAG GAG CCC TTC GTG TAC GTC AAG CCC ACG CTG AGT GAT      816
Thr Ile His Gln Glu Pro Phe Val Tyr Val Lys Pro Thr Leu Ser Asp
            260                 265                 270

GGG ACA TGC AAG GAG GAG TTC ACA GTC AAC GGC GAC CCA GTC AAG AAG      864
Gly Thr Cys Lys Glu Glu Phe Thr Val Asn Gly Asp Pro Val Lys Lys
        275                 280                 285

GTG ATC TGC ACC GGG CCC AAC GAC ACG TCG CCG GGC AGC CCC CGC CAC      912
Val Ile Cys Thr Gly Pro Asn Asp Thr Ser Pro Gly Ser Pro Arg His
    290                 295                 300

ACG GTG CCT CAG TGT TGC TAC GGC TTT TGC ATC GAC CTG CTC ATC AAG      960
Thr Val Pro Gln Cys Cys Tyr Gly Phe Cys Ile Asp Leu Leu Ile Lys
305                 310                 315                 320

CTG GCA CGG ACC ATG AAC TTC ACC TAC GAG GTG CAC CTG GTG GCA GAT     1008
Leu Ala Arg Thr Met Asn Phe Thr Tyr Glu Val His Leu Val Ala Asp
                325                 330                 335

GGC AAG TTC GGC ACA CAG GAG CGG GTG AAC AAC AGC AAC AAG AAG GAG     1056
Gly Lys Phe Gly Thr Gln Glu Arg Val Asn Asn Ser Asn Lys Lys Glu
            340                 345                 350

TGG AAT GGG ATG ATG GGC GAG CTG CTC AGC GGG CAG GCA GAC ATG ATC     1104
Trp Asn Gly Met Met Gly Glu Leu Leu Ser Gly Gln Ala Asp Met Ile
        355                 360                 365

GTG GCG CCG CTA ACC ATA AAC AAC GAG CGC GCG CAG TAC ATC GAG TTT     1152
Val Ala Pro Leu Thr Ile Asn Asn Glu Arg Ala Gln Tyr Ile Glu Phe
    370                 375                 380

TCC AAG CCC TTC AAG TAC CAG GGC CTG ACT ATT CTG GTC AAG AAG GAG     1200
Ser Lys Pro Phe Lys Tyr Gln Gly Leu Thr Ile Leu Val Lys Lys Glu
385                 390                 395                 400

ATT CCC CGG AGC ACG CTG GAC TCG TTC ATG CAG CCG TTC CAG AGC ACA     1248
Ile Pro Arg Ser Thr Leu Asp Ser Phe Met Gln Pro Phe Gln Ser Thr
                405                 410                 415

CTG TGG CTG CTG GTG GGG CTG TCG GTG CAC GTG GTG GCC GTG ATG CTG     1296
Leu Trp Leu Leu Val Gly Leu Ser Val His Val Val Ala Val Met Leu
            420                 425                 430

TAC CTG CTG GAC CGC TTC AGC CCC TTC GGC CGG TTC AAG GTG AAC AGC     1344
Tyr Leu Leu Asp Arg Phe Ser Pro Phe Gly Arg Phe Lys Val Asn Ser
        435                 440                 445

GAG GAG GAG GAG GAG GAC GCA CTG ACC CTG TCC TCG GCC ATG TGG TTC     1392
Glu Glu Glu Glu Glu Asp Ala Leu Thr Leu Ser Ser Ala Met Trp Phe
    450                 455                 460

TCC TGG GGC GTC CTG CTC AAC TCC GGC ATC GGG GAA GGC GCC CCC AGA     1440
Ser Trp Gly Val Leu Leu Asn Ser Gly Ile Gly Glu Gly Ala Pro Arg
465                 470                 475                 480
```

-continued

```
AGC TTC TCA GCG CGC ATC CTG GGC ATG GTG TGG GCC GGC TTT GCC ATG     1488
Ser Phe Ser Ala Arg Ile Leu Gly Met Val Trp Ala Gly Phe Ala Met
                485                 490                 495

ATC ATC GTG GCC TCC TAC ACC GCC AAC CTG GCG GCC TTC CTG GTG CTG     1536
Ile Ile Val Ala Ser Tyr Thr Ala Asn Leu Ala Ala Phe Leu Val Leu
            500                 505                 510

GAC CGG CCG GAG GAG CGC ATC ACG GGC ATC AAC GAC CCT CGG CTG AGG     1584
Asp Arg Pro Glu Glu Arg Ile Thr Gly Ile Asn Asp Pro Arg Leu Arg
        515                 520                 525

AAC CCC TCG GAC AAG TTT ATC TAC GCC ACG GTG AAG CAG AGC TCC GTG     1632
Asn Pro Ser Asp Lys Phe Ile Tyr Ala Thr Val Lys Gln Ser Ser Val
    530                 535                 540

GAT ATC TAC TTC CGG CGC CAG GTG GAG CTG AGC ACC ATG TAC CGG CAT     1680
Asp Ile Tyr Phe Arg Arg Gln Val Glu Leu Ser Thr Met Tyr Arg His
545                 550                 555                 560

ATG GAG AAG CAC AAC TAC GAG AGT GCG GCG GAG GCC ATC CAG GCC GTG     1728
Met Glu Lys His Asn Tyr Glu Ser Ala Ala Glu Ala Ile Gln Ala Val
                565                 570                 575

AGA GAC AAC AAG CTG CAT GCC TTC ATC TGG GAC TCG GCG GTG CTG GAG     1776
Arg Asp Asn Lys Leu His Ala Phe Ile Trp Asp Ser Ala Val Leu Glu
            580                 585                 590

TTC GAG GCC TCG CAG AAG TGC GAC CTG GTG ACG ACT GGA GAG CTG TTT     1824
Phe Glu Ala Ser Gln Lys Cys Asp Leu Val Thr Thr Gly Glu Leu Phe
        595                 600                 605

TTC CGC TCG GGC TTC GGC ATA GGC ATG CGC AAA GAC AGC CCC TGG AAG     1872
Phe Arg Ser Gly Phe Gly Ile Gly Met Arg Lys Asp Ser Pro Trp Lys
    610                 615                 620

CAG AAC GTC TCC CTG TCC ATC CTC AAG TCC CAC GAG AAT GGC TTC ATG     1920
Gln Asn Val Ser Leu Ser Ile Leu Lys Ser His Glu Asn Gly Phe Met
625                 630                 635                 640

GAA GAC CTG GAC AAG ACG TGG GTT CGG TAT CAG GAA TGT GAC TCG CGC     1968
Glu Asp Leu Asp Lys Thr Trp Val Arg Tyr Gln Glu Cys Asp Ser Arg
                645                 650                 655

AGC AAC GCC CCT GCG ACC CTT ACT TTT GAG AAC ATG GCC GGG GTC TTC     2016
Ser Asn Ala Pro Ala Thr Leu Thr Phe Glu Asn Met Ala Gly Val Phe
            660                 665                 670

ATG CTG GTA GCT GGG GGC ATC GTG GCC GGG ATC TTC CTG ATT TTC ATC     2064
Met Leu Val Ala Gly Gly Ile Val Ala Gly Ile Phe Leu Ile Phe Ile
        675                 680                 685

GAG ATT GCC TAC AAG CGG CAC AAG GAT GCT CGC CGG AAG CAG ATG CAG     2112
Glu Ile Ala Tyr Lys Arg His Lys Asp Ala Arg Arg Lys Gln Met Gln
    690                 695                 700

CTG GCC TTT GCC GCC GTT AAC GTG TGG CGG AAG AAC CTG CAG GAT AGA     2160
Leu Ala Phe Ala Ala Val Asn Val Trp Arg Lys Asn Leu Gln Asp Arg
705                 710                 715                 720

AAG AGT GGT AGA GCA GAG CCT GAC CCT AAA AAG AAA GCC ACA TTT AGG     2208
Lys Ser Gly Arg Ala Glu Pro Asp Pro Lys Lys Lys Ala Thr Phe Arg
                725                 730                 735

GCT ATC ACC TCC ACC CTG GCT TCC AGC TTC AAG AGG CGT AGG TCC TCC     2256
Ala Ile Thr Ser Thr Leu Ala Ser Ser Phe Lys Arg Arg Arg Ser Ser
            740                 745                 750

AAA GAC ACG CAG TAC CAT CCC ACT GAT ATC ACG GGC CCG CTC AAC CTC     2304
Lys Asp Thr Gln Tyr His Pro Thr Asp Ile Thr Gly Pro Leu Asn Leu
        755                 760                 765

TCA GAT CCC TCG GTC AGC ACC GTG GTG TGAGGCCCCC GGAGGCGCCC           2351
Ser Asp Pro Ser Val Ser Thr Val Val
    770                 775

ACCTGCCCAG TTAGCCCGGC CAAGGACACT GATGGGTCCT GCTGCTCGGG AAGGCCTGAG   2411

GGAAGCCCAC CCGCCCCAGA GACTGCCCAC CCTGGGCCTC CCGTCCGTCC GCCCGCCCAC   2471
```

-continued

```
CCCGCTGCCT GGCGGGCAGC CCCTGCTGGA CCAAGGTGCG GACCGGAGCG GCTGAGGACG   2531

GGGCAGAGC                                                           2540
```

(2) INFORMATION FOR SEQ ID NO:16:

(i) SEQUENCE CHARACTERISTICS:
(A) LENGTH: 777 amino acids
(B) TYPE: amino acid
(D) TOPOLOGY: linear (ii) MOLECULE TYPE: protein (xi) SEQUENCE DESCRIPTION: SEQ ID NO:16:

```
Asn Asp His Phe Thr Pro Thr Pro Val Ser Tyr Thr Ala Gly Phe Tyr
  1               5                  10                  15

Arg Ile Pro Val Leu Gly Leu Thr Thr Arg Met Ser Ile Tyr Ser Asp
             20                  25                  30

Lys Ser Ile His Leu Ser Phe Leu Arg Thr Val Pro Pro Tyr Ser His
         35                  40                  45

Gln Ser Ser Val Trp Phe Glu Met Met Arg Val Tyr Ser Trp Asn His
     50                  55                  60

Ile Ile Leu Leu Val Ser Asp Asp His Glu Gly Arg Ala Ala Gln Lys
 65                  70                  75                  80

Arg Leu Glu Thr Leu Leu Glu Glu Arg Glu Ser Lys Ser Lys Lys Arg
                 85                  90                  95

Asn Tyr Glu Asn Leu Asp Gln Leu Ser Tyr Asp Asn Lys Arg Gly Pro
            100                 105                 110

Lys Ala Glu Lys Val Leu Gln Phe Asp Pro Gly Thr Lys Asn Val Thr
        115                 120                 125

Ala Leu Leu Met Glu Ala Lys Glu Leu Glu Ala Arg Val Ile Ile Leu
    130                 135                 140

Ser Ala Ser Glu Asp Asp Ala Ala Thr Val Tyr Arg Ala Ala Ala Met
145                 150                 155                 160

Leu Asn Met Thr Gly Asn Thr Asn Ile Trp Lys Thr Gly Pro Leu Phe
                165                 170                 175

Lys Arg Val Leu Met Ser Ser Lys Tyr Ala Asp Gly Val Thr Gly Arg
            180                 185                 190

Val Glu Phe Asn Glu Asp Gly Asp Arg Lys Phe Ala Asn Tyr Ser Ile
        195                 200                 205

Met Asn Leu Gln Asn Arg Lys Leu Val Gln Val Gly Ile Tyr Asn Gly
    210                 215                 220

Thr His Val Ile Pro Asn Asp Arg Lys Ile Ile Trp Pro Gly Gly Glu
225                 230                 235                 240

Thr Glu Lys Pro Arg Gly Tyr Gln Met Ser Thr Arg Leu Lys Ile Val
                245                 250                 255

Thr Ile His Gln Glu Pro Phe Val Tyr Val Lys Pro Thr Leu Ser Asp
            260                 265                 270

Gly Thr Cys Lys Glu Glu Phe Thr Val Asn Gly Asp Pro Val Lys Lys
        275                 280                 285

Val Ile Cys Thr Gly Pro Asn Asp Thr Ser Pro Gly Ser Pro Arg His
    290                 295                 300

Thr Val Pro Gln Cys Cys Tyr Gly Phe Cys Ile Asp Leu Leu Ile Lys
305                 310                 315                 320

Leu Ala Arg Thr Met Asn Phe Thr Tyr Glu Val His Leu Val Ala Asp
                325                 330                 335
```

-continued

```
Gly Lys Phe Gly Thr Gln Glu Arg Val Asn Asn Ser Asn Lys Lys Glu
            340                 345                 350

Trp Asn Gly Met Met Gly Glu Leu Leu Ser Gly Gln Ala Asp Met Ile
        355                 360                 365

Val Ala Pro Leu Thr Ile Asn Asn Glu Arg Ala Gln Tyr Ile Glu Phe
    370                 375                 380

Ser Lys Pro Phe Lys Tyr Gln Gly Leu Thr Ile Leu Val Lys Lys Glu
385                 390                 395                 400

Ile Pro Arg Ser Thr Leu Asp Ser Phe Met Gln Pro Phe Gln Ser Thr
                405                 410                 415

Leu Trp Leu Leu Val Gly Leu Ser Val His Val Val Ala Val Met Leu
            420                 425                 430

Tyr Leu Leu Asp Arg Phe Ser Pro Phe Gly Arg Phe Lys Val Asn Ser
        435                 440                 445

Glu Glu Glu Glu Glu Asp Ala Leu Thr Leu Ser Ser Ala Met Trp Phe
    450                 455                 460

Ser Trp Gly Val Leu Leu Asn Ser Gly Ile Gly Glu Gly Ala Pro Arg
465                 470                 475                 480

Ser Phe Ser Ala Arg Ile Leu Gly Met Val Trp Ala Gly Phe Ala Met
                485                 490                 495

Ile Ile Val Ala Ser Tyr Thr Ala Asn Leu Ala Ala Phe Leu Val Leu
            500                 505                 510

Asp Arg Pro Glu Glu Arg Ile Thr Gly Ile Asn Asp Pro Arg Leu Arg
        515                 520                 525

Asn Pro Ser Asp Lys Phe Ile Tyr Ala Thr Val Lys Gln Ser Ser Val
    530                 535                 540

Asp Ile Tyr Phe Arg Arg Gln Val Glu Leu Ser Thr Met Tyr Arg His
545                 550                 555                 560

Met Glu Lys His Asn Tyr Glu Ser Ala Ala Glu Ala Ile Gln Ala Val
                565                 570                 575

Arg Asp Asn Lys Leu His Ala Phe Ile Trp Asp Ser Ala Val Leu Glu
            580                 585                 590

Phe Glu Ala Ser Gln Lys Cys Asp Leu Val Thr Thr Gly Glu Leu Phe
        595                 600                 605

Phe Arg Ser Gly Phe Gly Ile Gly Met Arg Lys Asp Ser Pro Trp Lys
    610                 615                 620

Gln Asn Val Ser Leu Ser Ile Leu Lys Ser His Glu Asn Gly Phe Met
625                 630                 635                 640

Glu Asp Leu Asp Lys Thr Trp Val Arg Tyr Gln Glu Cys Asp Ser Arg
                645                 650                 655

Ser Asn Ala Pro Ala Thr Leu Thr Phe Glu Asn Met Ala Gly Val Phe
            660                 665                 670

Met Leu Val Ala Gly Gly Ile Val Ala Gly Ile Phe Leu Ile Phe Ile
        675                 680                 685

Glu Ile Ala Tyr Lys Arg His Lys Asp Ala Arg Arg Lys Gln Met Gln
    690                 695                 700

Leu Ala Phe Ala Ala Val Asn Val Trp Arg Lys Asn Leu Gln Asp Arg
705                 710                 715                 720

Lys Ser Gly Arg Ala Glu Pro Asp Pro Lys Lys Lys Ala Thr Phe Arg
                725                 730                 735

Ala Ile Thr Ser Thr Leu Ala Ser Ser Phe Lys Arg Arg Arg Ser Ser
            740                 745                 750
```

-continued

```
Lys Asp Thr Gln Tyr His Pro Thr Asp Ile Thr Gly Pro Leu Asn Leu
        755                 760                 765

Ser Asp Pro Ser Val Ser Thr Val Val
    770                 775
```

(2) INFORMATION FOR SEQ ID NO:17:

(i) SEQUENCE CHARACTERISTICS:
(A) LENGTH: 595 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 1..576

(xi) SEQUENCE DESCRIPTION: SEQ ID NO:17:

```
GAA GAC CTG GAC AAG ACG TGG GTT CGG TAT CAG GAA TGT GAC TCG CGC       48
Glu Asp Leu Asp Lys Thr Trp Val Arg Tyr Gln Glu Cys Asp Ser Arg
  1               5                  10                  15

AGC AAC GCC CCT GCG ACC CTT ACT TTT GAG AAC ATG GCC GGG GTC TTC       96
Ser Asn Ala Pro Ala Thr Leu Thr Phe Glu Asn Met Ala Gly Val Phe
             20                  25                  30

ATG CTG GTA GCT GGG GGC ATC GTG GCC GGG ATC TTC CTG ATT TTC ATC      144
Met Leu Val Ala Gly Gly Ile Val Ala Gly Ile Phe Leu Ile Phe Ile
        35                  40                  45

GAG ATT GCC TAC AAG CGG CAC AAG GAT GCT CGC CGG AAG CAG ATG CAG      192
Glu Ile Ala Tyr Lys Arg His Lys Asp Ala Arg Arg Lys Gln Met Gln
    50                  55                  60

CTG GCC TTT GCC GCC GTT AAC GTG TGG CGG AAG AAC CTG CAG GAT AGA      240
Leu Ala Phe Ala Ala Val Asn Val Trp Arg Lys Asn Leu Gln Asp Arg
 65                  70                  75                  80

AAG AGT GGT AGA GCA GAG CCT GAC CCT AAA AAG AAA GCC ACA TTT AGG      288
Lys Ser Gly Arg Ala Glu Pro Asp Pro Lys Lys Lys Ala Thr Phe Arg
                 85                  90                  95

GCT ATC ACC TCC ACC CTG GCT TCC AGC TTC AAG AGG CGT AGG TCC TCC      336
Ala Ile Thr Ser Thr Leu Ala Ser Ser Phe Lys Arg Arg Arg Ser Ser
            100                 105                 110

AAA GAC ACG CTG GCT CGG GAC TGT CTT CAA CCC TGC CCT GCA CCT TGG      384
Lys Asp Thr Leu Ala Arg Asp Cys Leu Gln Pro Cys Pro Ala Pro Trp
        115                 120                 125

GCA CGG GAG AGC GCC ACC CGC CCG CCC CCG CCC TCG CTC CGG GTG CGT      432
Ala Arg Glu Ser Ala Thr Arg Pro Pro Pro Pro Ser Leu Arg Val Arg
    130                 135                 140

GAC CGG CCC GCC ACC TTG TAC AGA ACC AGC ACT CCC AGG GCC CGA GCG      480
Asp Arg Pro Ala Thr Leu Tyr Arg Thr Ser Thr Pro Arg Ala Arg Ala
145                 150                 155                 160

CGT GCC TTC CCC GTG CGC AGC CGC GCT CTG CCC CTC CGT CCC CAG GGT      528
Arg Ala Phe Pro Val Arg Ser Arg Ala Leu Pro Leu Arg Pro Gln Gly
                165                 170                 175

GCA GGC GCG CAC CGC CCA ACC CCC ACC TCC CGG TGT ATG CAG TGG TGATGCCTA583
Ala Gly Ala His Arg Pro Thr Pro Thr Ser Arg Cys Met Gln Trp
            180                 185                 190

AGGAATGTCA CG                                                        595
```

(2) INFORMATION FOR SEQ ID NO:18:

(i) SEQUENCE CHARACTERISTICS:
(A) LENGTH: 191 amino acids
(B) TYPE: amino acid

-continued (D) TOPOLOGY: linear (ii) MOLECULE TYPE: protein (xi) SEQUENCE DESCRIPTION: SEQ ID NO:18:

```
Glu Asp Leu Asp Lys Thr Trp Val Arg Tyr Gln Glu Cys Asp Ser Arg
  1               5                  10                  15

Ser Asn Ala Pro Ala Thr Leu Thr Phe Glu Asn Met Ala Gly Val Phe
             20                  25                  30

Met Leu Val Ala Gly Gly Ile Val Ala Gly Ile Phe Leu Ile Phe Ile
         35                  40                  45

Glu Ile Ala Tyr Lys Arg His Lys Asp Ala Arg Arg Lys Gln Met Gln
     50                  55                  60

Leu Ala Phe Ala Ala Val Asn Val Trp Arg Lys Asn Leu Gln Asp Arg
 65                  70                  75                  80

Lys Ser Gly Arg Ala Glu Pro Asp Pro Lys Lys Lys Ala Thr Phe Arg
                 85                  90                  95

Ala Ile Thr Ser Thr Leu Ala Ser Ser Phe Lys Arg Arg Arg Ser Ser
            100                 105                 110

Lys Asp Thr Leu Ala Arg Asp Cys Leu Gln Pro Cys Pro Ala Pro Trp
        115                 120                 125

Ala Arg Glu Ser Ala Thr Arg Pro Pro Pro Pro Ser Leu Arg Val Arg
    130                 135                 140

Asp Arg Pro Ala Thr Leu Tyr Arg Thr Ser Thr Pro Arg Ala Arg Ala
145                 150                 155                 160

Arg Ala Phe Pro Val Arg Ser Arg Ala Leu Pro Leu Arg Pro Gln Gly
                165                 170                 175

Ala Gly Ala His Arg Pro Thr Pro Thr Ser Arg Cys Met Gln Trp
            180                 185                 190
```

(2) INFORMATION FOR SEQ ID NO:19:

(i) SEQUENCE CHARACTERISTICS:
(A) LENGTH: 3935 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3030

(xi) SEQUENCE DESCRIPTION: SEQ ID NO:19:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
             30                  35                  40
```

-continued

```
CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG     1155
Asp Ala Val Gly Val Val Ala Gln Ala Val His Glu Leu Leu Glu Lys
        285                 290                 295

GAG AAC ATC ACC GAC CCG CCG CGG GGC TGC GTG GGC AAC ACC AAC ATC     1203
Glu Asn Ile Thr Asp Pro Pro Arg Gly Cys Val Gly Asn Thr Asn Ile
    300                 305                 310

TGG AAG ACC GGG CCG CTC TTC AAG AGA GTG CTG ATG TCT TCC AAG TAT     1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG     1299
Ala Asp Gly Val Thr Gly Arg Val Glu Phe Asn Glu Asp Gly Asp Arg
                335                 340                 345

AAG TTC GCC AAC TAC AGC ATC ATG AAC CTG CAG AAC CGC AAG CTG GTG     1347
Lys Phe Ala Asn Tyr Ser Ile Met Asn Leu Gln Asn Arg Lys Leu Val
            350                 355                 360
```

-continued

```
CAA GTG GGC ATC TAC AAT GGC ACC CAC GTC ATC CCT AAT GAC AGG AAG     1395
Gln Val Gly Ile Tyr Asn Gly Thr His Val Ile Pro Asn Asp Arg Lys
        365                 370                 375

ATC ATC TGG CCA GGC GGA GAG ACA GAG AAG CCT CGA GGG TAC CAG ATG     1443
Ile Ile Trp Pro Gly Gly Glu Thr Glu Lys Pro Arg Gly Tyr Gln Met
    380                 385                 390

TCC ACC AGA CTG AAG ATT GTG ACG ATC CAC CAG GAG CCC TTC GTG TAC     1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC     1539
Val Lys Pro Thr Leu Ser Asp Gly Thr Cys Lys Glu Glu Phe Thr Val
                415                 420                 425

AAC GGC GAC CCA GTC AAG AAG GTG ATC TGC ACC GGG CCC AAC GAC ACG     1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT     1635
Ser Pro Gly Ser Pro Arg His Thr Val Pro Gln Cys Cys Tyr Gly Phe
        445                 450                 455

TGC ATC GAC CTG CTC ATC AAG CTG GCA CGG ACC ATG AAC TTC ACC TAC     1683
Cys Ile Asp Leu Leu Ile Lys Leu Ala Arg Thr Met Asn Phe Thr Tyr
    460                 465                 470

GAG GTG CAC CTG GTG GCA GAT GGC AAG TTC GGC ACA CAG GAG CGG GTG     1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC     1779
Asn Asn Ser Asn Lys Lys Glu Trp Asn Gly Met Met Gly Glu Leu Leu
                495                 500                 505

AGC GGG CAG GCA GAC ATG ATC GTG GCG CCG CTA ACC ATA AAC AAC GAG     1827
Ser Gly Gln Ala Asp Met Ile Val Ala Pro Leu Thr Ile Asn Asn Glu
            510                 515                 520

CGC GCG CAG TAC ATC GAG TTT TCC AAG CCC TTC AAG TAC CAG GGC CTG     1875
Arg Ala Gln Tyr Ile Glu Phe Ser Lys Pro Phe Lys Tyr Gln Gly Leu
        525                 530                 535

ACT ATT CTG GTC AAG AAG GAG ATT CCC CGG AGC ACG CTG GAC TCG TTC     1923
Thr Ile Leu Val Lys Lys Glu Ile Pro Arg Ser Thr Leu Asp Ser Phe
    540                 545                 550

ATG CAG CCG TTC CAG AGC ACA CTG TGG CTG CTG GTG GGG CTG TCG GTG     1971
Met Gln Pro Phe Gln Ser Thr Leu Trp Leu Leu Val Gly Leu Ser Val
555                 560                 565                 570

CAC GTG GTG GCC GTG ATG CTG TAC CTG CTG GAC CGC TTC AGC CCC TTC     2019
His Val Val Ala Val Met Leu Tyr Leu Leu Asp Arg Phe Ser Pro Phe
                575                 580                 585

GGC CGG TTC AAG GTG AAC AGC GAG GAG GAG GAG GAG GAC GCA CTG ACC     2067
Gly Arg Phe Lys Val Asn Ser Glu Glu Glu Glu Glu Asp Ala Leu Thr
            590                 595                 600

CTG TCC TCG GCC ATG TGG TTC TCC TGG GGC GTC CTG CTC AAC TCC GGC     2115
Leu Ser Ser Ala Met Trp Phe Ser Trp Gly Val Leu Leu Asn Ser Gly
        605                 610                 615

ATC GGG GAA GGC GCC CCC AGA AGC TTC TCA GCG CGC ATC CTG GGC ATG     2163
Ile Gly Glu Gly Ala Pro Arg Ser Phe Ser Ala Arg Ile Leu Gly Met
    620                 625                 630

GTG TGG GCC GGC TTT GCC ATG ATC ATC GTG GCC TCC TAC ACC GCC AAC     2211
Val Trp Ala Gly Phe Ala Met Ile Ile Val Ala Ser Tyr Thr Ala Asn
635                 640                 645                 650

CTG GCG GCC TTC CTG GTG CTG GAC CGG CCG GAG GAG CGC ATC ACG GGC     2259
Leu Ala Ala Phe Leu Val Leu Asp Arg Pro Glu Glu Arg Ile Thr Gly
                655                 660                 665

ATC AAC GAC CCT CGG CTG AGG AAC CCC TCG GAC AAG TTT ATC TAC GCC     2307
Ile Asn Asp Pro Arg Leu Arg Asn Pro Ser Asp Lys Phe Ile Tyr Ala
```

-continued

```
            670                 675                 680

ACG GTG AAG CAG AGC TCC GTG GAT ATC TAC TTC CGG CGC CAG GTG GAG     2355
Thr Val Lys Gln Ser Ser Val Asp Ile Tyr Phe Arg Arg Gln Val Glu
        685                 690                 695

CTG AGC ACC ATG TAC CGG CAT ATG GAG AAG CAC AAC TAC GAG AGT GCG     2403
Leu Ser Thr Met Tyr Arg His Met Glu Lys His Asn Tyr Glu Ser Ala
    700                 705                 710

GCG GAG GCC ATC CAG GCC GTG AGA GAC AAC AAG CTG CAT GCC TTC ATC     2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG     2499
Trp Asp Ser Ala Val Leu Glu Phe Glu Ala Ser Gln Lys Cys Asp Leu
                735                 740                 745

GTG ACG ACT GGA GAG CTG TTT TTC CGC TCG GGC TTC GGC ATA GGC ATG     2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG     2595
Arg Lys Asp Ser Pro Trp Lys Gln Asn Val Ser Leu Ser Ile Leu Lys
        765                 770                 775

TCC CAC GAG AAT GGC TTC ATG GAA GAC CTG GAC AAG ACG TGG GTT CGG     2643
Ser His Glu Asn Gly Phe Met Glu Asp Leu Asp Lys Thr Trp Val Arg
    780                 785                 790

TAT CAG GAA TGT GAC TCG CGC AGC AAC GCC CCT GCG ACC CTT ACT TTT     2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC     2739
Glu Asn Met Ala Gly Val Phe Met Leu Val Ala Gly Gly Ile Val Ala
                815                 820                 825

GGG ATC TTC CTG ATT TTC ATC GAG ATT GCC TAC AAG CGG CAC AAG GAT     2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG     2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT     2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC     2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG CAG TAC CAT CCC ACT GAT     2979
Phe Lys Arg Arg Arg Ser Ser Lys Asp Thr Gln Tyr His Pro Thr Asp
                895                 900                 905

ATC ACG GGC CCG CTC AAC CTC TCA GAT CCC TCG GTC AGC ACC GTG GTG     3027
Ile Thr Gly Pro Leu Asn Leu Ser Asp Pro Ser Val Ser Thr Val Val
            910                 915                 920

TGAGGCCCCC GGAGGCGCCC ACCTGCCCAG TTAGCCCGGC CAAGGACACT GATGGGTCCT   3087

GCTGCTCGGG AAGGCCTGAG GGAAGCCCAC CCGCCCCAGA GACTGCCCAC CCTGGGCCTC   3147

CCGTCCGTCC GCCCGCCCAC CCCGCTGCCT GGCGGGCAGC CCCTGCTGGA CCAAGGTGCG   3207

GACCGGAGCG GCTGAGGACG GGGCAGAGCT GAGTCGGCTG GGCAGGGCCG CAGGGCGCTC   3267

CGGCAGAGGC AGGCCCCTGG GGTCTCTGAG CAGTGGGGAG CGGGGGCTAA CTGCCCCCAG   3327

GCGGAGGGGC TTGGAGCAGA GACGGCAGCC CCATCCTTCC CGCAGCACCA GCCTGAGCCA   3387

CAGTGGGGCC CATGGCCCCA GCTGGCTGGG TCGCCCCTCC TCGGGCGCCT GCGCTCCTCT   3447

GCAGCCTGAG CTCCACCCTC CCCTCTTCTT GCGGCACCGC CCACCAAACA CCCCGTCTGC   3507

CCCTTGACGC CACACGCCGG GGCTGGCGCT GCCCTCCCCC ACGGCCGTCC CTGACTTCCC   3567
```

-continued

```
AGCTGGCAGC GCCTCCCGCC GCCTCGGGCC GCCTCCTCCA GAATCGAGAG GGCTGAGCCC   3627

CTCCTCTCCT CGTCCGGCCT GCAGCACAGA AGGGGGCCTC CCCGGGGGTC CCCGGACGCT   3687

GGCTCGGGAC TGTCTTCAAC CCTGCCCTGC ACCTTGGGCA CGGGAGAGCG CCACCCGCCC   3747

GCCCCCGCCC TCGCTCCGGG TGCGTGACCG GCCCGCCACC TTGTACAGAA CCAGCACTCC   3807

CAGGGCCCGA GCGCGTGCCT TCCCCGTGCG CAGCCGCGCT CTGCCCCTCC GTCCCCAGGG   3867

TGCAGGCGCG CACCGCCCAA CCCCCACCTC CCGGTGTATG CAGTGGTGAT GCCTAAAGGA   3927

ATGTCACG                                                            3935
```

(2) INFORMATION FOR SEQ ID NO:20:

(i) SEQUENCE CHARACTERISTICS:
(A) LENGTH: 922 amino acids
(B) TYPE: amino acid
(D) TOPOLOGY: linear (ii) MOLECULE TYPE: protein (xi) SEQUENCE DESCRIPTION: SEQ ID NO:20:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
```

-continued

```
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700
```

-continued

```
His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780

Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
            900                 905                 910

Leu Ser Asp Pro Ser Val Ser Thr Val Val
        915                 920
```

(2) INFORMATION FOR SEQ ID NO:21:

(i) SEQUENCE CHARACTERISTICS:
(A) LENGTH: 3211 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3192

(xi) SEQUENCE DESCRIPTION: SEQ ID NO:21:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40
```

-continued

```
CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC TCC GGG TAC GTG TGG CTG GTC GGC     1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC     1059
Glu Arg Glu Ile Ser Gly Asn Ala Leu Arg Tyr Ala Pro Asp Gly Ile
                255                 260                 265

CTC GGG CTG CAG CTC ATC AAC GGC AAG AAC GAG TCG GCC CAC ATC AGC     1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG     1155
Asp Ala Val Gly Val Val Ala Gln Ala Val His Glu Leu Leu Glu Lys
        285                 290                 295

GAG AAC ATC ACC GAC CCG CCG CGG GGC TGC GTG GGC AAC ACC AAC ATC     1203
Glu Asn Ile Thr Asp Pro Pro Arg Gly Cys Val Gly Asn Thr Asn Ile
    300                 305                 310

TGG AAG ACC GGG CCG CTC TTC AAG AGA GTG CTG ATG TCT TCC AAG TAT     1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG     1299
Ala Asp Gly Val Thr Gly Arg Val Glu Phe Asn Glu Asp Gly Asp Arg
                335                 340                 345

AAG TTC GCC AAC TAC AGC ATC ATG AAC CTG CAG AAC CGC AAG CTG GTG     1347
Lys Phe Ala Asn Tyr Ser Ile Met Asn Leu Gln Asn Arg Lys Leu Val
```

-continued 350 355 360

CAA GTG GGC ATC TAC AAT GGC ACC CAC GTC ATC CCT AAT GAC AGG AAG 1395
Gln Val Gly Ile Tyr Asn Gly Thr His Val Ile Pro Asn Asp Arg Lys
365 370 375

ATC ATC TGG CCA GGC GGA GAG ACA GAG AAG CCT CGA GGG TAC CAG ATG 1443
Ile Ile Trp Pro Gly Gly Glu Thr Glu Lys Pro Arg Gly Tyr Gln Met
380 385 390

TCC ACC AGA CTG AAG ATT GTG ACG ATC CAC CAG GAG CCC TTC GTG TAC 1491
Ser Thr Arg Leu Lys Ile Val Thr Ile His Gln Glu Pro Phe Val Tyr
395 400 405 410

GTC AAG CCC ACG CTG AGT GAT GGG ACA TGC AAG GAG GAG TTC ACA GTC 1539
Val Lys Pro Thr Leu Ser Asp Gly Thr Cys Lys Glu Glu Phe Thr Val
415 420 425

AAC GGC GAC CCA GTC AAG AAG GTG ATC TGC ACC GGG CCC AAC GAC ACG 1587
Asn Gly Asp Pro Val Lys Lys Val Ile Cys Thr Gly Pro Asn Asp Thr
430 435 440

TCG CCG GGC AGC CCC CGC CAC ACG GTG CCT CAG TGT TGC TAC GGC TTT 1635
Ser Pro Gly Ser Pro Arg His Thr Val Pro Gln Cys Cys Tyr Gly Phe
445 450 455

TGC ATC GAC CTG CTC ATC AAG CTG GCA CGG ACC ATG AAC TTC ACC TAC 1683
Cys Ile Asp Leu Leu Ile Lys Leu Ala Arg Thr Met Asn Phe Thr Tyr
460 465 470

GAG GTG CAC CTG GTG GCA GAT GGC AAG TTC GGC ACA CAG GAG CGG GTG 1731
Glu Val His Leu Val Ala Asp Gly Lys Phe Gly Thr Gln Glu Arg Val
475 480 485 490

AAC AAC AGC AAC AAG AAG GAG TGG AAT GGG ATG ATG GGC GAG CTG CTC 1779
Asn Asn Ser Asn Lys Lys Glu Trp Asn Gly Met Met Gly Glu Leu Leu
495 500 505

AGC GGG CAG GCA GAC ATG ATC GTG GCG CCG CTA ACC ATA AAC AAC GAG 1827
Ser Gly Gln Ala Asp Met Ile Val Ala Pro Leu Thr Ile Asn Asn Glu
510 515 520

CGC GCG CAG TAC ATC GAG TTT TCC AAG CCC TTC AAG TAC CAG GGC CTG 1875
Arg Ala Gln Tyr Ile Glu Phe Ser Lys Pro Phe Lys Tyr Gln Gly Leu
525 530 535

ACT ATT CTG GTC AAG AAG GAG ATT CCC CGG AGC ACG CTG GAC TCG TTC 1923
Thr Ile Leu Val Lys Lys Glu Ile Pro Arg Ser Thr Leu Asp Ser Phe
540 545 550

ATG CAG CCG TTC CAG AGC ACA CTG TGG CTG CTG GTG GGG CTG TCG GTG 1971
Met Gln Pro Phe Gln Ser Thr Leu Trp Leu Leu Val Gly Leu Ser Val
555 560 565 570

CAC GTG GTG GCC GTG ATG CTG TAC CTG CTG GAC CGC TTC AGC CCC TTC 2019
His Val Val Ala Val Met Leu Tyr Leu Leu Asp Arg Phe Ser Pro Phe
575 580 585

GGC CGG TTC AAG GTG AAC AGC GAG GAG GAG GAG GAG GAC GCA CTG ACC 2067
Gly Arg Phe Lys Val Asn Ser Glu Glu Glu Glu Glu Asp Ala Leu Thr
590 595 600

CTG TCC TCG GCC ATG TGG TTC TCC TGG GGC GTC CTG CTC AAC TCC GGC 2115
Leu Ser Ser Ala Met Trp Phe Ser Trp Gly Val Leu Leu Asn Ser Gly
605 610 615

ATC GGG GAA GGC GCC CCC AGA AGC TTC TCA GCG CGC ATC CTG GGC ATG 2163
Ile Gly Glu Gly Ala Pro Arg Ser Phe Ser Ala Arg Ile Leu Gly Met
620 625 630

GTG TGG GCC GGC TTT GCC ATG ATC ATC GTG GCC TCC TAC ACC GCC AAC 2211
Val Trp Ala Gly Phe Ala Met Ile Ile Val Ala Ser Tyr Thr Ala Asn
635 640 645 650

CTG GCG GCC TTC CTG GTG CTG GAC CGG CCG GAG GAG CGC ATC ACG GGC 2259
Leu Ala Ala Phe Leu Val Leu Asp Arg Pro Glu Glu Arg Ile Thr Gly
655 660 665

ATC AAC GAC CCT CGG CTG AGG AAC CCC TCG GAC AAG TTT ATC TAC GCC 2307

-continued

```
Ile Asn Asp Pro Arg Leu Arg Asn Pro Ser Asp Lys Phe Ile Tyr Ala
            670                 675                 680

ACG GTG AAG CAG AGC TCC GTG GAT ATC TAC TTC CGG CGC CAG GTG GAG      2355
Thr Val Lys Gln Ser Ser Val Asp Ile Tyr Phe Arg Arg Gln Val Glu
        685                 690                 695

CTG AGC ACC ATG TAC CGG CAT ATG GAG AAG CAC AAC TAC GAG AGT GCG      2403
Leu Ser Thr Met Tyr Arg His Met Glu Lys His Asn Tyr Glu Ser Ala
    700                 705                 710

GCG GAG GCC ATC CAG GCC GTG AGA GAC AAC AAG CTG CAT GCC TTC ATC      2451
Ala Glu Ala Ile Gln Ala Val Arg Asp Asn Lys Leu His Ala Phe Ile
715                 720                 725                 730

TGG GAC TCG GCG GTG CTG GAG TTC GAG GCC TCG CAG AAG TGC GAC CTG      2499
Trp Asp Ser Ala Val Leu Glu Phe Glu Ala Ser Gln Lys Cys Asp Leu
            735                 740                 745

GTG ACG ACT GGA GAG CTG TTT TTC CGC TCG GGC TTC GGC ATA GGC ATG      2547
Val Thr Thr Gly Glu Leu Phe Phe Arg Ser Gly Phe Gly Ile Gly Met
            750                 755                 760

CGC AAA GAC AGC CCC TGG AAG CAG AAC GTC TCC CTG TCC ATC CTC AAG      2595
Arg Lys Asp Ser Pro Trp Lys Gln Asn Val Ser Leu Ser Ile Leu Lys
        765                 770                 775

TCC CAC GAG AAT GGC TTC ATG GAA GAC CTG GAC AAG ACG TGG GTT CGG      2643
Ser His Glu Asn Gly Phe Met Glu Asp Leu Asp Lys Thr Trp Val Arg
    780                 785                 790

TAT CAG GAA TGT GAC TCG CGC AGC AAC GCC CCT GCG ACC CTT ACT TTT      2691
Tyr Gln Glu Cys Asp Ser Arg Ser Asn Ala Pro Ala Thr Leu Thr Phe
795                 800                 805                 810

GAG AAC ATG GCC GGG GTC TTC ATG CTG GTA GCT GGG GGC ATC GTG GCC      2739
Glu Asn Met Ala Gly Val Phe Met Leu Val Ala Gly Gly Ile Val Ala
            815                 820                 825

GGG ATC TTC CTG ATT TTC ATC GAG ATT GCC TAC AAG CGG CAC AAG GAT      2787
Gly Ile Phe Leu Ile Phe Ile Glu Ile Ala Tyr Lys Arg His Lys Asp
            830                 835                 840

GCT CGC CGG AAG CAG ATG CAG CTG GCC TTT GCC GCC GTT AAC GTG TGG      2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT      2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC      2931
Lys Lys Lys Ala Thr Phe Arg Ala Ile Thr Ser Thr Leu Ala Ser Ser
875                 880                 885                 890

TTC AAG AGG CGT AGG TCC TCC AAA GAC ACG CTG GCT CGG GAC TGT CTT      2979
Phe Lys Arg Arg Arg Ser Ser Lys Asp Thr Leu Ala Arg Asp Cys Leu
            895                 900                 905

CAA CCC TGC CCT GCA CCT TGG GCA CGG GAG AGC GCC ACC CGC CCG CCC      3027
Gln Pro Cys Pro Ala Pro Trp Ala Arg Glu Ser Ala Thr Arg Pro Pro
            910                 915                 920

CCG CCC TCG CTC CGG GTG CGT GAC CGG CCC GCC ACC TTG TAC AGA ACC      3075
Pro Pro Ser Leu Arg Val Arg Asp Arg Pro Ala Thr Leu Tyr Arg Thr
        925                 930                 935

AGC ACT CCC AGG GCC CGA GCG CGT GCC TTC CCC GTG CGC AGC CGC GCT      3123
Ser Thr Pro Arg Ala Arg Ala Arg Ala Phe Pro Val Arg Ser Arg Ala
    940                 945                 950

CTG CCC CTC CGT CCC CAG GGT GCA GGC GCG CAC CGC CCA ACC CCC ACC      3171
Leu Pro Leu Arg Pro Gln Gly Ala Gly Ala His Arg Pro Thr Pro Thr
955                 960                 965                 970

TCC CGG TGT ATG CAG TGG TGATGCCTAA AGGAATGTCA CG                    3211
Ser Arg Cys Met Gln Trp
                975
```

-continued (2) INFORMATION FOR SEQ ID NO:22:

(i) SEQUENCE CHARACTERISTICS:
(A) LENGTH: 976 amino acids
(B) TYPE: amino acid
(D) TOPOLOGY: linear (ii) MOLECULE TYPE: protein (xi) SEQUENCE DESCRIPTION: SEQ ID NO:22:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300

Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
```

-continued

```
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Gly Ser Pro Arg
        435                 440                 445

His Thr Val Pro Gln Cys Cys Tyr Gly Phe Cys Ile Asp Leu Leu Ile
    450                 455                 460

Lys Leu Ala Arg Thr Met Asn Phe Thr Tyr Glu Val His Leu Val Ala
465                 470                 475                 480

Asp Gly Lys Phe Gly Thr Gln Glu Arg Val Asn Asn Ser Asn Lys Lys
                485                 490                 495

Glu Trp Asn Gly Met Met Gly Glu Leu Leu Ser Gly Gln Ala Asp Met
            500                 505                 510

Ile Val Ala Pro Leu Thr Ile Asn Asn Glu Arg Ala Gln Tyr Ile Glu
        515                 520                 525

Phe Ser Lys Pro Phe Lys Tyr Gln Gly Leu Thr Ile Leu Val Lys Lys
    530                 535                 540

Glu Ile Pro Arg Ser Thr Leu Asp Ser Phe Met Gln Pro Phe Gln Ser
545                 550                 555                 560

Thr Leu Trp Leu Leu Val Gly Leu Ser Val His Val Val Ala Val Met
                565                 570                 575

Leu Tyr Leu Leu Asp Arg Phe Ser Pro Phe Gly Arg Phe Lys Val Asn
            580                 585                 590

Ser Glu Glu Glu Glu Glu Asp Ala Leu Thr Leu Ser Ser Ala Met Trp
        595                 600                 605

Phe Ser Trp Gly Val Leu Leu Asn Ser Gly Ile Gly Glu Gly Ala Pro
    610                 615                 620

Arg Ser Phe Ser Ala Arg Ile Leu Gly Met Val Trp Ala Gly Phe Ala
625                 630                 635                 640

Met Ile Ile Val Ala Ser Tyr Thr Ala Asn Leu Ala Ala Phe Leu Val
                645                 650                 655

Leu Asp Arg Pro Glu Glu Arg Ile Thr Gly Ile Asn Asp Pro Arg Leu
            660                 665                 670

Arg Asn Pro Ser Asp Lys Phe Ile Tyr Ala Thr Val Lys Gln Ser Ser
        675                 680                 685

Val Asp Ile Tyr Phe Arg Arg Gln Val Glu Leu Ser Thr Met Tyr Arg
    690                 695                 700

His Met Glu Lys His Asn Tyr Glu Ser Ala Ala Glu Ala Ile Gln Ala
705                 710                 715                 720

Val Arg Asp Asn Lys Leu His Ala Phe Ile Trp Asp Ser Ala Val Leu
                725                 730                 735

Glu Phe Glu Ala Ser Gln Lys Cys Asp Leu Val Thr Thr Gly Glu Leu
            740                 745                 750

Phe Phe Arg Ser Gly Phe Gly Ile Gly Met Arg Lys Asp Ser Pro Trp
        755                 760                 765

Lys Gln Asn Val Ser Leu Ser Ile Leu Lys Ser His Glu Asn Gly Phe
    770                 775                 780
```

-continued

```
Met Glu Asp Leu Asp Lys Thr Trp Val Arg Tyr Gln Glu Cys Asp Ser
785                 790                 795                 800

Arg Ser Asn Ala Pro Ala Thr Leu Thr Phe Glu Asn Met Ala Gly Val
                805                 810                 815

Phe Met Leu Val Ala Gly Gly Ile Val Ala Gly Ile Phe Leu Ile Phe
            820                 825                 830

Ile Glu Ile Ala Tyr Lys Arg His Lys Asp Ala Arg Arg Lys Gln Met
        835                 840                 845

Gln Leu Ala Phe Ala Ala Val Asn Val Trp Arg Lys Asn Leu Gln Asp
    850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Leu Ala Arg Asp Cys Leu Gln Pro Cys Pro Ala Pro
            900                 905                 910

Trp Ala Arg Glu Ser Ala Thr Arg Pro Pro Pro Pro Ser Leu Arg Val
        915                 920                 925

Arg Asp Arg Pro Ala Thr Leu Tyr Arg Thr Ser Thr Pro Arg Ala Arg
    930                 935                 940

Ala Arg Ala Phe Pro Val Arg Ser Arg Ala Leu Pro Leu Arg Pro Gln
945                 950                 955                 960

Gly Ala Gly Ala His Arg Pro Thr Pro Thr Ser Arg Cys Met Gln Trp
                965                 970                 975
```

(2) INFORMATION FOR SEQ ID NO:23:

(i) SEQUENCE CHARACTERISTICS:
(A) LENGTH: 4361 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3141

(xi) SEQUENCE DESCRIPTION: SEQ ID NO:23:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT       435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG       483
```

-continued

```
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC     1059
Thr Val Tyr Arg Ala Ala Ala Met Leu Asn Met Thr Gly Ser Gly Tyr
                255                 260                 265

GTG TGG CTG GTC GGC GAG CGC GAG ATC TCG GGG AAC GCC CTG CGC TAC     1107
Val Trp Leu Val Gly Glu Arg Glu Ile Ser Gly Asn Ala Leu Arg Tyr
            270                 275                 280

GCC CCA GAC GGC ATC CTC GGG CTG CAG CTC ATC AAC GGC AAG AAC GAG     1155
Ala Pro Asp Gly Ile Leu Gly Leu Gln Leu Ile Asn Gly Lys Asn Glu
        285                 290                 295

TCG GCC CAC ATC AGC GAC GCC GTG GGC GTG GTG GCC CAG GCC GTG CAC     1203
Ser Ala His Ile Ser Asp Ala Val Gly Val Val Ala Gln Ala Val His
    300                 305                 310

GAG CTC CTC GAG AAG GAG AAC ATC ACC GAC CCG CCG CGG GGC TGC GTG     1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG     1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT     1347
Met Ser Ser Lys Tyr Ala Asp Gly Val Thr Gly Arg Val Glu Phe Asn
            350                 355                 360

GAG GAT GGG GAC CGG AAG TTC GCC AAC TAC AGC ATC ATG AAC CTG CAG     1395
Glu Asp Gly Asp Arg Lys Phe Ala Asn Tyr Ser Ile Met Asn Leu Gln
        365                 370                 375
```

-continued

```
AAC CGC AAG CTG GTG CAA GTG GGC ATC TAC AAT GGC ACC CAC GTC ATC      1443
Asn Arg Lys Leu Val Gln Val Gly Ile Tyr Asn Gly Thr His Val Ile
    380                 385                 390

CCT AAT GAC AGG AAG ATC ATC TGG CCA GGC GGA GAG ACA GAG AAG CCT      1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG      1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG      1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC      1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG      1683
Gly Pro Asn Asp Thr Ser Pro Gly Ser Pro Arg His Thr Val Pro Gln
    460                 465                 470

TGT TGC TAC GGC TTT TGC ATC GAC CTG CTC ATC AAG CTG GCA CGG ACC      1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC      1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG      1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA      1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC      1923
Thr Ile Asn Asn Glu Arg Ala Gln Tyr Ile Glu Phe Ser Lys Pro Phe
    540                 545                 550

AAG TAC CAG GGC CTG ACT ATT CTG GTC AAG AAG GAG ATT CCC CGG AGC      1971
Lys Tyr Gln Gly Leu Thr Ile Leu Val Lys Lys Glu Ile Pro Arg Ser
555                 560                 565                 570

ACG CTG GAC TCG TTC ATG CAG CCG TTC CAG AGC ACA CTG TGG CTG CTG      2019
Thr Leu Asp Ser Phe Met Gln Pro Phe Gln Ser Thr Leu Trp Leu Leu
                575                 580                 585

GTG GGG CTG TCG GTG CAC GTG GTG GCC GTG ATG CTG TAC CTG CTG GAC      2067
Val Gly Leu Ser Val His Val Val Ala Val Met Leu Tyr Leu Leu Asp
            590                 595                 600

CGC TTC AGC CCC TTC GGC CGG TTC AAG GTG AAC AGC GAG GAG GAG GAG      2115
Arg Phe Ser Pro Phe Gly Arg Phe Lys Val Asn Ser Glu Glu Glu Glu
        605                 610                 615

GAG GAC GCA CTG ACC CTG TCC TCG GCC ATG TGG TTC TCC TGG GGC GTC      2163
Glu Asp Ala Leu Thr Leu Ser Ser Ala Met Trp Phe Ser Trp Gly Val
    620                 625                 630

CTG CTC AAC TCC GGC ATC GGG GAA GGC GCC CCC AGA AGC TTC TCA GCG      2211
Leu Leu Asn Ser Gly Ile Gly Glu Gly Ala Pro Arg Ser Phe Ser Ala
635                 640                 645                 650

CGC ATC CTG GGC ATG GTG TGG GCC GGC TTT GCC ATG ATC ATC GTG GCC      2259
Arg Ile Leu Gly Met Val Trp Ala Gly Phe Ala Met Ile Ile Val Ala
                655                 660                 665

TCC TAC ACC GCC AAC CTG GCG GCC TTC CTG GTG CTG GAC CGG CCG GAG      2307
Ser Tyr Thr Ala Asn Leu Ala Ala Phe Leu Val Leu Asp Arg Pro Glu
            670                 675                 680

GAG CGC ATC ACG GGC ATC AAC GAC CCT CGG CTG AGG AAC CCC TCG GAC      2355
Glu Arg Ile Thr Gly Ile Asn Asp Pro Arg Leu Arg Asn Pro Ser Asp
        685                 690                 695
```

-continued

```
AAG TTT ATC TAC GCC ACG GTG AAG CAG AGC TCC GTG GAT ATC TAC TTC      2403
Lys Phe Ile Tyr Ala Thr Val Lys Gln Ser Ser Val Asp Ile Tyr Phe
    700                 705                 710

CGG CGC CAG GTG GAG CTG AGC ACC ATG TAC CGG CAT ATG GAG AAG CAC      2451
Arg Arg Gln Val Glu Leu Ser Thr Met Tyr Arg His Met Glu Lys His
715                 720                 725                 730

AAC TAC GAG AGT GCG GCG GAG GCC ATC CAG GCC GTG AGA GAC AAC AAG      2499
Asn Tyr Glu Ser Ala Ala Glu Ala Ile Gln Ala Val Arg Asp Asn Lys
                735                 740                 745

CTG CAT GCC TTC ATC TGG GAC TCG GCG GTG CTG GAG TTC GAG GCC TCG      2547
Leu His Ala Phe Ile Trp Asp Ser Ala Val Leu Glu Phe Glu Ala Ser
            750                 755                 760

CAG AAG TGC GAC CTG GTG ACG ACT GGA GAG CTG TTT TTC CGC TCG GGC      2595
Gln Lys Cys Asp Leu Val Thr Thr Gly Glu Leu Phe Phe Arg Ser Gly
        765                 770                 775

TTC GGC ATA GGC ATG CGC AAA GAC AGC CCC TGG AAG CAG AAC GTC TCC      2643
Phe Gly Ile Gly Met Arg Lys Asp Ser Pro Trp Lys Gln Asn Val Ser
    780                 785                 790

CTG TCC ATC CTC AAG TCC CAC GAG AAT GGC TTC ATG GAA GAC CTG GAC      2691
Leu Ser Ile Leu Lys Ser His Glu Asn Gly Phe Met Glu Asp Leu Asp
795                 800                 805                 810

AAG ACG TGG GTT CGG TAT CAG GAA TGT GAC TCG CGC AGC AAC GCC CCT      2739
Lys Thr Trp Val Arg Tyr Gln Glu Cys Asp Ser Arg Ser Asn Ala Pro
                815                 820                 825

GCG ACC CTT ACT TTT GAG AAC ATG GCC GGG GTC TTC ATG CTG GTA GCT      2787
Ala Thr Leu Thr Phe Glu Asn Met Ala Gly Val Phe Met Leu Val Ala
            830                 835                 840

GGG GGC ATC GTG GCC GGG ATC TTC CTG ATT TTC ATC GAG ATT GCC TAC      2835
Gly Gly Ile Val Ala Gly Ile Phe Leu Ile Phe Ile Glu Ile Ala Tyr
        845                 850                 855

AAG CGG CAC AAG GAT GCT CGC CGG AAG CAG ATG CAG CTG GCC TTT GCC      2883
Lys Arg His Lys Asp Ala Arg Arg Lys Gln Met Gln Leu Ala Phe Ala
    860                 865                 870

GCC GTT AAC GTG TGG CGG AAG AAC CTG CAG GAT AGA AAG AGT GGT AGA      2931
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC      2979
Ala Glu Pro Asp Pro Lys Lys Lys Ala Thr Phe Arg Ala Ile Thr Ser
                895                 900                 905

ACC CTG GCT TCC AGC TTC AAG AGG CGT AGG TCC TCC AAA GAC ACG AGC      3027
Thr Leu Ala Ser Ser Phe Lys Arg Arg Arg Ser Ser Lys Asp Thr Ser
            910                 915                 920

ACC GGG GGT GGA CGC GGT GCT TTG CAA AAC CAA AAA GAC ACA GTG CTG      3075
Thr Gly Gly Gly Arg Gly Ala Leu Gln Asn Gln Lys Asp Thr Val Leu
        925                 930                 935

CCG CGA CGC GCT ATT GAG AGG GAG GAG GGC CAG CTG CAG CTG TGT TCC      3123
Pro Arg Arg Ala Ile Glu Arg Glu Glu Gly Gln Leu Gln Leu Cys Ser
    940                 945                 950

CGT CAT AGG GAG AGC TGAGACTCCC CGCCCGCCCT CCTCTGCCCC CTCCCCCGCA      3178
Arg His Arg Glu Ser
955                 960

GACAGACAGA CAGACGGACG GGACAGCGGC CCGGCCCACG CAGAGCCCCG GAGCACCACG    3238

GGGTCGGGGG AGGAGCACCC CCAGCCTCCC CCAGGCTGCG CCTGCCCGCC CGCCGGTTGG    3298

CCGGCTGGCC GGTCCACCCC GTCCCGGCCC CGCGCGTGCC CCCAGCGTGG GGCTAACGGG    3358

CGCCTTGTCT GTGTATTTCT ATTTTGCAGC AGTACCATCC CACTGATATC ACGGGCCCGC    3418

TCAACCTCTC AGATCCCTCG GTCAGCACCG TGGTGTGAGG CCCCCGGAGG CGCCCACCTG    3478
```

-continued

```
CCCAGTTAGC CCGGCCAAGG ACACTGATGG GTCCTGCTGC TCGGGAAGGC CTGAGGGAAG   3538

CCCACCCGCC CCAGAGACTG CCCACCCTGG GCCTCCCGTC CGTCCGCCCG CCCACCCCGC   3598

TGCCTGGCGG GCAGCCCCTG CTGGACCAAG GTGCGGACCG GAGCGGCTGA GGACGGGGCA   3658

GAGCTGAGTC GGCTGGGCAG GGCCGCAGGG CGCTCCGGCA GAGGCAGGCC CCTGGGGTCT   3718

CTGAGCAGTG GGGAGCGGGG GCTAACTGCC CCCAGGCGGA GGGGCTTGGA GCAGAGACGG   3778

CAGCCCCATC CTTCCCGCAG CACCAGCCTG AGCCACAGTG GGGCCCATGG CCCCAGCTGG   3838

CTGGGTCGCC CCTCCTCGGG CGCCTGCGCT CCTCTGCAGC CTGAGCTCCA CCCTCCCCTC   3898

TTCTTGCGGC ACCGCCCACC AAACACCCCG TCTGCCCCTT GACGCCACAC GCCGGGGCTG   3958

GCGCTGCCCT CCCCCACGGC CGTCCCTGAC TTCCCAGCTG GCAGCGCCTC CCGCCGCCTC   4018

GGGCCGCCTC CTCCAGAATC GAGAGGGCTG AGCCCCTCCT CTCCTCGTCC GGCCTGCAGC   4078

ACAGAAGGGG GCCTCCCCGG GGGTCCCCGG ACGCTGGCTC GGGACTGTCT TCAACCCTGC   4138

CCTGCACCTT GGGCACGGGA GAGCGCCACC CGCCCGCCCC CGCCCTCGCT CCGGGTGCGT   4198

GACCGGCCCG CCACCTTGTA CAGAACCAGC ACTCCCAGGG CCCGAGCGCG TGCCTTCCCC   4258

GTGCGCAGCC GCGCTCTGCC CCTCCGTCCC CAGGGTGCAG GCGCGCACCG CCCAACCCCC   4318

ACCTCCCGGT GTATGCAGTG GTGATGCCTA AAGGAATGTC ACG                     4361
```

(2) INFORMATION FOR SEQ ID NO:24:

(i) SEQUENCE CHARACTERISTICS:
(A) LENGTH: 959 amino acids
(B) TYPE: amino acid
(D) TOPOLOGY: linear (ii) MOLECULE TYPE: protein (xi) SEQUENCE DESCRIPTION: SEQ ID NO:24:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
```

-continued

```
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Glu Asp Ala Leu Thr Leu
    610                 615                 620
```

-continued

```
Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
    690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Asp Arg Lys Ser Gly Arg Ala Glu Pro Asp Pro Lys
                885                 890                 895

Lys Lys Ala Thr Phe Arg Ala Ile Thr Ser Thr Leu Ala Ser Ser Phe
            900                 905                 910

Lys Arg Arg Arg Ser Ser Lys Asp Thr Ser Thr Gly Gly Gly Arg Gly
        915                 920                 925

Ala Leu Gln Asn Gln Lys Asp Thr Val Leu Pro Arg Arg Ala Ile Glu
    930                 935                 940

Arg Glu Glu Gly Gln Leu Gln Leu Cys Ser Arg His Arg Glu Ser
945                 950                 955
```

(2) INFORMATION FOR SEQ ID NO:25:

(i) SEQUENCE CHARACTERISTICS:
(A) LENGTH: 4157 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..2937

-continued (xi) SEQUENCE DESCRIPTION: SEQ ID NO:25:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC     1059
Thr Val Tyr Arg Ala Ala Ala Met Leu Asn Met Thr Gly Asn Thr Asn
                255                 260                 265

ATC TGG AAG ACC GGG CCG CTC TTC AAG AGA GTG CTG ATG TCT TCC AAG     1107
```

-continued

```
Ile Trp Lys Thr Gly Pro Leu Phe Lys Arg Val Leu Met Ser Ser Lys
            270                 275                 280

TAT GCG GAT GGG GTG ACT GGT CGC GTG GAG TTC AAT GAG GAT GGG GAC      1155
Tyr Ala Asp Gly Val Thr Gly Arg Val Glu Phe Asn Glu Asp Gly Asp
        285                 290                 295

CGG AAG TTC GCC AAC TAC AGC ATC ATG AAC CTG CAG AAC CGC AAG CTG      1203
Arg Lys Phe Ala Asn Tyr Ser Ile Met Asn Leu Gln Asn Arg Lys Leu
    300                 305                 310

GTG CAA GTG GGC ATC TAC AAT GGC ACC CAC GTC ATC CCT AAT GAC AGG      1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG      1299
Lys Ile Ile Trp Pro Gly Gly Glu Thr Glu Lys Pro Arg Gly Tyr Gln
                335                 340                 345

ATG TCC ACC AGA CTG AAG ATT GTG ACG ATC CAC CAG GAG CCC TTC GTG      1347
Met Ser Thr Arg Leu Lys Ile Val Thr Ile His Gln Glu Pro Phe Val
            350                 355                 360

TAC GTC AAG CCC ACG CTG AGT GAT GGG ACA TGC AAG GAG GAG TTC ACA      1395
Tyr Val Lys Pro Thr Leu Ser Asp Gly Thr Cys Lys Glu Glu Phe Thr
        365                 370                 375

GTC AAC GGC GAC CCA GTC AAG AAG GTG ATC TGC ACC GGG CCC AAC GAC      1443
Val Asn Gly Asp Pro Val Lys Lys Val Ile Cys Thr Gly Pro Asn Asp
    380                 385                 390

ACG TCG CCG GGC AGC CCC CGC CAC ACG GTG CCT CAG TGT TGC TAC GGC      1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC      1539
Phe Cys Ile Asp Leu Leu Ile Lys Leu Ala Arg Thr Met Asn Phe Thr
                415                 420                 425

TAC GAG GTG CAC CTG GTG GCA GAT GGC AAG TTC GGC ACA CAG GAG CGG      1587
Tyr Glu Val His Leu Val Ala Asp Gly Lys Phe Gly Thr Gln Glu Arg
            430                 435                 440

GTG AAC AAC AGC AAC AAG AAG GAG TGG AAT GGG ATG ATG GGC GAG CTG      1635
Val Asn Asn Ser Asn Lys Lys Glu Trp Asn Gly Met Met Gly Glu Leu
        445                 450                 455

CTC AGC GGG CAG GCA GAC ATG ATC GTG GCG CCG CTA ACC ATA AAC AAC      1683
Leu Ser Gly Gln Ala Asp Met Ile Val Ala Pro Leu Thr Ile Asn Asn
    460                 465                 470

GAG CGC GCG CAG TAC ATC GAG TTT TCC AAG CCC TTC AAG TAC CAG GGC      1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG      1779
Leu Thr Ile Leu Val Lys Lys Glu Ile Pro Arg Ser Thr Leu Asp Ser
                495                 500                 505

TTC ATG CAG CCG TTC CAG AGC ACA CTG TGG CTG CTG GTG GGG CTG TCG      1827
Phe Met Gln Pro Phe Gln Ser Thr Leu Trp Leu Leu Val Gly Leu Ser
            510                 515                 520

GTG CAC GTG GTG GCC GTG ATG CTG TAC CTG CTG GAC CGC TTC AGC CCC      1875
Val His Val Val Ala Val Met Leu Tyr Leu Leu Asp Arg Phe Ser Pro
        525                 530                 535

TTC GGC CGG TTC AAG GTG AAC AGC GAG GAG GAG GAG GAG GAC GCA CTG      1923
Phe Gly Arg Phe Lys Val Asn Ser Glu Glu Glu Glu Glu Asp Ala Leu
    540                 545                 550

ACC CTG TCC TCG GCC ATG TGG TTC TCC TGG GGC GTC CTG CTC AAC TCC      1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC      2019
Gly Ile Gly Glu Gly Ala Pro Arg Ser Phe Ser Ala Arg Ile Leu Gly
                575                 580                 585
```

-continued

```
ATG GTG TGG GCC GGC TTT GCC ATG ATC ATC GTG GCC TCC TAC ACC GCC      2067
Met Val Trp Ala Gly Phe Ala Met Ile Ile Val Ala Ser Tyr Thr Ala
            590                 595                 600

AAC CTG GCG GCC TTC CTG GTG CTG GAC CGG CCG GAG GAG CGC ATC ACG      2115
Asn Leu Ala Ala Phe Leu Val Leu Asp Arg Pro Glu Glu Arg Ile Thr
        605                 610                 615

GGC ATC AAC GAC CCT CGG CTG AGG AAC CCC TCG GAC AAG TTT ATC TAC      2163
Gly Ile Asn Asp Pro Arg Leu Arg Asn Pro Ser Asp Lys Phe Ile Tyr
    620                 625                 630

GCC ACG GTG AAG CAG AGC TCC GTG GAT ATC TAC TTC CGG CGC CAG GTG      2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT      2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC      2307
Ala Ala Glu Ala Ile Gln Ala Val Arg Asp Asn Lys Leu His Ala Phe
            670                 675                 680

ATC TGG GAC TCG GCG GTG CTG GAG TTC GAG GCC TCG CAG AAG TGC GAC      2355
Ile Trp Asp Ser Ala Val Leu Glu Phe Glu Ala Ser Gln Lys Cys Asp
        685                 690                 695

CTG GTG ACG ACT GGA GAG CTG TTT TTC CGC TCG GGC TTC GGC ATA GGC      2403
Leu Val Thr Thr Gly Glu Leu Phe Phe Arg Ser Gly Phe Gly Ile Gly
    700                 705                 710

ATG CGC AAA GAC AGC CCC TGG AAG CAG AAC GTC TCC CTG TCC ATC CTC      2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT      2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT      2547
Arg Tyr Gln Glu Cys Asp Ser Arg Ser Asn Ala Pro Ala Thr Leu Thr
            750                 755                 760

TTT GAG AAC ATG GCC GGG GTC TTC ATG CTG GTA GCT GGG GGC ATC GTG      2595
Phe Glu Asn Met Ala Gly Val Phe Met Leu Val Ala Gly Gly Ile Val
        765                 770                 775

GCC GGG ATC TTC CTG ATT TTC ATC GAG ATT GCC TAC AAG CGG CAC AAG      2643
Ala Gly Ile Phe Leu Ile Phe Ile Glu Ile Ala Tyr Lys Arg His Lys
    780                 785                 790

GAT GCT CGC CGG AAG CAG ATG CAG CTG GCC TTT GCC GCC GTT AAC GTG      2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC      2739
Trp Arg Lys Asn Leu Gln Asp Arg Lys Ser Gly Arg Ala Glu Pro Asp
                815                 820                 825

CCT AAA AAG AAA GCC ACA TTT AGG GCT ATC ACC TCC ACC CTG GCT TCC      2787
Pro Lys Lys Lys Ala Thr Phe Arg Ala Ile Thr Ser Thr Leu Ala Ser
            830                 835                 840

AGC TTC AAG AGG CGT AGG TCC TCC AAA GAC ACG AGC ACC GGG GGT GGA      2835
Ser Phe Lys Arg Arg Arg Ser Ser Lys Asp Thr Ser Thr Gly Gly Gly
        845                 850                 855

CGC GGT GCT TTG CAA AAC CAA AAA GAC ACA GTG CTG CCG CGA CGC GCT      2883
Arg Gly Ala Leu Gln Asn Gln Lys Asp Thr Val Leu Pro Arg Arg Ala
    860                 865                 870

ATT GAG AGG GAG GAG GGC CAG CTG CAG CTG TGT TCC CGT CAT AGG GAG      2931
Ile Glu Arg Glu Glu Gly Gln Leu Gln Leu Cys Ser Arg His Arg Glu
875                 880                 885                 890

AGC TGAGACTCCC CGCCCGCCCT CCTCTGCCCC CTCCCCCGCA GACAGACAGA           2984
Ser
```

-continued

```
CAGACGGACG GGACAGCGGC CCGGCCCACG CAGAGCCCCG GAGCACCACG GGGTCGGGGG   3044

AGGAGCACCC CCAGCCTCCC CCAGGCTGCG CCTGCCCGCC CGCCGGTTGG CCGGCTGGCC   3104

GGTCCACCCC GTCCCGGCCC CGCGCGTGCC CCCAGCGTGG GGCTAACGGG CGCCTTGTCT   3164

GTGTATTTCT ATTTTGCAGC AGTACCATCC CACTGATATC ACGGGCCCGC TCAACCTCTC   3224

AGATCCCTCG GTCAGCACCG TGGTGTGAGG CCCCCGGAGG CGCCCACCTG CCCAGTTAGC   3284

CCGGCCAAGG ACACTGATGG GTCCTGCTGC TCGGGAAGGC CTGAGGGAAG CCCACCCGCC   3344

CCAGAGACTG CCCACCCTGG GCCTCCCGTC CGTCCGCCCG CCCACCCCGC TGCCTGGCGG   3404

GCAGCCCCTG CTGGACCAAG GTGCGGACCG GAGCGGCTGA GGACGGGGCA GAGCTGAGTC   3464

GGCTGGGCAG GGCCGCAGGG CGCTCCGGCA GAGGCAGGCC CCTGGGGTCT CTGAGCAGTG   3524

GGGAGCGGGG GCTAACTGCC CCCAGGCGGA GGGGCTTGGA GCAGAGACGG CAGCCCCATC   3584

CTTCCCGCAG CACCAGCCTG AGCCACAGTG GGGCCCATGG CCCCAGCTGG CTGGGTCGCC   3644

CCTCCTCGGG CGCCTGCGCT CCTCTGCAGC CTGAGCTCCA CCCTCCCCTC TTCTTGCGGC   3704

ACCGCCCACC AAACACCCCG TCTGCCCCTT GACGCCACAC GCCGGGGCTG GCGCTGCCCT   3764

CCCCCACGGC CGTCCCTGAC TTCCCAGCTG GCAGCGCCTC CCGCCGCCTC GGGCCGCCTC   3824

CTCCAGAATC GAGAGGGCTG AGCCCCTCCT CTCCTCGTCC GGCCTGCAGC ACAGAAGGGG   3884

GCCTCCCCGG GGGTCCCCGG ACGCTGGCTC GGGACTGTCT TCAACCCTGC CCTGCACCTT   3944

GGGCACGGGA GAGCGCCACC CGCCCGCCCC CGCCCTCGCT CCGGGTGCGT GACCGGCCCG   4004

CCACCTTGTA CAGAACCAGC ACTCCCAGGG CCCGAGCGCG TGCCTTCCCC GTGCGCAGCC   4064

GCGCTCTGCC CCTCCGTCCC CAGGGTGCAG GCGCGCACCG CCCAACCCCC ACCTCCCGGT   4124

GTATGCAGTG GTGATGCCTA AAGGAATGTC ACG                                4157
```

(2) INFORMATION FOR SEQ ID NO:26:

(i) SEQUENCE CHARACTERISTICS:
(A) LENGTH: 891 amino acids
(B) TYPE: amino acid
(D) TOPOLOGY: linear (ii) MOLECULE TYPE: protein (xi) SEQUENCE DESCRIPTION: SEQ ID NO:26:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140
```

-continued

```
Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Asn Thr Asn Ile Trp Lys Thr Gly Pro
            260                 265                 270

Leu Phe Lys Arg Val Leu Met Ser Ser Lys Tyr Ala Asp Gly Val Thr
        275                 280                 285

Gly Arg Val Glu Phe Asn Glu Asp Gly Asp Arg Lys Phe Ala Asn Tyr
    290                 295                 300

Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                325                 330                 335

Gly Glu Thr Glu Lys Pro Arg Gly Tyr Gln Met Ser Thr Arg Leu Lys
            340                 345                 350

Ile Val Thr Ile His Gln Glu Pro Phe Val Tyr Val Lys Pro Thr Leu
        355                 360                 365

Ser Asp Gly Thr Cys Lys Glu Glu Phe Thr Val Asn Gly Asp Pro Val
    370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                405                 410                 415

Ile Lys Leu Ala Arg Thr Met Asn Phe Thr Tyr Glu Val His Leu Val
            420                 425                 430

Ala Asp Gly Lys Phe Gly Thr Gln Glu Arg Val Asn Asn Ser Asn Lys
        435                 440                 445

Lys Glu Trp Asn Gly Met Met Gly Glu Leu Leu Ser Gly Gln Ala Asp
    450                 455                 460

Met Ile Val Ala Pro Leu Thr Ile Asn Asn Glu Arg Ala Gln Tyr Ile
465                 470                 475                 480

Glu Phe Ser Lys Pro Phe Lys Tyr Gln Gly Leu Thr Ile Leu Val Lys
                485                 490                 495

Lys Glu Ile Pro Arg Ser Thr Leu Asp Ser Phe Met Gln Pro Phe Gln
            500                 505                 510

Ser Thr Leu Trp Leu Leu Val Gly Leu Ser Val His Val Val Ala Val
        515                 520                 525

Met Leu Tyr Leu Leu Asp Arg Phe Ser Pro Phe Gly Arg Phe Lys Val
    530                 535                 540

Asn Ser Glu Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
```

-continued

```
                565                 570                 575

Pro Arg Ser Phe Ser Ala Arg Ile Leu Gly Met Val Trp Ala Gly Phe
            580                 585                 590

Ala Met Ile Ile Val Ala Ser Tyr Thr Ala Asn Leu Ala Ala Phe Leu
        595                 600                 605

Val Leu Asp Arg Pro Glu Glu Arg Ile Thr Gly Ile Asn Asp Pro Arg
    610                 615                 620

Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
                645                 650                 655

Arg His Met Glu Lys His Asn Tyr Glu Ser Ala Ala Glu Ala Ile Gln
            660                 665                 670

Ala Val Arg Asp Asn Lys Leu His Ala Phe Ile Trp Asp Ser Ala Val
        675                 680                 685

Leu Glu Phe Glu Ala Ser Gln Lys Cys Asp Leu Val Thr Thr Gly Glu
    690                 695                 700

Leu Phe Phe Arg Ser Gly Phe Gly Ile Gly Met Arg Lys Asp Ser Pro
705                 710                 715                 720

Trp Lys Gln Asn Val Ser Leu Ser Ile Leu Lys Ser His Glu Asn Gly
                725                 730                 735

Phe Met Glu Asp Leu Asp Lys Thr Trp Val Arg Tyr Gln Glu Cys Asp
            740                 745                 750

Ser Arg Ser Asn Ala Pro Ala Thr Leu Thr Phe Glu Asn Met Ala Gly
        755                 760                 765

Val Phe Met Leu Val Ala Gly Gly Ile Val Ala Gly Ile Phe Leu Ile
    770                 775                 780

Phe Ile Glu Ile Ala Tyr Lys Arg His Lys Asp Ala Arg Arg Lys Gln
785                 790                 795                 800

Met Gln Leu Ala Phe Ala Ala Val Asn Val Trp Arg Lys Asn Leu Gln
                805                 810                 815

Asp Arg Lys Ser Gly Arg Ala Glu Pro Asp Pro Lys Lys Lys Ala Thr
            820                 825                 830

Phe Arg Ala Ile Thr Ser Thr Leu Ala Ser Ser Phe Lys Arg Arg Arg
        835                 840                 845

Ser Ser Lys Asp Thr Ser Thr Gly Gly Gly Arg Gly Ala Leu Gln Asn
    850                 855                 860

Gln Lys Asp Thr Val Leu Pro Arg Arg Ala Ile Glu Arg Glu Glu Gly
865                 870                 875                 880

Gln Leu Gln Leu Cys Ser Arg His Arg Glu Ser
                885                 890
```

(2) INFORMATION FOR SEQ ID NO:27:

(i) SEQUENCE CHARACTERISTICS:
- (A) LENGTH: 3794 base pairs
- (B) TYPE: nucleic acid
- (C) STRANDEDNESS: both
- (D) TOPOLOGY: both (ii) MOLECULE TYPE: cDNA (ix) FEATURE:
- (A) NAME/KEY: CDS
- (B) LOCATION: 262..2889

(xi) SEQUENCE DESCRIPTION: SEQ ID NO:27:

-continued

```
CAAGCCGGGC GTTCGGAGCT GTGCCCGGCC CCGCTTCAGC ACCGCGGACA GCGCCGGCCG     60

CGTGGGGCTG AGCGCCGAGC CCCCGCGCAC GCTTCAGCCC CCCTTCCCTC GGCCGACGTC    120

CCGGGACCGC CGCTCCGGGG GAGACGTGGC GTCCGCAGCC CGCGGGGCCG GGCGAGCGCA    180

GGACGGCCCG GAAGCCCCGC GGGGGATGCG CCGAGGGCCC CGCGTTCGCG CCGCGCAGAG    240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC     1059
Thr Val Tyr Arg Ala Ala Ala Met Leu Asn Met Thr Gly Asn Thr Asn
                255                 260                 265

ATC TGG AAG ACC GGG CCG CTC TTC AAG AGA GTG CTG ATG TCT TCC AAG     1107
Ile Trp Lys Thr Gly Pro Leu Phe Lys Arg Val Leu Met Ser Ser Lys
            270                 275                 280
```

-continued

```
TAT GCG GAT GGG GTG ACT GGT CGC GTG GAG TTC AAT GAG GAT GGG GAC      1155
Tyr Ala Asp Gly Val Thr Gly Arg Val Glu Phe Asn Glu Asp Gly Asp
        285                 290                 295

CGG AAG TTC GCC AAC TAC AGC ATC ATG AAC CTG CAG AAC CGC AAG CTG      1203
Arg Lys Phe Ala Asn Tyr Ser Ile Met Asn Leu Gln Asn Arg Lys Leu
    300                 305                 310

GTG CAA GTG GGC ATC TAC AAT GGC ACC CAC GTC ATC CCT AAT GAC AGG      1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG      1299
Lys Ile Ile Trp Pro Gly Gly Glu Thr Glu Lys Pro Arg Gly Tyr Gln
                335                 340                 345

ATG TCC ACC AGA CTG AAG ATT GTG ACG ATC CAC CAG GAG CCC TTC GTG      1347
Met Ser Thr Arg Leu Lys Ile Val Thr Ile His Gln Glu Pro Phe Val
            350                 355                 360

TAC GTC AAG CCC ACG CTG AGT GAT GGG ACA TGC AAG GAG GAG TTC ACA      1395
Tyr Val Lys Pro Thr Leu Ser Asp Gly Thr Cys Lys Glu Glu Phe Thr
        365                 370                 375

GTC AAC GGC GAC CCA GTC AAG AAG GTG ATC TGC ACC GGG CCC AAC GAC      1443
Val Asn Gly Asp Pro Val Lys Lys Val Ile Cys Thr Gly Pro Asn Asp
    380                 385                 390

ACG TCG CCG GGC AGC CCC CGC CAC ACG GTG CCT CAG TGT TGC TAC GGC      1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC      1539
Phe Cys Ile Asp Leu Leu Ile Lys Leu Ala Arg Thr Met Asn Phe Thr
                415                 420                 425

TAC GAG GTG CAC CTG GTG GCA GAT GGC AAG TTC GGC ACA CAG GAG CGG      1587
Tyr Glu Val His Leu Val Ala Asp Gly Lys Phe Gly Thr Gln Glu Arg
            430                 435                 440

GTG AAC AAC AGC AAC AAG AAG GAG TGG AAT GGG ATG ATG GGC GAG CTG      1635
Val Asn Asn Ser Asn Lys Lys Glu Trp Asn Gly Met Met Gly Glu Leu
        445                 450                 455

CTC AGC GGG CAG GCA GAC ATG ATC GTG GCG CCG CTA ACC ATA AAC AAC      1683
Leu Ser Gly Gln Ala Asp Met Ile Val Ala Pro Leu Thr Ile Asn Asn
    460                 465                 470

GAG CGC GCG CAG TAC ATC GAG TTT TCC AAG CCC TTC AAG TAC CAG GGC      1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG      1779
Leu Thr Ile Leu Val Lys Lys Glu Ile Pro Arg Ser Thr Leu Asp Ser
                495                 500                 505

TTC ATG CAG CCG TTC CAG AGC ACA CTG TGG CTG CTG GTG GGG CTG TCG      1827
Phe Met Gln Pro Phe Gln Ser Thr Leu Trp Leu Leu Val Gly Leu Ser
            510                 515                 520

GTG CAC GTG GTG GCC GTG ATG CTG TAC CTG CTG GAC CGC TTC AGC CCC      1875
Val His Val Val Ala Val Met Leu Tyr Leu Leu Asp Arg Phe Ser Pro
        525                 530                 535

TTC GGC CGG TTC AAG GTG AAC AGC GAG GAG GAG GAG GAG GAC GCA CTG      1923
Phe Gly Arg Phe Lys Val Asn Ser Glu Glu Glu Glu Glu Asp Ala Leu
    540                 545                 550

ACC CTG TCC TCG GCC ATG TGG TTC TCC TGG GGC GTC CTG CTC AAC TCC      1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC      2019
Gly Ile Gly Glu Gly Ala Pro Arg Ser Phe Ser Ala Arg Ile Leu Gly
                575                 580                 585

ATG GTG TGG GCC GGC TTT GCC ATG ATC ATC GTG GCC TCC TAC ACC GCC      2067
Met Val Trp Ala Gly Phe Ala Met Ile Ile Val Ala Ser Tyr Thr Ala
```

-continued

```
            590                 595                 600

AAC CTG GCG GCC TTC CTG GTG CTG GAC CGG CCG GAG GAG CGC ATC ACG     2115
Asn Leu Ala Ala Phe Leu Val Leu Asp Arg Pro Glu Glu Arg Ile Thr
        605                 610                 615

GGC ATC AAC GAC CCT CGG CTG AGG AAC CCC TCG GAC AAG TTT ATC TAC     2163
Gly Ile Asn Asp Pro Arg Leu Arg Asn Pro Ser Asp Lys Phe Ile Tyr
    620                 625                 630

GCC ACG GTG AAG CAG AGC TCC GTG GAT ATC TAC TTC CGG CGC CAG GTG     2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT     2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC     2307
Ala Ala Glu Ala Ile Gln Ala Val Arg Asp Asn Lys Leu His Ala Phe
            670                 675                 680

ATC TGG GAC TCG GCG GTG CTG GAG TTC GAG GCC TCG CAG AAG TGC GAC     2355
Ile Trp Asp Ser Ala Val Leu Glu Phe Glu Ala Ser Gln Lys Cys Asp
        685                 690                 695

CTG GTG ACG ACT GGA GAG CTG TTT TTC CGC TCG GGC TTC GGC ATA GGC     2403
Leu Val Thr Thr Gly Glu Leu Phe Phe Arg Ser Gly Phe Gly Ile Gly
    700                 705                 710

ATG CGC AAA GAC AGC CCC TGG AAG CAG AAC GTC TCC CTG TCC ATC CTC     2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT     2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT     2547
Arg Tyr Gln Glu Cys Asp Ser Arg Ser Asn Ala Pro Ala Thr Leu Thr
            750                 755                 760

TTT GAG AAC ATG GCC GGG GTC TTC ATG CTG GTA GCT GGG GGC ATC GTG     2595
Phe Glu Asn Met Ala Gly Val Phe Met Leu Val Ala Gly Gly Ile Val
        765                 770                 775

GCC GGG ATC TTC CTG ATT TTC ATC GAG ATT GCC TAC AAG CGG CAC AAG     2643
Ala Gly Ile Phe Leu Ile Phe Ile Glu Ile Ala Tyr Lys Arg His Lys
    780                 785                 790

GAT GCT CGC CGG AAG CAG ATG CAG CTG GCC TTT GCC GCC GTT AAC GTG     2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC     2739
Trp Arg Lys Asn Leu Gln Asp Arg Lys Ser Gly Arg Ala Glu Pro Asp
                815                 820                 825

CCT AAA AAG AAA GCC ACA TTT AGG GCT ATC ACC TCC ACC CTG GCT TCC     2787
Pro Lys Lys Lys Ala Thr Phe Arg Ala Ile Thr Ser Thr Leu Ala Ser
            830                 835                 840

AGC TTC AAG AGG CGT AGG TCC TCC AAA GAC ACG CAG TAC CAT CCC ACT     2835
Ser Phe Lys Arg Arg Arg Ser Ser Lys Asp Thr Gln Tyr His Pro Thr
        845                 850                 855

GAT ATC ACG GGC CCG CTC AAC CTC TCA GAT CCC TCG GTC AGC ACC GTG     2883
Asp Ile Thr Gly Pro Leu Asn Leu Ser Asp Pro Ser Val Ser Thr Val
    860                 865                 870

GTG TGAGGCCCCC GGAGGCGCCC ACCTGCCCAG TTAGCCCGGC CAAGGACACT          2936
Val
875

GATGGGTCCT GCTGCTCGGG AAGGCCTGAG GGAAGCCCAC CCGCCCCAGA GACTGCCCAC   2996

CCTGGGCCTC CCGTCCGTCC GCCCGCCCAC CCCGCTGCCT GGCGGGCAGC CCCTGCTGGA   3056

CCAAGGTGCG GACCGGAGCG GCTGAGGACG GGCAGAGCT GAGTCGGCTG GGCAGGGCCG    3116
```

-continued

```
CAGGGCGCTC CGGCAGAGGC AGGCCCCTGG GGTCTCTGAG CAGTGGGGAG CGGGGGCTAA   3176

CTGCCCCCAG GCGGAGGGGC TTGGAGCAGA GACGGCAGCC CCATCCTTCC CGCAGCACCA   3236

GCCTGAGCCA CAGTGGGGCC CATGGCCCCA GCTGGCTGGG TCGCCCCTCC TCGGGCGCCT   3296

GCGCTCCTCT GCAGCCTGAG CTCCACCCTC CCCTCTTCTT GCGGCACCGC CCACCAAACA   3356

CCCCGTCTGC CCCTTGACGC CACACGCCGG GGCTGGCGCT GCCCTCCCCC ACGGCCGTCC   3416

CTGACTTCCC AGCTGGCAGC GCCTCCCGCC GCCTCGGGCC GCCTCCTCCA GAATCGAGAG   3476

GGCTGAGCCC CTCCTCTCCT CGTCCGGCCT GCAGCACAGA AGGGGGCCTC CCCGGGGGTC   3536

CCCGGACGCT GGCTCGGGAC TGTCTTCAAC CCTGCCCTGC ACCTTGGGCA CGGGAGAGCG   3596

CCACCCGCCC GCCCCCGCCC TCGCTCCGGG TGCGTGACCG GCCCGCCACC TTGTACAGAA   3656

CCAGCACTCC CAGGGCCCGA GCGCGTGCCT TCCCCGTGCG CAGCCGCGCT CTGCCCCTCC   3716

GTCCCCAGGG TGCAGGCGCG CACCGCCCAA CCCCCACCTC CCGGTGTATG CAGTGGTGAT   3776

GCCTAAAGGA ATGTCACG                                                 3794
```

(2) INFORMATION FOR SEQ ID NO:28:

(i) SEQUENCE CHARACTERISTICS:
(A) LENGTH: 875 amino acids
(B) TYPE: amino acid
(D) TOPOLOGY: linear (ii) MOLECULE TYPE: protein (xi) SEQUENCE DESCRIPTION: SEQ ID NO:28:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220
```

-continued

```
Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Asn Thr Asn Ile Trp Lys Thr Gly Pro
            260                 265                 270

Leu Phe Lys Arg Val Leu Met Ser Ser Lys Tyr Ala Asp Gly Val Thr
        275                 280                 285

Gly Arg Val Glu Phe Asn Glu Asp Gly Asp Arg Lys Phe Ala Asn Tyr
    290                 295                 300

Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                325                 330                 335

Gly Glu Thr Glu Lys Pro Arg Gly Tyr Gln Met Ser Thr Arg Leu Lys
            340                 345                 350

Ile Val Thr Ile His Gln Glu Pro Phe Val Tyr Val Lys Pro Thr Leu
        355                 360                 365

Ser Asp Gly Thr Cys Lys Glu Glu Phe Thr Val Asn Gly Asp Pro Val
    370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                405                 410                 415

Ile Lys Leu Ala Arg Thr Met Asn Phe Thr Tyr Glu Val His Leu Val
            420                 425                 430

Ala Asp Gly Lys Phe Gly Thr Gln Glu Arg Val Asn Asn Ser Asn Lys
        435                 440                 445

Lys Glu Trp Asn Gly Met Met Gly Glu Leu Leu Ser Gly Gln Ala Asp
    450                 455                 460

Met Ile Val Ala Pro Leu Thr Ile Asn Asn Glu Arg Ala Gln Tyr Ile
465                 470                 475                 480

Glu Phe Ser Lys Pro Phe Lys Tyr Gln Gly Leu Thr Ile Leu Val Lys
                485                 490                 495

Lys Glu Ile Pro Arg Ser Thr Leu Asp Ser Phe Met Gln Pro Phe Gln
            500                 505                 510

Ser Thr Leu Trp Leu Leu Val Gly Leu Ser Val His Val Val Ala Val
        515                 520                 525

Met Leu Tyr Leu Leu Asp Arg Phe Ser Pro Phe Gly Arg Phe Lys Val
    530                 535                 540

Asn Ser Glu Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
                565                 570                 575

Pro Arg Ser Phe Ser Ala Arg Ile Leu Gly Met Val Trp Ala Gly Phe
            580                 585                 590

Ala Met Ile Ile Val Ala Ser Tyr Thr Ala Asn Leu Ala Ala Phe Leu
        595                 600                 605

Val Leu Asp Arg Pro Glu Glu Arg Ile Thr Gly Ile Asn Asp Pro Arg
    610                 615                 620

Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
```

-continued

```
            645                 650                 655

Arg His Met Glu Lys His Asn Tyr Glu Ser Ala Ala Glu Ala Ile Gln
        660                 665                 670

Ala Val Arg Asp Asn Lys Leu His Ala Phe Ile Trp Asp Ser Ala Val
    675                 680                 685

Leu Glu Phe Glu Ala Ser Gln Lys Cys Asp Leu Val Thr Thr Gly Glu
    690                 695                 700

Leu Phe Phe Arg Ser Gly Phe Gly Ile Gly Met Arg Lys Asp Ser Pro
705                 710                 715                 720

Trp Lys Gln Asn Val Ser Leu Ser Ile Leu Lys Ser His Glu Asn Gly
            725                 730                 735

Phe Met Glu Asp Leu Asp Lys Thr Trp Val Arg Tyr Gln Glu Cys Asp
        740                 745                 750

Ser Arg Ser Asn Ala Pro Ala Thr Leu Thr Phe Glu Asn Met Ala Gly
    755                 760                 765

Val Phe Met Leu Val Ala Gly Gly Ile Val Ala Gly Ile Phe Leu Ile
    770                 775                 780

Phe Ile Glu Ile Ala Tyr Lys Arg His Lys Asp Ala Arg Arg Lys Gln
785                 790                 795                 800

Met Gln Leu Ala Phe Ala Ala Val Asn Val Trp Arg Lys Asn Leu Gln
            805                 810                 815

Asp Arg Lys Ser Gly Arg Ala Glu Pro Asp Pro Lys Lys Lys Ala Thr
        820                 825                 830

Phe Arg Ala Ile Thr Ser Thr Leu Ala Ser Ser Phe Lys Arg Arg Arg
    835                 840                 845

Ser Ser Lys Asp Thr Gln Tyr His Pro Thr Asp Ile Thr Gly Pro Leu
    850                 855                 860

Asn Leu Ser Asp Pro Ser Val Ser Thr Val Val
865                 870                 875
```

(2) INFORMATION FOR SEQ ID NO:29:

(i) SEQUENCE CHARACTERISTICS:
(A) LENGTH: 4094 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..2874

(xi) SEQUENCE DESCRIPTION: SEQ ID NO:29:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
```

-continued

```
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC AAC ACC AAC ATC TGG AAG ACC GGG     1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG     1059
Pro Leu Phe Lys Arg Val Leu Met Ser Ser Lys Tyr Ala Asp Gly Val
                255                 260                 265

ACT GGT CGC GTG GAG TTC AAT GAG GAT GGG GAC CGG AAG TTC GCC AAC     1107
Thr Gly Arg Val Glu Phe Asn Glu Asp Gly Asp Arg Lys Phe Ala Asn
            270                 275                 280

TAC AGC ATC ATG AAC CTG CAG AAC CGC AAG CTG GTG CAA GTG GGC ATC     1155
Tyr Ser Ile Met Asn Leu Gln Asn Arg Lys Leu Val Gln Val Gly Ile
        285                 290                 295

TAC AAT GGC ACC CAC GTC ATC CCT AAT GAC AGG AAG ATC ATC TGG CCA     1203
Tyr Asn Gly Thr His Val Ile Pro Asn Asp Arg Lys Ile Ile Trp Pro
    300                 305                 310

GGC GGA GAG ACA GAG AAG CCT CGA GGG TAC CAG ATG TCC ACC AGA CTG     1251
Gly Gly Glu Thr Glu Lys Pro Arg Gly Tyr Gln Met Ser Thr Arg Leu
315                 320                 325                 330

AAG ATT GTG ACG ATC CAC CAG GAG CCC TTC GTG TAC GTC AAG CCC ACG     1299
Lys Ile Val Thr Ile His Gln Glu Pro Phe Val Tyr Val Lys Pro Thr
                335                 340                 345

CTG AGT GAT GGG ACA TGC AAG GAG GAG TTC ACA GTC AAC GGC GAC CCA     1347
```

-continued

Leu Ser Asp Gly Thr Cys Lys Glu Glu Phe Thr Val Asn Gly Asp Pro
350 355 360

GTC AAG AAG GTG ATC TGC ACC GGG CCC AAC GAC ACG TCG CCG GGC AGC 1395
Val Lys Lys Val Ile Cys Thr Gly Pro Asn Asp Thr Ser Pro Gly Ser
365 370 375

CCC CGC CAC ACG GTG CCT CAG TGT TGC TAC GGC TTT TGC ATC GAC CTG 1443
Pro Arg His Thr Val Pro Gln Cys Cys Tyr Gly Phe Cys Ile Asp Leu
380 385 390

CTC ATC AAG CTG GCA CGG ACC ATG AAC TTC ACC TAC GAG GTG CAC CTG 1491
Leu Ile Lys Leu Ala Arg Thr Met Asn Phe Thr Tyr Glu Val His Leu
395 400 405 410

GTG GCA GAT GGC AAG TTC GGC ACA CAG GAG CGG GTG AAC AAC AGC AAC 1539
Val Ala Asp Gly Lys Phe Gly Thr Gln Glu Arg Val Asn Asn Ser Asn
415 420 425

AAG AAG GAG TGG AAT GGG ATG ATG GGC GAG CTG CTC AGC GGG CAG GCA 1587
Lys Lys Glu Trp Asn Gly Met Met Gly Glu Leu Leu Ser Gly Gln Ala
430 435 440

GAC ATG ATC GTG GCG CCG CTA ACC ATA AAC AAC GAG CGC GCG CAG TAC 1635
Asp Met Ile Val Ala Pro Leu Thr Ile Asn Asn Glu Arg Ala Gln Tyr
445 450 455

ATC GAG TTT TCC AAG CCC TTC AAG TAC CAG GGC CTG ACT ATT CTG GTC 1683
Ile Glu Phe Ser Lys Pro Phe Lys Tyr Gln Gly Leu Thr Ile Leu Val
460 465 470

AAG AAG GAG ATT CCC CGG AGC ACG CTG GAC TCG TTC ATG CAG CCG TTC 1731
Lys Lys Glu Ile Pro Arg Ser Thr Leu Asp Ser Phe Met Gln Pro Phe
475 480 485 490

CAG AGC ACA CTG TGG CTG CTG GTG GGG CTG TCG GTG CAC GTG GTG GCC 1779
Gln Ser Thr Leu Trp Leu Leu Val Gly Leu Ser Val His Val Val Ala
495 500 505

GTG ATG CTG TAC CTG CTG GAC CGC TTC AGC CCC TTC GGC CGG TTC AAG 1827
Val Met Leu Tyr Leu Leu Asp Arg Phe Ser Pro Phe Gly Arg Phe Lys
510 515 520

GTG AAC AGC GAG GAG GAG GAG GAG GAC GCA CTG ACC CTG TCC TCG GCC 1875
Val Asn Ser Glu Glu Glu Glu Glu Asp Ala Leu Thr Leu Ser Ser Ala
525 530 535

ATG TGG TTC TCC TGG GGC GTC CTG CTC AAC TCC GGC ATC GGG GAA GGC 1923
Met Trp Phe Ser Trp Gly Val Leu Leu Asn Ser Gly Ile Gly Glu Gly
540 545 550

GCC CCC AGA AGC TTC TCA GCG CGC ATC CTG GGC ATG GTG TGG GCC GGC 1971
Ala Pro Arg Ser Phe Ser Ala Arg Ile Leu Gly Met Val Trp Ala Gly
555 560 565 570

TTT GCC ATG ATC ATC GTG GCC TCC TAC ACC GCC AAC CTG GCG GCC TTC 2019
Phe Ala Met Ile Ile Val Ala Ser Tyr Thr Ala Asn Leu Ala Ala Phe
575 580 585

CTG GTG CTG GAC CGG CCG GAG GAG CGC ATC ACG GGC ATC AAC GAC CCT 2067
Leu Val Leu Asp Arg Pro Glu Glu Arg Ile Thr Gly Ile Asn Asp Pro
590 595 600

CGG CTG AGG AAC CCC TCG GAC AAG TTT ATC TAC GCC ACG GTG AAG CAG 2115
Arg Leu Arg Asn Pro Ser Asp Lys Phe Ile Tyr Ala Thr Val Lys Gln
605 610 615

AGC TCC GTG GAT ATC TAC TTC CGG CGC CAG GTG GAG CTG AGC ACC ATG 2163
Ser Ser Val Asp Ile Tyr Phe Arg Arg Gln Val Glu Leu Ser Thr Met
620 625 630

TAC CGG CAT ATG GAG AAG CAC AAC TAC GAG AGT GCG GCG GAG GCC ATC 2211
Tyr Arg His Met Glu Lys His Asn Tyr Glu Ser Ala Ala Glu Ala Ile
635 640 645 650

CAG GCC GTG AGA GAC AAC AAG CTG CAT GCC TTC ATC TGG GAC TCG GCG 2259
Gln Ala Val Arg Asp Asn Lys Leu His Ala Phe Ile Trp Asp Ser Ala
655 660 665

-continued

```
GTG CTG GAG TTC GAG GCC TCG CAG AAG TGC GAC CTG GTG ACG ACT GGA      2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC      2355
Glu Leu Phe Phe Arg Ser Gly Phe Gly Ile Gly Met Arg Lys Asp Ser
        685                 690                 695

CCC TGG AAG CAG AAC GTC TCC CTG TCC ATC CTC AAG TCC CAC GAG AAT      2403
Pro Trp Lys Gln Asn Val Ser Leu Ser Ile Leu Lys Ser His Glu Asn
    700                 705                 710

GGC TTC ATG GAA GAC CTG GAC AAG ACG TGG GTT CGG TAT CAG GAA TGT      2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC      2499
Asp Ser Arg Ser Asn Ala Pro Ala Thr Leu Thr Phe Glu Asn Met Ala
                735                 740                 745

GGG GTC TTC ATG CTG GTA GCT GGG GGC ATC GTG GCC GGG ATC TTC CTG      2547
Gly Val Phe Met Leu Val Ala Gly Gly Ile Val Ala Gly Ile Phe Leu
            750                 755                 760

ATT TTC ATC GAG ATT GCC TAC AAG CGG CAC AAG GAT GCT CGC CGG AAG      2595
Ile Phe Ile Glu Ile Ala Tyr Lys Arg His Lys Asp Ala Arg Arg Lys
        765                 770                 775

CAG ATG CAG CTG GCC TTT GCC GCC GTT AAC GTG TGG CGG AAG AAC CTG      2643
Gln Met Gln Leu Ala Phe Ala Ala Val Asn Val Trp Arg Lys Asn Leu
    780                 785                 790

CAG GAT AGA AAG AGT GGT AGA GCA GAG CCT GAC CCT AAA AAG AAA GCC      2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT      2739
Thr Phe Arg Ala Ile Thr Ser Thr Leu Ala Ser Ser Phe Lys Arg Arg
                815                 820                 825

AGG TCC TCC AAA GAC ACG AGC ACC GGG GGT GGA CGC GGT GCT TTG CAA      2787
Arg Ser Ser Lys Asp Thr Ser Thr Gly Gly Gly Arg Gly Ala Leu Gln
            830                 835                 840

AAC CAA AAA GAC ACA GTG CTG CCG CGA CGC GCT ATT GAG AGG GAG GAG      2835
Asn Gln Lys Asp Thr Val Leu Pro Arg Arg Ala Ile Glu Arg Glu Glu
        845                 850                 855

GGC CAG CTG CAG CTG TGT TCC CGT CAT AGG GAG AGC TGAGACTCCC           2881
Gly Gln Leu Gln Leu Cys Ser Arg His Arg Glu Ser
    860                 865                 870

CGCCCGCCCT CCTCTGCCCC CTCCCCCGCA GACAGACAGA CAGACGGACG GGACAGCGGC   2941

CCGGCCCACG CAGAGCCCCG GAGCACCACG GGGTCGGGGG AGGAGCACCC CCAGCCTCCC   3001

CCAGGCTGCG CCTGCCCGCC CGCCGGTTGG CCGGCTGGCC GGTCCACCCC GTCCCGGCCC   3061

CGCGCGTGCC CCCAGCGTGG GGCTAACGGG CGCCTTGTCT GTGTATTTCT ATTTTGCAGC   3121

AGTACCATCC CACTGATATC ACGGGCCCGC TCAACCTCTC AGATCCCTCG GTCAGCACCG   3181

TGGTGTGAGG CCCCCGGAGG CGCCCACCTG CCCAGTTAGC CCGGCCAAGG ACACTGATGG   3241

GTCCTGCTGC TCGGGAAGGC CTGAGGGAAG CCCACCCGCC CCAGAGACTG CCCACCCTGG   3301

GCCTCCCGTC CGTCCGCCCG CCCACCCCGC TGCCTGGCGG GCAGCCCCTG CTGGACCAAG   3361

GTGCGGACCG GAGCGGCTGA GGACGGGGCA GAGCTGAGTC GGCTGGGCAG GGCCGCAGGG   3421

CGCTCCGGCA GAGGCAGGCC CCTGGGGTCT CTGAGCAGTG GGGAGCGGGG GCTAACTGCC   3481

CCCAGGCGGA GGGGCTTGGA GCAGAGACGG CAGCCCCATC CTTCCCGCAG CACCAGCCTG   3541

AGCCACAGTG GGGCCCATGG CCCCAGCTGG CTGGGTCGCC CCTCCTCGGG CGCCTGCGCT   3601

CCTCTGCAGC CTGAGCTCCA CCCTCCCCTC TTCTTGCGGC ACCGCCCACC AAACACCCCG   3661

TCTGCCCCTT GACGCCACAC GCCGGGGCTG GCGCTGCCCT CCCCCACGGC CGTCCCTGAC   3721
```

-continued

```
TTCCCAGCTG GCAGCGCCTC CCGCCGCCTC GGGCCGCCTC CTCCAGAATC GAGAGGGCTG   3781

AGCCCCTCCT CTCCTCGTCC GGCCTGCAGC ACAGAAGGGG GCCTCCCCGG GGGTCCCCGG   3841

ACGCTGGCTC GGGACTGTCT TCAACCCTGC CCTGCACCTT GGGCACGGGA GAGCGCCACC   3901

CGCCCGCCCC CGCCCTCGCT CCGGGTGCGT GACCGGCCCG CCACCTTGTA CAGAACCAGC   3961

ACTCCCAGGG CCCGAGCGCG TGCCTTCCCC GTGCGCAGCC GCGCTCTGCC CCTCCGTCCC   4021

CAGGGTGCAG GCGCGCACCG CCCAACCCCC ACCTCCCGGT GTATGCAGTG GTGATGCCTA   4081

AAGGAATGTC ACG                                                      4094
```

(2) INFORMATION FOR SEQ ID NO:30:

(i) SEQUENCE CHARACTERISTICS:
(A) LENGTH: 870 amino acids
(B) TYPE: amino acid
(D) TOPOLOGY: linear (ii) MOLECULE TYPE: protein (xi) SEQUENCE DESCRIPTION: SEQ ID NO:30:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Asn Thr Asn Ile Trp Lys Thr Gly Pro Leu Phe Lys Arg Val
                245                 250                 255

Leu Met Ser Ser Lys Tyr Ala Asp Gly Val Thr Gly Arg Val Glu Phe
            260                 265                 270

Asn Glu Asp Gly Asp Arg Lys Phe Ala Asn Tyr Ser Ile Met Asn Leu
```

-continued

```
        275                 280                 285

Gln Asn Arg Lys Leu Val Gln Val Gly Ile Tyr Asn Gly Thr His Val
    290                 295                 300

Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
                325                 330                 335

Gln Glu Pro Phe Val Tyr Val Lys Pro Thr Leu Ser Asp Gly Thr Cys
            340                 345                 350

Lys Glu Glu Phe Thr Val Asn Gly Asp Pro Val Lys Lys Val Ile Cys
        355                 360                 365

Thr Gly Pro Asn Asp Thr Ser Pro Gly Ser Pro Arg His Thr Val Pro
    370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                405                 410                 415

Gly Thr Gln Glu Arg Val Asn Asn Ser Asn Lys Lys Glu Trp Asn Gly
            420                 425                 430

Met Met Gly Glu Leu Leu Ser Gly Gln Ala Asp Met Ile Val Ala Pro
        435                 440                 445

Leu Thr Ile Asn Asn Glu Arg Ala Gln Tyr Ile Glu Phe Ser Lys Pro
    450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                485                 490                 495

Leu Val Gly Leu Ser Val His Val Val Ala Val Met Leu Tyr Leu Leu
            500                 505                 510

Asp Arg Phe Ser Pro Phe Gly Arg Phe Lys Val Asn Ser Glu Glu Glu
        515                 520                 525

Glu Glu Asp Ala Leu Thr Leu Ser Ser Ala Met Trp Phe Ser Trp Gly
    530                 535                 540

Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590

Glu Glu Arg Ile Thr Gly Ile Asn Asp Pro Arg Leu Arg Asn Pro Ser
        595                 600                 605

Asp Lys Phe Ile Tyr Ala Thr Val Lys Gln Ser Ser Val Asp Ile Tyr
    610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655

Lys Leu His Ala Phe Ile Trp Asp Ser Ala Val Leu Glu Phe Glu Ala
            660                 665                 670

Ser Gln Lys Cys Asp Leu Val Thr Thr Gly Glu Leu Phe Phe Arg Ser
        675                 680                 685

Gly Phe Gly Ile Gly Met Arg Lys Asp Ser Pro Trp Lys Gln Asn Val
    690                 695                 700
```

-continued

```
Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
                725                 730                 735

Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
        755                 760                 765

Tyr Lys Arg His Lys Asp Ala Arg Arg Lys Gln Met Gln Leu Ala Phe
    770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Lys Ala Thr Phe Arg Ala Ile Thr
                805                 810                 815

Ser Thr Leu Ala Ser Ser Phe Lys Arg Arg Arg Ser Ser Lys Asp Thr
            820                 825                 830

Ser Thr Gly Gly Gly Arg Gly Ala Leu Gln Asn Gln Lys Asp Thr Val
        835                 840                 845

Leu Pro Arg Arg Ala Ile Glu Arg Glu Glu Gly Gln Leu Gln Leu Cys
    850                 855                 860

Ser Arg His Arg Glu Ser
865                 870
```

(2) INFORMATION FOR SEQ ID NO:31:

(i) SEQUENCE CHARACTERISTICS:
(A) LENGTH: 3731 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..2826

(xi) SEQUENCE DESCRIPTION: SEQ ID NO:31:

```
CAAGCCGGGC GTTCGGAGCT GTGCCCGGCC CCGCTTCAGC ACCGCGGACA GCGCCGGCCG     60

CGTGGGGCTG AGCGCCGAGC CCCCGCGCAC GCTTCAGCCC CCCTTCCCTC GGCCGACGTC    120

CCGGGACCGC CGCTCCGGGG GAGACGTGGC GTCCGCAGCC CGCGGGGCCG GGCGAGCGCA    180

GGACGGCCCG GAAGCCCCGC GGGGGATGCG CCGAGGGCCC CGCGTTCGCG CCGCGCAGAG    240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70
```

-continued

```
GCT CTG TCG GTG TGC GAG GAC CTC ATC TCC AGC CAG GTC TAC GCC ATC        531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT        579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC        627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG        675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG        723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC        771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG        819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG        867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC        915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA        963
Ile Ile Leu Ser Ala Ser Glu Asp Asp Ala Ala Thr Val Tyr Arg Ala
    220                 225                 230

GCC GCG ATG CTG AAC ATG ACG GGC AAC ACC AAC ATC TGG AAG ACC GGG       1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG       1059
Pro Leu Phe Lys Arg Val Leu Met Ser Ser Lys Tyr Ala Asp Gly Val
                255                 260                 265

ACT GGT CGC GTG GAG TTC AAT GAG GAT GGG GAC CGG AAG TTC GCC AAC       1107
Thr Gly Arg Val Glu Phe Asn Glu Asp Gly Asp Arg Lys Phe Ala Asn
            270                 275                 280

TAC AGC ATC ATG AAC CTG CAG AAC CGC AAG CTG GTG CAA GTG GGC ATC       1155
Tyr Ser Ile Met Asn Leu Gln Asn Arg Lys Leu Val Gln Val Gly Ile
        285                 290                 295

TAC AAT GGC ACC CAC GTC ATC CCT AAT GAC AGG AAG ATC ATC TGG CCA       1203
Tyr Asn Gly Thr His Val Ile Pro Asn Asp Arg Lys Ile Ile Trp Pro
    300                 305                 310

GGC GGA GAG ACA GAG AAG CCT CGA GGG TAC CAG ATG TCC ACC AGA CTG       1251
Gly Gly Glu Thr Glu Lys Pro Arg Gly Tyr Gln Met Ser Thr Arg Leu
315                 320                 325                 330

AAG ATT GTG ACG ATC CAC CAG GAG CCC TTC GTG TAC GTC AAG CCC ACG       1299
Lys Ile Val Thr Ile His Gln Glu Pro Phe Val Tyr Val Lys Pro Thr
                335                 340                 345

CTG AGT GAT GGG ACA TGC AAG GAG GAG TTC ACA GTC AAC GGC GAC CCA       1347
Leu Ser Asp Gly Thr Cys Lys Glu Glu Phe Thr Val Asn Gly Asp Pro
            350                 355                 360

GTC AAG AAG GTG ATC TGC ACC GGG CCC AAC GAC ACG TCG CCG GGC AGC       1395
Val Lys Lys Val Ile Cys Thr Gly Pro Asn Asp Thr Ser Pro Gly Ser
        365                 370                 375

CCC CGC CAC ACG GTG CCT CAG TGT TGC TAC GGC TTT TGC ATC GAC CTG       1443
Pro Arg His Thr Val Pro Gln Cys Cys Tyr Gly Phe Cys Ile Asp Leu
    380                 385                 390
```

-continued

```
CTC ATC AAG CTG GCA CGG ACC ATG AAC TTC ACC TAC GAG GTG CAC CTG     1491
Leu Ile Lys Leu Ala Arg Thr Met Asn Phe Thr Tyr Glu Val His Leu
395                 400                 405                 410

GTG GCA GAT GGC AAG TTC GGC ACA CAG GAG CGG GTG AAC AAC AGC AAC     1539
Val Ala Asp Gly Lys Phe Gly Thr Gln Glu Arg Val Asn Asn Ser Asn
                415                 420                 425

AAG AAG GAG TGG AAT GGG ATG ATG GGC GAG CTG CTC AGC GGG CAG GCA     1587
Lys Lys Glu Trp Asn Gly Met Met Gly Glu Leu Leu Ser Gly Gln Ala
            430                 435                 440

GAC ATG ATC GTG GCG CCG CTA ACC ATA AAC AAC GAG CGC GCG CAG TAC     1635
Asp Met Ile Val Ala Pro Leu Thr Ile Asn Asn Glu Arg Ala Gln Tyr
        445                 450                 455

ATC GAG TTT TCC AAG CCC TTC AAG TAC CAG GGC CTG ACT ATT CTG GTC     1683
Ile Glu Phe Ser Lys Pro Phe Lys Tyr Gln Gly Leu Thr Ile Leu Val
    460                 465                 470

AAG AAG GAG ATT CCC CGG AGC ACG CTG GAC TCG TTC ATG CAG CCG TTC     1731
Lys Lys Glu Ile Pro Arg Ser Thr Leu Asp Ser Phe Met Gln Pro Phe
475                 480                 485                 490

CAG AGC ACA CTG TGG CTG CTG GTG GGG CTG TCG GTG CAC GTG GTG GCC     1779
Gln Ser Thr Leu Trp Leu Leu Val Gly Leu Ser Val His Val Val Ala
                495                 500                 505

GTG ATG CTG TAC CTG CTG GAC CGC TTC AGC CCC TTC GGC CGG TTC AAG     1827
Val Met Leu Tyr Leu Leu Asp Arg Phe Ser Pro Phe Gly Arg Phe Lys
            510                 515                 520

GTG AAC AGC GAG GAG GAG GAG GAG GAC GCA CTG ACC CTG TCC TCG GCC     1875
Val Asn Ser Glu Glu Glu Glu Glu Asp Ala Leu Thr Leu Ser Ser Ala
        525                 530                 535

ATG TGG TTC TCC TGG GGC GTC CTG CTC AAC TCC GGC ATC GGG GAA GGC     1923
Met Trp Phe Ser Trp Gly Val Leu Leu Asn Ser Gly Ile Gly Glu Gly
    540                 545                 550

GCC CCC AGA AGC TTC TCA GCG CGC ATC CTG GGC ATG GTG TGG GCC GGC     1971
Ala Pro Arg Ser Phe Ser Ala Arg Ile Leu Gly Met Val Trp Ala Gly
555                 560                 565                 570

TTT GCC ATG ATC ATC GTG GCC TCC TAC ACC GCC AAC CTG GCG GCC TTC     2019
Phe Ala Met Ile Ile Val Ala Ser Tyr Thr Ala Asn Leu Ala Ala Phe
                575                 580                 585

CTG GTG CTG GAC CGG CCG GAG GAG CGC ATC ACG GGC ATC AAC GAC CCT     2067
Leu Val Leu Asp Arg Pro Glu Glu Arg Ile Thr Gly Ile Asn Asp Pro
            590                 595                 600

CGG CTG AGG AAC CCC TCG GAC AAG TTT ATC TAC GCC ACG GTG AAG CAG     2115
Arg Leu Arg Asn Pro Ser Asp Lys Phe Ile Tyr Ala Thr Val Lys Gln
        605                 610                 615

AGC TCC GTG GAT ATC TAC TTC CGG CGC CAG GTG GAG CTG AGC ACC ATG     2163
Ser Ser Val Asp Ile Tyr Phe Arg Arg Gln Val Glu Leu Ser Thr Met
    620                 625                 630

TAC CGG CAT ATG GAG AAG CAC AAC TAC GAG AGT GCG GCG GAG GCC ATC     2211
Tyr Arg His Met Glu Lys His Asn Tyr Glu Ser Ala Ala Glu Ala Ile
635                 640                 645                 650

CAG GCC GTG AGA GAC AAC AAG CTG CAT GCC TTC ATC TGG GAC TCG GCG     2259
Gln Ala Val Arg Asp Asn Lys Leu His Ala Phe Ile Trp Asp Ser Ala
                655                 660                 665

GTG CTG GAG TTC GAG GCC TCG CAG AAG TGC GAC CTG GTG ACG ACT GGA     2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC     2355
Glu Leu Phe Phe Arg Ser Gly Phe Gly Ile Gly Met Arg Lys Asp Ser
        685                 690                 695

CCC TGG AAG CAG AAC GTC TCC CTG TCC ATC CTC AAG TCC CAC GAG AAT     2403
Pro Trp Lys Gln Asn Val Ser Leu Ser Ile Leu Lys Ser His Glu Asn
```

-continued

```
    700                 705                 710

GGC TTC ATG GAA GAC CTG GAC AAG ACG TGG GTT CGG TAT CAG GAA TGT      2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC      2499
Asp Ser Arg Ser Asn Ala Pro Ala Thr Leu Thr Phe Glu Asn Met Ala
                735                 740                 745

GGG GTC TTC ATG CTG GTA GCT GGG GGC ATC GTG GCC GGG ATC TTC CTG      2547
Gly Val Phe Met Leu Val Ala Gly Gly Ile Val Ala Gly Ile Phe Leu
            750                 755                 760

ATT TTC ATC GAG ATT GCC TAC AAG CGG CAC AAG GAT GCT CGC CGG AAG      2595
Ile Phe Ile Glu Ile Ala Tyr Lys Arg His Lys Asp Ala Arg Arg Lys
        765                 770                 775

CAG ATG CAG CTG GCC TTT GCC GCC GTT AAC GTG TGG CGG AAG AAC CTG      2643
Gln Met Gln Leu Ala Phe Ala Ala Val Asn Val Trp Arg Lys Asn Leu
    780                 785                 790

CAG GAT AGA AAG AGT GGT AGA GCA GAG CCT GAC CCT AAA AAG AAA GCC      2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT      2739
Thr Phe Arg Ala Ile Thr Ser Thr Leu Ala Ser Ser Phe Lys Arg Arg
                815                 820                 825

AGG TCC TCC AAA GAC ACG CAG TAC CAT CCC ACT GAT ATC ACG GGC CCG      2787
Arg Ser Ser Lys Asp Thr Gln Tyr His Pro Thr Asp Ile Thr Gly Pro
            830                 835                 840

CTC AAC CTC TCA GAT CCC TCG GTC AGC ACC GTG GTG TGAGGCCCCC          2833
Leu Asn Leu Ser Asp Pro Ser Val Ser Thr Val Val
        845                 850                 855

GGAGGCGCCC ACCTGCCCAG TTAGCCCGGC CAAGGACACT GATGGGTCCT GCTGCTCGGG   2893

AAGGCCTGAG GGAAGCCCAC CCGCCCCAGA GACTGCCCAC CCTGGGCCTC CCGTCCGTCC   2953

GCCCGCCCAC CCCGCTGCCT GGCGGGCAGC CCCTGCTGGA CCAAGGTGCG GACCGGAGCG   3013

GCTGAGGACG GGGCAGAGCT GAGTCGGCTG GGCAGGGCCG CAGGGCGCTC CGGCAGAGGC   3073

AGGCCCCTGG GGTCTCTGAG CAGTGGGGAG CGGGGGCTAA CTGCCCCCAG GCGGAGGGGC   3133

TTGGAGCAGA GACGGCAGCC CCATCCTTCC CGCAGCACCA GCCTGAGCCA CAGTGGGGCC   3193

CATGGCCCCA GCTGGCTGGG TCGCCCCTCC TCGGGCGCCT GCGCTCCTCT GCAGCCTGAG   3253

CTCCACCCTC CCCTCTTCTT GCGGCACCGC CCACCAAACA CCCCGTCTGC CCCTTGACGC   3313

CACACGCCGG GGCTGGCGCT GCCCTCCCCC ACGGCCGTCC CTGACTTCCC AGCTGGCAGC   3373

GCCTCCCGCC GCCTCGGGCC GCCTCCTCCA GAATCGAGAG GGCTGAGCCC CTCCTCTCCT   3433

CGTCCGGCCT GCAGCACAGA AGGGGGCCTC CCCGGGGGTC CCCGGACGCT GGCTCGGGAC   3493

TGTCTTCAAC CCTGCCCTGC ACCTTGGGCA CGGGAGAGCG CCACCCGCCC GCCCCCGCCC   3553

TCGCTCCGGG TGCGTGACCG GCCCGCCACC TTGTACAGAA CCAGCACTCC CAGGGCCCGA   3613

GCGCGTGCCT TCCCCGTGCG CAGCCGCGCT CTGCCCCTCC GTCCCCAGGG TGCAGGCGCG   3673

CACCGCCCAA CCCCCACCTC CCGGTGTATG CAGTGGTGAT GCCTAAAGGA ATGTCACG     3731
```

(2) INFORMATION FOR SEQ ID NO:32:

(i) SEQUENCE CHARACTERISTICS:
(A) LENGTH: 854 amino acids
(B) TYPE: amino acid
(D) TOPOLOGY: linear (ii) MOLECULE TYPE: protein (xi) SEQUENCE DESCRIPTION: SEQ ID NO:32:

-continued

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
225                 230                 235                 240

Thr Gly Asn Thr Asn Ile Trp Lys Thr Gly Pro Leu Phe Lys Arg Val
                245                 250                 255

Leu Met Ser Ser Lys Tyr Ala Asp Gly Val Thr Gly Arg Val Glu Phe
            260                 265                 270

Asn Glu Asp Gly Asp Arg Lys Phe Ala Asn Tyr Ser Ile Met Asn Leu
        275                 280                 285

Gln Asn Arg Lys Leu Val Gln Val Gly Ile Tyr Asn Gly Thr His Val
    290                 295                 300

Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
                325                 330                 335

Gln Glu Pro Phe Val Tyr Val Lys Pro Thr Leu Ser Asp Gly Thr Cys
            340                 345                 350

Lys Glu Glu Phe Thr Val Asn Gly Asp Pro Val Lys Lys Val Ile Cys
        355                 360                 365

Thr Gly Pro Asn Asp Thr Ser Pro Gly Ser Pro Arg His Thr Val Pro
    370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                405                 410                 415
```

-continued

```
Gly Thr Gln Glu Arg Val Asn Asn Ser Asn Lys Lys Glu Trp Asn Gly
            420                 425                 430

Met Met Gly Glu Leu Leu Ser Gly Gln Ala Asp Met Ile Val Ala Pro
        435                 440                 445

Leu Thr Ile Asn Asn Glu Arg Ala Gln Tyr Ile Glu Phe Ser Lys Pro
    450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                485                 490                 495

Leu Val Gly Leu Ser Val His Val Val Ala Val Met Leu Tyr Leu Leu
            500                 505                 510

Asp Arg Phe Ser Pro Phe Gly Arg Phe Lys Val Asn Ser Glu Glu Glu
        515                 520                 525

Glu Glu Asp Ala Leu Thr Leu Ser Ser Ala Met Trp Phe Ser Trp Gly
    530                 535                 540

Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590

Glu Glu Arg Ile Thr Gly Ile Asn Asp Pro Arg Leu Arg Asn Pro Ser
        595                 600                 605

Asp Lys Phe Ile Tyr Ala Thr Val Lys Gln Ser Ser Val Asp Ile Tyr
    610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655

Lys Leu His Ala Phe Ile Trp Asp Ser Ala Val Leu Glu Phe Glu Ala
            660                 665                 670

Ser Gln Lys Cys Asp Leu Val Thr Thr Gly Glu Leu Phe Phe Arg Ser
        675                 680                 685

Gly Phe Gly Ile Gly Met Arg Lys Asp Ser Pro Trp Lys Gln Asn Val
    690                 695                 700

Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
                725                 730                 735

Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
        755                 760                 765

Tyr Lys Arg His Lys Asp Ala Arg Arg Lys Gln Met Gln Leu Ala Phe
    770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Lys Ala Thr Phe Arg Ala Ile Thr
                805                 810                 815

Ser Thr Leu Ala Ser Ser Phe Lys Arg Arg Arg Ser Ser Lys Asp Thr
            820                 825                 830

Gln Tyr His Pro Thr Asp Ile Thr Gly Pro Leu Asn Leu Ser Asp Pro
```

-continued

```
        835                 840                 845

Ser Val Ser Thr Val Val
    850
```

(2) INFORMATION FOR SEQ ID NO:33:

(i) SEQUENCE CHARACTERISTICS:
(A) LENGTH: 3007 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..2988

(xi) SEQUENCE DESCRIPTION: SEQ ID NO:33:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG GCA GAG AAG GTG CTG CAG TTT GAC CCA GGG ACC AAG      867
```

-continued

```
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC      915
Asn Val Thr Ala Leu Leu Met Glu Ala Lys Glu Leu Glu Ala Arg Val
        205                 210                 215

ATC ATC CTT TCT GCC AGC GAG GAC GAT GCT GCC ACT GTA TAC CGC GCA      963
Ile Ile Leu Ser Ala Ser Glu Asp Asp Ala Ala Thr Val Tyr Arg Ala
    220                 225                 230

GCC GCG ATG CTG AAC ATG ACG GGC AAC ACC AAC ATC TGG AAG ACC GGG     1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG     1059
Pro Leu Phe Lys Arg Val Leu Met Ser Ser Lys Tyr Ala Asp Gly Val
                255                 260                 265

ACT GGT CGC GTG GAG TTC AAT GAG GAT GGG GAC CGG AAG TTC GCC AAC     1107
Thr Gly Arg Val Glu Phe Asn Glu Asp Gly Asp Arg Lys Phe Ala Asn
            270                 275                 280

TAC AGC ATC ATG AAC CTG CAG AAC CGC AAG CTG GTG CAA GTG GGC ATC     1155
Tyr Ser Ile Met Asn Leu Gln Asn Arg Lys Leu Val Gln Val Gly Ile
        285                 290                 295

TAC AAT GGC ACC CAC GTC ATC CCT AAT GAC AGG AAG ATC ATC TGG CCA     1203
Tyr Asn Gly Thr His Val Ile Pro Asn Asp Arg Lys Ile Ile Trp Pro
    300                 305                 310

GGC GGA GAG ACA GAG AAG CCT CGA GGG TAC CAG ATG TCC ACC AGA CTG     1251
Gly Gly Glu Thr Glu Lys Pro Arg Gly Tyr Gln Met Ser Thr Arg Leu
315                 320                 325                 330

AAG ATT GTG ACG ATC CAC CAG GAG CCC TTC GTG TAC GTC AAG CCC ACG     1299
Lys Ile Val Thr Ile His Gln Glu Pro Phe Val Tyr Val Lys Pro Thr
                335                 340                 345

CTG AGT GAT GGG ACA TGC AAG GAG GAG TTC ACA GTC AAC GGC GAC CCA     1347
Leu Ser Asp Gly Thr Cys Lys Glu Glu Phe Thr Val Asn Gly Asp Pro
            350                 355                 360

GTC AAG AAG GTG ATC TGC ACC GGG CCC AAC GAC ACG TCG CCG GGC AGC     1395
Val Lys Lys Val Ile Cys Thr Gly Pro Asn Asp Thr Ser Pro Gly Ser
        365                 370                 375

CCC CGC CAC ACG GTG CCT CAG TGT TGC TAC GGC TTT TGC ATC GAC CTG     1443
Pro Arg His Thr Val Pro Gln Cys Cys Tyr Gly Phe Cys Ile Asp Leu
    380                 385                 390

CTC ATC AAG CTG GCA CGG ACC ATG AAC TTC ACC TAC GAG GTG CAC CTG     1491
Leu Ile Lys Leu Ala Arg Thr Met Asn Phe Thr Tyr Glu Val His Leu
395                 400                 405                 410

GTG GCA GAT GGC AAG TTC GGC ACA CAG GAG CGG GTG AAC AAC AGC AAC     1539
Val Ala Asp Gly Lys Phe Gly Thr Gln Glu Arg Val Asn Asn Ser Asn
                415                 420                 425

AAG AAG GAG TGG AAT GGG ATG ATG GGC GAG CTG CTC AGC GGG CAG GCA     1587
Lys Lys Glu Trp Asn Gly Met Met Gly Glu Leu Leu Ser Gly Gln Ala
            430                 435                 440

GAC ATG ATC GTG GCG CCG CTA ACC ATA AAC AAC GAG CGC GCG CAG TAC     1635
Asp Met Ile Val Ala Pro Leu Thr Ile Asn Asn Glu Arg Ala Gln Tyr
        445                 450                 455

ATC GAG TTT TCC AAG CCC TTC AAG TAC CAG GGC CTG ACT ATT CTG GTC     1683
Ile Glu Phe Ser Lys Pro Phe Lys Tyr Gln Gly Leu Thr Ile Leu Val
    460                 465                 470

AAG AAG GAG ATT CCC CGG AGC ACG CTG GAC TCG TTC ATG CAG CCG TTC     1731
Lys Lys Glu Ile Pro Arg Ser Thr Leu Asp Ser Phe Met Gln Pro Phe
475                 480                 485                 490

CAG AGC ACA CTG TGG CTG CTG GTG GGG CTG TCG GTG CAC GTG GTG GCC     1779
Gln Ser Thr Leu Trp Leu Leu Val Gly Leu Ser Val His Val Val Ala
                495                 500                 505
```

-continued

```
GTG ATG CTG TAC CTG CTG GAC CGC TTC AGC CCC TTC GGC CGG TTC AAG      1827
Val Met Leu Tyr Leu Leu Asp Arg Phe Ser Pro Phe Gly Arg Phe Lys
            510                 515                 520

GTG AAC AGC GAG GAG GAG GAG GAG GAC GCA CTG ACC CTG TCC TCG GCC      1875
Val Asn Ser Glu Glu Glu Glu Glu Asp Ala Leu Thr Leu Ser Ser Ala
        525                 530                 535

ATG TGG TTC TCC TGG GGC GTC CTG CTC AAC TCC GGC ATC GGG GAA GGC      1923
Met Trp Phe Ser Trp Gly Val Leu Leu Asn Ser Gly Ile Gly Glu Gly
    540                 545                 550

GCC CCC AGA AGC TTC TCA GCG CGC ATC CTG GGC ATG GTG TGG GCC GGC      1971
Ala Pro Arg Ser Phe Ser Ala Arg Ile Leu Gly Met Val Trp Ala Gly
555                 560                 565                 570

TTT GCC ATG ATC ATC GTG GCC TCC TAC ACC GCC AAC CTG GCG GCC TTC      2019
Phe Ala Met Ile Ile Val Ala Ser Tyr Thr Ala Asn Leu Ala Ala Phe
                575                 580                 585

CTG GTG CTG GAC CGG CCG GAG GAG CGC ATC ACG GGC ATC AAC GAC CCT      2067
Leu Val Leu Asp Arg Pro Glu Glu Arg Ile Thr Gly Ile Asn Asp Pro
            590                 595                 600

CGG CTG AGG AAC CCC TCG GAC AAG TTT ATC TAC GCC ACG GTG AAG CAG      2115
Arg Leu Arg Asn Pro Ser Asp Lys Phe Ile Tyr Ala Thr Val Lys Gln
        605                 610                 615

AGC TCC GTG GAT ATC TAC TTC CGG CGC CAG GTG GAG CTG AGC ACC ATG      2163
Ser Ser Val Asp Ile Tyr Phe Arg Arg Gln Val Glu Leu Ser Thr Met
    620                 625                 630

TAC CGG CAT ATG GAG AAG CAC AAC TAC GAG AGT GCG GCG GAG GCC ATC      2211
Tyr Arg His Met Glu Lys His Asn Tyr Glu Ser Ala Ala Glu Ala Ile
635                 640                 645                 650

CAG GCC GTG AGA GAC AAC AAG CTG CAT GCC TTC ATC TGG GAC TCG GCG      2259
Gln Ala Val Arg Asp Asn Lys Leu His Ala Phe Ile Trp Asp Ser Ala
                655                 660                 665

GTG CTG GAG TTC GAG GCC TCG CAG AAG TGC GAC CTG GTG ACG ACT GGA      2307
Val Leu Glu Phe Glu Ala Ser Gln Lys Cys Asp Leu Val Thr Thr Gly
            670                 675                 680

GAG CTG TTT TTC CGC TCG GGC TTC GGC ATA GGC ATG CGC AAA GAC AGC      2355
Glu Leu Phe Phe Arg Ser Gly Phe Gly Ile Gly Met Arg Lys Asp Ser
        685                 690                 695

CCC TGG AAG CAG AAC GTC TCC CTG TCC ATC CTC AAG TCC CAC GAG AAT      2403
Pro Trp Lys Gln Asn Val Ser Leu Ser Ile Leu Lys Ser His Glu Asn
    700                 705                 710

GGC TTC ATG GAA GAC CTG GAC AAG ACG TGG GTT CGG TAT CAG GAA TGT      2451
Gly Phe Met Glu Asp Leu Asp Lys Thr Trp Val Arg Tyr Gln Glu Cys
715                 720                 725                 730

GAC TCG CGC AGC AAC GCC CCT GCG ACC CTT ACT TTT GAG AAC ATG GCC      2499
Asp Ser Arg Ser Asn Ala Pro Ala Thr Leu Thr Phe Glu Asn Met Ala
                735                 740                 745

GGG GTC TTC ATG CTG GTA GCT GGG GGC ATC GTG GCC GGG ATC TTC CTG      2547
Gly Val Phe Met Leu Val Ala Gly Gly Ile Val Ala Gly Ile Phe Leu
            750                 755                 760

ATT TTC ATC GAG ATT GCC TAC AAG CGG CAC AAG GAT GCT CGC CGG AAG      2595
Ile Phe Ile Glu Ile Ala Tyr Lys Arg His Lys Asp Ala Arg Arg Lys
        765                 770                 775

CAG ATG CAG CTG GCC TTT GCC GCC GTT AAC GTG TGG CGG AAG AAC CTG      2643
Gln Met Gln Leu Ala Phe Ala Ala Val Asn Val Trp Arg Lys Asn Leu
    780                 785                 790

CAG GAT AGA AAG AGT GGT AGA GCA GAG CCT GAC CCT AAA AAG AAA GCC      2691
Gln Asp Arg Lys Ser Gly Arg Ala Glu Pro Asp Pro Lys Lys Lys Ala
795                 800                 805                 810

ACA TTT AGG GCT ATC ACC TCC ACC CTG GCT TCC AGC TTC AAG AGG CGT      2739
Thr Phe Arg Ala Ile Thr Ser Thr Leu Ala Ser Ser Phe Lys Arg Arg
                815                 820                 825
```

-continued

```
AGG TCC TCC AAA GAC ACG CTG GCT CGG GAC TGT CTT CAA CCC TGC CCT     2787
Arg Ser Ser Lys Asp Thr Leu Ala Arg Asp Cys Leu Gln Pro Cys Pro
            830                 835                 840

GCA CCT TGG GCA CGG GAG AGC GCC ACC CGC CCG CCC CCG CCC TCG CTC     2835
Ala Pro Trp Ala Arg Glu Ser Ala Thr Arg Pro Pro Pro Pro Ser Leu
        845                 850                 855

CGG GTG CGT GAC CGG CCC GCC ACC TTG TAC AGA ACC AGC ACT CCC AGG     2883
Arg Val Arg Asp Arg Pro Ala Thr Leu Tyr Arg Thr Ser Thr Pro Arg
    860                 865                 870

GCC CGA GCG CGT GCC TTC CCC GTG CGC AGC CGC GCT CTG CCC CTC CGT     2931
Ala Arg Ala Arg Ala Phe Pro Val Arg Ser Arg Ala Leu Pro Leu Arg
875                 880                 885                 890

CCC CAG GGT GCA GGC GCG CAC CGC CCA ACC CCC ACC TCC CGG TGT ATG     2979
Pro Gln Gly Ala Gly Ala His Arg Pro Thr Pro Thr Ser Arg Cys Met
                895                 900                 905

CAG TGG TGATGCCTAA AGGAATGTCA CG                                    3007
Gln Trp
```

(2) INFORMATION FOR SEQ ID NO:34:

(i) SEQUENCE CHARACTERISTICS:
(A) LENGTH: 908 amino acids
(B) TYPE: amino acid
(D) TOPOLOGY: linear (ii) MOLECULE TYPE: protein (xi) SEQUENCE DESCRIPTION: SEQ ID NO:34:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Ala Met Leu Asn Met
```

-continued

```
225                 230                 235                 240

Thr Gly Asn Thr Asn Ile Trp Lys Thr Gly Pro Leu Phe Lys Arg Val
                245                 250                 255

Leu Met Ser Ser Lys Tyr Ala Asp Gly Val Thr Gly Arg Val Glu Phe
            260                 265                 270

Asn Glu Asp Gly Asp Arg Lys Phe Ala Asn Tyr Ser Ile Met Asn Leu
        275                 280                 285

Gln Asn Arg Lys Leu Val Gln Val Gly Ile Tyr Asn Gly Thr His Val
    290                 295                 300

Ile Pro Asn Asp Arg Lys Ile Ile Trp Pro Gly Gly Glu Thr Glu Lys
305                 310                 315                 320

Pro Arg Gly Tyr Gln Met Ser Thr Arg Leu Lys Ile Val Thr Ile His
                325                 330                 335

Gln Glu Pro Phe Val Tyr Val Lys Pro Thr Leu Ser Asp Gly Thr Cys
            340                 345                 350

Lys Glu Glu Phe Thr Val Asn Gly Asp Pro Val Lys Lys Val Ile Cys
        355                 360                 365

Thr Gly Pro Asn Asp Thr Ser Pro Gly Ser Pro Arg His Thr Val Pro
    370                 375                 380

Gln Cys Cys Tyr Gly Phe Cys Ile Asp Leu Leu Ile Lys Leu Ala Arg
385                 390                 395                 400

Thr Met Asn Phe Thr Tyr Glu Val His Leu Val Ala Asp Gly Lys Phe
                405                 410                 415

Gly Thr Gln Glu Arg Val Asn Asn Ser Asn Lys Lys Glu Trp Asn Gly
            420                 425                 430

Met Met Gly Glu Leu Leu Ser Gly Gln Ala Asp Met Ile Val Ala Pro
        435                 440                 445

Leu Thr Ile Asn Asn Glu Arg Ala Gln Tyr Ile Glu Phe Ser Lys Pro
    450                 455                 460

Phe Lys Tyr Gln Gly Leu Thr Ile Leu Val Lys Lys Glu Ile Pro Arg
465                 470                 475                 480

Ser Thr Leu Asp Ser Phe Met Gln Pro Phe Gln Ser Thr Leu Trp Leu
                485                 490                 495

Leu Val Gly Leu Ser Val His Val Val Ala Val Met Leu Tyr Leu Leu
            500                 505                 510

Asp Arg Phe Ser Pro Phe Gly Arg Phe Lys Val Asn Ser Glu Glu Glu
        515                 520                 525

Glu Glu Asp Ala Leu Thr Leu Ser Ser Ala Met Trp Phe Ser Trp Gly
    530                 535                 540

Val Leu Leu Asn Ser Gly Ile Gly Glu Gly Ala Pro Arg Ser Phe Ser
545                 550                 555                 560

Ala Arg Ile Leu Gly Met Val Trp Ala Gly Phe Ala Met Ile Ile Val
                565                 570                 575

Ala Ser Tyr Thr Ala Asn Leu Ala Ala Phe Leu Val Leu Asp Arg Pro
            580                 585                 590

Glu Glu Arg Ile Thr Gly Ile Asn Asp Pro Arg Leu Arg Asn Pro Ser
        595                 600                 605

Asp Lys Phe Ile Tyr Ala Thr Val Lys Gln Ser Ser Val Asp Ile Tyr
    610                 615                 620

Phe Arg Arg Gln Val Glu Leu Ser Thr Met Tyr Arg His Met Glu Lys
625                 630                 635                 640

His Asn Tyr Glu Ser Ala Ala Glu Ala Ile Gln Ala Val Arg Asp Asn
                645                 650                 655
```

```
Lys Leu His Ala Phe Ile Trp Asp Ser Ala Val Leu Glu Phe Glu Ala
            660                 665                 670

Ser Gln Lys Cys Asp Leu Val Thr Thr Gly Glu Leu Phe Phe Arg Ser
        675                 680                 685

Gly Phe Gly Ile Gly Met Arg Lys Asp Ser Pro Trp Lys Gln Asn Val
    690                 695                 700

Ser Leu Ser Ile Leu Lys Ser His Glu Asn Gly Phe Met Glu Asp Leu
705                 710                 715                 720

Asp Lys Thr Trp Val Arg Tyr Gln Glu Cys Asp Ser Arg Ser Asn Ala
                725                 730                 735

Pro Ala Thr Leu Thr Phe Glu Asn Met Ala Gly Val Phe Met Leu Val
            740                 745                 750

Ala Gly Gly Ile Val Ala Gly Ile Phe Leu Ile Phe Ile Glu Ile Ala
        755                 760                 765

Tyr Lys Arg His Lys Asp Ala Arg Arg Lys Gln Met Gln Leu Ala Phe
    770                 775                 780

Ala Ala Val Asn Val Trp Arg Lys Asn Leu Gln Asp Arg Lys Ser Gly
785                 790                 795                 800

Arg Ala Glu Pro Asp Pro Lys Lys Lys Ala Thr Phe Arg Ala Ile Thr
                805                 810                 815

Ser Thr Leu Ala Ser Ser Phe Lys Arg Arg Arg Ser Ser Lys Asp Thr
            820                 825                 830

Leu Ala Arg Asp Cys Leu Gln Pro Cys Pro Ala Pro Trp Ala Arg Glu
        835                 840                 845

Ser Ala Thr Arg Pro Pro Pro Pro Ser Leu Arg Val Arg Asp Arg Pro
    850                 855                 860

Ala Thr Leu Tyr Arg Thr Ser Thr Pro Arg Ala Arg Ala Arg Ala Phe
865                 870                 875                 880

Pro Val Arg Ser Arg Ala Leu Pro Leu Arg Pro Gln Gly Ala Gly Ala
                885                 890                 895

His Arg Pro Thr Pro Thr Ser Arg Cys Met Gln Trp
            900                 905
```

(2) INFORMATION FOR SEQ ID NO:35:

(i) SEQUENCE CHARACTERISTICS:
(A) LENGTH: 3998 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3093

(xi) SEQUENCE DESCRIPTION: SEQ ID NO:35:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC       339
```

-continued

```
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC     1059
Thr Val Tyr Arg Ala Ala Ala Met Leu Asn Met Thr Gly Ser Gly Tyr
                255                 260                 265

GTG TGG CTG GTC GGC GAG CGC GAG ATC TCG GGG AAC GCC CTG CGC TAC     1107
Val Trp Leu Val Gly Glu Arg Glu Ile Ser Gly Asn Ala Leu Arg Tyr
            270                 275                 280

GCC CCA GAC GGC ATC CTC GGG CTG CAG CTC ATC AAC GGC AAG AAC GAG     1155
Ala Pro Asp Gly Ile Leu Gly Leu Gln Leu Ile Asn Gly Lys Asn Glu
        285                 290                 295

TCG GCC CAC ATC AGC GAC GCC GTG GGC GTG GTG GCC CAG GCC GTG CAC     1203
Ser Ala His Ile Ser Asp Ala Val Gly Val Val Ala Gln Ala Val His
    300                 305                 310

GAG CTC CTC GAG AAG GAG AAC ATC ACC GAC CCG CCG CGG GGC TGC GTG     1251
Glu Leu Leu Glu Lys Glu Asn Ile Thr Asp Pro Pro Arg Gly Cys Val
315                 320                 325                 330
```

-continued

```
GGC AAC ACC AAC ATC TGG AAG ACC GGG CCG CTC TTC AAG AGA GTG CTG      1299
Gly Asn Thr Asn Ile Trp Lys Thr Gly Pro Leu Phe Lys Arg Val Leu
            335                 340                 345

ATG TCT TCC AAG TAT GCG GAT GGG GTG ACT GGT CGC GTG GAG TTC AAT      1347
Met Ser Ser Lys Tyr Ala Asp Gly Val Thr Gly Arg Val Glu Phe Asn
            350                 355                 360

GAG GAT GGG GAC CGG AAG TTC GCC AAC TAC AGC ATC ATG AAC CTG CAG      1395
Glu Asp Gly Asp Arg Lys Phe Ala Asn Tyr Ser Ile Met Asn Leu Gln
        365                 370                 375

AAC CGC AAG CTG GTG CAA GTG GGC ATC TAC AAT GGC ACC CAC GTC ATC      1443
Asn Arg Lys Leu Val Gln Val Gly Ile Tyr Asn Gly Thr His Val Ile
    380                 385                 390

CCT AAT GAC AGG AAG ATC ATC TGG CCA GGC GGA GAG ACA GAG AAG CCT      1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG      1539
Arg Gly Tyr Gln Met Ser Thr Arg Leu Lys Ile Val Thr Ile His Gln
            415                 420                 425

GAG CCC TTC GTG TAC GTC AAG CCC ACG CTG AGT GAT GGG ACA TGC AAG      1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC      1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG      1683
Gly Pro Asn Asp Thr Ser Pro Gly Ser Pro Arg His Thr Val Pro Gln
    460                 465                 470

TGT TGC TAC GGC TTT TGC ATC GAC CTG CTC ATC AAG CTG GCA CGG ACC      1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC      1779
Met Asn Phe Thr Tyr Glu Val His Leu Val Ala Asp Gly Lys Phe Gly
            495                 500                 505

ACA CAG GAG CGG GTG AAC AAC AGC AAC AAG AAG GAG TGG AAT GGG ATG      1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA      1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC      1923
Thr Ile Asn Asn Glu Arg Ala Gln Tyr Ile Glu Phe Ser Lys Pro Phe
    540                 545                 550

AAG TAC CAG GGC CTG ACT ATT CTG GTC AAG AAG GAG ATT CCC CGG AGC      1971
Lys Tyr Gln Gly Leu Thr Ile Leu Val Lys Lys Glu Ile Pro Arg Ser
555                 560                 565                 570

ACG CTG GAC TCG TTC ATG CAG CCG TTC CAG AGC ACA CTG TGG CTG CTG      2019
Thr Leu Asp Ser Phe Met Gln Pro Phe Gln Ser Thr Leu Trp Leu Leu
            575                 580                 585

GTG GGG CTG TCG GTG CAC GTG GTG GCC GTG ATG CTG TAC CTG CTG GAC      2067
Val Gly Leu Ser Val His Val Val Ala Val Met Leu Tyr Leu Leu Asp
            590                 595                 600

CGC TTC AGC CCC TTC GGC CGG TTC AAG GTG AAC AGC GAG GAG GAG GAG      2115
Arg Phe Ser Pro Phe Gly Arg Phe Lys Val Asn Ser Glu Glu Glu Glu
        605                 610                 615

GAG GAC GCA CTG ACC CTG TCC TCG GCC ATG TGG TTC TCC TGG GGC GTC      2163
Glu Asp Ala Leu Thr Leu Ser Ser Ala Met Trp Phe Ser Trp Gly Val
    620                 625                 630

CTG CTC AAC TCC GGC ATC GGG GAA GGC GCC CCC AGA AGC TTC TCA GCG      2211
Leu Leu Asn Ser Gly Ile Gly Glu Gly Ala Pro Arg Ser Phe Ser Ala
635                 640                 645                 650
```

-continued

```
CGC ATC CTG GGC ATG GTG TGG GCC GGC TTT GCC ATG ATC ATC GTG GCC      2259
Arg Ile Leu Gly Met Val Trp Ala Gly Phe Ala Met Ile Ile Val Ala
                655                 660                 665

TCC TAC ACC GCC AAC CTG GCG GCC TTC CTG GTG CTG GAC CGG CCG GAG      2307
Ser Tyr Thr Ala Asn Leu Ala Ala Phe Leu Val Leu Asp Arg Pro Glu
            670                 675                 680

GAG CGC ATC ACG GGC ATC AAC GAC CCT CGG CTG AGG AAC CCC TCG GAC      2355
Glu Arg Ile Thr Gly Ile Asn Asp Pro Arg Leu Arg Asn Pro Ser Asp
        685                 690                 695

AAG TTT ATC TAC GCC ACG GTG AAG CAG AGC TCC GTG GAT ATC TAC TTC      2403
Lys Phe Ile Tyr Ala Thr Val Lys Gln Ser Ser Val Asp Ile Tyr Phe
    700                 705                 710

CGG CGC CAG GTG GAG CTG AGC ACC ATG TAC CGG CAT ATG GAG AAG CAC      2451
Arg Arg Gln Val Glu Leu Ser Thr Met Tyr Arg His Met Glu Lys His
715                 720                 725                 730

AAC TAC GAG AGT GCG GCG GAG GCC ATC CAG GCC GTG AGA GAC AAC AAG      2499
Asn Tyr Glu Ser Ala Ala Glu Ala Ile Gln Ala Val Arg Asp Asn Lys
                735                 740                 745

CTG CAT GCC TTC ATC TGG GAC TCG GCG GTG CTG GAG TTC GAG GCC TCG      2547
Leu His Ala Phe Ile Trp Asp Ser Ala Val Leu Glu Phe Glu Ala Ser
            750                 755                 760

CAG AAG TGC GAC CTG GTG ACG ACT GGA GAG CTG TTT TTC CGC TCG GGC      2595
Gln Lys Cys Asp Leu Val Thr Thr Gly Glu Leu Phe Phe Arg Ser Gly
        765                 770                 775

TTC GGC ATA GGC ATG CGC AAA GAC AGC CCC TGG AAG CAG AAC GTC TCC      2643
Phe Gly Ile Gly Met Arg Lys Asp Ser Pro Trp Lys Gln Asn Val Ser
    780                 785                 790

CTG TCC ATC CTC AAG TCC CAC GAG AAT GGC TTC ATG GAA GAC CTG GAC      2691
Leu Ser Ile Leu Lys Ser His Glu Asn Gly Phe Met Glu Asp Leu Asp
795                 800                 805                 810

AAG ACG TGG GTT CGG TAT CAG GAA TGT GAC TCG CGC AGC AAC GCC CCT      2739
Lys Thr Trp Val Arg Tyr Gln Glu Cys Asp Ser Arg Ser Asn Ala Pro
                815                 820                 825

GCG ACC CTT ACT TTT GAG AAC ATG GCC GGG GTC TTC ATG CTG GTA GCT      2787
Ala Thr Leu Thr Phe Glu Asn Met Ala Gly Val Phe Met Leu Val Ala
            830                 835                 840

GGG GGC ATC GTG GCC GGG ATC TTC CTG ATT TTC ATC GAG ATT GCC TAC      2835
Gly Gly Ile Val Ala Gly Ile Phe Leu Ile Phe Ile Glu Ile Ala Tyr
        845                 850                 855

AAG CGG CAC AAG GAT GCT CGC CGG AAG CAG ATG CAG CTG GCC TTT GCC      2883
Lys Arg His Lys Asp Ala Arg Arg Lys Gln Met Gln Leu Ala Phe Ala
    860                 865                 870

GCC GTT AAC GTG TGG CGG AAG AAC CTG CAG GAT AGA AAG AGT GGT AGA      2931
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC      2979
Ala Glu Pro Asp Pro Lys Lys Lys Ala Thr Phe Arg Ala Ile Thr Ser
                895                 900                 905

ACC CTG GCT TCC AGC TTC AAG AGG CGT AGG TCC TCC AAA GAC ACG CAG      3027
Thr Leu Ala Ser Ser Phe Lys Arg Arg Arg Ser Ser Lys Asp Thr Gln
            910                 915                 920

TAC CAT CCC ACT GAT ATC ACG GGC CCG CTC AAC CTC TCA GAT CCC TCG      3075
Tyr His Pro Thr Asp Ile Thr Gly Pro Leu Asn Leu Ser Asp Pro Ser
        925                 930                 935

GTC AGC ACC GTG GTG TGAGGCCCCC GGAGGCGCCC ACCTGCCCAG TTAGCCCGGC      3130
Val Ser Thr Val Val
    940

CAAGGACACT GATGGGTCCT GCTGCTCGGG AAGGCCTGAG GGAAGCCCAC CCGCCCCAGA   3190
```

-continued

GACTGCCCAC CCTGGGCCTC CCGTCCGTCC GCCCGCCCAC CCCGCTGCCT GGCGGGCAGC 3250

CCCTGCTGGA CCAAGGTGCG GACCGGAGCG GCTGAGGACG GGCAGAGCT GAGTCGGCTG 3310

GGCAGGGCCG CAGGGCGCTC CGGCAGAGGC AGGCCCCTGG GGTCTCTGAG CAGTGGGGAG 3370

CGGGGGCTAA CTGCCCCCAG GCGGAGGGGC TTGGAGCAGA GACGGCAGCC CCATCCTTCC 3430

CGCAGCACCA GCCTGAGCCA CAGTGGGGCC CATGGCCCCA GCTGGCTGGG TCGCCCCTCC 3490

TCGGGCGCCT GCGCTCCTCT GCAGCCTGAG CTCCACCCTC CCCTCTTCTT GCGGCACCGC 3550

CCACCAAACA CCCCGTCTGC CCCTTGACGC CACACGCCGG GGCTGGCGCT GCCCTCCCCC 3610

ACGGCCGTCC CTGACTTCCC AGCTGGCAGC GCCTCCCGCC GCCTCGGGCC GCCTCCTCCA 3670

GAATCGAGAG GGCTGAGCCC CTCCTCTCCT CGTCCGGCCT GCAGCACAGA AGGGGGCCTC 3730

CCCGGGGGTC CCCGGACGCT GGCTCGGGAC TGTCTTCAAC CCTGCCCTGC ACCTTGGGCA 3790

CGGGAGAGCG CCACCCGCCC GCCCCCGCCC TCGCTCCGGG TGCGTGACCG GCCCGCCACC 3850

TTGTACAGAA CCAGCACTCC CAGGGCCCGA GCGCGTGCCT TCCCCGTGCG CAGCCGCGCT 3910

CTGCCCCTCC GTCCCCAGGG TGCAGGCGCG CACCGCCCAA CCCCCACCTC CCGGTGTATG 3970

CAGTGGTGAT GCCTAAAGGA ATGTCACG 3998

(2) INFORMATION FOR SEQ ID NO:36:

(i) SEQUENCE CHARACTERISTICS:
(A) LENGTH: 943 amino acids
(B) TYPE: amino acid
(D) TOPOLOGY: linear (ii) MOLECULE TYPE: protein (xi) SEQUENCE DESCRIPTION: SEQ ID NO:36:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205
```

-continued

```
Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Glu Asp Ala Leu Thr Leu
    610                 615                 620

Ser Ser Ala Met Trp Phe Ser Trp Gly Val Leu Leu Asn Ser Gly Ile
```

-continued

```
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
    690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Asp Arg Lys Ser Gly Arg Ala Glu Pro Asp Pro Lys
                885                 890                 895

Lys Lys Ala Thr Phe Arg Ala Ile Thr Ser Thr Leu Ala Ser Ser Phe
            900                 905                 910

Lys Arg Arg Arg Ser Ser Lys Asp Thr Gln Tyr His Pro Thr Asp Ile
        915                 920                 925

Thr Gly Pro Leu Asn Leu Ser Asp Pro Ser Val Ser Thr Val Val
    930                 935                 940
```

(2) INFORMATION FOR SEQ ID NO:37:

(i) SEQUENCE CHARACTERISTICS:
(A) LENGTH: 3274 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3255

(xi) SEQUENCE DESCRIPTION: SEQ ID NO:37:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120
```

-continued

```
CCGGGACCGC CGCTCCGGGG GAGACGTGGC GTCCGCAGCC CGCGGGGCCG GGCGAGCGCA    180

GGACGGCCCG GAAGCCCCGC GGGGGATGCG CCGAGGGCCC CGCGTTCGCG CCGCGCAGAG    240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC     1059
Thr Val Tyr Arg Ala Ala Ala Met Leu Asn Met Thr Gly Ser Gly Tyr
                255                 260                 265

GTG TGG CTG GTC GGC GAG CGC GAG ATC TCG GGG AAC GCC CTG CGC TAC     1107
Val Trp Leu Val Gly Glu Arg Glu Ile Ser Gly Asn Ala Leu Arg Tyr
            270                 275                 280

GCC CCA GAC GGC ATC CTC GGG CTG CAG CTC ATC AAC GGC AAG AAC GAG     1155
Ala Pro Asp Gly Ile Leu Gly Leu Gln Leu Ile Asn Gly Lys Asn Glu
```

-continued

```
        285                 290                 295

TCG GCC CAC ATC AGC GAC GCC GTG GGC GTG GTG GCC CAG GCC GTG CAC      1203
Ser Ala His Ile Ser Asp Ala Val Gly Val Val Ala Gln Ala Val His
    300                 305                 310

GAG CTC CTC GAG AAG GAG AAC ATC ACC GAC CCG CCG CGG GGC TGC GTG      1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG      1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT      1347
Met Ser Ser Lys Tyr Ala Asp Gly Val Thr Gly Arg Val Glu Phe Asn
            350                 355                 360

GAG GAT GGG GAC CGG AAG TTC GCC AAC TAC AGC ATC ATG AAC CTG CAG      1395
Glu Asp Gly Asp Arg Lys Phe Ala Asn Tyr Ser Ile Met Asn Leu Gln
        365                 370                 375

AAC CGC AAG CTG GTG CAA GTG GGC ATC TAC AAT GGC ACC CAC GTC ATC      1443
Asn Arg Lys Leu Val Gln Val Gly Ile Tyr Asn Gly Thr His Val Ile
    380                 385                 390

CCT AAT GAC AGG AAG ATC ATC TGG CCA GGC GGA GAG ACA GAG AAG CCT      1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG      1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG      1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC      1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG      1683
Gly Pro Asn Asp Thr Ser Pro Gly Ser Pro Arg His Thr Val Pro Gln
    460                 465                 470

TGT TGC TAC GGC TTT TGC ATC GAC CTG CTC ATC AAG CTG GCA CGG ACC      1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC      1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG      1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA      1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC      1923
Thr Ile Asn Asn Glu Arg Ala Gln Tyr Ile Glu Phe Ser Lys Pro Phe
    540                 545                 550

AAG TAC CAG GGC CTG ACT ATT CTG GTC AAG AAG GAG ATT CCC CGG AGC      1971
Lys Tyr Gln Gly Leu Thr Ile Leu Val Lys Lys Glu Ile Pro Arg Ser
555                 560                 565                 570

ACG CTG GAC TCG TTC ATG CAG CCG TTC CAG AGC ACA CTG TGG CTG CTG      2019
Thr Leu Asp Ser Phe Met Gln Pro Phe Gln Ser Thr Leu Trp Leu Leu
                575                 580                 585

GTG GGG CTG TCG GTG CAC GTG GTG GCC GTG ATG CTG TAC CTG CTG GAC      2067
Val Gly Leu Ser Val His Val Val Ala Val Met Leu Tyr Leu Leu Asp
            590                 595                 600

CGC TTC AGC CCC TTC GGC CGG TTC AAG GTG AAC AGC GAG GAG GAG GAG      2115
```

-continued

```
Arg Phe Ser Pro Phe Gly Arg Phe Lys Val Asn Ser Glu Glu Glu Glu
        605                 610                 615

GAG GAC GCA CTG ACC CTG TCC TCG GCC ATG TGG TTC TCC TGG GGC GTC      2163
Glu Asp Ala Leu Thr Leu Ser Ser Ala Met Trp Phe Ser Trp Gly Val
    620                 625                 630

CTG CTC AAC TCC GGC ATC GGG GAA GGC GCC CCC AGA AGC TTC TCA GCG      2211
Leu Leu Asn Ser Gly Ile Gly Glu Gly Ala Pro Arg Ser Phe Ser Ala
635                 640                 645                 650

CGC ATC CTG GGC ATG GTG TGG GCC GGC TTT GCC ATG ATC ATC GTG GCC      2259
Arg Ile Leu Gly Met Val Trp Ala Gly Phe Ala Met Ile Ile Val Ala
                655                 660                 665

TCC TAC ACC GCC AAC CTG GCG GCC TTC CTG GTG CTG GAC CGG CCG GAG      2307
Ser Tyr Thr Ala Asn Leu Ala Ala Phe Leu Val Leu Asp Arg Pro Glu
            670                 675                 680

GAG CGC ATC ACG GGC ATC AAC GAC CCT CGG CTG AGG AAC CCC TCG GAC      2355
Glu Arg Ile Thr Gly Ile Asn Asp Pro Arg Leu Arg Asn Pro Ser Asp
        685                 690                 695

AAG TTT ATC TAC GCC ACG GTG AAG CAG AGC TCC GTG GAT ATC TAC TTC      2403
Lys Phe Ile Tyr Ala Thr Val Lys Gln Ser Ser Val Asp Ile Tyr Phe
    700                 705                 710

CGG CGC CAG GTG GAG CTG AGC ACC ATG TAC CGG CAT ATG GAG AAG CAC      2451
Arg Arg Gln Val Glu Leu Ser Thr Met Tyr Arg His Met Glu Lys His
715                 720                 725                 730

AAC TAC GAG AGT GCG GCG GAG GCC ATC CAG GCC GTG AGA GAC AAC AAG      2499
Asn Tyr Glu Ser Ala Ala Glu Ala Ile Gln Ala Val Arg Asp Asn Lys
                735                 740                 745

CTG CAT GCC TTC ATC TGG GAC TCG GCG GTG CTG GAG TTC GAG GCC TCG      2547
Leu His Ala Phe Ile Trp Asp Ser Ala Val Leu Glu Phe Glu Ala Ser
            750                 755                 760

CAG AAG TGC GAC CTG GTG ACG ACT GGA GAG CTG TTT TTC CGC TCG GGC      2595
Gln Lys Cys Asp Leu Val Thr Thr Gly Glu Leu Phe Phe Arg Ser Gly
        765                 770                 775

TTC GGC ATA GGC ATG CGC AAA GAC AGC CCC TGG AAG CAG AAC GTC TCC      2643
Phe Gly Ile Gly Met Arg Lys Asp Ser Pro Trp Lys Gln Asn Val Ser
    780                 785                 790

CTG TCC ATC CTC AAG TCC CAC GAG AAT GGC TTC ATG GAA GAC CTG GAC      2691
Leu Ser Ile Leu Lys Ser His Glu Asn Gly Phe Met Glu Asp Leu Asp
795                 800                 805                 810

AAG ACG TGG GTT CGG TAT CAG GAA TGT GAC TCG CGC AGC AAC GCC CCT      2739
Lys Thr Trp Val Arg Tyr Gln Glu Cys Asp Ser Arg Ser Asn Ala Pro
                815                 820                 825

GCG ACC CTT ACT TTT GAG AAC ATG GCC GGG GTC TTC ATG CTG GTA GCT      2787
Ala Thr Leu Thr Phe Glu Asn Met Ala Gly Val Phe Met Leu Val Ala
            830                 835                 840

GGG GGC ATC GTG GCC GGG ATC TTC CTG ATT TTC ATC GAG ATT GCC TAC      2835
Gly Gly Ile Val Ala Gly Ile Phe Leu Ile Phe Ile Glu Ile Ala Tyr
        845                 850                 855

AAG CGG CAC AAG GAT GCT CGC CGG AAG CAG ATG CAG CTG GCC TTT GCC      2883
Lys Arg His Lys Asp Ala Arg Arg Lys Gln Met Gln Leu Ala Phe Ala
    860                 865                 870

GCC GTT AAC GTG TGG CGG AAG AAC CTG CAG GAT AGA AAG AGT GGT AGA      2931
Ala Val Asn Val Trp Arg Lys Asn Leu Gln Asp Arg Lys Ser Gly Arg
875                 880                 885                 890

GCA GAG CCT GAC CCT AAA AAG AAA GCC ACA TTT AGG GCT ATC ACC TCC      2979
Ala Glu Pro Asp Pro Lys Lys Lys Ala Thr Phe Arg Ala Ile Thr Ser
                895                 900                 905

ACC CTG GCT TCC AGC TTC AAG AGG CGT AGG TCC TCC AAA GAC ACG CTG      3027
Thr Leu Ala Ser Ser Phe Lys Arg Arg Arg Ser Ser Lys Asp Thr Leu
            910                 915                 920
```

-continued

```
GCT CGG GAC TGT CTT CAA CCC TGC CCT GCA CCT TGG GCA CGG GAG AGC     3075
Ala Arg Asp Cys Leu Gln Pro Cys Pro Ala Pro Trp Ala Arg Glu Ser
        925                 930                 935

GCC ACC CGC CCG CCC CCG CCC TCG CTC CGG GTG CGT GAC CGG CCC GCC     3123
Ala Thr Arg Pro Pro Pro Pro Ser Leu Arg Val Arg Asp Arg Pro Ala
    940                 945                 950

ACC TTG TAC AGA ACC AGC ACT CCC AGG GCC CGA GCG CGT GCC TTC CCC     3171
Thr Leu Tyr Arg Thr Ser Thr Pro Arg Ala Arg Ala Arg Ala Phe Pro
955                 960                 965                 970

GTG CGC AGC CGC GCT CTG CCC CTC CGT CCC CAG GGT GCA GGC GCG CAC     3219
Val Arg Ser Arg Ala Leu Pro Leu Arg Pro Gln Gly Ala Gly Ala His
                975                 980                 985

CGC CCA ACC CCC ACC TCC CGG TGT ATG CAG TGG TGATGCCTAA AGGAATGTCA   3272
Arg Pro Thr Pro Thr Ser Arg Cys Met Gln Trp
            990                 995

CG                                                                  3274
```

(2) INFORMATION FOR SEQ ID NO:38:

(i) SEQUENCE CHARACTERISTICS:
(A) LENGTH: 997 amino acids
(B) TYPE: amino acid
(D) TOPOLOGY: linear (ii) MOLECULE TYPE: protein (xi) SEQUENCE DESCRIPTION: SEQ ID NO:38:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240
```

-continued

```
Ile Leu Ser Ala Ser Glu Asp Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
    450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

Val Val Ala Val Met Leu Tyr Leu Leu Asp Arg Phe Ser Pro Phe Gly
        595                 600                 605

Arg Phe Lys Val Asn Ser Glu Glu Glu Glu Glu Asp Ala Leu Thr Leu
    610                 615                 620

Ser Ser Ala Met Trp Phe Ser Trp Gly Val Leu Leu Asn Ser Gly Ile
625                 630                 635                 640

Gly Glu Gly Ala Pro Arg Ser Phe Ser Ala Arg Ile Leu Gly Met Val
                645                 650                 655

Trp Ala Gly Phe Ala Met Ile Ile Val Ala Ser Tyr Thr Ala Asn Leu
```

-continued

```
            660                 665                 670

Ala Ala Phe Leu Val Leu Asp Arg Pro Glu Glu Arg Ile Thr Gly Ile
        675                 680                 685

Asn Asp Pro Arg Leu Arg Asn Pro Ser Asp Lys Phe Ile Tyr Ala Thr
    690                 695                 700

Val Lys Gln Ser Ser Val Asp Ile Tyr Phe Arg Arg Gln Val Glu Leu
705                 710                 715                 720

Ser Thr Met Tyr Arg His Met Glu Lys His Asn Tyr Glu Ser Ala Ala
                725                 730                 735

Glu Ala Ile Gln Ala Val Arg Asp Asn Lys Leu His Ala Phe Ile Trp
            740                 745                 750

Asp Ser Ala Val Leu Glu Phe Glu Ala Ser Gln Lys Cys Asp Leu Val
        755                 760                 765

Thr Thr Gly Glu Leu Phe Phe Arg Ser Gly Phe Gly Ile Gly Met Arg
    770                 775                 780

Lys Asp Ser Pro Trp Lys Gln Asn Val Ser Leu Ser Ile Leu Lys Ser
785                 790                 795                 800

His Glu Asn Gly Phe Met Glu Asp Leu Asp Lys Thr Trp Val Arg Tyr
                805                 810                 815

Gln Glu Cys Asp Ser Arg Ser Asn Ala Pro Ala Thr Leu Thr Phe Glu
            820                 825                 830

Asn Met Ala Gly Val Phe Met Leu Val Ala Gly Gly Ile Val Ala Gly
        835                 840                 845

Ile Phe Leu Ile Phe Ile Glu Ile Ala Tyr Lys Arg His Lys Asp Ala
    850                 855                 860

Arg Arg Lys Gln Met Gln Leu Ala Phe Ala Ala Val Asn Val Trp Arg
865                 870                 875                 880

Lys Asn Leu Gln Asp Arg Lys Ser Gly Arg Ala Glu Pro Asp Pro Lys
                885                 890                 895

Lys Lys Ala Thr Phe Arg Ala Ile Thr Ser Thr Leu Ala Ser Ser Phe
            900                 905                 910

Lys Arg Arg Arg Ser Ser Lys Asp Thr Leu Ala Arg Asp Cys Leu Gln
        915                 920                 925

Pro Cys Pro Ala Pro Trp Ala Arg Glu Ser Ala Thr Arg Pro Pro Pro
    930                 935                 940

Pro Ser Leu Arg Val Arg Asp Arg Pro Ala Thr Leu Tyr Arg Thr Ser
945                 950                 955                 960

Thr Pro Arg Ala Arg Ala Arg Ala Phe Pro Val Arg Ser Arg Ala Leu
                965                 970                 975

Pro Leu Arg Pro Gln Gly Ala Gly Ala His Arg Pro Thr Pro Thr Ser
            980                 985                 990

Arg Cys Met Gln Trp
        995
```

(2) INFORMATION FOR SEQ ID NO:39:

(i) SEQUENCE CHARACTERISTICS:
(A) LENGTH: 3070 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 262..3051

-continued (xi) SEQUENCE DESCRIPTION: SEQ ID NO:39:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                        Met Ser Thr Met Arg Leu Leu Thr Leu Ala
                          1               5                  10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
                 15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
     60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC AAC ACC AAC     1059
Thr Val Tyr Arg Ala Ala Ala Met Leu Asn Met Thr Gly Asn Thr Asn
                255                 260                 265
```

-continued

```
ATC TGG AAG ACC GGG CCG CTC TTC AAG AGA GTG CTG ATG TCT TCC AAG      1107
Ile Trp Lys Thr Gly Pro Leu Phe Lys Arg Val Leu Met Ser Ser Lys
            270                 275                 280

TAT GCG GAT GGG GTG ACT GGT CGC GTG GAG TTC AAT GAG GAT GGG GAC      1155
Tyr Ala Asp Gly Val Thr Gly Arg Val Glu Phe Asn Glu Asp Gly Asp
        285                 290                 295

CGG AAG TTC GCC AAC TAC AGC ATC ATG AAC CTG CAG AAC CGC AAG CTG      1203
Arg Lys Phe Ala Asn Tyr Ser Ile Met Asn Leu Gln Asn Arg Lys Leu
    300                 305                 310

GTG CAA GTG GGC ATC TAC AAT GGC ACC CAC GTC ATC CCT AAT GAC AGG      1251
Val Gln Val Gly Ile Tyr Asn Gly Thr His Val Ile Pro Asn Asp Arg
315                 320                 325                 330

AAG ATC ATC TGG CCA GGC GGA GAG ACA GAG AAG CCT CGA GGG TAC CAG      1299
Lys Ile Ile Trp Pro Gly Gly Glu Thr Glu Lys Pro Arg Gly Tyr Gln
                335                 340                 345

ATG TCC ACC AGA CTG AAG ATT GTG ACG ATC CAC CAG GAG CCC TTC GTG      1347
Met Ser Thr Arg Leu Lys Ile Val Thr Ile His Gln Glu Pro Phe Val
            350                 355                 360

TAC GTC AAG CCC ACG CTG AGT GAT GGG ACA TGC AAG GAG GAG TTC ACA      1395
Tyr Val Lys Pro Thr Leu Ser Asp Gly Thr Cys Lys Glu Glu Phe Thr
        365                 370                 375

GTC AAC GGC GAC CCA GTC AAG AAG GTG ATC TGC ACC GGG CCC AAC GAC      1443
Val Asn Gly Asp Pro Val Lys Lys Val Ile Cys Thr Gly Pro Asn Asp
    380                 385                 390

ACG TCG CCG GGC AGC CCC CGC CAC ACG GTG CCT CAG TGT TGC TAC GGC      1491
Thr Ser Pro Gly Ser Pro Arg His Thr Val Pro Gln Cys Cys Tyr Gly
395                 400                 405                 410

TTT TGC ATC GAC CTG CTC ATC AAG CTG GCA CGG ACC ATG AAC TTC ACC      1539
Phe Cys Ile Asp Leu Leu Ile Lys Leu Ala Arg Thr Met Asn Phe Thr
                415                 420                 425

TAC GAG GTG CAC CTG GTG GCA GAT GGC AAG TTC GGC ACA CAG GAG CGG      1587
Tyr Glu Val His Leu Val Ala Asp Gly Lys Phe Gly Thr Gln Glu Arg
            430                 435                 440

GTG AAC AAC AGC AAC AAG AAG GAG TGG AAT GGG ATG ATG GGC GAG CTG      1635
Val Asn Asn Ser Asn Lys Lys Glu Trp Asn Gly Met Met Gly Glu Leu
        445                 450                 455

CTC AGC GGG CAG GCA GAC ATG ATC GTG GCG CCG CTA ACC ATA AAC AAC      1683
Leu Ser Gly Gln Ala Asp Met Ile Val Ala Pro Leu Thr Ile Asn Asn
    460                 465                 470

GAG CGC GCG CAG TAC ATC GAG TTT TCC AAG CCC TTC AAG TAC CAG GGC      1731
Glu Arg Ala Gln Tyr Ile Glu Phe Ser Lys Pro Phe Lys Tyr Gln Gly
475                 480                 485                 490

CTG ACT ATT CTG GTC AAG AAG GAG ATT CCC CGG AGC ACG CTG GAC TCG      1779
Leu Thr Ile Leu Val Lys Lys Glu Ile Pro Arg Ser Thr Leu Asp Ser
                495                 500                 505

TTC ATG CAG CCG TTC CAG AGC ACA CTG TGG CTG CTG GTG GGG CTG TCG      1827
Phe Met Gln Pro Phe Gln Ser Thr Leu Trp Leu Leu Val Gly Leu Ser
            510                 515                 520

GTG CAC GTG GTG GCC GTG ATG CTG TAC CTG CTG GAC CGC TTC AGC CCC      1875
Val His Val Val Ala Val Met Leu Tyr Leu Leu Asp Arg Phe Ser Pro
        525                 530                 535

TTC GGC CGG TTC AAG GTG AAC AGC GAG GAG GAG GAG GAG GAC GCA CTG      1923
Phe Gly Arg Phe Lys Val Asn Ser Glu Glu Glu Glu Glu Asp Ala Leu
    540                 545                 550

ACC CTG TCC TCG GCC ATG TGG TTC TCC TGG GGC GTC CTG CTC AAC TCC      1971
Thr Leu Ser Ser Ala Met Trp Phe Ser Trp Gly Val Leu Leu Asn Ser
555                 560                 565                 570

GGC ATC GGG GAA GGC GCC CCC AGA AGC TTC TCA GCG CGC ATC CTG GGC      2019
Gly Ile Gly Glu Gly Ala Pro Arg Ser Phe Ser Ala Arg Ile Leu Gly
                575                 580                 585
```

-continued

```
ATG GTG TGG GCC GGC TTT GCC ATG ATC ATC GTG GCC TCC TAC ACC GCC     2067
Met Val Trp Ala Gly Phe Ala Met Ile Ile Val Ala Ser Tyr Thr Ala
            590                 595                 600

AAC CTG GCG GCC TTC CTG GTG CTG GAC CGG CCG GAG GAG CGC ATC ACG     2115
Asn Leu Ala Ala Phe Leu Val Leu Asp Arg Pro Glu Glu Arg Ile Thr
        605                 610                 615

GGC ATC AAC GAC CCT CGG CTG AGG AAC CCC TCG GAC AAG TTT ATC TAC     2163
Gly Ile Asn Asp Pro Arg Leu Arg Asn Pro Ser Asp Lys Phe Ile Tyr
    620                 625                 630

GCC ACG GTG AAG CAG AGC TCC GTG GAT ATC TAC TTC CGG CGC CAG GTG     2211
Ala Thr Val Lys Gln Ser Ser Val Asp Ile Tyr Phe Arg Arg Gln Val
635                 640                 645                 650

GAG CTG AGC ACC ATG TAC CGG CAT ATG GAG AAG CAC AAC TAC GAG AGT     2259
Glu Leu Ser Thr Met Tyr Arg His Met Glu Lys His Asn Tyr Glu Ser
                655                 660                 665

GCG GCG GAG GCC ATC CAG GCC GTG AGA GAC AAC AAG CTG CAT GCC TTC     2307
Ala Ala Glu Ala Ile Gln Ala Val Arg Asp Asn Lys Leu His Ala Phe
            670                 675                 680

ATC TGG GAC TCG GCG GTG CTG GAG TTC GAG GCC TCG CAG AAG TGC GAC     2355
Ile Trp Asp Ser Ala Val Leu Glu Phe Glu Ala Ser Gln Lys Cys Asp
        685                 690                 695

CTG GTG ACG ACT GGA GAG CTG TTT TTC CGC TCG GGC TTC GGC ATA GGC     2403
Leu Val Thr Thr Gly Glu Leu Phe Phe Arg Ser Gly Phe Gly Ile Gly
    700                 705                 710

ATG CGC AAA GAC AGC CCC TGG AAG CAG AAC GTC TCC CTG TCC ATC CTC     2451
Met Arg Lys Asp Ser Pro Trp Lys Gln Asn Val Ser Leu Ser Ile Leu
715                 720                 725                 730

AAG TCC CAC GAG AAT GGC TTC ATG GAA GAC CTG GAC AAG ACG TGG GTT     2499
Lys Ser His Glu Asn Gly Phe Met Glu Asp Leu Asp Lys Thr Trp Val
                735                 740                 745

CGG TAT CAG GAA TGT GAC TCG CGC AGC AAC GCC CCT GCG ACC CTT ACT     2547
Arg Tyr Gln Glu Cys Asp Ser Arg Ser Asn Ala Pro Ala Thr Leu Thr
            750                 755                 760

TTT GAG AAC ATG GCC GGG GTC TTC ATG CTG GTA GCT GGG GGC ATC GTG     2595
Phe Glu Asn Met Ala Gly Val Phe Met Leu Val Ala Gly Gly Ile Val
        765                 770                 775

GCC GGG ATC TTC CTG ATT TTC ATC GAG ATT GCC TAC AAG CGG CAC AAG     2643
Ala Gly Ile Phe Leu Ile Phe Ile Glu Ile Ala Tyr Lys Arg His Lys
    780                 785                 790

GAT GCT CGC CGG AAG CAG ATG CAG CTG GCC TTT GCC GCC GTT AAC GTG     2691
Asp Ala Arg Arg Lys Gln Met Gln Leu Ala Phe Ala Ala Val Asn Val
795                 800                 805                 810

TGG CGG AAG AAC CTG CAG GAT AGA AAG AGT GGT AGA GCA GAG CCT GAC     2739
Trp Arg Lys Asn Leu Gln Asp Arg Lys Ser Gly Arg Ala Glu Pro Asp
                815                 820                 825

CCT AAA AAG AAA GCC ACA TTT AGG GCT ATC ACC TCC ACC CTG GCT TCC     2787
Pro Lys Lys Lys Ala Thr Phe Arg Ala Ile Thr Ser Thr Leu Ala Ser
            830                 835                 840

AGC TTC AAG AGG CGT AGG TCC TCC AAA GAC ACG CTG GCT CGG GAC TGT     2835
Ser Phe Lys Arg Arg Arg Ser Ser Lys Asp Thr Leu Ala Arg Asp Cys
        845                 850                 855

CTT CAA CCC TGC CCT GCA CCT TGG GCA CGG GAG AGC GCC ACC CGC CCG     2883
Leu Gln Pro Cys Pro Ala Pro Trp Ala Arg Glu Ser Ala Thr Arg Pro
    860                 865                 870

CCC CCG CCC TCG CTC CGG GTG CGT GAC CGG CCC GCC ACC TTG TAC AGA     2931
Pro Pro Pro Ser Leu Arg Val Arg Asp Arg Pro Ala Thr Leu Tyr Arg
875                 880                 885                 890

ACC AGC ACT CCC AGG GCC CGA GCG CGT GCC TTC CCC GTG CGC AGC CGC     2979
Thr Ser Thr Pro Arg Ala Arg Ala Arg Ala Phe Pro Val Arg Ser Arg
```

-continued

```
              895                 900                 905

GCT CTG CCC CTC CGT CCC CAG GGT GCA GGC GCG CAC CGC CCA ACC CCC      3027
Ala Leu Pro Leu Arg Pro Gln Gly Ala Gly Ala His Arg Pro Thr Pro
            910                 915                 920

ACC TCC CGG TGT ATG CAG TGG TGATGCCTAA AGGAATGTCA CG                 3070
Thr Ser Arg Cys Met Gln Trp
        925                 930
```

(2) INFORMATION FOR SEQ ID NO:40:

(i) SEQUENCE CHARACTERISTICS:
(A) LENGTH: 929 amino acids
(B) TYPE: amino acid
(D) TOPOLOGY: linear (ii) MOLECULE TYPE: protein (xi) SEQUENCE DESCRIPTION: SEQ ID NO:40:

```
Met Ser Thr Met Arg Leu Leu Thr Leu Ala Leu Leu Phe Ser Cys Ser
  1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Asp Ala Ala Thr Val Tyr Arg Ala Ala
                245                 250                 255

Ala Met Leu Asn Met Thr Gly Asn Thr Asn Ile Trp Lys Thr Gly Pro
            260                 265                 270

Leu Phe Lys Arg Val Leu Met Ser Ser Lys Tyr Ala Asp Gly Val Thr
        275                 280                 285

Gly Arg Val Glu Phe Asn Glu Asp Gly Asp Arg Lys Phe Ala Asn Tyr
    290                 295                 300
```

-continued

```
Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                325                 330                 335

Gly Glu Thr Glu Lys Pro Arg Gly Tyr Gln Met Ser Thr Arg Leu Lys
            340                 345                 350

Ile Val Thr Ile His Gln Glu Pro Phe Val Tyr Val Lys Pro Thr Leu
        355                 360                 365

Ser Asp Gly Thr Cys Lys Glu Glu Phe Thr Val Asn Gly Asp Pro Val
    370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                405                 410                 415

Ile Lys Leu Ala Arg Thr Met Asn Phe Thr Tyr Glu Val His Leu Val
            420                 425                 430

Ala Asp Gly Lys Phe Gly Thr Gln Glu Arg Val Asn Asn Ser Asn Lys
        435                 440                 445

Lys Glu Trp Asn Gly Met Met Gly Glu Leu Leu Ser Gly Gln Ala Asp
    450                 455                 460

Met Ile Val Ala Pro Leu Thr Ile Asn Asn Glu Arg Ala Gln Tyr Ile
465                 470                 475                 480

Glu Phe Ser Lys Pro Phe Lys Tyr Gln Gly Leu Thr Ile Leu Val Lys
                485                 490                 495

Lys Glu Ile Pro Arg Ser Thr Leu Asp Ser Phe Met Gln Pro Phe Gln
            500                 505                 510

Ser Thr Leu Trp Leu Leu Val Gly Leu Ser Val His Val Val Ala Val
        515                 520                 525

Met Leu Tyr Leu Leu Asp Arg Phe Ser Pro Phe Gly Arg Phe Lys Val
    530                 535                 540

Asn Ser Glu Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
                565                 570                 575

Pro Arg Ser Phe Ser Ala Arg Ile Leu Gly Met Val Trp Ala Gly Phe
            580                 585                 590

Ala Met Ile Ile Val Ala Ser Tyr Thr Ala Asn Leu Ala Ala Phe Leu
        595                 600                 605

Val Leu Asp Arg Pro Glu Glu Arg Ile Thr Gly Ile Asn Asp Pro Arg
    610                 615                 620

Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
                645                 650                 655

Arg His Met Glu Lys His Asn Tyr Glu Ser Ala Ala Glu Ala Ile Gln
            660                 665                 670

Ala Val Arg Asp Asn Lys Leu His Ala Phe Ile Trp Asp Ser Ala Val
        675                 680                 685

Leu Glu Phe Glu Ala Ser Gln Lys Cys Asp Leu Val Thr Thr Gly Glu
    690                 695                 700

Leu Phe Phe Arg Ser Gly Phe Gly Ile Gly Met Arg Lys Asp Ser Pro
705                 710                 715                 720

Trp Lys Gln Asn Val Ser Leu Ser Ile Leu Lys Ser His Glu Asn Gly
```

-continued

```
            725                 730                 735

Phe Met Glu Asp Leu Asp Lys Thr Trp Val Arg Tyr Gln Glu Cys Asp
            740                 745                 750

Ser Arg Ser Asn Ala Pro Ala Thr Leu Thr Phe Glu Asn Met Ala Gly
        755                 760                 765

Val Phe Met Leu Val Ala Gly Gly Ile Val Ala Gly Ile Phe Leu Ile
    770                 775                 780

Phe Ile Glu Ile Ala Tyr Lys Arg His Lys Asp Ala Arg Arg Lys Gln
785                 790                 795                 800

Met Gln Leu Ala Phe Ala Ala Val Asn Val Trp Arg Lys Asn Leu Gln
                805                 810                 815

Asp Arg Lys Ser Gly Arg Ala Glu Pro Asp Pro Lys Lys Lys Ala Thr
            820                 825                 830

Phe Arg Ala Ile Thr Ser Thr Leu Ala Ser Ser Phe Lys Arg Arg Arg
        835                 840                 845

Ser Ser Lys Asp Thr Leu Ala Arg Asp Cys Leu Gln Pro Cys Pro Ala
    850                 855                 860

Pro Trp Ala Arg Glu Ser Ala Thr Arg Pro Pro Pro Pro Ser Leu Arg
865                 870                 875                 880

Val Arg Asp Arg Pro Ala Thr Leu Tyr Arg Thr Ser Thr Pro Arg Ala
                885                 890                 895

Arg Ala Arg Ala Phe Pro Val Arg Ser Arg Ala Leu Pro Leu Arg Pro
            900                 905                 910

Gln Gly Ala Gly Ala His Arg Pro Thr Pro Thr Ser Arg Cys Met Gln
        915                 920                 925

Trp
```

(2) INFORMATION FOR SEQ ID NO:41:

(i) SEQUENCE CHARACTERISTICS:
(A) LENGTH: 2326 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 3..2324

(xi) SEQUENCE DESCRIPTION: SEQ ID NO:41:

```
CC GGC CAC GTG TGG CTG GTG CCC AAC CTG GCG CTG GGC AGC ACC GAT         47
   Gly His Val Trp Leu Val Pro Asn Leu Ala Leu Gly Ser Thr Asp
     1               5                  10                  15

GCG CCC CCC GCC ACC TTC CCC GTG GGC CTC ATC AGC GTC GTC ACC GAG        95
Ala Pro Pro Ala Thr Phe Pro Val Gly Leu Ile Ser Val Val Thr Glu
                20                  25                  30

AGC TGG CGC CTC AGC CTG CGC CAG AAG GTG CGC GAC GGC GTG GCC ATT       143
Ser Trp Arg Leu Ser Leu Arg Gln Lys Val Arg Asp Gly Val Ala Ile
            35                  40                  45

CTG GCC CTG GGC GCC CAC AGC TAC TGG CGC CAG CAT GGA ACC CTG CCA       191
Leu Ala Leu Gly Ala His Ser Tyr Trp Arg Gln His Gly Thr Leu Pro
        50                  55                  60

GCC CCG GCC GGG GAC TGC CGT GTT CAC CCT GGG CCC GTC AGC CCT GCC       239
Ala Pro Ala Gly Asp Cys Arg Val His Pro Gly Pro Val Ser Pro Ala
    65                  70                  75

CGG GAG GCC TTC TAC AGG CAC CTA CTG AAT GTC ACC TGG GAG GGC CGA       287
Arg Glu Ala Phe Tyr Arg His Leu Leu Asn Val Thr Trp Glu Gly Arg
```

-continued

```
 80                  85                  90                  95

GAC TTC TCC TTC AGC CCT GGT GGG TAC CTG GTC CAG CCC ACC ATG GTG      335
Asp Phe Ser Phe Ser Pro Gly Gly Tyr Leu Val Gln Pro Thr Met Val
                100                 105                 110

GTG ATC GCC CTC AAC CGG CAC CGC CTC TGG GAG ATG GTG GGG CGC TGG      383
Val Ile Ala Leu Asn Arg His Arg Leu Trp Glu Met Val Gly Arg Trp
            115                 120                 125

GAG CAT GGC GTC CTA TAC ATG AAG TAC CCC GTG TGG CCT CGC TAC AGT      431
Glu His Gly Val Leu Tyr Met Lys Tyr Pro Val Trp Pro Arg Tyr Ser
        130                 135                 140

GCC TCT CTG CAG CCT GTG GTG GAC AGT CGG CAC CTG ACG GTG GCC ACG      479
Ala Ser Leu Gln Pro Val Val Asp Ser Arg His Leu Thr Val Ala Thr
    145                 150                 155

CTG GAA GAG CGG CCC TTT GTC ATC GTG GAG AGC CCT GAC CCT GGC ACA      527
Leu Glu Glu Arg Pro Phe Val Ile Val Glu Ser Pro Asp Pro Gly Thr
160                 165                 170                 175

GGA GGC TGT GTC CCC AAC ACC GTG CCC TGC CGC AGG CAG AGC AAC CAC      575
Gly Gly Cys Val Pro Asn Thr Val Pro Cys Arg Arg Gln Ser Asn His
                180                 185                 190

ACC TTC AGC AGC GGG GAC GTG GCC CCC TAC ACC AAG CTC TGC TGT AAG      623
Thr Phe Ser Ser Gly Asp Val Ala Pro Tyr Thr Lys Leu Cys Cys Lys
            195                 200                 205

GGA TTC TGC ATC GAC ATC CTC AAG AAG CTG GCC AGA GTG GTC AAA TTC      671
Gly Phe Cys Ile Asp Ile Leu Lys Lys Leu Ala Arg Val Val Lys Phe
        210                 215                 220

TCC TAC GAC CTG TAC CTG GTG ACC AAC GGC AAG CAT GGC AAG CGG GTG      719
Ser Tyr Asp Leu Tyr Leu Val Thr Asn Gly Lys His Gly Lys Arg Val
    225                 230                 235

CGC GGC GTA TGG AAC GGC ATG ATT GGG GAG GTG TAC TAC AAG CGG GCA      767
Arg Gly Val Trp Asn Gly Met Ile Gly Glu Val Tyr Tyr Lys Arg Ala
240                 245                 250                 255

GAC ATG GCC ATC GGC TCC CTC ACC ATC AAT GAG GAA CGC TCC GAG ATC      815
Asp Met Ala Ile Gly Ser Leu Thr Ile Asn Glu Glu Arg Ser Glu Ile
                260                 265                 270

GTA GAC TTC TCT GTA CCC TTT GTG GAG ACG GGC ATC AGT GTG ATG GTG      863
Val Asp Phe Ser Val Pro Phe Val Glu Thr Gly Ile Ser Val Met Val
            275                 280                 285

GCT CGC AGC AAT GGC ACC GTC TCC CCC TCG GCC TTC TTG GAG CCA TAT      911
Ala Arg Ser Asn Gly Thr Val Ser Pro Ser Ala Phe Leu Glu Pro Tyr
        290                 295                 300

AGC CCT GCA GTG TGG GTG ATG ATG TTT GTC ATG TGC CTC ACT GTG GTG      959
Ser Pro Ala Val Trp Val Met Met Phe Val Met Cys Leu Thr Val Val
    305                 310                 315

GCC ATC ACC GTC TTC ATG TTC GAG TAC TTC AGC CCT GTC AGC TAC AAC     1007
Ala Ile Thr Val Phe Met Phe Glu Tyr Phe Ser Pro Val Ser Tyr Asn
320                 325                 330                 335

CAG AAC CTC ACC AGA GGC AAG AAG TCC GGG GGC CCA GCT TTC ACT ATC     1055
Gln Asn Leu Thr Arg Gly Lys Lys Ser Gly Gly Pro Ala Phe Thr Ile
                340                 345                 350

GGC AAG TCC GTG TGG CTG CTG TGG GCG CTG GTC TTC AAC AAC TCA GTG     1103
Gly Lys Ser Val Trp Leu Leu Trp Ala Leu Val Phe Asn Asn Ser Val
            355                 360                 365

CCC ATC GAG AAC CCG CGG GGC ACC ACC AGC AAG ATC ATG GTT CTG GTC     1151
Pro Ile Glu Asn Pro Arg Gly Thr Thr Ser Lys Ile Met Val Leu Val
        370                 375                 380

TGG GCC TTC TTT GCT GTC ATC TTC CTC GCC AGA TAC ACG GCC AAC CTG     1199
Trp Ala Phe Phe Ala Val Ile Phe Leu Ala Arg Tyr Thr Ala Asn Leu
    385                 390                 395

GCC GCC TTC ATG ATC CAA GAG CAA TAC ATC GAC ACT GTG TCG GGC CTC     1247
```

-continued

Ala Ala Phe Met Ile Gln Glu Gln Tyr Ile Asp Thr Val Ser Gly Leu
400 405 410 415

AGT GAC AAG AAG TTT CAG CGG CCT CAA GAT CAG TAC CCA CCT TTC CGC 1295
Ser Asp Lys Lys Phe Gln Arg Pro Gln Asp Gln Tyr Pro Pro Phe Arg
420 425 430

TTC GGC ACG GTG CCC AAC GGC AGC ACG GAG CGG AAC ATC CGC AGT AAC 1343
Phe Gly Thr Val Pro Asn Gly Ser Thr Glu Arg Asn Ile Arg Ser Asn
435 440 445

TAC CGT GAC ATG CAC ACC CAC ATG GTC AAG TTC AAC CAG CGC TCG GTG 1391
Tyr Arg Asp Met His Thr His Met Val Lys Phe Asn Gln Arg Ser Val
450 455 460

GAG GAC GCG CTC ACC AGC CTC AAG ATG GGC AAG GAC GAG GGC TGC AAG 1439
Glu Asp Ala Leu Thr Ser Leu Lys Met Gly Lys Asp Glu Gly Cys Lys
465 470 475

CTG GTC ACC ATT GGG TCT GGC AAG GTC TTT GCT ACC ACT GGC TAC GGC 1487
Leu Val Thr Ile Gly Ser Gly Lys Val Phe Ala Thr Thr Gly Tyr Gly
480 485 490 495

ATC GCC ATG CAG AAG GAC TCC CAC TGG AAG CGG GCC ATA GAC CTG GCG 1535
Ile Ala Met Gln Lys Asp Ser His Trp Lys Arg Ala Ile Asp Leu Ala
500 505 510

CTC TTG CAG TTC CTG GGG GAC GGA GAG ACA CAG AAA CTG GAG ACA GTG 1583
Leu Leu Gln Phe Leu Gly Asp Gly Glu Thr Gln Lys Leu Glu Thr Val
515 520 525

TGG CTC TCA GGG ATC TGC CAG AAT GAG AAG AAC GAG GTG ATG AGC AGC 1631
Trp Leu Ser Gly Ile Cys Gln Asn Glu Lys Asn Glu Val Met Ser Ser
530 535 540

AAG CTG GAC ATC GAC AAC ATG GGA GGC GTC TTC TAC ATG CTG CTG GTG 1679
Lys Leu Asp Ile Asp Asn Met Gly Gly Val Phe Tyr Met Leu Leu Val
545 550 555

GCC ATG GGG CTG GCC CTG CTG GTC TTC GCC TGG GAG CAC CTG GTC TAC 1727
Ala Met Gly Leu Ala Leu Leu Val Phe Ala Trp Glu His Leu Val Tyr
560 565 570 575

TGG AAG CTG CGC CAC TCG GTG CCC AAC TCA TCC CAG CTG GAC TTC CTG 1775
Trp Lys Leu Arg His Ser Val Pro Asn Ser Ser Gln Leu Asp Phe Leu
580 585 590

CTG GCT TTC AGC AGG GGC ATC TAC AGC TGC TTC AGC GGG GTG CAG AGC 1823
Leu Ala Phe Ser Arg Gly Ile Tyr Ser Cys Phe Ser Gly Val Gln Ser
595 600 605

CTC GCC AGC CCA CCG CGG CAG GCC AGC CCG GAC CTC ACG GCC AGC TCG 1871
Leu Ala Ser Pro Pro Arg Gln Ala Ser Pro Asp Leu Thr Ala Ser Ser
610 615 620

GCC CAG GCC AGC GTG CTC AAG ATT CTG CAG GCA GCC CGC GAC ATG GTG 1919
Ala Gln Ala Ser Val Leu Lys Ile Leu Gln Ala Ala Arg Asp Met Val
625 630 635

ACC ACG GCG GGC GTA AGC AAC TCC CTG GAC CGC GCC ACT CGC ACC ATC 1967
Thr Thr Ala Gly Val Ser Asn Ser Leu Asp Arg Ala Thr Arg Thr Ile
640 645 650 655

GAG AAT TGG GGT GGC GGC CGC CGT GCG CCC CCA CCG TCC CCC TGC CCG 2015
Glu Asn Trp Gly Gly Gly Arg Arg Ala Pro Pro Pro Ser Pro Cys Pro
660 665 670

ACC CCG CGG TCT GGC CCC AGC CCA TGC CTG CCC ACC CCC GAC CCG CCC 2063
Thr Pro Arg Ser Gly Pro Ser Pro Cys Leu Pro Thr Pro Asp Pro Pro
675 680 685

CCA GAG CCG AGC CCC ACG GGC TGG GGA CCG CCA GAC GGG GGT CGC GCG 2111
Pro Glu Pro Ser Pro Thr Gly Trp Gly Pro Pro Asp Gly Gly Arg Ala
690 695 700

GCG CTT GTG CGC AGG GCT CCG CAG CCC CCG GGC CGC CCC CCG ACG CCG 2159
Ala Leu Val Arg Arg Ala Pro Gln Pro Pro Gly Arg Pro Pro Thr Pro
705 710 715

-continued

```
GGG CCG CCC CTG TCC GAC GTC TCC CGA GTG TCG CGC CGC CCA GCC TGG      2207
Gly Pro Pro Leu Ser Asp Val Ser Arg Val Ser Arg Arg Pro Ala Trp
720                 725                 730                 735

GAG GCG CGG TGG CCG GTG CGG ACC GGG CAC TGC GGG AGG CAC CTC TCG      2255
Glu Ala Arg Trp Pro Val Arg Thr Gly His Cys Gly Arg His Leu Ser
                740                 745                 750

GCC TCC GAG CGG CCC CTG TCG CCC GCG CGC TGT CAC TAC AGC TCC TTT      2303
Ala Ser Glu Arg Pro Leu Ser Pro Ala Arg Cys His Tyr Ser Ser Phe
            755                 760                 765

CCT CGA GCC GAC CGA TCC GGC CG                                       2326
Pro Arg Ala Asp Arg Ser Gly
        770
```

(2) INFORMATION FOR SEQ ID NO:42:

(i) SEQUENCE CHARACTERISTICS:
(A) LENGTH: 774 amino acids
(B) TYPE: amino acid
(D) TOPOLOGY: linear (ii) MOLECULE TYPE: protein (xi) SEQUENCE DESCRIPTION: SEQ ID NO:42:

```
Gly His Val Trp Leu Val Pro Asn Leu Ala Leu Gly Ser Thr Asp Ala
  1               5                  10                  15

Pro Pro Ala Thr Phe Pro Val Gly Leu Ile Ser Val Val Thr Glu Ser
             20                  25                  30

Trp Arg Leu Ser Leu Arg Gln Lys Val Arg Asp Gly Val Ala Ile Leu
         35                  40                  45

Ala Leu Gly Ala His Ser Tyr Trp Arg Gln His Gly Thr Leu Pro Ala
     50                  55                  60

Pro Ala Gly Asp Cys Arg Val His Pro Gly Pro Val Ser Pro Ala Arg
 65                  70                  75                  80

Glu Ala Phe Tyr Arg His Leu Leu Asn Val Thr Trp Glu Gly Arg Asp
                 85                  90                  95

Phe Ser Phe Ser Pro Gly Gly Tyr Leu Val Gln Pro Thr Met Val Val
            100                 105                 110

Ile Ala Leu Asn Arg His Arg Leu Trp Glu Met Val Gly Arg Trp Glu
        115                 120                 125

His Gly Val Leu Tyr Met Lys Tyr Pro Val Trp Pro Arg Tyr Ser Ala
    130                 135                 140

Ser Leu Gln Pro Val Val Asp Ser Arg His Leu Thr Val Ala Thr Leu
145                 150                 155                 160

Glu Glu Arg Pro Phe Val Ile Val Glu Ser Pro Asp Pro Gly Thr Gly
                165                 170                 175

Gly Cys Val Pro Asn Thr Val Pro Cys Arg Arg Gln Ser Asn His Thr
            180                 185                 190

Phe Ser Ser Gly Asp Val Ala Pro Tyr Thr Lys Leu Cys Cys Lys Gly
        195                 200                 205

Phe Cys Ile Asp Ile Leu Lys Lys Leu Ala Arg Val Val Lys Phe Ser
    210                 215                 220

Tyr Asp Leu Tyr Leu Val Thr Asn Gly Lys His Gly Lys Arg Val Arg
225                 230                 235                 240

Gly Val Trp Asn Gly Met Ile Gly Glu Val Tyr Tyr Lys Arg Ala Asp
                245                 250                 255

Met Ala Ile Gly Ser Leu Thr Ile Asn Glu Glu Arg Ser Glu Ile Val
            260                 265                 270
```

-continued

Asp Phe Ser Val Pro Phe Val Glu Thr Gly Ile Ser Val Met Val Ala
275 280 285

Arg Ser Asn Gly Thr Val Ser Pro Ser Ala Phe Leu Glu Pro Tyr Ser
290 295 300

Pro Ala Val Trp Val Met Met Phe Val Met Cys Leu Thr Val Val Ala
305 310 315 320

Ile Thr Val Phe Met Phe Glu Tyr Phe Ser Pro Val Ser Tyr Asn Gln
325 330 335

Asn Leu Thr Arg Gly Lys Lys Ser Gly Gly Pro Ala Phe Thr Ile Gly
340 345 350

Lys Ser Val Trp Leu Leu Trp Ala Leu Val Phe Asn Asn Ser Val Pro
355 360 365

Ile Glu Asn Pro Arg Gly Thr Thr Ser Lys Ile Met Val Leu Val Trp
370 375 380

Ala Phe Phe Ala Val Ile Phe Leu Ala Arg Tyr Thr Ala Asn Leu Ala
385 390 395 400

Ala Phe Met Ile Gln Glu Gln Tyr Ile Asp Thr Val Ser Gly Leu Ser
405 410 415

Asp Lys Lys Phe Gln Arg Pro Gln Asp Gln Tyr Pro Pro Phe Arg Phe
420 425 430

Gly Thr Val Pro Asn Gly Ser Thr Glu Arg Asn Ile Arg Ser Asn Tyr
435 440 445

Arg Asp Met His Thr His Met Val Lys Phe Asn Gln Arg Ser Val Glu
450 455 460

Asp Ala Leu Thr Ser Leu Lys Met Gly Lys Asp Glu Gly Cys Lys Leu
465 470 475 480

Val Thr Ile Gly Ser Gly Lys Val Phe Ala Thr Thr Gly Tyr Gly Ile
485 490 495

Ala Met Gln Lys Asp Ser His Trp Lys Arg Ala Ile Asp Leu Ala Leu
500 505 510

Leu Gln Phe Leu Gly Asp Gly Glu Thr Gln Lys Leu Glu Thr Val Trp
515 520 525

Leu Ser Gly Ile Cys Gln Asn Glu Lys Asn Glu Val Met Ser Ser Lys
530 535 540

Leu Asp Ile Asp Asn Met Gly Gly Val Phe Tyr Met Leu Leu Val Ala
545 550 555 560

Met Gly Leu Ala Leu Leu Val Phe Ala Trp Glu His Leu Val Tyr Trp
565 570 575

Lys Leu Arg His Ser Val Pro Asn Ser Ser Gln Leu Asp Phe Leu Leu
580 585 590

Ala Phe Ser Arg Gly Ile Tyr Ser Cys Phe Ser Gly Val Gln Ser Leu
595 600 605

Ala Ser Pro Pro Arg Gln Ala Ser Pro Asp Leu Thr Ala Ser Ser Ala
610 615 620

Gln Ala Ser Val Leu Lys Ile Leu Gln Ala Ala Arg Asp Met Val Thr
625 630 635 640

Thr Ala Gly Val Ser Asn Ser Leu Asp Arg Ala Thr Arg Thr Ile Glu
645 650 655

Asn Trp Gly Gly Gly Arg Arg Ala Pro Pro Pro Ser Pro Cys Pro Thr
660 665 670

Pro Arg Ser Gly Pro Ser Pro Cys Leu Pro Thr Pro Asp Pro Pro Pro
675 680 685

Glu Pro Ser Pro Thr Gly Trp Gly Pro Pro Asp Gly Gly Arg Ala Ala

-continued

```
    690                 695                 700

Leu Val Arg Arg Ala Pro Gln Pro Pro Gly Arg Pro Pro Thr Pro Gly
705                 710                 715                 720

Pro Pro Leu Ser Asp Val Ser Arg Val Ser Arg Arg Pro Ala Trp Glu
                725                 730                 735

Ala Arg Trp Pro Val Arg Thr Gly His Cys Gly Arg His Leu Ser Ala
            740                 745                 750

Ser Glu Arg Pro Leu Ser Pro Ala Arg Cys His Tyr Ser Ser Phe Pro
        755                 760                 765

Arg Ala Asp Arg Ser Gly
    770
```

(2) INFORMATION FOR SEQ ID NO:43:

(i) SEQUENCE CHARACTERISTICS:
(A) LENGTH: 3698 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: Coding Sequence
(B) LOCATION: 3...3698

(xi) SEQUENCE DESCRIPTION: SEQ ID NO:43:

```
TG GAG ATC CAG CCG CTC ACA GTT GGG GTC AAC ACC ACC AAC CCC AGC         47
   Glu Ile Gln Pro Leu Thr Val Gly Val Asn Thr Thr Asn Pro Ser
    1               5                  10                  15

AGC CTC CTC ACC CAG ATC TGC GGC CTC CTG GGT GCT GCC CAC GTC CAC        95
Ser Leu Leu Thr Gln Ile Cys Gly Leu Leu Gly Ala Ala His Val His
                20                  25                  30

GGC ATT GTC TTT GAG GAC AAC GTG GAC ACC GAG GCG GTG GCC CAG ATC       143
Gly Ile Val Phe Glu Asp Asn Val Asp Thr Glu Ala Val Ala Gln Ile
            35                  40                  45

CTT GAC TTC ATC TCC TCC CAG ACC CAT GTG CCC ATC CTC AGC ATC AGC       191
Leu Asp Phe Ile Ser Ser Gln Thr His Val Pro Ile Leu Ser Ile Ser
        50                  55                  60

GGA GGC TCT GCT GTG GTC CTC ACC CCC AAG GAG CCG GGC TCC GCC TTC       239
Gly Gly Ser Ala Val Val Leu Thr Pro Lys Glu Pro Gly Ser Ala Phe
    65                  70                  75

CTG CAG CTG GGC GTG TCC CTG GAG CAG CAG CTG CAG GTG CTG TTC AAG       287
Leu Gln Leu Gly Val Ser Leu Glu Gln Gln Leu Gln Val Leu Phe Lys
80                  85                  90                  95

GTG CTG GAA GAG TAC GAC TGG AGC GCC TTC GCC GTC ATC ACC AGC CTG       335
Val Leu Glu Glu Tyr Asp Trp Ser Ala Phe Ala Val Ile Thr Ser Leu
                100                 105                 110

CAC CCG GGC CAC GCG CTC TTC CTG GAG GGC GTG CGC GCC GTC GCC GAC       383
His Pro Gly His Ala Leu Phe Leu Glu Gly Val Arg Ala Val Ala Asp
            115                 120                 125

GCC AGC CAC GTG AGT TGG CGG CTG CTG GAC GTG GTC ACG CTG GAA CTG       431
Ala Ser His Val Ser Trp Arg Leu Leu Asp Val Val Thr Leu Glu Leu
        130                 135                 140

GAC CCG GGA GGG CCG CGC GCG CGC ACG CAG CGC CTG CTG CGC CAG CTC       479
Asp Pro Gly Gly Pro Arg Ala Arg Thr Gln Arg Leu Leu Arg Gln Leu
    145                 150                 155

GAC GCG CCC GTG TTT GTG GCC TAC TGC TCG CGC GAG GAG GCC GAG GTG       527
Asp Ala Pro Val Phe Val Ala Tyr Cys Ser Arg Glu Glu Ala Glu Val
160                 165                 170                 175

CTC TTC GCC GAG GCG GCG CAG GCC GGT CTG GTG GGG CCC GGC CAC GTG       575
```

-continued

```
Leu Phe Ala Glu Ala Ala Gln Ala Gly Leu Val Gly Pro Gly His Val
                180                 185                 190

TGG CTG GTG CCC AAC CTG GCG CTG GGC AGC ACC GAT GCG CCC CCC GCC      623
Trp Leu Val Pro Asn Leu Ala Leu Gly Ser Thr Asp Ala Pro Pro Ala
            195                 200                 205

ACC TTC CCC GTG GGC CTC ATC AGC GTC GTC ACC GAG AGC TGG CGC CTC      671
Thr Phe Pro Val Gly Leu Ile Ser Val Val Thr Glu Ser Trp Arg Leu
        210                 215                 220

AGC CTG CGC CAG AAG GTG CGC GAC GGC GTG GCC ATT CTG GCC CTG GGC      719
Ser Leu Arg Gln Lys Val Arg Asp Gly Val Ala Ile Leu Ala Leu Gly
    225                 230                 235

GCC CAC AGC TAC TGG CGC CAG CAT GGA ACC CAG AAG GGG GTG TGC CAG      767
Ala His Ser Tyr Trp Arg Gln His Gly Thr Gln Lys Gly Val Cys Gln
240                 245                 250                 255

CCC CGG CCG GGG ACT GCC GTG TTC ACC CTG GGC CCG TCA GCC CTG CCC      815
Pro Arg Pro Gly Thr Ala Val Phe Thr Leu Gly Pro Ser Ala Leu Pro
                260                 265                 270

GGG AGG CCT TCT ACA GGC ACC TAC TGA ATG TCA CCT GGG AGG GCC GAG      863
Gly Arg Pro Ser Thr Gly Thr Tyr  *  Met Ser Pro Gly Arg Ala Glu
            275                 280                 285

ACT TCT CCT TCA GCC CTG GTG GGT ACC TGG TCC AGC CCA CCA TGG TGG      911
Thr Ser Pro Ser Ala Leu Val Gly Thr Trp Ser Ser Pro Pro Trp Trp
        290                 295                 300

TGA TCG CCC TCA ACC GGC ACC GCC TCT GGG AGA TGG TGG GGC GCT GGG      959
 *  Ser Pro Ser Thr Gly Thr Ala Ser Gly Arg Trp Trp Gly Ala Gly
    305                 310                 315

AGC ATG GCG TCC TAT ACA TGA AGT ACC CCG TGT GGC CTC GCT ACA GTG     1007
Ser Met Ala Ser Tyr Thr  *  Ser Thr Pro Cys Gly Leu Ala Thr Val
320                 325                 330                 335

CCT CTC TGC AGC CTG TGG TGG ACA GTC GGC ACC TGA CGG TGG CCA CGC     1055
Pro Leu Cys Ser Leu Trp Trp Thr Val Gly Thr  *  Arg Trp Pro Arg
                340                 345                 350

TGG AAG AGC GGC CCT TTG TCA TCG TGG AGA GCC CTG ACC CTG GCA CAG     1103
Trp Lys Ser Gly Pro Leu Ser Ser Trp Arg Ala Leu Thr Leu Ala Gln
            355                 360                 365

GAG GCT GTG TCC CCA ACA CCG TGC CCT GCC GCA GGC AGA GCA ACC ACA     1151
Glu Ala Val Ser Pro Thr Pro Cys Pro Ala Ala Gly Arg Ala Thr Thr
        370                 375                 380

CCT TCA GCA GCG GGG ACG TGG CCC CCT ACA CCA AGC TCT GCT GTA AGG     1199
Pro Ser Ala Ala Gly Thr Trp Pro Pro Thr Pro Ser Ser Ala Val Arg
    385                 390                 395

GAT TCT GCA TCG ACA TCC TCA AGA AGC TGG CCA GAG TGG TCA AAT TCT     1247
Asp Ser Ala Ser Thr Ser Ser Arg Ser Trp Pro Glu Trp Ser Asn Ser
400                 405                 410                 415

CCT ACG ACC TGT ACC TGG TGA CCA ACG GCA AGC ATG GCA AGC GGG TGC     1295
Pro Thr Thr Cys Thr Trp  *  Pro Thr Ala Ser Met Ala Ser Gly Cys
                420                 425                 430

GCG GCG TAT GGA ACG GCA TGA TTG GGG AGG TGT ACT ACA AGC GGG CAG     1343
Ala Ala Tyr Gly Thr Ala  *  Leu Gly Arg Cys Thr Thr Ser Gly Gln
            435                 440                 445

ACA TGG CCA TCG GCT CCC TCA CCA TCA ATG AGG AAC GCT CCG AGA TCG     1391
Thr Trp Pro Ser Ala Pro Ser Pro Ser Met Arg Asn Ala Pro Arg Ser
        450                 455                 460

TAG ACT TCT CTG TAC CCT TTG TGG AGA CGG GCA TCA GTG TGA TGG TGG     1439
 *  Thr Ser Leu Tyr Pro Leu Trp Arg Arg Ala Ser Val  *  Trp Trp
    465                 470                 475

CTC GCA GCA ATG GCA CCG TCT CCC CCT CGG CCT TCT TGG AGC CAT ATA      1487
Leu Ala Ala Met Ala Pro Ser Pro Pro Arg Pro Ser Trp Ser His Ile
480                 485                 490                 495
```

-continued

```
GCC CTG CAG TGT GGG TGA TGA TGT TTG TCA TGT GCC TCA CTG TGG TGG      1535
Ala Leu Gln Cys Gly  *   *  Cys Leu Ser Cys Ala Ser Leu Trp Trp
                500                 505                 510

CCA TCA CCG TCT TCA TGT TCG AGT ACT TCA GCC CTG TCA GCT ACA ACC      1583
Pro Ser Pro Ser Ser Cys Ser Ser Thr Ser Ala Leu Ser Ala Thr Thr
            515                 520                 525

AGA ACC TCA CCA GAG GCA AGA CTT TCA CTA TCG GCA AGT CCG TGT GGC      1631
Arg Thr Ser Pro Glu Ala Arg Leu Ser Leu Ser Ala Ser Pro Cys Gly
        530                 535                 540

TGC TGT GGG CGC TGG TCT TCA ACA ACT CAG TGC CCA TCG AGA ACC CGC      1679
Cys Cys Gly Arg Trp Ser Ser Thr Thr Gln Cys Pro Ser Arg Thr Arg
    545                 550                 555

GGG GCA CCA CCA GCA AGA TCA TGG TTC TGG TCT GGG CCT TCT TTG CTG      1727
Gly Ala Pro Pro Ala Arg Ser Trp Phe Trp Ser Gly Pro Ser Leu Leu
560                 565                 570                 575

TCA TCT TCC TCG CCA GAT ACA CGG CCA ACC TGG CCG CCT TCA TGA TCC      1775
Ser Ser Ser Ser Pro Asp Thr Arg Pro Thr Trp Pro Pro Ser  *  Ser
                580                 585                 590

AAG AGC AAT ACA TCG ACA CTG TGT CGG GCC TCA GTG ACA AGA AGT TTC      1823
Lys Ser Asn Thr Ser Thr Leu Cys Arg Ala Ser Val Thr Arg Ser Phe
            595                 600                 605

AGC GGC CTC AAG ATC AGT ACC CAC CTT TCC GCT TCG GCA CGG TGC CCA      1871
Ser Gly Leu Lys Ile Ser Thr His Leu Ser Ala Ser Ala Arg Cys Pro
        610                 615                 620

ACG GCA GCA CGG AGC GGA ACA TCC GCA GTA ACT ACC GTG ACA TGC ACA      1919
Thr Ala Ala Arg Ser Gly Thr Ser Ala Val Thr Thr Val Thr Cys Thr
    625                 630                 635

CCC ACA TGG TCA AGT TCA ACC AGC GCT CGG TGG AGG ACG CGC TCA CCA      1967
Pro Thr Trp Ser Ser Ser Thr Ser Ala Arg Trp Arg Thr Arg Ser Pro
640                 645                 650                 655

GCC TCA AGA TGG GGA AGC TGG ATG CCT TCA TCT ATG ATG CTG CTG TCC      2015
Ala Ser Arg Trp Gly Ser Trp Met Pro Ser Ser Met Met Leu Leu Ser
                660                 665                 670

TCA ACT ACA TGG CAG GCA AGG ACG AGG GCT GCA AGC TGG TCA CCA TTG      2063
Ser Thr Thr Trp Gln Ala Arg Thr Arg Ala Ala Ser Trp Ser Pro Leu
            675                 680                 685

GGT CTG GCA AGG TCT TTG CTA CCA CTG GCT ACG GCA TCG CCA TGC AGA      2111
Gly Leu Ala Arg Ser Leu Leu Pro Leu Ala Thr Ala Ser Pro Cys Arg
        690                 695                 700

AGG ACT CCC ACT GGA AGC GGG CCA TAG ACC TGG CGC TCT TGC AGT TCC      2159
Arg Thr Pro Thr Gly Ser Gly Pro  *  Thr Trp Arg Ser Cys Ser Ser
    705                 710                 715

TGG GGG ACG GAG AGA CAC AGA AAC TGG AGA CAG TGT GGC TCT CAG GGA      2207
Trp Gly Thr Glu Arg His Arg Asn Trp Arg Gln Cys Gly Ser Gln Gly
720                 725                 730                 735

TCT GCC AGA ATG AGA AGA ACG AGG TGA TGA GCA GCA AGC TGG ACA TCG      2255
Ser Ala Arg Met Arg Arg Thr Arg  *   *  Ala Ala Ser Trp Thr Ser
                740                 745                 750

ACA ACA TGG GAG GCG TCT TCT ACA TGC TGC TGG TGG CCA TGG GGC TGG      2303
Thr Thr Trp Glu Ala Ser Ser Thr Cys Cys Trp Trp Pro Trp Gly Trp
            755                 760                 765

CCC TGC TGG TCT TCG CCT GGG AGC ACC TGG TCT ACT GGA AGC TGC GCC      2351
Pro Cys Trp Ser Ser Pro Gly Ser Thr Trp Ser Thr Gly Ser Cys Ala
        770                 775                 780

ACT CGG TGC CCA ACT CAT CCC AGC TGG ACT TCC TGC TGG CTT TCA GCA      2399
Thr Arg Cys Pro Thr His Pro Ser Trp Thr Ser Cys Trp Leu Ser Ala
    785                 790                 795

GGG GCA TCT ACA GCT GCT TCA GCG GGG TGC AGA GCC TCG CCA GCC CAC      2447
Gly Ala Ser Thr Ala Ala Ser Ala Gly Cys Arg Ala Ser Pro Ala His
800                 805                 810                 815
```

-continued

```
CGC GGC AGG CCA GCC CGG ACC TCA CGG CCA GCT CGG CCC AGG CCA GCG     2495
Arg Gly Arg Pro Ala Arg Thr Ser Arg Pro Ala Arg Pro Arg Pro Ala
                820                 825                 830

TGC TCA AGA TTC TGC AGG CAG CCC GCG ACA TGG TGA CCA CGG CGG GCG     2543
Cys Ser Arg Phe Cys Arg Gln Pro Ala Thr Trp  *  Pro Arg Arg Ala
            835                 840                 845

TAA GCA ACT CCC TGG ACC GCG CCA CTC GCA CCA TCG AGA ATT GGG GTG     2591
 *  Ala Thr Pro Trp Thr Ala Pro Leu Ala Pro Ser Arg Ile Gly Val
        850                 855                 860

GCG GCC GCC GTG CGC CCC CAC CGT CCC CCT GCC CGA CCC CGC GGT CTG    2639
Ala Ala Ala Val Arg Pro His Arg Pro Pro Ala Arg Pro Arg Gly Leu
    865                 870                 875

GCC CCA GCC CAT GCC TGC CCA CCC CCG ACC CGC CCC CAG AGC CGA GCC    2687
Ala Pro Ala His Ala Cys Pro Pro Pro Thr Arg Pro Gln Ser Arg Ala
880                 885                 890                 895

CCA CGG GCT GGG GAC CGC CAG ACG GGG GTC GCG CGG CGC TTG TGC GCA    2735
Pro Arg Ala Gly Asp Arg Gln Thr Gly Val Ala Arg Arg Leu Cys Ala
                900                 905                 910

GGG CTC CGC AGC CCC CGG GCC GCC CCC CGA CGC CGG GGC CGC CCC TGT    2783
Gly Leu Arg Ser Pro Arg Ala Ala Pro Arg Arg Arg Gly Arg Pro Cys
            915                 920                 925

CCG ACG TCT CCC GAG TGT CGC GCC GCC CAG CCT GGG AGG CGC GGT GGC    2831
Pro Thr Ser Pro Glu Cys Arg Ala Ala Gln Pro Gly Arg Arg Gly Gly
        930                 935                 940

CGG TGC GGA CCG GGC ACT GCG GGA GGC ACC TCT CGG CCT CCG AGC GGC    2879
Arg Cys Gly Pro Gly Thr Ala Gly Gly Thr Ser Arg Pro Pro Ser Gly
    945                 950                 955

CCC TGT CGC CCG CGC GCT GTC ACT ACA GCT CCT TTC CTC GAG CCG ACC    2927
Pro Cys Arg Pro Arg Ala Val Thr Thr Ala Pro Phe Leu Glu Pro Thr
960                 965                 970                 975

GAT CCG GCC GCC CCT TCC TCC CGC TCT TCC CGG AGC CCC CGG AGC TGG    2975
Asp Pro Ala Ala Pro Ser Ser Arg Ser Ser Arg Ser Pro Arg Ser Trp
                980                 985                 990

AGG ACC TGC CGC TGC TCG GTC CGG AGC AGC TGG CCC GGC GGG AGG CCC    3023
Arg Thr Cys Arg Cys Ser Val Arg Ser Ser Trp Pro Gly Gly Arg Pro
            995                1000                1005

TGC TGA ACG CGG CCT GGG CCC GGG GCT CGC GCC CGA GTC ACG CTT CCC    3071
Cys  *  Thr Arg Pro Gly Pro Gly Ala Arg Ala Arg Val Thr Leu Pro
       1010                1015                1020

TGC CCA GCT CCG TGG CCG AGG CCT TCG CTC GGC CCA GCT CGC TGC CCG    3119
Cys Pro Ala Pro Trp Pro Arg Pro Ser Leu Gly Pro Ala Arg Cys Pro
   1025                1030                1035

CTG GGT GCA CCG GCC CCG CCT GCG CCC GCC CCG ACG GCC ACT CGG CCT    3167
Leu Gly Ala Pro Ala Pro Pro Ala Pro Ala Pro Thr Ala Thr Arg Pro
1040                1045                1050                1055

GCA GGC GCT TGG CGC AGG CGC AGT CGA TGT GCT TGC CGA TCT ACC GGG    3215
Ala Gly Ala Trp Arg Arg Arg Ser Arg Cys Ala Cys Arg Ser Thr Gly
               1060                1065                1070

AGG CCT GCC AGG AGG GCG AGC AGG CAG GGG CCC CCG CCT GGC AGC ACA    3263
Arg Pro Ala Arg Arg Ala Ser Arg Gln Gly Pro Pro Pro Gly Ser Thr
           1075                1080                1085

GAC AGC ACG TCT GCC TGC ACG CCC ACG CCC ACC TGC CAT TGT GCT GGG    3311
Asp Ser Thr Ser Ala Cys Thr Pro Thr Pro Thr Cys His Cys Ala Gly
       1090                1095                1100

GGG CTG TCT GTC CTC ACC TTC CAC CCT GTG ACA GCC ACG GCT CCT GGC    3359
Gly Leu Ser Val Leu Thr Phe His Pro Val Thr Ala Thr Ala Pro Gly
   1105                1110                1115

TCT CCG GCG CCT GGG GGC CTC TGG GGC ACA GCG GCA GGA CTC TGG GGC    3407
Ser Pro Ala Pro Gly Gly Leu Trp Gly Thr Ala Ala Gly Leu Trp Gly
```

-continued

```
1120                1125                1130                1135

TGG GCA CAG GCT ACA GAG ACA GTG GGG GAC TGG ACG AGA TCA GCA GTG    3455
Trp Ala Gln Ala Thr Glu Thr Val Gly Asp Trp Thr Arg Ser Ala Val
               1140                1145                1150

TAG CCC GTG GGA CGC AAG GCT TCC CGG GAC CCT GCA CCT GGA GAC GGA    3503
 *  Pro Val Gly Arg Lys Ala Ser Arg Asp Pro Ala Pro Gly Asp Gly
           1155                1160                1165

TCT CCA GTC TGG AGT CAG AAG TGT GAG TTA TCA GCC ACT CAG GCT CCG     3551
Ser Pro Val Trp Ser Gln Lys Cys Glu Leu Ser Ala Thr Gln Ala Pro
       1170                1175                1180

AGC CAG CTG GAT TCT CTG CCT GCC ACT GTC AGG GTT AAG CGG CAG GCA     3599
Ser Gln Leu Asp Ser Leu Pro Ala Thr Val Arg Val Lys Arg Gln Ala
   1185                1190                1195

GGA TTG GCC CTT CTC TGG CTT CTA CCA TGA AAT CCT GGC CAT GGC ACC     3647
Gly Leu Ala Leu Leu Trp Leu Leu Pro  *  Asn Pro Gly His Gly Thr
1200                1205                1210                1215

CCA GTG ACA GAT GAT GTC TTC CAT GGT CAT CAG TGA CCT CAG CTA GCC     3695
Pro Val Thr Asp Asp Val Phe His Gly His Gln  *  Pro Gln Leu Ala
               1220                1225                1230

TCA                                                                 3698
Ser
```

(2) INFORMATION FOR SEQ ID NO:44:

(i) SEQUENCE CHARACTERISTICS:
(A) LENGTH: 3243 base pairs
(B) TYPE: nucleic acid
(C) STRANDEDNESS: unknown
(D) TOPOLOGY: unknown (ii) MOLECULE TYPE: cDNA (ix) FEATURE:
(A) NAME/KEY: Coding Sequence
(B) LOCATION: 1...3243

(xi) SEQUENCE DESCRIPTION: SEQ ID NO:44:

```
GTG GCC TAC TGC TCG CGC GAG GAG GCC GAG GTG CTC TTC GCC GAG GCG       48
Val Ala Tyr Cys Ser Arg Glu Glu Ala Glu Val Leu Phe Ala Glu Ala
 1               5                  10                  15

GCG CAG GCC GGT CTG GTG GGG CCC GGC CAC GTG TGG CTG GTG CCC AAC       96
Ala Gln Ala Gly Leu Val Gly Pro Gly His Val Trp Leu Val Pro Asn
            20                  25                  30

CTG GCG CTG GGC AGC ACC GAT GCG CCC CCC GCC ACC TTC CCC GTG GGC      144
Leu Ala Leu Gly Ser Thr Asp Ala Pro Pro Ala Thr Phe Pro Val Gly
        35                  40                  45

CTC ATC AGC GTC GTC ACC GAG AGC TGG CGC CTC AGC CTG CGC CAG AAG      192
Leu Ile Ser Val Val Thr Glu Ser Trp Arg Leu Ser Leu Arg Gln Lys
    50                  55                  60

GTG CGC GAC GGC GTG GCC ATT CTG GCC CTG GGC GCC CAC AGC TAC TGG      240
Val Arg Asp Gly Val Ala Ile Leu Ala Leu Gly Ala His Ser Tyr Trp
65                  70                  75                  80

CGC CAG CAT GGA ACC CAG AAG GGG GTG TGC CAG CCC CGG CCG GGG ACT      288
Arg Gln His Gly Thr Gln Lys Gly Val Cys Gln Pro Arg Pro Gly Thr
               85                  90                  95

GCC GTG TTC ACC CTG GGC CCG TCA GCC CTG CCC GGG AGG CCT TCT ACA      336
Ala Val Phe Thr Leu Gly Pro Ser Ala Leu Pro Gly Arg Pro Ser Thr
            100                 105                 110

GGC ACC TAC TGA ATG TCA CCT GGG AGG GCC GAG ACT TCT CCT TCA GCC      384
Gly Thr Tyr  *  Met Ser Pro Gly Arg Ala Glu Thr Ser Pro Ser Ala
        115                 120                 125

CTG GTG GGT ACC TGG TCC AGC CCA CCA TGG TGG TGA TCG CCC TCA ACC      432
```

-continued

```
Leu Val Gly Thr Trp Ser Ser Pro Pro Trp Trp  *  Ser Pro Ser Thr
    130                 135                 140

GGC ACC GCC TCT GGG AGA TGG TGG GGC GCT GGG AGC ATG GCG TCC TAT      480
Gly Thr Ala Ser Gly Arg Trp Trp Gly Ala Gly Ser Met Ala Ser Tyr
145                 150                 155                 160

ACA TGA AGT ACC CCG TGT GGC CTC GCT ACA GTG CCT CTC TGC AGC CTG      528
Thr  *  Ser Thr Pro Cys Gly Leu Ala Thr Val Pro Leu Cys Ser Leu
                165                 170                 175

TGG TGG ACA GTC GGC ACC TGA CGG TGG CCA CGC TGG AAG AGC GGC CCT      576
Trp Trp Thr Val Gly Thr  *  Arg Trp Pro Arg Trp Lys Ser Gly Pro
            180                 185                 190

TTG TCA TCG TGG AGA GCC CTG ACC CTG GCA CAG GAG GCT GTG TCC CCA      624
Leu Ser Ser Trp Arg Ala Leu Thr Leu Ala Gln Glu Ala Val Ser Pro
        195                 200                 205

ACA CCG TGC CCT GCC GCA GGC AGA GCA ACC ACA CCT TCA GCA GCG GGG      672
Thr Pro Cys Pro Ala Ala Gly Arg Ala Thr Thr Pro Ser Ala Ala Gly
    210                 215                 220

ACG TGG CCC CCT ACA CCA AGC TCT GCT GTA AGG GAT TCT GCA TCG ACA      720
Thr Trp Pro Pro Thr Pro Ser Ser Ala Val Arg Asp Ser Ala Ser Thr
225                 230                 235                 240

TCC TCA AGA AGC TGG CCA GAG TGG TCA AAT TCT CCT ACG ACC TGT ACC      768
Ser Ser Arg Ser Trp Pro Glu Trp Ser Asn Ser Pro Thr Thr Cys Thr
                245                 250                 255

TGG TGA CCA ACG GCA AGC ATG GCA AGC GGG TGC GCG GCG TAT GGA ACG      816
Trp  *  Pro Thr Ala Ser Met Ala Ser Gly Cys Ala Ala Tyr Gly Thr
            260                 265                 270

GCA TGA TTG GGG AGG TGT ACT ACA AGC GGG CAG ACA TGG CCA TCG GCT      864
Ala  *  Leu Gly Arg Cys Thr Thr Ser Gly Gln Thr Trp Pro Ser Ala
        275                 280                 285

CCC TCA CCA TCA ATG AGG AAC GCT CCG AGA TCG TAG ACT TCT CTG TAC      912
Pro Ser Pro Ser Met Arg Asn Ala Pro Arg Ser  *  Thr Ser Leu Tyr
    290                 295                 300

CCT TTG TGG AGA CGG GCA TCA GTG TGA TGG TGG CTC GCA GCA ATG GCA      960
Pro Leu Trp Arg Arg Ala Ser Val  *  Trp Trp Leu Ala Ala Met Ala
305                 310                 315                 320

CCG TCT CCC CCT CGG CCT TCT TGG AGC CAT ATA GCC CTG CAG TGT GGG     1008
Pro Ser Pro Pro Arg Pro Ser Trp Ser His Ile Ala Leu Gln Cys Gly
                325                 330                 335

TGA TGA TGT TTG TCA TGT GCC TCA CTG TGG TGG CCA TCA CCG TCT TCA     1056
 *   *  Cys Leu Ser Cys Ala Ser Leu Trp Trp Pro Ser Pro Ser Ser
            340                 345                 350

TGT TCG AGT ACT TCA GCC CTG TCA GCT ACA ACC AGA ACC TCA CCA GAG     1104
Cys Ser Ser Thr Ser Ala Leu Ser Ala Thr Thr Arg Thr Ser Pro Glu
        355                 360                 365

GCA AGA AGT CCG GGG GCC CAG CTT TCA CTA TCG GCA AGT CCG TGT GGC     1152
Ala Arg Ser Pro Gly Ala Gln Leu Ser Leu Ser Ala Ser Pro Cys Gly
    370                 375                 380

TGC TGT GGG CGC TGG TCT TCA ACA ACT CAG TGC CCA TCG AGA ACC CGC     1200
Cys Cys Gly Arg Trp Ser Ser Thr Thr Gln Cys Pro Ser Arg Thr Arg
385                 390                 395                 400

GGG GCA CCA CCA GCA AGA TCA TGG TTC TGG TCT GGG CCT TCT TTG CTG     1248
Gly Ala Pro Pro Ala Arg Ser Trp Phe Trp Ser Gly Pro Ser Leu Leu
                405                 410                 415

TCA TCT TCC TCG CCA GAT ACA CGG CCA ACC TGG CCG CCT TCA TGA TCC     1296
Ser Ser Ser Ser Pro Asp Thr Arg Pro Thr Trp Pro Pro Ser  *  Ser
            420                 425                 430

AAG AGC AAT ACA TCG ACA CTG TGT CGG GCC TCA GTG ACA AGA AGT TTC     1344
Lys Ser Asn Thr Ser Thr Leu Cys Arg Ala Ser Val Thr Arg Ser Phe
        435                 440                 445
```

-continued

```
AGC GGC CTC AAG ATC AGT ACC CAC CTT TCC GCT TCG GCA CGG TGC CCA     1392
Ser Gly Leu Lys Ile Ser Thr His Leu Ser Ala Ser Ala Arg Cys Pro
    450                 455                 460

ACG GCA GCA CGG AGC GGA ACA TCC GCA GTA ACT ACC GTG ACA TGC ACA     1440
Thr Ala Ala Arg Ser Gly Thr Ser Ala Val Thr Thr Val Thr Cys Thr
465                 470                 475                 480

CCC ACA TGG TCA AGT TCA ACC AGC GCT CGG TGG AGG ACG CGC TCA CCA     1488
Pro Thr Trp Ser Ser Ser Thr Ser Ala Arg Trp Arg Thr Arg Ser Pro
                485                 490                 495

GCC TCA AGA TGG GCT CTG AGG CTC AGC CTG TCC CCA GGA AGC TGG ATG     1536
Ala Ser Arg Trp Ala Leu Arg Leu Ser Leu Ser Pro Gly Ser Trp Met
            500                 505                 510

CCT TCA TCT ATG ATG CTG CTG TCC TCA ACT ACA TGG CAG GCA AGG ACG     1584
Pro Ser Ser Met Met Leu Leu Ser Ser Thr Thr Trp Gln Ala Arg Thr
        515                 520                 525

AGG GCT GCA AGC TGG TCA CCA TTG GGT CTG GCA AGG TCT TTG CTA CCA     1632
Arg Ala Ala Ser Trp Ser Pro Leu Gly Leu Ala Arg Ser Leu Leu Pro
    530                 535                 540

CTG GCT ACG GCA TCG CCA TGC AGA AGG ACT CCC ACT GGA AGC GGG CCA     1680
Leu Ala Thr Ala Ser Pro Cys Arg Arg Thr Pro Thr Gly Ser Gly Pro
545                 550                 555                 560

TAG ACC TGG CGC TCT TGC AGT TCC TGG GGG ACG GAG AGA CAC AGA AAC     1728
 *  Thr Trp Arg Ser Cys Ser Ser Trp Gly Thr Glu Arg His Arg Asn
                565                 570                 575

TGG AGA CAG TGT GGC TCT CAG GGA TCT GCC AGA ATG AGA AGA ACG AGG    1776
Trp Arg Gln Cys Gly Ser Gln Gly Ser Ala Arg Met Arg Arg Thr Arg
            580                 585                 590

TGA TGA GCA GCA AGC TGG ACA TCG ACA ACA TGG GAG GCG TCT TCT ACA    1824
 *   *  Ala Ala Ser Trp Thr Ser Thr Thr Trp Glu Ala Ser Ser Thr
        595                 600                 605

TGC TGC TGG TGG CCA TGG GGC TGG CCC TGC TGG TCT TCG CCT GGG AGC    1872
Cys Cys Trp Trp Pro Trp Gly Trp Pro Cys Trp Ser Ser Pro Gly Ser
    610                 615                 620

ACC TGG TCT ACT GGA AGC TGC GCC ACT CGG TGC CCA ACT CAT CCC AGC    1920
Thr Trp Ser Thr Gly Ser Cys Ala Thr Arg Cys Pro Thr His Pro Ser
625                 630                 635                 640

TGG ACT TCC TGC TGG CTT TCA GCA GGG GCA TCT ACA GCT GCT TCA GCG    1968
Trp Thr Ser Cys Trp Leu Ser Ala Gly Ala Ser Thr Ala Ala Ser Ala
                645                 650                 655

GGG TGC AGA GCC TCG CCA GCC CAC CGC GGC AGG CCA GCC CGG ACC TCA    2016
Gly Cys Arg Ala Ser Pro Ala His Arg Gly Arg Pro Ala Arg Thr Ser
            660                 665                 670

CGG CCA GCT CGG CCC AGG CCA GCG TGC TCA AGA TTC TGC AGG CAG CCC    2064
Arg Pro Ala Arg Pro Arg Pro Ala Cys Ser Arg Phe Cys Arg Gln Pro
        675                 680                 685

GCG ACA TGG TGA CCA CGG CGG GCG TAA GCA ACT CCC TGG ACC GCG CCA    2112
Ala Thr Trp  *  Pro Arg Arg Ala  *  Ala Thr Pro Trp Thr Ala ProZ
    690                 695                 700

CTC GCA CCA TCG AGA ATT GGG GTG GCG GCC GCC GTG CGC CCC CAC CGT    2160
Leu Ala Pro Ser Arg Ile Gly Val Ala Ala Ala Val Arg Pro His Arg
705                 710                 715                 720

CCC CCT GCC CGA CCC CGC GGT CTG GCC CCA GCC CAT GCC TGC CCA CCC    2208
Pro Pro Ala Arg Pro Arg Gly Leu Ala Pro Ala His Ala Cys Pro Pro
                725                 730                 735

CCG ACC CGC CCC CAG AGC CGA GCC CCA CGG GCT GGG GAC CGC CAG ACG    2256
Pro Thr Arg Pro Gln Ser Arg Ala Pro Arg Ala Gly Asp Arg Gln Thr
            740                 745                 750

GGG GTC GCG CGG CGC TTG TGC GCA GGG CTC CGC AGC CCC CGG GCC GCC    2304
Gly Val Ala Arg Arg Leu Cys Ala Gly Leu Arg Ser Pro Arg Ala Ala
        755                 760                 765
```

-continued

```
CCC CGA CGC CGG GGC CGC CCC TGT CCG ACG TCT CCC GAG TGT CGC GCC    2352
Pro Arg Arg Arg Gly Arg Pro Cys Pro Thr Ser Pro Glu Cys Arg Ala
    770                 775                 780

GCC CAG CCT GGG AGG CGC GGT GGC CGG TGC GGA CCG GGC ACT GCG GGA    2400
Ala Gln Pro Gly Arg Arg Gly Gly Arg Cys Gly Pro Gly Thr Ala Gly
785                 790                 795                 800

GGC ACC TCT CGG CCT CCG AGC GGC CCC TGT CGC CCG CGC GCT GTC ACT    2448
Gly Thr Ser Arg Pro Pro Ser Gly Pro Cys Arg Pro Arg Ala Val Thr
                805                 810                 815

ACA GCT CCT TTC CTC GAG CCG ACC GAT CCG GCC GCC CCT TCC TCC CGC    2496
Thr Ala Pro Phe Leu Glu Pro Thr Asp Pro Ala Ala Pro Ser Ser Arg
            820                 825                 830

TCT TCC CGG AGC CCC CGG AGC TGG AGG ACC TGC CGC TGC TCG GTC CGG    2544
Ser Ser Arg Ser Pro Arg Ser Trp Arg Thr Cys Arg Cys Ser Val Arg
        835                 840                 845

AGC AGC TGG CCC GGC GGG AGG CCC TGC TGA ACG CGG CCT GGG CCC GGG    2592
Ser Ser Trp Pro Gly Gly Arg Pro Cys  *  Thr Arg Pro Gly Pro Gly
    850                 855                 860

GCT CGC GCC CGA GTC ACG CTT CCC TGC CCA GCT CCG TGG CCG AGG CCT    2640
Ala Arg Ala Arg Val Thr Leu Pro Cys Pro Ala Pro Trp Pro Arg Pro
865                 870                 875                 880

TCG CTC GGC CCA GCT CGC TGC CCG CTG GGT GCA CCG GCC CCG CCT GCG    2688
Ser Leu Gly Pro Ala Arg Cys Pro Leu Gly Ala Pro Ala Pro Pro Ala
                885                 890                 895

CCC GCC CCG ACG GCC ACT CGG CCT GCA GGC GCT TGG CGC AGG CGC AGT    2736
Pro Ala Pro Thr Ala Thr Arg Pro Ala Gly Ala Trp Arg Arg Arg Ser
            900                 905                 910

CGA TGT GCT TGC CGA TCT ACC GGG AGG CCT GCC AGG AGG GCG AGC AGG    2784
Arg Cys Ala Cys Arg Ser Thr Gly Arg Pro Ala Arg Arg Ala Ser Arg
        915                 920                 925

CAG GGG CCC CCG CCT GGC AGC ACA GAC AGC ACG TCT GCC TGC ACG CCC    2832
Gln Gly Pro Pro Pro Gly Ser Thr Asp Ser Thr Ser Ala Cys Thr Pro
    930                 935                 940

ACG CCC ACC TGC CAT TGT GCT GGG GGG CTG TCT GTC CTC ACC TTC CAC    2880
Thr Pro Thr Cys His Cys Ala Gly Gly Leu Ser Val Leu Thr Phe His
945                 950                 955                 960

CCT GTG ACA GCC ACG GCT CCT GGC TCT CCG GCG CCT GGG GGC CTC TGG    2928
Pro Val Thr Ala Thr Ala Pro Gly Ser Pro Ala Pro Gly Gly Leu Trp
                965                 970                 975

GGC ACA GCG GCA GGA CTC TGG GGC TGG GCA CAG GCT ACA GAG ACA GTG    2976
Gly Thr Ala Ala Gly Leu Trp Gly Trp Ala Gln Ala Thr Glu Thr Val
            980                 985                 990

GGG GAC TGG ACG AGA TCA GCA GTG TAG CCC GTG GGA CGC AAG GCT TCC    3024
Gly Asp Trp Thr Arg Ser Ala Val  *  Pro Val Gly Arg Lys Ala Ser
        995                1000                1005

CGG GAC CCT GCA CCT GGA GAC GGA TCT CCA GTC TGG AGT CAG AAG TGT    3072
Arg Asp Pro Ala Pro Gly Asp Gly Ser Pro Val Trp Ser Gln Lys Cys
   1010                1015                1020

GAG TTA TCA GCC ACT CAG GCT CCG AGC CAG CTG GAT TCT CTG CCT GCC    3120
Glu Leu Ser Ala Thr Gln Ala Pro Ser Gln Leu Asp Ser Leu Pro Ala
1025                1030                1035                1040

ACT GTC AGG GTT AAG CGG CAG GCA GGA TTG GCC CTT CTC TGG CTT CTA    3168
Thr Val Arg Val Lys Arg Gln Ala Gly Leu Ala Leu Leu Trp Leu Leu
               1045                1050                1055

CCA TGA AAT CCT GGC CAT GGC ACC CCA GTG ACA GAT GAT GTC TTC CAT    3216
Pro  *  Asn Pro Gly His Gly Thr Pro Val Thr Asp Asp Val Phe His
           1060                1065                1070

GGT CAT CAG TGA CCT CAG CTA GCC TCA                                3243
Gly His Gln  *  Pro Gln Leu Ala Ser
```

-continued 1075 1080

(2) INFORMATION FOR SEQ ID NO:45:

(i) SEQUENCE CHARACTERISTICS:
(A) LENGTH: 4092 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 189..3923

(xi) SEQUENCE DESCRIPTION: SEQ ID NO:45:

```
CCCTTAATAA GATTTGCNAC GTACACTCGA GCCATCGCGA GTGTCCTTGA GCCGCGGGTG     60

ACGGTGGCTC TCGCTGCTCG CGCCCCCTCC TCCCGCGGGG GGAGCCTGAT GCCACGTTCC    120

CTATGAATTA TTTATCGCCG GCCTAAAAAT ACCCCGAACT TCACAGCCCG AGTGACCCTC    180

CGGTGGAC ATG GGT GGG GCC CTG GGG CCG GCC CTG TTG CTC ACC TCG CTC     230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG      278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC      326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC      374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC      422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC      758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA      806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC      854
Gly Pro Arg Ala Arg Thr Gln Arg Leu Leu Arg Gln Leu Asp Ala Pro
```

-continued

```
            210                 215                 220

GTG TTT GTG GCC TAC TGC TCG CGC GAG GAG GCC GAG GTG CTC TTC GCC      902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG      950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC      998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC     1046
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC     1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT     1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC     1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT     1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC     1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG     1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG     1382
Lys Tyr Pro Val Trp Pro Arg Tyr Ser Ala Ser Leu Gln Pro Val Val
        385                 390                 395

GAC AGT CGG CAC CTG ACG GTG GCC ACG CTG GAA GAG CGG CCC TTT GTC     1430
Asp Ser Arg His Leu Thr Val Ala Thr Leu Glu Glu Arg Pro Phe Val
    400                 405                 410

ATC GTG GAG AGC CCT GAC CCT GGC ACA GGA GGC TGT GTC CCC AAC ACC     1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG     1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC     1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG     1622
Lys Lys Leu Ala Arg Val Val Lys Phe Ser Tyr Asp Leu Tyr Leu Val
        465                 470                 475

ACC AAC GGC AAG CAT GGC AAG CGG GTG CGC GGC GTA TGG AAC GGC ATG     1670
Thr Asn Gly Lys His Gly Lys Arg Val Arg Gly Val Trp Asn Gly Met
    480                 485                 490

ATT GGG GAG GTG TAC TAC AAG CGG GCA GAC ATG GCC ATC GGC TCC CTC     1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT     1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC     1814
```

-continued

```
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG      1862
Ser Pro Ser Ala Phe Leu Glu Pro Tyr Ser Pro Ala Val Trp Val Met
        545                 550                 555

ATG TTT GTC ATG TGC CTC ACT GTG GTG GCC ATC ACC GTC TTC ATG TTC      1910
Met Phe Val Met Cys Leu Thr Val Val Ala Ile Thr Val Phe Met Phe
    560                 565                 570

GAG TAC TTC AGC CCT GTC AGC TAC AAC CAG AAC CTC ACC AGA GGC AAG      1958
Glu Tyr Phe Ser Pro Val Ser Tyr Asn Gln Asn Leu Thr Arg Gly Lys
575                 580                 585                 590

AAG TCC GGG GGC CCA GCT TTC ACT ATC GGC AAG TCC GTG TGG CTG CTG      2006
Lys Ser Gly Gly Pro Ala Phe Thr Ile Gly Lys Ser Val Trp Leu Leu
                595                 600                 605

TGG GCG CTG GTC TTC AAC AAC TCA GTG CCC ATC GAG AAC CCG CGG GGC      2054
Trp Ala Leu Val Phe Asn Asn Ser Val Pro Ile Glu Asn Pro Arg Gly
            610                 615                 620

ACC ACC AGC AAG ATC ATG GTT CTG GTC TGG GCC TTC TTT GCT GTC ATC      2102
Thr Thr Ser Lys Ile Met Val Leu Val Trp Ala Phe Phe Ala Val Ile
        625                 630                 635

TTC CTC GCC AGA TAC ACG GCC AAC CTG GCC GCC TTC ATG ATC CAA GAG      2150
Phe Leu Ala Arg Tyr Thr Ala Asn Leu Ala Ala Phe Met Ile Gln Glu
    640                 645                 650

CAA TAC ATC GAC ACT GTG TCG GGC CTC AGT GAC AAG AAG TTT CAG CGG      2198
Gln Tyr Ile Asp Thr Val Ser Gly Leu Ser Asp Lys Lys Phe Gln Arg
655                 660                 665                 670

CCT CAA GAT CAG TAC CCA CCT TTC CGC TTC GGC ACG GTG CCC AAC GGC      2246
Pro Gln Asp Gln Tyr Pro Pro Phe Arg Phe Gly Thr Val Pro Asn Gly
                675                 680                 685

AGC ACG GAG CGG AAC ATC CGC AGT AAC TAC CGT GAC ATG CAC ACC CAC      2294
Ser Thr Glu Arg Asn Ile Arg Ser Asn Tyr Arg Asp Met His Thr His
            690                 695                 700

ATG GTC AAG TTC AAC CAG CGC TCG GTG GAG GAC GCG CTC ACC AGC CTC      2342
Met Val Lys Phe Asn Gln Arg Ser Val Glu Asp Ala Leu Thr Ser Leu
        705                 710                 715

AAG ATG GGC TCT GAG GCT CAG CCT GTC CCC AGG AAG CTG GAT GCC TTC      2390
Lys Met Gly Ser Glu Ala Gln Pro Val Pro Arg Lys Leu Asp Ala Phe
    720                 725                 730

ATC TAT GAT GCT GCT GTC CTC AAC TAC ATG GCA GGC AAG GAC GAG GGC      2438
Ile Tyr Asp Ala Ala Val Leu Asn Tyr Met Ala Gly Lys Asp Glu Gly
735                 740                 745                 750

TGC AAG CTG GTC ACC ATT GGG TCT GGC AAG GTC TTT GCT ACC ACT GGC      2486
Cys Lys Leu Val Thr Ile Gly Ser Gly Lys Val Phe Ala Thr Thr Gly
                755                 760                 765

TAC GGC ATC GCC ATG CAG AAG GAC TCC CAC TGG AAG CGG GCC ATA GAC      2534
Tyr Gly Ile Ala Met Gln Lys Asp Ser His Trp Lys Arg Ala Ile Asp
            770                 775                 780

CTG GCG CTC TTG CAG TTC CTG GGG GAC GGA GAG ACA CAG AAA CTG GAG      2582
Leu Ala Leu Leu Gln Phe Leu Gly Asp Gly Glu Thr Gln Lys Leu Glu
        785                 790                 795

ACA GTG TGG CTC TCA GGG ATC TGC CAG AAT GAG AAG AAC GAG GTG ATG      2630
Thr Val Trp Leu Ser Gly Ile Cys Gln Asn Glu Lys Asn Glu Val Met
    800                 805                 810

AGC AGC AAG CTG GAC ATC GAC AAC ATG GGA GGC GTC TTC TAC ATG CTG      2678
Ser Ser Lys Leu Asp Ile Asp Asn Met Gly Gly Val Phe Tyr Met Leu
815                 820                 825                 830

CTG GTG GCC ATG GGG CTG GCC CTG CTG GTC TTC GCC TGG GAG CAC CTG      2726
Leu Val Ala Met Gly Leu Ala Leu Leu Val Phe Ala Trp Glu His Leu
                835                 840                 845
```

-continued

```
GTC TAC TGG AAG CTG CGC CAC TCG GTG CCC AAC TCA TCC CAG CTG GAC      2774
Val Tyr Trp Lys Leu Arg His Ser Val Pro Asn Ser Ser Gln Leu Asp
            850                 855                 860

TTC CTG CTG GCT TTC AGC AGG GGC ATC TAC AGC TGC TTC AGC GGG GTG      2822
Phe Leu Leu Ala Phe Ser Arg Gly Ile Tyr Ser Cys Phe Ser Gly Val
        865                 870                 875

CAG AGC CTC GCC AGC CCA CCG CGG CAG GCC AGC CCG GAC CTC ACG GCC      2870
Gln Ser Leu Ala Ser Pro Pro Arg Gln Ala Ser Pro Asp Leu Thr Ala
    880                 885                 890

AGC TCG GCC CAG GCC AGC GTG CTC AAG ATT CTG CAG GCA GCC CGC GAC      2918
Ser Ser Ala Gln Ala Ser Val Leu Lys Ile Leu Gln Ala Ala Arg Asp
895                 900                 905                 910

ATG GTG ACC ACG GCG GGC GTA AGC AAC TCC CTG GAC CGC GCC ACT CGC      2966
Met Val Thr Thr Ala Gly Val Ser Asn Ser Leu Asp Arg Ala Thr Arg
                915                 920                 925

ACC ATC GAG AAT TGG GGT GGC GGC CGC CGT GCG CCC CCA CCG TCC CCC      3014
Thr Ile Glu Asn Trp Gly Gly Gly Arg Arg Ala Pro Pro Pro Ser Pro
            930                 935                 940

TGC CCG ACC CCG CGG TCT GGC CCC AGC CCA TGC CTG CCC ACC CCC GAC      3062
Cys Pro Thr Pro Arg Ser Gly Pro Ser Pro Cys Leu Pro Thr Pro Asp
        945                 950                 955

CCG CCC CCA GAG CCG AGC CCC ACG GGC TGG GGA CCG CCA GAC GGG GGT      3110
Pro Pro Pro Glu Pro Ser Pro Thr Gly Trp Gly Pro Pro Asp Gly Gly
    960                 965                 970

CGC GCG GCG CTT GTG CGC AGG GCT CCG CAG CCC CCG GGC CGC CCC CCG      3158
Arg Ala Ala Leu Val Arg Arg Ala Pro Gln Pro Pro Gly Arg Pro Pro
975                 980                 985                 990

ACG CCG GGG CCG CCC CTG TCC GAC GTC TCC CGA GTG TCG CGC CGC CCA      3206
Thr Pro Gly Pro Pro Leu Ser Asp Val Ser Arg Val Ser Arg Arg Pro
                995                1000                1005

GCC TGG GAG GCG CGG TGG CCG GTG CGG ACC GGG CAC TGC GGG AGG CAC      3254
Ala Trp Glu Ala Arg Trp Pro Val Arg Thr Gly His Cys Gly Arg His
            1010                1015                1020

CTC TCG GCC TCC GAG CGG CCC CTG TCG CCC GCG CGC TGT CAC TAC AGC      3302
Leu Ser Ala Ser Glu Arg Pro Leu Ser Pro Ala Arg Cys His Tyr Ser
        1025                1030                1035

TCC TTT CCT CGA GCC GAC CGA TCC GGC CGC CCC TTC CTC CCG CTC TTC      3350
Ser Phe Pro Arg Ala Asp Arg Ser Gly Arg Pro Phe Leu Pro Leu Phe
    1040                1045                1050

CCG GAG CCC CCG GAG CTG GAG GAC CTG CCG CTG CTC GGT CCG GAG CAG      3398
Pro Glu Pro Pro Glu Leu Glu Asp Leu Pro Leu Leu Gly Pro Glu Gln
1055                1060                1065                1070

CTG GCC CGG CGG GAG GCC CTG CTG AAC GCG GCC TGG GCC CGG GGC TCG      3446
Leu Ala Arg Arg Glu Ala Leu Leu Asn Ala Ala Trp Ala Arg Gly Ser
                1075                1080                1085

CGC CCG AGT CAC GCT TCC CTG CCC AGC TCC GTG GCC GAG GCC TTC GCT      3494
Arg Pro Ser His Ala Ser Leu Pro Ser Ser Val Ala Glu Ala Phe Ala
            1090                1095                1100

CGG CCC AGC TCG CTG CCC GCT GGG TGC ACC GGC CCC GCC TGC GCC CGC      3542
Arg Pro Ser Ser Leu Pro Ala Gly Cys Thr Gly Pro Ala Cys Ala Arg
        1105                1110                1115

CCC GAC GGC CAC TCG GCC TGC AGG CGC TTG GCG CAG GCG CAG TCG ATG      3590
Pro Asp Gly His Ser Ala Cys Arg Arg Leu Ala Gln Ala Gln Ser Met
    1120                1125                1130

TGC TTG CCG ATC TAC CGG GAG GCC TGC CAG GAG GGC GAG CAG GCA GGG      3638
Cys Leu Pro Ile Tyr Arg Glu Ala Cys Gln Glu Gly Glu Gln Ala Gly
1135                1140                1145                1150

GCC CCC GCC TGG CAG CAC AGA CAG CAC GTC TGC CTG CAC GCC CAC GCC      3686
Ala Pro Ala Trp Gln His Arg Gln His Val Cys Leu His Ala His Ala
                1155                1160                1165
```

-continued

CAC CTG CCA TTG TGC TGG GGG GCT GTC TGT CCT CAC CTT CCA CCC TGT 3734
His Leu Pro Leu Cys Trp Gly Ala Val Cys Pro His Leu Pro Pro Cys
1170 1175 1180

GAC AGC CAC GGC TCC TGG CTC TCC GGC GCC TGG GGG CCT CTG GGG CAC 3782
Asp Ser His Gly Ser Trp Leu Ser Gly Ala Trp Gly Pro Leu Gly His
1185 1190 1195

AGC GGC AGG ACT CTG GGG CTG GGC ACA GGC TAC AGA GAC AGT GGG GGA 3830
Ser Gly Arg Thr Leu Gly Leu Gly Thr Gly Tyr Arg Asp Ser Gly Gly
1200 1205 1210

CTG GAC GAG ATC AGC AGT GTA GCC CGT GGG ACG CAA GGC TTC CCG GGA 3878
Leu Asp Glu Ile Ser Ser Val Ala Arg Gly Thr Gln Gly Phe Pro Gly
1215 1220 1225 1230

CCC TGC ACC TGG AGA CGG ATC TCC AGT CTG GAG TCA GAA GTG TGAGTTATCA 3930
Pro Cys Thr Trp Arg Arg Ile Ser Ser Leu Glu Ser Glu Val
1235 1240 124

GCCACTCAGG CTCCGAGCCA GCTGGATTCT CTGCCTGCCA CTGTCAGGGT TAAGCGGCAG 3990

GCAGGATTGG CCCTTCTCTG GCTTCTACCA TGAAATCCTG GCCATGGCAC CCCAGTGACA 4050

GATGATGTCT TCCATGGTCA TCAGTGACCT CAGCTAGCCT CA 4092

(2) INFORMATION FOR SEQ ID NO:46:

(i) SEQUENCE CHARACTERISTICS:
(A) LENGTH: 1244 amino acids
(B) TYPE: amino acid
(D) TOPOLOGY: linear (ii) MOLECULE TYPE: protein (xi) SEQUENCE DESCRIPTION: SEQ ID NO:46:

Met Gly Gly Ala Leu Gly Pro Ala Leu Leu Leu Thr Ser Leu Phe Gly
1 5 10 15

Ala Trp Ala Gly Leu Gly Pro Gly Gln Gly Glu Gln Gly Met Thr Val
20 25 30

Ala Val Val Phe Ser Ser Ser Gly Pro Pro Gln Ala Gln Phe Arg Val
35 40 45

Arg Leu Thr Pro Gln Ser Phe Leu Asp Leu Pro Leu Glu Ile Gln Pro
50 55 60

Leu Thr Val Gly Val Asn Thr Thr Asn Pro Ser Ser Leu Leu Thr Gln
65 70 75 80

Ile Cys Gly Leu Leu Gly Ala Ala His Val His Gly Ile Val Phe Glu
85 90 95

Asp Asn Val Asp Thr Glu Ala Val Ala Gln Ile Leu Asp Phe Ile Ser
100 105 110

Ser Gln Thr His Val Pro Ile Leu Ser Ile Ser Gly Gly Ser Ala Val
115 120 125

Val Leu Thr Pro Lys Glu Pro Gly Ser Ala Phe Leu Gln Leu Gly Val
130 135 140

Ser Leu Glu Gln Gln Leu Gln Val Leu Phe Lys Val Leu Glu Glu Tyr
145 150 155 160

Asp Trp Ser Ala Phe Ala Val Ile Thr Ser Leu His Pro Gly His Ala
165 170 175

Leu Phe Leu Glu Gly Val Arg Ala Val Ala Asp Ala Ser His Val Ser
180 185 190

Trp Arg Leu Leu Asp Val Val Thr Leu Glu Leu Asp Pro Gly Gly Pro
195 200 205

Arg Ala Arg Thr Gln Arg Leu Leu Arg Gln Leu Asp Ala Pro Val Phe

-continued

```
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
    370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
    450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Lys Ser
            580                 585                 590

Gly Gly Pro Ala Phe Thr Ile Gly Lys Ser Val Trp Leu Leu Trp Ala
        595                 600                 605

Leu Val Phe Asn Asn Ser Val Pro Ile Glu Asn Pro Arg Gly Thr Thr
    610                 615                 620

Ser Lys Ile Met Val Leu Val Trp Ala Phe Phe Ala Val Ile Phe Leu
625                 630                 635                 640
```

-continued

```
Ala Arg Tyr Thr Ala Asn Leu Ala Ala Phe Met Ile Gln Glu Gln Tyr
                645                 650                 655

Ile Asp Thr Val Ser Gly Leu Ser Asp Lys Lys Phe Gln Arg Pro Gln
            660                 665                 670

Asp Gln Tyr Pro Pro Phe Arg Phe Gly Thr Val Pro Asn Gly Ser Thr
        675                 680                 685

Glu Arg Asn Ile Arg Ser Asn Tyr Arg Asp Met His Thr His Met Val
    690                 695                 700

Lys Phe Asn Gln Arg Ser Val Glu Asp Ala Leu Thr Ser Leu Lys Met
705                 710                 715                 720

Gly Ser Glu Ala Gln Pro Val Pro Arg Lys Leu Asp Ala Phe Ile Tyr
                725                 730                 735

Asp Ala Ala Val Leu Asn Tyr Met Ala Gly Lys Asp Glu Gly Cys Lys
            740                 745                 750

Leu Val Thr Ile Gly Ser Gly Lys Val Phe Ala Thr Thr Gly Tyr Gly
        755                 760                 765

Ile Ala Met Gln Lys Asp Ser His Trp Lys Arg Ala Ile Asp Leu Ala
    770                 775                 780

Leu Leu Gln Phe Leu Gly Asp Gly Glu Thr Gln Lys Leu Glu Thr Val
785                 790                 795                 800

Trp Leu Ser Gly Ile Cys Gln Asn Glu Lys Asn Glu Val Met Ser Ser
                805                 810                 815

Lys Leu Asp Ile Asp Asn Met Gly Gly Val Phe Tyr Met Leu Leu Val
            820                 825                 830

Ala Met Gly Leu Ala Leu Leu Val Phe Ala Trp Glu His Leu Val Tyr
        835                 840                 845

Trp Lys Leu Arg His Ser Val Pro Asn Ser Ser Gln Leu Asp Phe Leu
    850                 855                 860

Leu Ala Phe Ser Arg Gly Ile Tyr Ser Cys Phe Ser Gly Val Gln Ser
865                 870                 875                 880

Leu Ala Ser Pro Pro Arg Gln Ala Ser Pro Asp Leu Thr Ala Ser Ser
                885                 890                 895

Ala Gln Ala Ser Val Leu Lys Ile Leu Gln Ala Ala Arg Asp Met Val
            900                 905                 910

Thr Thr Ala Gly Val Ser Asn Ser Leu Asp Arg Ala Thr Arg Thr Ile
        915                 920                 925

Glu Asn Trp Gly Gly Gly Arg Arg Ala Pro Pro Pro Ser Pro Cys Pro
    930                 935                 940

Thr Pro Arg Ser Gly Pro Ser Pro Cys Leu Pro Thr Pro Asp Pro Pro
945                 950                 955                 960

Pro Glu Pro Ser Pro Thr Gly Trp Gly Pro Pro Asp Gly Gly Arg Ala
                965                 970                 975

Ala Leu Val Arg Arg Ala Pro Gln Pro Pro Gly Arg Pro Pro Thr Pro
            980                 985                 990

Gly Pro Pro Leu Ser Asp Val Ser Arg Val Ser Arg Arg Pro Ala Trp
        995                 1000                1005

Glu Ala Arg Trp Pro Val Arg Thr Gly His Cys Gly Arg His Leu Ser
    1010                1015                1020

Ala Ser Glu Arg Pro Leu Ser Pro Ala Arg Cys His Tyr Ser Ser Phe
1025                1030                1035                1040

Pro Arg Ala Asp Arg Ser Gly Arg Pro Phe Leu Pro Leu Phe Pro Glu
                1045                1050                1055
```

-continued

```
Pro Pro Glu Leu Glu Asp Leu Pro Leu Leu Gly Pro Glu Gln Leu Ala
            1060                1065                1070

Arg Arg Glu Ala Leu Leu Asn Ala Ala Trp Ala Arg Gly Ser Arg Pro
        1075                1080                1085

Ser His Ala Ser Leu Pro Ser Ser Val Ala Glu Ala Phe Ala Arg Pro
    1090                1095                1100

Ser Ser Leu Pro Ala Gly Cys Thr Gly Pro Ala Cys Ala Arg Pro Asp
1105                1110                1115                1120

Gly His Ser Ala Cys Arg Arg Leu Ala Gln Ala Gln Ser Met Cys Leu
                1125                1130                1135

Pro Ile Tyr Arg Glu Ala Cys Gln Glu Gly Glu Gln Ala Gly Ala Pro
            1140                1145                1150

Ala Trp Gln His Arg Gln His Val Cys Leu His Ala His Ala His Leu
        1155                1160                1165

Pro Leu Cys Trp Gly Ala Val Cys Pro His Leu Pro Pro Cys Asp Ser
    1170                1175                1180

His Gly Ser Trp Leu Ser Gly Ala Trp Gly Pro Leu Gly His Ser Gly
1185                1190                1195                1200

Arg Thr Leu Gly Leu Gly Thr Gly Tyr Arg Asp Ser Gly Gly Leu Asp
                1205                1210                1215

Glu Ile Ser Ser Val Ala Arg Gly Thr Gln Gly Phe Pro Gly Pro Cys
            1220                1225                1230

Thr Trp Arg Arg Ile Ser Ser Leu Glu Ser Glu Val
        1235                1240
```

(2) INFORMATION FOR SEQ ID NO:47:

(i) SEQUENCE CHARACTERISTICS:
(A) LENGTH: 4053 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 189..3884

(xi) SEQUENCE DESCRIPTION: SEQ ID NO:47:

```
CCCTTAATAA GATTTGCNAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC      230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG       278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC       326
Thr Val Ala Val Val Phe Ser Ser Ser Gly Pro Pro Gln Ala Gln Phe
                35                  40                  45

CGT GTC CGC CTC ACC CCC CAG AGC TTC CTG GAC CTA CCC CTG GAG ATC       374
Arg Val Arg Leu Thr Pro Gln Ser Phe Leu Asp Leu Pro Leu Glu Ile
            50                  55                  60

CAG CCG CTC ACA GTT GGG GTC AAC ACC ACC AAC CCC AGC AGC CTC CTC       422
Gln Pro Leu Thr Val Gly Val Asn Thr Thr Asn Pro Ser Ser Leu Leu
        65                  70                  75
```

-continued

```
ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                   85                   90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC      758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA      806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC      854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC      902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG      950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC      998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC     1046
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC     1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT     1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC     1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT     1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC     1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG     1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG     1382
Lys Tyr Pro Val Trp Pro Arg Tyr Ser Ala Ser Leu Gln Pro Val Val
        385                 390                 395
```

-continued

GAC AGT CGG CAC CTG ACG GTG GCC ACG CTG GAA GAG CGG CCC TTT GTC 1430
Asp Ser Arg His Leu Thr Val Ala Thr Leu Glu Glu Arg Pro Phe Val
400 405 410

ATC GTG GAG AGC CCT GAC CCT GGC ACA GGA GGC TGT GTC CCC AAC ACC 1478
Ile Val Glu Ser Pro Asp Pro Gly Thr Gly Gly Cys Val Pro Asn Thr
415 420 425 430

GTG CCC TGC CGC AGG CAG AGC AAC CAC ACC TTC AGC AGC GGG GAC GTG 1526
Val Pro Cys Arg Arg Gln Ser Asn His Thr Phe Ser Ser Gly Asp Val
435 440 445

GCC CCC TAC ACC AAG CTC TGC TGT AAG GGA TTC TGC ATC GAC ATC CTC 1574
Ala Pro Tyr Thr Lys Leu Cys Cys Lys Gly Phe Cys Ile Asp Ile Leu
450 455 460

AAG AAG CTG GCC AGA GTG GTC AAA TTC TCC TAC GAC CTG TAC CTG GTG 1622
Lys Lys Leu Ala Arg Val Val Lys Phe Ser Tyr Asp Leu Tyr Leu Val
465 470 475

ACC AAC GGC AAG CAT GGC AAG CGG GTG CGC GGC GTA TGG AAC GGC ATG 1670
Thr Asn Gly Lys His Gly Lys Arg Val Arg Gly Val Trp Asn Gly Met
480 485 490

ATT GGG GAG GTG TAC TAC AAG CGG GCA GAC ATG GCC ATC GGC TCC CTC 1718
Ile Gly Glu Val Tyr Tyr Lys Arg Ala Asp Met Ala Ile Gly Ser Leu
495 500 505 510

ACC ATC AAT GAG GAA CGC TCC GAG ATC GTA GAC TTC TCT GTA CCC TTT 1766
Thr Ile Asn Glu Glu Arg Ser Glu Ile Val Asp Phe Ser Val Pro Phe
515 520 525

GTG GAG ACG GGC ATC AGT GTG ATG GTG GCT CGC AGC AAT GGC ACC GTC 1814
Val Glu Thr Gly Ile Ser Val Met Val Ala Arg Ser Asn Gly Thr Val
530 535 540

TCC CCC TCG GCC TTC TTG GAG CCA TAT AGC CCT GCA GTG TGG GTG ATG 1862
Ser Pro Ser Ala Phe Leu Glu Pro Tyr Ser Pro Ala Val Trp Val Met
545 550 555

ATG TTT GTC ATG TGC CTC ACT GTG GTG GCC ATC ACC GTC TTC ATG TTC 1910
Met Phe Val Met Cys Leu Thr Val Val Ala Ile Thr Val Phe Met Phe
560 565 570

GAG TAC TTC AGC CCT GTC AGC TAC AAC CAG AAC CTC ACC AGA GGC AAG 1958
Glu Tyr Phe Ser Pro Val Ser Tyr Asn Gln Asn Leu Thr Arg Gly Lys
575 580 585 590

ACT TTC ACT ATC GGC AAG TCC GTG TGG CTG CTG TGG GCG CTG GTC TTC 2006
Thr Phe Thr Ile Gly Lys Ser Val Trp Leu Leu Trp Ala Leu Val Phe
595 600 605

AAC AAC TCA GTG CCC ATC GAG AAC CCG CGG GGC ACC ACC AGC AAG ATC 2054
Asn Asn Ser Val Pro Ile Glu Asn Pro Arg Gly Thr Thr Ser Lys Ile
610 615 620

ATG GTT CTG GTC TGG GCC TTC TTT GCT GTC ATC TTC CTC GCC AGA TAC 2102
Met Val Leu Val Trp Ala Phe Phe Ala Val Ile Phe Leu Ala Arg Tyr
625 630 635

ACG GCC AAC CTG GCC GCC TTC ATG ATC CAA GAG CAA TAC ATC GAC ACT 2150
Thr Ala Asn Leu Ala Ala Phe Met Ile Gln Glu Gln Tyr Ile Asp Thr
640 645 650

GTG TCG GGC CTC AGT GAC AAG AAG TTT CAG CGG CCT CAA GAT CAG TAC 2198
Val Ser Gly Leu Ser Asp Lys Lys Phe Gln Arg Pro Gln Asp Gln Tyr
655 660 665 670

CCA CCT TTC CGC TTC GGC ACG GTG CCC AAC GGC AGC ACG GAG CGG AAC 2246
Pro Pro Phe Arg Phe Gly Thr Val Pro Asn Gly Ser Thr Glu Arg Asn
675 680 685

ATC CGC AGT AAC TAC CGT GAC ATG CAC ACC CAC ATG GTC AAG TTC AAC 2294
Ile Arg Ser Asn Tyr Arg Asp Met His Thr His Met Val Lys Phe Asn
690 695 700

CAG CGC TCG GTG GAG GAC GCG CTC ACC AGC CTC AAG ATG GGG AAG CTG 2342
Gln Arg Ser Val Glu Asp Ala Leu Thr Ser Leu Lys Met Gly Lys Leu

-continued

```
        705                 710                 715

GAT GCC TTC ATC TAT GAT GCT GCT GTC CTC AAC TAC ATG GCA GGC AAG     2390
Asp Ala Phe Ile Tyr Asp Ala Ala Val Leu Asn Tyr Met Ala Gly Lys
    720                 725                 730

GAC GAG GGC TGC AAG CTG GTC ACC ATT GGG TCT GGC AAG GTC TTT GCT     2438
Asp Glu Gly Cys Lys Leu Val Thr Ile Gly Ser Gly Lys Val Phe Ala
735                 740                 745                 750

ACC ACT GGC TAC GGC ATC GCC ATG CAG AAG GAC TCC CAC TGG AAG CGG     2486
Thr Thr Gly Tyr Gly Ile Ala Met Gln Lys Asp Ser His Trp Lys Arg
                755                 760                 765

GCC ATA GAC CTG GCG CTC TTG CAG TTC CTG GGG GAC GGA GAG ACA CAG     2534
Ala Ile Asp Leu Ala Leu Leu Gln Phe Leu Gly Asp Gly Glu Thr Gln
            770                 775                 780

AAA CTG GAG ACA GTG TGG CTC TCA GGG ATC TGC CAG AAT GAG AAG AAC     2582
Lys Leu Glu Thr Val Trp Leu Ser Gly Ile Cys Gln Asn Glu Lys Asn
        785                 790                 795

GAG GTG ATG AGC AGC AAG CTG GAC ATC GAC AAC ATG GGA GGC GTC TTC     2630
Glu Val Met Ser Ser Lys Leu Asp Ile Asp Asn Met Gly Gly Val Phe
    800                 805                 810

TAC ATG CTG CTG GTG GCC ATG GGG CTG GCC CTG CTG GTC TTC GCC TGG     2678
Tyr Met Leu Leu Val Ala Met Gly Leu Ala Leu Leu Val Phe Ala Trp
815                 820                 825                 830

GAG CAC CTG GTC TAC TGG AAG CTG CGC CAC TCG GTG CCC AAC TCA TCC     2726
Glu His Leu Val Tyr Trp Lys Leu Arg His Ser Val Pro Asn Ser Ser
                835                 840                 845

CAG CTG GAC TTC CTG CTG GCT TTC AGC AGG GGC ATC TAC AGC TGC TTC     2774
Gln Leu Asp Phe Leu Leu Ala Phe Ser Arg Gly Ile Tyr Ser Cys Phe
            850                 855                 860

AGC GGG GTG CAG AGC CTC GCC AGC CCA CCG CGG CAG GCC AGC CCG GAC     2822
Ser Gly Val Gln Ser Leu Ala Ser Pro Pro Arg Gln Ala Ser Pro Asp
        865                 870                 875

CTC ACG GCC AGC TCG GCC CAG GCC AGC GTG CTC AAG ATT CTG CAG GCA     2870
Leu Thr Ala Ser Ser Ala Gln Ala Ser Val Leu Lys Ile Leu Gln Ala
    880                 885                 890

GCC CGC GAC ATG GTG ACC ACG GCG GGC GTA AGC AAC TCC CTG GAC CGC     2918
Ala Arg Asp Met Val Thr Thr Ala Gly Val Ser Asn Ser Leu Asp Arg
895                 900                 905                 910

GCC ACT CGC ACC ATC GAG AAT TGG GGT GGC GGC CGC CGT GCG CCC CCA     2966
Ala Thr Arg Thr Ile Glu Asn Trp Gly Gly Gly Arg Arg Ala Pro Pro
                915                 920                 925

CCG TCC CCC TGC CCG ACC CCG CGG TCT GGC CCC AGC CCA TGC CTG CCC     3014
Pro Ser Pro Cys Pro Thr Pro Arg Ser Gly Pro Ser Pro Cys Leu Pro
            930                 935                 940

ACC CCC GAC CCG CCC CCA GAG CCG AGC CCC ACG GGC TGG GGA CCG CCA     3062
Thr Pro Asp Pro Pro Pro Glu Pro Ser Pro Thr Gly Trp Gly Pro Pro
        945                 950                 955

GAC GGG GGT CGC GCG GCG CTT GTG CGC AGG GCT CCG CAG CCC CCG GGC     3110
Asp Gly Gly Arg Ala Ala Leu Val Arg Arg Ala Pro Gln Pro Pro Gly
    960                 965                 970

CGC CCC CCG ACG CCG GGG CCG CCC CTG TCC GAC GTC TCC CGA GTG TCG     3158
Arg Pro Pro Thr Pro Gly Pro Pro Leu Ser Asp Val Ser Arg Val Ser
975                 980                 985                 990

CGC CGC CCA GCC TGG GAG GCG CGG TGG CCG GTG CGG ACC GGG CAC TGC     3206
Arg Arg Pro Ala Trp Glu Ala Arg Trp Pro Val Arg Thr Gly His Cys
                995                1000                1005

GGG AGG CAC CTC TCG GCC TCC GAG CGG CCC CTG TCG CCC GCG CGC TGT     3254
Gly Arg His Leu Ser Ala Ser Glu Arg Pro Leu Ser Pro Ala Arg Cys
            1010                1015                1020

CAC TAC AGC TCC TTT CCT CGA GCC GAC CGA TCC GGC CGC CCC TTC CTC     3302
```

-continued

```
His Tyr Ser Ser Phe Pro Arg Ala Asp Arg Ser Gly Arg Pro Phe Leu
        1025                1030                1035

CCG CTC TTC CCG GAG CCC CCG GAG CTG GAG GAC CTG CCG CTG CTC GGT      3350
Pro Leu Phe Pro Glu Pro Pro Glu Leu Glu Asp Leu Pro Leu Leu Gly
    1040                1045                1050

CCG GAG CAG CTG GCC CGG CGG GAG GCC CTG CTG AAC GCG GCC TGG GCC      3398
Pro Glu Gln Leu Ala Arg Arg Glu Ala Leu Leu Asn Ala Ala Trp Ala
1055                1060                1065                1070

CGG GGC TCG CGC CCG AGT CAC GCT TCC CTG CCC AGC TCC GTG GCC GAG      3446
Arg Gly Ser Arg Pro Ser His Ala Ser Leu Pro Ser Ser Val Ala Glu
                1075                1080                1085

GCC TTC GCT CGG CCC AGC TCG CTG CCC GCT GGG TGC ACC GGC CCC GCC      3494
Ala Phe Ala Arg Pro Ser Ser Leu Pro Ala Gly Cys Thr Gly Pro Ala
            1090                1095                1100

TGC GCC CGC CCC GAC GGC CAC TCG GCC TGC AGG CGC TTG GCG CAG GCG      3542
Cys Ala Arg Pro Asp Gly His Ser Ala Cys Arg Arg Leu Ala Gln Ala
        1105                1110                1115

CAG TCG ATG TGC TTG CCG ATC TAC CGG GAG GCC TGC CAG GAG GGC GAG      3590
Gln Ser Met Cys Leu Pro Ile Tyr Arg Glu Ala Cys Gln Glu Gly Glu
    1120                1125                1130

CAG GCA GGG GCC CCC GCC TGG CAG CAC AGA CAG CAC GTC TGC CTG CAC      3638
Gln Ala Gly Ala Pro Ala Trp Gln His Arg Gln His Val Cys Leu His
1135                1140                1145                1150

GCC CAC GCC CAC CTG CCA TTG TGC TGG GGG GCT GTC TGT CCT CAC CTT      3686
Ala His Ala His Leu Pro Leu Cys Trp Gly Ala Val Cys Pro His Leu
                1155                1160                1165

CCA CCC TGT GAC AGC CAC GGC TCC TGG CTC TCC GGC GCC TGG GGG CCT      3734
Pro Pro Cys Asp Ser His Gly Ser Trp Leu Ser Gly Ala Trp Gly Pro
            1170                1175                1180

CTG GGG CAC AGC GGC AGG ACT CTG GGG CTG GGC ACA GGC TAC AGA GAC      3782
Leu Gly His Ser Gly Arg Thr Leu Gly Leu Gly Thr Gly Tyr Arg Asp
        1185                1190                1195

AGT GGG GGA CTG GAC GAG ATC AGC AGT GTA GCC CGT GGG ACG CAA GGC      3830
Ser Gly Gly Leu Asp Glu Ile Ser Ser Val Ala Arg Gly Thr Gln Gly
    1200                1205                1210

TTC CCG GGA CCC TGC ACC TGG AGA CGG ATC TCC AGT CTG GAG TCA GAA      3878
Phe Pro Gly Pro Cys Thr Trp Arg Arg Ile Ser Ser Leu Glu Ser Glu
1215                1220                1225                1230

GTG TGAGTTATCA GCCACTCAGG CTCCGAGCCA GCTGGATTCT CTGCCTGCCA           3931
Val

CTGTCAGGGT TAAGCGGCAG GCAGGATTGG CCCTTCTCTG GCTTCTACCA TGAAATCCTG   3991

GCCATGGCAC CCCAGTGACA GATGATGTCT TCCATGGTCA TCAGTGACCT CAGCTAGCCT   4051

CA                                                                  4053
```

(2) INFORMATION FOR SEQ ID NO:48:

(i) SEQUENCE CHARACTERISTICS:
(A) LENGTH: 1231 amino acids
(B) TYPE: amino acid
(D) TOPOLOGY: linear (ii) MOLECULE TYPE: protein (xi) SEQUENCE DESCRIPTION: SEQ ID NO:48:

```
Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
            20                  25                  30

Ala Val Val Phe Ser Ser Ser Gly Pro Pro Gln Ala Gln Phe Arg Val
```

-continued

```
        35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
    370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
    450                 455                 460
```

-continued

```
Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Thr Phe
            580                 585                 590

Thr Ile Gly Lys Ser Val Trp Leu Leu Trp Ala Leu Val Phe Asn Asn
        595                 600                 605

Ser Val Pro Ile Glu Asn Pro Arg Gly Thr Thr Ser Lys Ile Met Val
    610                 615                 620

Leu Val Trp Ala Phe Phe Ala Val Ile Phe Leu Ala Arg Tyr Thr Ala
625                 630                 635                 640

Asn Leu Ala Ala Phe Met Ile Gln Glu Gln Tyr Ile Asp Thr Val Ser
                645                 650                 655

Gly Leu Ser Asp Lys Lys Phe Gln Arg Pro Gln Asp Gln Tyr Pro Pro
            660                 665                 670

Phe Arg Phe Gly Thr Val Pro Asn Gly Ser Thr Glu Arg Asn Ile Arg
        675                 680                 685

Ser Asn Tyr Arg Asp Met His Thr His Met Val Lys Phe Asn Gln Arg
    690                 695                 700

Ser Val Glu Asp Ala Leu Thr Ser Leu Lys Met Gly Lys Leu Asp Ala
705                 710                 715                 720

Phe Ile Tyr Asp Ala Ala Val Leu Asn Tyr Met Ala Gly Lys Asp Glu
                725                 730                 735

Gly Cys Lys Leu Val Thr Ile Gly Ser Gly Lys Val Phe Ala Thr Thr
            740                 745                 750

Gly Tyr Gly Ile Ala Met Gln Lys Asp Ser His Trp Lys Arg Ala Ile
        755                 760                 765

Asp Leu Ala Leu Leu Gln Phe Leu Gly Asp Gly Glu Thr Gln Lys Leu
    770                 775                 780

Glu Thr Val Trp Leu Ser Gly Ile Cys Gln Asn Glu Lys Asn Glu Val
785                 790                 795                 800

Met Ser Ser Lys Leu Asp Ile Asp Asn Met Gly Gly Val Phe Tyr Met
                805                 810                 815

Leu Leu Val Ala Met Gly Leu Ala Leu Leu Val Phe Ala Trp Glu His
            820                 825                 830

Leu Val Tyr Trp Lys Leu Arg His Ser Val Pro Asn Ser Ser Gln Leu
        835                 840                 845

Asp Phe Leu Leu Ala Phe Ser Arg Gly Ile Tyr Ser Cys Phe Ser Gly
    850                 855                 860

Val Gln Ser Leu Ala Ser Pro Pro Arg Gln Ala Ser Pro Asp Leu Thr
865                 870                 875                 880
```

-continued

```
Ala Ser Ser Ala Gln Ala Ser Val Leu Lys Ile Leu Gln Ala Ala Arg
                885                 890                 895

Asp Met Val Thr Thr Ala Gly Val Ser Asn Ser Leu Asp Arg Ala Thr
            900                 905                 910

Arg Thr Ile Glu Asn Trp Gly Gly Gly Arg Arg Ala Pro Pro Pro Ser
        915                 920                 925

Pro Cys Pro Thr Pro Arg Ser Gly Pro Ser Pro Cys Leu Pro Thr Pro
    930                 935                 940

Asp Pro Pro Pro Glu Pro Ser Pro Thr Gly Trp Gly Pro Pro Asp Gly
945                 950                 955                 960

Gly Arg Ala Ala Leu Val Arg Arg Ala Pro Gln Pro Pro Gly Arg Pro
                965                 970                 975

Pro Thr Pro Gly Pro Pro Leu Ser Asp Val Ser Arg Val Ser Arg Arg
            980                 985                 990

Pro Ala Trp Glu Ala Arg Trp Pro Val Arg Thr Gly His Cys Gly Arg
        995                 1000                1005

His Leu Ser Ala Ser Glu Arg Pro Leu Ser Pro Ala Arg Cys His Tyr
    1010                1015                1020

Ser Ser Phe Pro Arg Ala Asp Arg Ser Gly Arg Pro Phe Leu Pro Leu
1025                1030                1035                1040

Phe Pro Glu Pro Pro Glu Leu Glu Asp Leu Pro Leu Leu Gly Pro Glu
                1045                1050                1055

Gln Leu Ala Arg Arg Glu Ala Leu Leu Asn Ala Ala Trp Ala Arg Gly
            1060                1065                1070

Ser Arg Pro Ser His Ala Ser Leu Pro Ser Ser Val Ala Glu Ala Phe
        1075                1080                1085

Ala Arg Pro Ser Ser Leu Pro Ala Gly Cys Thr Gly Pro Ala Cys Ala
    1090                1095                1100

Arg Pro Asp Gly His Ser Ala Cys Arg Arg Leu Ala Gln Ala Gln Ser
1105                1110                1115                1120

Met Cys Leu Pro Ile Tyr Arg Glu Ala Cys Gln Glu Gly Glu Gln Ala
                1125                1130                1135

Gly Ala Pro Ala Trp Gln His Arg Gln His Val Cys Leu His Ala His
            1140                1145                1150

Ala His Leu Pro Leu Cys Trp Gly Ala Val Cys Pro His Leu Pro Pro
        1155                1160                1165

Cys Asp Ser His Gly Ser Trp Leu Ser Gly Ala Trp Gly Pro Leu Gly
    1170                1175                1180

His Ser Gly Arg Thr Leu Gly Leu Gly Thr Gly Tyr Arg Asp Ser Gly
1185                1190                1195                1200

Gly Leu Asp Glu Ile Ser Ser Val Ala Arg Gly Thr Gln Gly Phe Pro
                1205                1210                1215

Gly Pro Cys Thr Trp Arg Arg Ile Ser Ser Leu Glu Ser Glu Val
            1220                1225                1230
```

(2) INFORMATION FOR SEQ ID NO:49:

(i) SEQUENCE CHARACTERISTICS:
(A) LENGTH: 4017 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS -continued

```
          (B) LOCATION: 189..3848

    (xi) SEQUENCE DESCRIPTION: SEQ ID NO:49:

CCCTTAATAA GATTTGCNAC GTACACTCGA GCCATCGCGA GTGTCCTTGA GCCGCGGGTG     60

ACGGTGGCTC TCGCTGCTCG CGCCCCCTCC TCCCGCGGGG GGAGCCTGAT GCCACGTTCC    120

CTATGAATTA TTTATCGCCG GCCTAAAAAT ACCCCGAACT TCACAGCCCG AGTGACCCTC    180

CGGTGGAC ATG GGT GGG GCC CTG GGG CCG GCC CTG TTG CTC ACC TCG CTC     230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG      278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC      326
Thr Val Ala Val Val Phe Ser Ser Ser Gly Pro Pro Gln Ala Gln Phe
                35                  40                  45

CGT GTC CGC CTC ACC CCC CAG AGC TTC CTG GAC CTA CCC CTG GAG ATC      374
Arg Val Arg Leu Thr Pro Gln Ser Phe Leu Asp Leu Pro Leu Glu Ile
            50                  55                  60

CAG CCG CTC ACA GTT GGG GTC AAC ACC ACC AAC CCC AGC AGC CTC CTC      422
Gln Pro Leu Thr Val Gly Val Asn Thr Thr Asn Pro Ser Ser Leu Leu
        65                  70                  75

ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
               115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
           130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC      758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA      806
Val Ser Trp Arg Leu Leu Asp Val Val Thr Leu Glu Leu Asp Pro Gly
               195                 200                 205

GGG CCG CGC GCG CGC ACG CAG CGC CTG CTG CGC CAG CTC GAC GCG CCC      854
Gly Pro Arg Ala Arg Thr Gln Arg Leu Leu Arg Gln Leu Asp Ala Pro
           210                 215                 220

GTG TTT GTG GCC TAC TGC TCG CGC GAG GAG GCC GAG GTG CTC TTC GCC      902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG      950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC      998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC     1046
```

-continued

```
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC     1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT     1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC     1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT     1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC     1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG     1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG     1382
Lys Tyr Pro Val Trp Pro Arg Tyr Ser Ala Ser Leu Gln Pro Val Val
        385                 390                 395

GAC AGT CGG CAC CTG ACG GTG GCC ACG CTG GAA GAG CGG CCC TTT GTC     1430
Asp Ser Arg His Leu Thr Val Ala Thr Leu Glu Glu Arg Pro Phe Val
    400                 405                 410

ATC GTG GAG AGC CCT GAC CCT GGC ACA GGA GGC TGT GTC CCC AAC ACC     1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG     1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC     1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG     1622
Lys Lys Leu Ala Arg Val Val Lys Phe Ser Tyr Asp Leu Tyr Leu Val
        465                 470                 475

ACC AAC GGC AAG CAT GGC AAG CGG GTG CGC GGC GTA TGG AAC GGC ATG     1670
Thr Asn Gly Lys His Gly Lys Arg Val Arg Gly Val Trp Asn Gly Met
    480                 485                 490

ATT GGG GAG GTG TAC TAC AAG CGG GCA GAC ATG GCC ATC GGC TCC CTC     1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT     1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC     1814
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG     1862
Ser Pro Ser Ala Phe Leu Glu Pro Tyr Ser Pro Ala Val Trp Val Met
        545                 550                 555

ATG TTT GTC ATG TGC CTC ACT GTG GTG GCC ATC ACC GTC TTC ATG TTC     1910
Met Phe Val Met Cys Leu Thr Val Val Ala Ile Thr Val Phe Met Phe
    560                 565                 570

GAG TAC TTC AGC CCT GTC AGC TAC AAC CAG AAC CTC ACC AGA GGC AAG     1958
Glu Tyr Phe Ser Pro Val Ser Tyr Asn Gln Asn Leu Thr Arg Gly Lys
575                 580                 585                 590
```

-continued

AAG TCC GGG GGC CCA GCT TTC ACT ATC GGC AAG TCC GTG TGG CTG CTG 2006
Lys Ser Gly Gly Pro Ala Phe Thr Ile Gly Lys Ser Val Trp Leu Leu
595 600 605

TGG GCG CTG GTC TTC AAC AAC TCA GTG CCC ATC GAG AAC CCG CGG GGC 2054
Trp Ala Leu Val Phe Asn Asn Ser Val Pro Ile Glu Asn Pro Arg Gly
610 615 620

ACC ACC AGC AAG ATC ATG GTT CTG GTC TGG GCC TTC TTT GCT GTC ATC 2102
Thr Thr Ser Lys Ile Met Val Leu Val Trp Ala Phe Phe Ala Val Ile
625 630 635

TTC CTC GCC AGA TAC ACG GCC AAC CTG GCC GCC TTC ATG ATC CAA GAG 2150
Phe Leu Ala Arg Tyr Thr Ala Asn Leu Ala Ala Phe Met Ile Gln Glu
640 645 650

CAA TAC ATC GAC ACT GTG TCG GGC CTC AGT GAC AAG AAG TTT CAG CGG 2198
Gln Tyr Ile Asp Thr Val Ser Gly Leu Ser Asp Lys Lys Phe Gln Arg
655 660 665 670

CCT CAA GAT CAG TAC CCA CCT TTC CGC TTC GGC ACG GTG CCC AAC GGC 2246
Pro Gln Asp Gln Tyr Pro Pro Phe Arg Phe Gly Thr Val Pro Asn Gly
675 680 685

AGC ACG GAG CGG AAC ATC CGC AGT AAC TAC CGT GAC ATG CAC ACC CAC 2294
Ser Thr Glu Arg Asn Ile Arg Ser Asn Tyr Arg Asp Met His Thr His
690 695 700

ATG GTC AAG TTC AAC CAG CGC TCG GTG GAG GAC GCG CTC ACC AGC CTC 2342
Met Val Lys Phe Asn Gln Arg Ser Val Glu Asp Ala Leu Thr Ser Leu
705 710 715

AAG ATG GGC AAG GAC GAG GGC TGC AAG CTG GTC ACC ATT GGG TCT GGC 2390
Lys Met Gly Lys Asp Glu Gly Cys Lys Leu Val Thr Ile Gly Ser Gly
720 725 730

AAG GTC TTT GCT ACC ACT GGC TAC GGC ATC GCC ATG CAG AAG GAC TCC 2438
Lys Val Phe Ala Thr Thr Gly Tyr Gly Ile Ala Met Gln Lys Asp Ser
735 740 745 750

CAC TGG AAG CGG GCC ATA GAC CTG GCG CTC TTG CAG TTC CTG GGG GAC 2486
His Trp Lys Arg Ala Ile Asp Leu Ala Leu Leu Gln Phe Leu Gly Asp
755 760 765

GGA GAG ACA CAG AAA CTG GAG ACA GTG TGG CTC TCA GGG ATC TGC CAG 2534
Gly Glu Thr Gln Lys Leu Glu Thr Val Trp Leu Ser Gly Ile Cys Gln
770 775 780

AAT GAG AAG AAC GAG GTG ATG AGC AGC AAG CTG GAC ATC GAC AAC ATG 2582
Asn Glu Lys Asn Glu Val Met Ser Ser Lys Leu Asp Ile Asp Asn Met
785 790 795

GGA GGC GTC TTC TAC ATG CTG CTG GTG GCC ATG GGG CTG GCC CTG CTG 2630
Gly Gly Val Phe Tyr Met Leu Leu Val Ala Met Gly Leu Ala Leu Leu
800 805 810

GTC TTC GCC TGG GAG CAC CTG GTC TAC TGG AAG CTG CGC CAC TCG GTG 2678
Val Phe Ala Trp Glu His Leu Val Tyr Trp Lys Leu Arg His Ser Val
815 820 825 830

CCC AAC TCA TCC CAG CTG GAC TTC CTG CTG GCT TTC AGC AGG GGC ATC 2726
Pro Asn Ser Ser Gln Leu Asp Phe Leu Leu Ala Phe Ser Arg Gly Ile
835 840 845

TAC AGC TGC TTC AGC GGG GTG CAG AGC CTC GCC AGC CCA CCG CGG CAG 2774
Tyr Ser Cys Phe Ser Gly Val Gln Ser Leu Ala Ser Pro Pro Arg Gln
850 855 860

GCC AGC CCG GAC CTC ACG GCC AGC TCG GCC CAG GCC AGC GTG CTC AAG 2822
Ala Ser Pro Asp Leu Thr Ala Ser Ser Ala Gln Ala Ser Val Leu Lys
865 870 875

ATT CTG CAG GCA GCC CGC GAC ATG GTG ACC ACG GCG GGC GTA AGC AAC 2870
Ile Leu Gln Ala Ala Arg Asp Met Val Thr Thr Ala Gly Val Ser Asn
880 885 890

TCC CTG GAC CGC GCC ACT CGC ACC ATC GAG AAT TGG GGT GGC GGC CGC 2918
Ser Leu Asp Arg Ala Thr Arg Thr Ile Glu Asn Trp Gly Gly Gly Arg
895 900 905 910

-continued

```
CGT GCG CCC CCA CCG TCC CCC TGC CCG ACC CCG CGG TCT GGC CCC AGC      2966
Arg Ala Pro Pro Pro Ser Pro Cys Pro Thr Pro Arg Ser Gly Pro Ser
                915                 920                 925

CCA TGC CTG CCC ACC CCC GAC CCG CCC CCA GAG CCG AGC CCC ACG GGC      3014
Pro Cys Leu Pro Thr Pro Asp Pro Pro Pro Glu Pro Ser Pro Thr Gly
            930                 935                 940

TGG GGA CCG CCA GAC GGG GGT CGC GCG GCG CTT GTG CGC AGG GCT CCG      3062
Trp Gly Pro Pro Asp Gly Gly Arg Ala Ala Leu Val Arg Arg Ala Pro
        945                 950                 955

CAG CCC CCG GGC CGC CCC CCG ACG CCG GGG CCG CCC CTG TCC GAC GTC      3110
Gln Pro Pro Gly Arg Pro Pro Thr Pro Gly Pro Pro Leu Ser Asp Val
    960                 965                 970

TCC CGA GTG TCG CGC CGC CCA GCC TGG GAG GCG CGG TGG CCG GTG CGG      3158
Ser Arg Val Ser Arg Arg Pro Ala Trp Glu Ala Arg Trp Pro Val Arg
975                 980                 985                 990

ACC GGG CAC TGC GGG AGG CAC CTC TCG GCC TCC GAG CGG CCC CTG TCG      3206
Thr Gly His Cys Gly Arg His Leu Ser Ala Ser Glu Arg Pro Leu Ser
                995                1000                1005

CCC GCG CGC TGT CAC TAC AGC TCC TTT CCT CGA GCC GAC CGA TCC GGC      3254
Pro Ala Arg Cys His Tyr Ser Ser Phe Pro Arg Ala Asp Arg Ser Gly
            1010                1015                1020

CGC CCC TTC CTC CCG CTC TTC CCG GAG CCC CCG GAG CTG GAG GAC CTG      3302
Arg Pro Phe Leu Pro Leu Phe Pro Glu Pro Pro Glu Leu Glu Asp Leu
        1025                1030                1035

CCG CTG CTC GGT CCG GAG CAG CTG GCC CGG CGG GAG GCC CTG CTG AAC      3350
Pro Leu Leu Gly Pro Glu Gln Leu Ala Arg Arg Glu Ala Leu Leu Asn
    1040                1045                1050

GCG GCC TGG GCC CGG GGC TCG CGC CCG AGT CAC GCT TCC CTG CCC AGC      3398
Ala Ala Trp Ala Arg Gly Ser Arg Pro Ser His Ala Ser Leu Pro Ser
1055                1060                1065                1070

TCC GTG GCC GAG GCC TTC GCT CGG CCC AGC TCG CTG CCC GCT GGG TGC      3446
Ser Val Ala Glu Ala Phe Ala Arg Pro Ser Ser Leu Pro Ala Gly Cys
                1075                1080                1085

ACC GGC CCC GCC TGC GCC CGC CCC GAC GGC CAC TCG GCC TGC AGG CGC      3494
Thr Gly Pro Ala Cys Ala Arg Pro Asp Gly His Ser Ala Cys Arg Arg
            1090                1095                1100

TTG GCG CAG GCG CAG TCG ATG TGC TTG CCG ATC TAC CGG GAG GCC TGC      3542
Leu Ala Gln Ala Gln Ser Met Cys Leu Pro Ile Tyr Arg Glu Ala Cys
        1105                1110                1115

CAG GAG GGC GAG CAG GCA GGG GCC CCC GCC TGG CAG CAC AGA CAG CAC      3590
Gln Glu Gly Glu Gln Ala Gly Ala Pro Ala Trp Gln His Arg Gln His
    1120                1125                1130

GTC TGC CTG CAC GCC CAC GCC CAC CTG CCA TTG TGC TGG GGG GCT GTC      3638
Val Cys Leu His Ala His Ala His Leu Pro Leu Cys Trp Gly Ala Val
1135                1140                1145                1150

TGT CCT CAC CTT CCA CCC TGT GAC AGC CAC GGC TCC TGG CTC TCC GGC      3686
Cys Pro His Leu Pro Pro Cys Asp Ser His Gly Ser Trp Leu Ser Gly
                1155                1160                1165

GCC TGG GGG CCT CTG GGG CAC AGC GGC AGG ACT CTG GGG CTG GGC ACA      3734
Ala Trp Gly Pro Leu Gly His Ser Gly Arg Thr Leu Gly Leu Gly Thr
            1170                1175                1180

GGC TAC AGA GAC AGT GGG GGA CTG GAC GAG ATC AGC AGT GTA GCC CGT      3782
Gly Tyr Arg Asp Ser Gly Gly Leu Asp Glu Ile Ser Ser Val Ala Arg
        1185                1190                1195

GGG ACG CAA GGC TTC CCG GGA CCC TGC ACC TGG AGA CGG ATC TCC AGT      3830
Gly Thr Gln Gly Phe Pro Gly Pro Cys Thr Trp Arg Arg Ile Ser Ser
    1200                1205                1210

CTG GAG TCA GAA GTG TGAGTTATCA GCCACTCAGG CTCCGAGCCA GCTGGATTCT      3885
Leu Glu Ser Glu Val
```

-continued 1215 122

CTGCCTGCCA CTGTCAGGGT TAAGCGGCAG GCAGGATTGG CCCTTCTCTG GCTTCTACCA 3945

TGAAATCCTG GCCATGGCAC CCCAGTGACA GATGATGTCT TCCATGGTCA TCAGTGACCT 4005

CAGCTAGCCT CA 4017

(2) INFORMATION FOR SEQ ID NO:50:

(i) SEQUENCE CHARACTERISTICS:
(A) LENGTH: 1219 amino acids
(B) TYPE: amino acid
(D) TOPOLOGY: linear (ii) MOLECULE TYPE: protein (xi) SEQUENCE DESCRIPTION: SEQ ID NO:50:

```
Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
             20                  25                  30

Ala Val Val Phe Ser Ser Ser Gly Pro Pro Gln Ala Gln Phe Arg Val
         35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320
```

-continued

```
Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
    370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
    450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Lys Ser
            580                 585                 590

Gly Gly Pro Ala Phe Thr Ile Gly Lys Ser Val Trp Leu Leu Trp Ala
        595                 600                 605

Leu Val Phe Asn Asn Ser Val Pro Ile Glu Asn Pro Arg Gly Thr Thr
    610                 615                 620

Ser Lys Ile Met Val Leu Val Trp Ala Phe Phe Ala Val Ile Phe Leu
625                 630                 635                 640

Ala Arg Tyr Thr Ala Asn Leu Ala Ala Phe Met Ile Gln Glu Gln Tyr
                645                 650                 655

Ile Asp Thr Val Ser Gly Leu Ser Asp Lys Lys Phe Gln Arg Pro Gln
            660                 665                 670

Asp Gln Tyr Pro Pro Phe Arg Phe Gly Thr Val Pro Asn Gly Ser Thr
        675                 680                 685

Glu Arg Asn Ile Arg Ser Asn Tyr Arg Asp Met His Thr His Met Val
    690                 695                 700

Lys Phe Asn Gln Arg Ser Val Glu Asp Ala Leu Thr Ser Leu Lys Met
705                 710                 715                 720

Gly Lys Asp Glu Gly Cys Lys Leu Val Thr Ile Gly Ser Gly Lys Val
                725                 730                 735
```

-continued

Phe Ala Thr Thr Gly Tyr Gly Ile Ala Met Gln Lys Asp Ser His Trp
740 745 750

Lys Arg Ala Ile Asp Leu Ala Leu Leu Gln Phe Leu Gly Asp Gly Glu
755 760 765

Thr Gln Lys Leu Glu Thr Val Trp Leu Ser Gly Ile Cys Gln Asn Glu
770 775 780

Lys Asn Glu Val Met Ser Ser Lys Leu Asp Ile Asp Asn Met Gly Gly
785 790 795 800

Val Phe Tyr Met Leu Leu Val Ala Met Gly Leu Ala Leu Leu Val Phe
805 810 815

Ala Trp Glu His Leu Val Tyr Trp Lys Leu Arg His Ser Val Pro Asn
820 825 830

Ser Ser Gln Leu Asp Phe Leu Leu Ala Phe Ser Arg Gly Ile Tyr Ser
835 840 845

Cys Phe Ser Gly Val Gln Ser Leu Ala Ser Pro Pro Arg Gln Ala Ser
850 855 860

Pro Asp Leu Thr Ala Ser Ser Ala Gln Ala Ser Val Leu Lys Ile Leu
865 870 875 880

Gln Ala Ala Arg Asp Met Val Thr Thr Ala Gly Val Ser Asn Ser Leu
885 890 895

Asp Arg Ala Thr Arg Thr Ile Glu Asn Trp Gly Gly Gly Arg Arg Ala
900 905 910

Pro Pro Pro Ser Pro Cys Pro Thr Pro Arg Ser Gly Pro Ser Pro Cys
915 920 925

Leu Pro Thr Pro Asp Pro Pro Pro Glu Pro Ser Pro Thr Gly Trp Gly
930 935 940

Pro Pro Asp Gly Gly Arg Ala Ala Leu Val Arg Arg Ala Pro Gln Pro
945 950 955 960

Pro Gly Arg Pro Pro Thr Pro Gly Pro Pro Leu Ser Asp Val Ser Arg
965 970 975

Val Ser Arg Arg Pro Ala Trp Glu Ala Arg Trp Pro Val Arg Thr Gly
980 985 990

His Cys Gly Arg His Leu Ser Ala Ser Glu Arg Pro Leu Ser Pro Ala
995 1000 1005

Arg Cys His Tyr Ser Ser Phe Pro Arg Ala Asp Arg Ser Gly Arg Pro
1010 1015 1020

Phe Leu Pro Leu Phe Pro Glu Pro Pro Glu Leu Glu Asp Leu Pro Leu
1025 1030 1035 1040

Leu Gly Pro Glu Gln Leu Ala Arg Arg Glu Ala Leu Leu Asn Ala Ala
1045 1050 1055

Trp Ala Arg Gly Ser Arg Pro Ser His Ala Ser Leu Pro Ser Ser Val
1060 1065 1070

Ala Glu Ala Phe Ala Arg Pro Ser Ser Leu Pro Ala Gly Cys Thr Gly
1075 1080 1085

Pro Ala Cys Ala Arg Pro Asp Gly His Ser Ala Cys Arg Arg Leu Ala
1090 1095 1100

Gln Ala Gln Ser Met Cys Leu Pro Ile Tyr Arg Glu Ala Cys Gln Glu
1105 1110 1115 1120

Gly Glu Gln Ala Gly Ala Pro Ala Trp Gln His Arg Gln His Val Cys
1125 1130 1135

Leu His Ala His Ala His Leu Pro Leu Cys Trp Gly Ala Val Cys Pro
1140 1145 1150

His Leu Pro Pro Cys Asp Ser His Gly Ser Trp Leu Ser Gly Ala Trp

-continued

```
        1155                1160                1165

Gly Pro Leu Gly His Ser Gly Arg Thr Leu Gly Leu Gly Thr Gly Tyr
    1170                1175                1180

Arg Asp Ser Gly Gly Leu Asp Glu Ile Ser Ser Val Ala Arg Gly Thr
1185                1190                1195                1200

Gln Gly Phe Pro Gly Pro Cys Thr Trp Arg Arg Ile Ser Ser Leu Glu
                1205                1210                1215

Ser Glu Val
```

(2) INFORMATION FOR SEQ ID NO:51:

(i) SEQUENCE CHARACTERISTICS:
(A) LENGTH: 4077 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 189..3908

(xi) SEQUENCE DESCRIPTION: SEQ ID NO:51:

```
CCCTTAATAA GATTTGCNAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC      230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG      278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC      326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC      374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC      422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170
```

-continued

```
CAC GCG CTC TTC CTG GAG GGC GTG CGC GCC GTC GCC GAC GCC AGC CAC       758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA       806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC       854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC       902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG       950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC       998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC      1046
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC      1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT      1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC      1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT      1238
Leu Leu Asn Val Thr Trp Glu Gly Arg Asp Phe Ser Phe Ser Pro Gly
335                 340                 345                 350

GGG TAC CTG GTC CAG CCC ACC ATG GTG GTG ATC GCC CTC AAC CGG CAC      1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG      1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG      1382
Lys Tyr Pro Val Trp Pro Arg Tyr Ser Ala Ser Leu Gln Pro Val Val
        385                 390                 395

GAC AGT CGG CAC CTG ACG GTG GCC ACG CTG GAA GAG CGG CCC TTT GTC      1430
Asp Ser Arg His Leu Thr Val Ala Thr Leu Glu Glu Arg Pro Phe Val
    400                 405                 410

ATC GTG GAG AGC CCT GAC CCT GGC ACA GGA GGC TGT GTC CCC AAC ACC      1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG      1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC      1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG      1622
Lys Lys Leu Ala Arg Val Val Lys Phe Ser Tyr Asp Leu Tyr Leu Val
        465                 470                 475

ACC AAC GGC AAG CAT GGC AAG CGG GTG CGC GGC GTA TGG AAC GGC ATG      1670
Thr Asn Gly Lys His Gly Lys Arg Val Arg Gly Val Trp Asn Gly Met
```

-continued

```
    480                 485                 490

ATT GGG GAG GTG TAC TAC AAG CGG GCA GAC ATG GCC ATC GGC TCC CTC      1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT      1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC      1814
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG      1862
Ser Pro Ser Ala Phe Leu Glu Pro Tyr Ser Pro Ala Val Trp Val Met
        545                 550                 555

ATG TTT GTC ATG TGC CTC ACT GTG GTG GCC ATC ACC GTC TTC ATG TTC      1910
Met Phe Val Met Cys Leu Thr Val Val Ala Ile Thr Val Phe Met Phe
    560                 565                 570

GAG TAC TTC AGC CCT GTC AGC TAC AAC CAG AAC CTC ACC AGA GGC AAG      1958
Glu Tyr Phe Ser Pro Val Ser Tyr Asn Gln Asn Leu Thr Arg Gly Lys
575                 580                 585                 590

ACT TTC ACT ATC GGC AAG TCC GTG TGG CTG CTG TGG GCG CTG GTC TTC      2006
Thr Phe Thr Ile Gly Lys Ser Val Trp Leu Leu Trp Ala Leu Val Phe
                595                 600                 605

AAC AAC TCA GTG CCC ATC GAG AAC CCG CGG GGC ACC ACC AGC AAG ATC      2054
Asn Asn Ser Val Pro Ile Glu Asn Pro Arg Gly Thr Thr Ser Lys Ile
            610                 615                 620

ATG GTT CTG GTC TGG GCC TTC TTT GCT GTC ATC TTC CTC GCC AGA TAC      2102
Met Val Leu Val Trp Ala Phe Phe Ala Val Ile Phe Leu Ala Arg Tyr
        625                 630                 635

ACG GCC AAC CTG GCC GCC TTC ATG ATC CAA GAG CAA TAC ATC GAC ACT      2150
Thr Ala Asn Leu Ala Ala Phe Met Ile Gln Glu Gln Tyr Ile Asp Thr
    640                 645                 650

GTG TCG GGC CTC AGT GAC AAG AAG TTT CAG CGG CCT CAA GAT CAG TAC      2198
Val Ser Gly Leu Ser Asp Lys Lys Phe Gln Arg Pro Gln Asp Gln Tyr
655                 660                 665                 670

CCA CCT TTC CGC TTC GGC ACG GTG CCC AAC GGC AGC ACG GAG CGG AAC      2246
Pro Pro Phe Arg Phe Gly Thr Val Pro Asn Gly Ser Thr Glu Arg Asn
                675                 680                 685

ATC CGC AGT AAC TAC CGT GAC ATG CAC ACC CAC ATG GTC AAG TTC AAC      2294
Ile Arg Ser Asn Tyr Arg Asp Met His Thr His Met Val Lys Phe Asn
            690                 695                 700

CAG CGC TCG GTG GAG GAC GCG CTC ACC AGC CTC AAG ATG GGC TCT GAG      2342
Gln Arg Ser Val Glu Asp Ala Leu Thr Ser Leu Lys Met Gly Ser Glu
        705                 710                 715

GCT CAG CCT GTC CCC AGG AAG CTG GAT GCC TTC ATC TAT GAT GCT GCT      2390
Ala Gln Pro Val Pro Arg Lys Leu Asp Ala Phe Ile Tyr Asp Ala Ala
    720                 725                 730

GTC CTC AAC TAC ATG GCA GGC AAG GAC GAG GGC TGC AAG CTG GTC ACC      2438
Val Leu Asn Tyr Met Ala Gly Lys Asp Glu Gly Cys Lys Leu Val Thr
735                 740                 745                 750

ATT GGG TCT GGC AAG GTC TTT GCT ACC ACT GGC TAC GGC ATC GCC ATG      2486
Ile Gly Ser Gly Lys Val Phe Ala Thr Thr Gly Tyr Gly Ile Ala Met
                755                 760                 765

CAG AAG GAC TCC CAC TGG AAG CGG GCC ATA GAC CTG GCG CTC TTG CAG      2534
Gln Lys Asp Ser His Trp Lys Arg Ala Ile Asp Leu Ala Leu Leu Gln
            770                 775                 780

TTC CTG GGG GAC GGA GAG ACA CAG AAA CTG GAG ACA GTG TGG CTC TCA      2582
Phe Leu Gly Asp Gly Glu Thr Gln Lys Leu Glu Thr Val Trp Leu Ser
        785                 790                 795

GGG ATC TGC CAG AAT GAG AAG AAC GAG GTG ATG AGC AGC AAG CTG GAC      2630
```

-continued

Gly Ile Cys Gln Asn Glu Lys Asn Glu Val Met Ser Ser Lys Leu Asp
800 805 810

ATC GAC AAC ATG GGA GGC GTC TTC TAC ATG CTG CTG GTG GCC ATG GGG 2678
Ile Asp Asn Met Gly Gly Val Phe Tyr Met Leu Leu Val Ala Met Gly
815 820 825 830

CTG GCC CTG CTG GTC TTC GCC TGG GAG CAC CTG GTC TAC TGG AAG CTG 2726
Leu Ala Leu Leu Val Phe Ala Trp Glu His Leu Val Tyr Trp Lys Leu
835 840 845

CGC CAC TCG GTG CCC AAC TCA TCC CAG CTG GAC TTC CTG CTG GCT TTC 2774
Arg His Ser Val Pro Asn Ser Ser Gln Leu Asp Phe Leu Leu Ala Phe
850 855 860

AGC AGG GGC ATC TAC AGC TGC TTC AGC GGG GTG CAG AGC CTC GCC AGC 2822
Ser Arg Gly Ile Tyr Ser Cys Phe Ser Gly Val Gln Ser Leu Ala Ser
865 870 875

CCA CCG CGG CAG GCC AGC CCG GAC CTC ACG GCC AGC TCG GCC CAG GCC 2870
Pro Pro Arg Gln Ala Ser Pro Asp Leu Thr Ala Ser Ser Ala Gln Ala
880 885 890

AGC GTG CTC AAG ATT CTG CAG GCA GCC CGC GAC ATG GTG ACC ACG GCG 2918
Ser Val Leu Lys Ile Leu Gln Ala Ala Arg Asp Met Val Thr Thr Ala
895 900 905 910

GGC GTA AGC AAC TCC CTG GAC CGC GCC ACT CGC ACC ATC GAG AAT TGG 2966
Gly Val Ser Asn Ser Leu Asp Arg Ala Thr Arg Thr Ile Glu Asn Trp
915 920 925

GGT GGC GGC CGC CGT GCG CCC CCA CCG TCC CCC TGC CCG ACC CCG CGG 3014
Gly Gly Gly Arg Arg Ala Pro Pro Pro Ser Pro Cys Pro Thr Pro Arg
930 935 940

TCT GGC CCC AGC CCA TGC CTG CCC ACC CCC GAC CCG CCC CCA GAG CCG 3062
Ser Gly Pro Ser Pro Cys Leu Pro Thr Pro Asp Pro Pro Pro Glu Pro
945 950 955

AGC CCC ACG GGC TGG GGA CCG CCA GAC GGG GGT CGC GCG GCG CTT GTG 3110
Ser Pro Thr Gly Trp Gly Pro Pro Asp Gly Gly Arg Ala Ala Leu Val
960 965 970

CGC AGG GCT CCG CAG CCC CCG GGC CGC CCC CCG ACG CCG GGG CCG CCC 3158
Arg Arg Ala Pro Gln Pro Pro Gly Arg Pro Pro Thr Pro Gly Pro Pro
975 980 985 990

CTG TCC GAC GTC TCC CGA GTG TCG CGC CGC CCA GCC TGG GAG GCG CGG 3206
Leu Ser Asp Val Ser Arg Val Ser Arg Arg Pro Ala Trp Glu Ala Arg
995 1000 1005

TGG CCG GTG CGG ACC GGG CAC TGC GGG AGG CAC CTC TCG GCC TCC GAG 3254
Trp Pro Val Arg Thr Gly His Cys Gly Arg His Leu Ser Ala Ser Glu
1010 1015 1020

CGG CCC CTG TCG CCC GCG CGC TGT CAC TAC AGC TCC TTT CCT CGA GCC 3302
Arg Pro Leu Ser Pro Ala Arg Cys His Tyr Ser Ser Phe Pro Arg Ala
1025 1030 1035

GAC CGA TCC GGC CGC CCC TTC CTC CCG CTC TTC CCG GAG CCC CCG GAG 3350
Asp Arg Ser Gly Arg Pro Phe Leu Pro Leu Phe Pro Glu Pro Pro Glu
1040 1045 1050

CTG GAG GAC CTG CCG CTG CTC GGT CCG GAG CAG CTG GCC CGG CGG GAG 3398
Leu Glu Asp Leu Pro Leu Leu Gly Pro Glu Gln Leu Ala Arg Arg Glu
1055 1060 1065 1070

GCC CTG CTG AAC GCG GCC TGG GCC CGG GGC TCG CGC CCG AGT CAC GCT 3446
Ala Leu Leu Asn Ala Ala Trp Ala Arg Gly Ser Arg Pro Ser His Ala
1075 1080 1085

TCC CTG CCC AGC TCC GTG GCC GAG GCC TTC GCT CGG CCC AGC TCG CTG 3494
Ser Leu Pro Ser Ser Val Ala Glu Ala Phe Ala Arg Pro Ser Ser Leu
1090 1095 1100

CCC GCT GGG TGC ACC GGC CCC GCC TGC GCC CGC CCC GAC GGC CAC TCG 3542
Pro Ala Gly Cys Thr Gly Pro Ala Cys Ala Arg Pro Asp Gly His Ser
1105 1110 1115

-continued

```
GCC TGC AGG CGC TTG GCG CAG GCG CAG TCG ATG TGC TTG CCG ATC TAC      3590
Ala Cys Arg Arg Leu Ala Gln Ala Gln Ser Met Cys Leu Pro Ile Tyr
    1120                1125                1130

CGG GAG GCC TGC CAG GAG GGC GAG CAG GCA GGG GCC CCC GCC TGG CAG      3638
Arg Glu Ala Cys Gln Glu Gly Glu Gln Ala Gly Ala Pro Ala Trp Gln
1135                1140                1145                1150

CAC AGA CAG CAC GTC TGC CTG CAC GCC CAC GCC CAC CTG CCA TTG TGC      3686
His Arg Gln His Val Cys Leu His Ala His Ala His Leu Pro Leu Cys
                1155                1160                1165

TGG GGG GCT GTC TGT CCT CAC CTT CCA CCC TGT GAC AGC CAC GGC TCC      3734
Trp Gly Ala Val Cys Pro His Leu Pro Pro Cys Asp Ser His Gly Ser
            1170                1175                1180

TGG CTC TCC GGC GCC TGG GGG CCT CTG GGG CAC AGC GGC AGG ACT CTG      3782
Trp Leu Ser Gly Ala Trp Gly Pro Leu Gly His Ser Gly Arg Thr Leu
        1185                1190                1195

GGG CTG GGC ACA GGC TAC AGA GAC AGT GGG GGA CTG GAC GAG ATC AGC      3830
Gly Leu Gly Thr Gly Tyr Arg Asp Ser Gly Gly Leu Asp Glu Ile Ser
    1200                1205                1210

AGT GTA GCC CGT GGG ACG CAA GGC TTC CCG GGA CCC TGC ACC TGG AGA      3878
Ser Val Ala Arg Gly Thr Gln Gly Phe Pro Gly Pro Cys Thr Trp Arg
1215                1220                1225                1230

CGG ATC TCC AGT CTG GAG TCA GAA GTG TGAGTTATCA GCCACTCAGG            3925
Arg Ile Ser Ser Leu Glu Ser Glu Val
                1235                124

CTCCGAGCCA GCTGGATTCT CTGCCTGCCA CTGTCAGGGT TAAGCGGCAG GCAGGATTGG    3985

CCCTTCTCTG GCTTCTACCA TGAAATCCTG GCCATGGCAC CCCAGTGACA GATGATGTCT    4045

TCCATGGTCA TCAGTGACCT CAGCTAGCCT CA                                  4077
```

(2) INFORMATION FOR SEQ ID NO:52:

(i) SEQUENCE CHARACTERISTICS:
(A) LENGTH: 1239 amino acids
(B) TYPE: amino acid
(D) TOPOLOGY: linear (ii) MOLECULE TYPE: protein (xi) SEQUENCE DESCRIPTION: SEQ ID NO:52:

```
Met Gly Gly Ala Leu Gly Pro Ala Leu Leu Leu Thr Ser Leu Phe Gly
  1               5                  10                  15

Ala Trp Ala Gly Leu Gly Pro Gly Gln Gly Glu Gln Gly Met Thr Val
             20                  25                  30

Ala Val Val Phe Ser Ser Ser Gly Pro Pro Gln Ala Gln Phe Arg Val
         35                  40                  45

Arg Leu Thr Pro Gln Ser Phe Leu Asp Leu Pro Leu Glu Ile Gln Pro
     50                  55                  60

Leu Thr Val Gly Val Asn Thr Thr Asn Pro Ser Ser Leu Leu Thr Gln
 65                  70                  75                  80

Ile Cys Gly Leu Leu Gly Ala Ala His Val His Gly Ile Val Phe Glu
                 85                  90                  95

Asp Asn Val Asp Thr Glu Ala Val Ala Gln Ile Leu Asp Phe Ile Ser
            100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160
```

-continued

```
Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
            260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
    290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335

Asn Val Thr Trp Glu Gly Arg Asp Phe Ser Phe Ser Pro Gly Gly Tyr
            340                 345                 350

Leu Val Gln Pro Thr Met Val Val Ile Ala Leu Asn Arg His Arg Leu
        355                 360                 365

Trp Glu Met Val Gly Arg Trp Glu His Gly Val Leu Tyr Met Lys Tyr
    370                 375                 380

Pro Val Trp Pro Arg Tyr Ser Ala Ser Leu Gln Pro Val Val Asp Ser
385                 390                 395                 400

Arg His Leu Thr Val Ala Thr Leu Glu Glu Arg Pro Phe Val Ile Val
                405                 410                 415

Glu Ser Pro Asp Pro Gly Thr Gly Gly Cys Val Pro Asn Thr Val Pro
            420                 425                 430

Cys Arg Arg Gln Ser Asn His Thr Phe Ser Ser Gly Asp Val Ala Pro
        435                 440                 445

Tyr Thr Lys Leu Cys Cys Lys Gly Phe Cys Ile Asp Ile Leu Lys Lys
    450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575
```

-continued

```
Phe Ser Pro Val Ser Tyr Asn Gln Asn Leu Thr Arg Gly Lys Thr Phe
            580                 585                 590

Thr Ile Gly Lys Ser Val Trp Leu Leu Trp Ala Leu Val Phe Asn Asn
        595                 600                 605

Ser Val Pro Ile Glu Asn Pro Arg Gly Thr Thr Ser Lys Ile Met Val
    610                 615                 620

Leu Val Trp Ala Phe Phe Ala Val Ile Phe Leu Ala Arg Tyr Thr Ala
625                 630                 635                 640

Asn Leu Ala Ala Phe Met Ile Gln Glu Gln Tyr Ile Asp Thr Val Ser
                645                 650                 655

Gly Leu Ser Asp Lys Lys Phe Gln Arg Pro Gln Asp Gln Tyr Pro Pro
            660                 665                 670

Phe Arg Phe Gly Thr Val Pro Asn Gly Ser Thr Glu Arg Asn Ile Arg
        675                 680                 685

Ser Asn Tyr Arg Asp Met His Thr His Met Val Lys Phe Asn Gln Arg
    690                 695                 700

Ser Val Glu Asp Ala Leu Thr Ser Leu Lys Met Gly Ser Glu Ala Gln
705                 710                 715                 720

Pro Val Pro Arg Lys Leu Asp Ala Phe Ile Tyr Asp Ala Ala Val Leu
                725                 730                 735

Asn Tyr Met Ala Gly Lys Asp Glu Gly Cys Lys Leu Val Thr Ile Gly
            740                 745                 750

Ser Gly Lys Val Phe Ala Thr Thr Gly Tyr Gly Ile Ala Met Gln Lys
        755                 760                 765

Asp Ser His Trp Lys Arg Ala Ile Asp Leu Ala Leu Leu Gln Phe Leu
    770                 775                 780

Gly Asp Gly Glu Thr Gln Lys Leu Glu Thr Val Trp Leu Ser Gly Ile
785                 790                 795                 800

Cys Gln Asn Glu Lys Asn Glu Val Met Ser Ser Lys Leu Asp Ile Asp
                805                 810                 815

Asn Met Gly Gly Val Phe Tyr Met Leu Leu Val Ala Met Gly Leu Ala
            820                 825                 830

Leu Leu Val Phe Ala Trp Glu His Leu Val Tyr Trp Lys Leu Arg His
        835                 840                 845

Ser Val Pro Asn Ser Ser Gln Leu Asp Phe Leu Leu Ala Phe Ser Arg
    850                 855                 860

Gly Ile Tyr Ser Cys Phe Ser Gly Val Gln Ser Leu Ala Ser Pro Pro
865                 870                 875                 880

Arg Gln Ala Ser Pro Asp Leu Thr Ala Ser Ser Ala Gln Ala Ser Val
                885                 890                 895

Leu Lys Ile Leu Gln Ala Ala Arg Asp Met Val Thr Thr Ala Gly Val
            900                 905                 910

Ser Asn Ser Leu Asp Arg Ala Thr Arg Thr Ile Glu Asn Trp Gly Gly
        915                 920                 925

Gly Arg Arg Ala Pro Pro Pro Ser Pro Cys Pro Thr Pro Arg Ser Gly
    930                 935                 940

Pro Ser Pro Cys Leu Pro Thr Pro Asp Pro Pro Pro Glu Pro Ser Pro
945                 950                 955                 960

Thr Gly Trp Gly Pro Pro Asp Gly Gly Arg Ala Ala Leu Val Arg Arg
                965                 970                 975

Ala Pro Gln Pro Pro Gly Arg Pro Pro Thr Pro Gly Pro Pro Leu Ser
            980                 985                 990

Asp Val Ser Arg Val Ser Arg Arg Pro Ala Trp Glu Ala Arg Trp Pro
```

-continued

```
        995                 1000                1005

Val Arg Thr Gly His Cys Gly Arg His Leu Ser Ala Ser Glu Arg Pro
    1010                1015                1020

Leu Ser Pro Ala Arg Cys His Tyr Ser Ser Phe Pro Arg Ala Asp Arg
1025                1030                1035                1040

Ser Gly Arg Pro Phe Leu Pro Leu Phe Pro Glu Pro Pro Glu Leu Glu
                1045                1050                1055

Asp Leu Pro Leu Leu Gly Pro Glu Gln Leu Ala Arg Arg Glu Ala Leu
            1060                1065                1070

Leu Asn Ala Ala Trp Ala Arg Gly Ser Arg Pro Ser His Ala Ser Leu
        1075                1080                1085

Pro Ser Ser Val Ala Glu Ala Phe Ala Arg Pro Ser Ser Leu Pro Ala
    1090                1095                1100

Gly Cys Thr Gly Pro Ala Cys Ala Arg Pro Asp Gly His Ser Ala Cys
1105                1110                1115                1120

Arg Arg Leu Ala Gln Ala Gln Ser Met Cys Leu Pro Ile Tyr Arg Glu
                1125                1130                1135

Ala Cys Gln Glu Gly Glu Gln Ala Gly Ala Pro Ala Trp Gln His Arg
            1140                1145                1150

Gln His Val Cys Leu His Ala His Ala His Leu Pro Leu Cys Trp Gly
        1155                1160                1165

Ala Val Cys Pro His Leu Pro Pro Cys Asp Ser His Gly Ser Trp Leu
    1170                1175                1180

Ser Gly Ala Trp Gly Pro Leu Gly His Ser Gly Arg Thr Leu Gly Leu
1185                1190                1195                1200

Gly Thr Gly Tyr Arg Asp Ser Gly Gly Leu Asp Glu Ile Ser Ser Val
                1205                1210                1215

Ala Arg Gly Thr Gln Gly Phe Pro Gly Pro Cys Thr Trp Arg Arg Ile
            1220                1225                1230

Ser Ser Leu Glu Ser Glu Val
        1235
```

(2) INFORMATION FOR SEQ ID NO:53:

(i) SEQUENCE CHARACTERISTICS:
(A) LENGTH: 4002 base pairs
(B) TYPE: nucleic acid
(C) STRANDEDNESS: both
(D) TOPOLOGY: both (ii) MOLECULE TYPE: cDNA (ix) FEATURE:
(A) NAME/KEY: CDS
(B) LOCATION: 189..3833

(xi) SEQUENCE DESCRIPTION: SEQ ID NO:53:

```
CCCTTAATAA GATTTGCNAC GTACACTCGA GCCATCGCGA GTGTCCTTGA GCCGCGGGTG      60

ACGGTGGCTC TCGCTGCTCG CGCCCCCTCC TCCCGCGGGG GGAGCCTGAT GCCACGTTCC     120

CTATGAATTA TTTATCGCCG GCCTAAAAAT ACCCCGAACT TCACAGCCCG AGTGACCCTC     180

CGGTGGAC ATG GGT GGG GCC CTG GGG CCG GCC CTG TTG CTC ACC TCG CTC      230
         Met Gly Gly Ala Leu Gly Pro Ala Leu Leu Leu Thr Ser Leu
           1               5                  10

TTC GGT GCC TGG GCA GGG CTG GGT CCG GGG CAG GGC GAG CAG GGC ATG      278
Phe Gly Ala Trp Ala Gly Leu Gly Pro Gly Gln Gly Glu Gln Gly Met
 15                  20                  25                  30

ACG GTG GCC GTG GTG TTT AGC AGC TCA GGG CCG CCC CAG GCC CAG TTC      326
```

-continued

```
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC      374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC      422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC      470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC      518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT      566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG      614
Ala Val Val Leu Thr Pro Lys Glu Pro Gly Ser Ala Phe Leu Gln Leu
            130                 135                 140

GGC GTG TCC CTG GAG CAG CAG CTG CAG GTG CTG TTC AAG GTG CTG GAA      662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC      710
Glu Tyr Asp Trp Ser Ala Phe Ala Val Ile Thr Ser Leu His Pro Gly
    160                 165                 170

CAC GCG CTC TTC CTG GAG GGC GTG CGC GCC GTC GCC GAC GCC AGC CAC      758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA      806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC      854
Gly Pro Arg Ala Arg Thr Gln Arg Leu Leu Arg Gln Leu Asp Ala Pro
            210                 215                 220

GTG TTT GTG GCC TAC TGC TCG CGC GAG GAG GCC GAG GTG CTC TTC GCC      902
Val Phe Val Ala Tyr Cys Ser Arg Glu Glu Ala Glu Val Leu Phe Ala
        225                 230                 235

GAG GCG GCG CAG GCC GGT CTG GTG GGG CCC GGC CAC GTG TGG CTG GTG      950
Glu Ala Ala Gln Ala Gly Leu Val Gly Pro Gly His Val Trp Leu Val
    240                 245                 250

CCC AAC CTG GCG CTG GGC AGC ACC GAT GCG CCC CCC GCC ACC TTC CCC      998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC     1046
Val Gly Leu Ile Ser Val Val Thr Glu Ser Trp Arg Leu Ser Leu Arg
                275                 280                 285

CAG AAG GTG CGC GAC GGC GTG GCC ATT CTG GCC CTG GGC GCC CAC AGC     1094
Gln Lys Val Arg Asp Gly Val Ala Ile Leu Ala Leu Gly Ala His Ser
            290                 295                 300

TAC TGG CGC CAG CAT GGA ACC CTG CCA GCC CCG GCC GGG GAC TGC CGT     1142
Tyr Trp Arg Gln His Gly Thr Leu Pro Ala Pro Ala Gly Asp Cys Arg
        305                 310                 315

GTT CAC CCT GGG CCC GTC AGC CCT GCC CGG GAG GCC TTC TAC AGG CAC     1190
Val His Pro Gly Pro Val Ser Pro Ala Arg Glu Ala Phe Tyr Arg His
    320                 325                 330

CTA CTG AAT GTC ACC TGG GAG GGC CGA GAC TTC TCC TTC AGC CCT GGT     1238
Leu Leu Asn Val Thr Trp Glu Gly Arg Asp Phe Ser Phe Ser Pro Gly
335                 340                 345                 350
```

-continued

```
GGG TAC CTG GTC CAG CCC ACC ATG GTG GTG ATC GCC CTC AAC CGG CAC      1286
Gly Tyr Leu Val Gln Pro Thr Met Val Val Ile Ala Leu Asn Arg His
                355                 360                 365

CGC CTC TGG GAG ATG GTG GGG CGC TGG GAG CAT GGC GTC CTA TAC ATG      1334
Arg Leu Trp Glu Met Val Gly Arg Trp Glu His Gly Val Leu Tyr Met
            370                 375                 380

AAG TAC CCC GTG TGG CCT CGC TAC AGT GCC TCT CTG CAG CCT GTG GTG      1382
Lys Tyr Pro Val Trp Pro Arg Tyr Ser Ala Ser Leu Gln Pro Val Val
        385                 390                 395

GAC AGT CGG CAC CTG ACG GTG GCC ACG CTG GAA GAG CGG CCC TTT GTC      1430
Asp Ser Arg His Leu Thr Val Ala Thr Leu Glu Glu Arg Pro Phe Val
    400                 405                 410

ATC GTG GAG AGC CCT GAC CCT GGC ACA GGA GGC TGT GTC CCC AAC ACC      1478
Ile Val Glu Ser Pro Asp Pro Gly Thr Gly Gly Cys Val Pro Asn Thr
415                 420                 425                 430

GTG CCC TGC CGC AGG CAG AGC AAC CAC ACC TTC AGC AGC GGG GAC GTG      1526
Val Pro Cys Arg Arg Gln Ser Asn His Thr Phe Ser Ser Gly Asp Val
                435                 440                 445

GCC CCC TAC ACC AAG CTC TGC TGT AAG GGA TTC TGC ATC GAC ATC CTC      1574
Ala Pro Tyr Thr Lys Leu Cys Cys Lys Gly Phe Cys Ile Asp Ile Leu
            450                 455                 460

AAG AAG CTG GCC AGA GTG GTC AAA TTC TCC TAC GAC CTG TAC CTG GTG      1622
Lys Lys Leu Ala Arg Val Val Lys Phe Ser Tyr Asp Leu Tyr Leu Val
        465                 470                 475

ACC AAC GGC AAG CAT GGC AAG CGG GTG CGC GGC GTA TGG AAC GGC ATG      1670
Thr Asn Gly Lys His Gly Lys Arg Val Arg Gly Val Trp Asn Gly Met
    480                 485                 490

ATT GGG GAG GTG TAC TAC AAG CGG GCA GAC ATG GCC ATC GGC TCC CTC      1718
Ile Gly Glu Val Tyr Tyr Lys Arg Ala Asp Met Ala Ile Gly Ser Leu
495                 500                 505                 510

ACC ATC AAT GAG GAA CGC TCC GAG ATC GTA GAC TTC TCT GTA CCC TTT      1766
Thr Ile Asn Glu Glu Arg Ser Glu Ile Val Asp Phe Ser Val Pro Phe
                515                 520                 525

GTG GAG ACG GGC ATC AGT GTG ATG GTG GCT CGC AGC AAT GGC ACC GTC      1814
Val Glu Thr Gly Ile Ser Val Met Val Ala Arg Ser Asn Gly Thr Val
            530                 535                 540

TCC CCC TCG GCC TTC TTG GAG CCA TAT AGC CCT GCA GTG TGG GTG ATG      1862
Ser Pro Ser Ala Phe Leu Glu Pro Tyr Ser Pro Ala Val Trp Val Met
        545                 550                 555

ATG TTT GTC ATG TGC CTC ACT GTG GTG GCC ATC ACC GTC TTC ATG TTC      1910
Met Phe Val Met Cys Leu Thr Val Val Ala Ile Thr Val Phe Met Phe
    560                 565                 570

GAG TAC TTC AGC CCT GTC AGC TAC AAC CAG AAC CTC ACC AGA GGC AAG      1958
Glu Tyr Phe Ser Pro Val Ser Tyr Asn Gln Asn Leu Thr Arg Gly Lys
575                 580                 585                 590

ACT TTC ACT ATC GGC AAG TCC GTG TGG CTG CTG TGG GCG CTG GTC TTC      2006
Thr Phe Thr Ile Gly Lys Ser Val Trp Leu Leu Trp Ala Leu Val Phe
                595                 600                 605

AAC AAC TCA GTG CCC ATC GAG AAC CCG CGG GGC ACC ACC AGC AAG ATC      2054
Asn Asn Ser Val Pro Ile Glu Asn Pro Arg Gly Thr Thr Ser Lys Ile
            610                 615                 620

ATG GTT CTG GTC TGG GCC TTC TTT GCT GTC ATC TTC CTC GCC AGA TAC      2102
Met Val Leu Val Trp Ala Phe Phe Ala Val Ile Phe Leu Ala Arg Tyr
        625                 630                 635

ACG GCC AAC CTG GCC GCC TTC ATG ATC CAA GAG CAA TAC ATC GAC ACT      2150
Thr Ala Asn Leu Ala Ala Phe Met Ile Gln Glu Gln Tyr Ile Asp Thr
    640                 645                 650

GTG TCG GGC CTC AGT GAC AAG AAG TTT CAG CGG CCT CAA GAT CAG TAC      2198
Val Ser Gly Leu Ser Asp Lys Lys Phe Gln Arg Pro Gln Asp Gln Tyr
655                 660                 665                 670
```

-continued

```
CCA CCT TTC CGC TTC GGC ACG GTG CCC AAC GGC AGC ACG GAG CGG AAC     2246
Pro Pro Phe Arg Phe Gly Thr Val Pro Asn Gly Ser Thr Glu Arg Asn
                675                 680                 685

ATC CGC AGT AAC TAC CGT GAC ATG CAC ACC CAC ATG GTC AAG TTC AAC     2294
Ile Arg Ser Asn Tyr Arg Asp Met His Thr His Met Val Lys Phe Asn
            690                 695                 700

CAG CGC TCG GTG GAG GAC GCG CTC ACC AGC CTC AAG ATG GGC AAG GAC     2342
Gln Arg Ser Val Glu Asp Ala Leu Thr Ser Leu Lys Met Gly Lys Asp
        705                 710                 715

GAG GGC TGC AAG CTG GTC ACC ATT GGG TCT GGC AAG GTC TTT GCT ACC     2390
Glu Gly Cys Lys Leu Val Thr Ile Gly Ser Gly Lys Val Phe Ala Thr
    720                 725                 730

ACT GGC TAC GGC ATC GCC ATG CAG AAG GAC TCC CAC TGG AAG CGG GCC     2438
Thr Gly Tyr Gly Ile Ala Met Gln Lys Asp Ser His Trp Lys Arg Ala
735                 740                 745                 750

ATA GAC CTG GCG CTC TTG CAG TTC CTG GGG GAC GGA GAG ACA CAG AAA     2486
Ile Asp Leu Ala Leu Leu Gln Phe Leu Gly Asp Gly Glu Thr Gln Lys
                755                 760                 765

CTG GAG ACA GTG TGG CTC TCA GGG ATC TGC CAG AAT GAG AAG AAC GAG     2534
Leu Glu Thr Val Trp Leu Ser Gly Ile Cys Gln Asn Glu Lys Asn Glu
            770                 775                 780

GTG ATG AGC AGC AAG CTG GAC ATC GAC AAC ATG GGA GGC GTC TTC TAC     2582
Val Met Ser Ser Lys Leu Asp Ile Asp Asn Met Gly Gly Val Phe Tyr
        785                 790                 795

ATG CTG CTG GTG GCC ATG GGG CTG GCC CTG CTG GTC TTC GCC TGG GAG     2630
Met Leu Leu Val Ala Met Gly Leu Ala Leu Leu Val Phe Ala Trp Glu
    800                 805                 810

CAC CTG GTC TAC TGG AAG CTG CGC CAC TCG GTG CCC AAC TCA TCC CAG     2678
His Leu Val Tyr Trp Lys Leu Arg His Ser Val Pro Asn Ser Ser Gln
815                 820                 825                 830

CTG GAC TTC CTG CTG GCT TTC AGC AGG GGC ATC TAC AGC TGC TTC AGC     2726
Leu Asp Phe Leu Leu Ala Phe Ser Arg Gly Ile Tyr Ser Cys Phe Ser
                835                 840                 845

GGG GTG CAG AGC CTC GCC AGC CCA CCG CGG CAG GCC AGC CCG GAC CTC     2774
Gly Val Gln Ser Leu Ala Ser Pro Pro Arg Gln Ala Ser Pro Asp Leu
            850                 855                 860

ACG GCC AGC TCG GCC CAG GCC AGC GTG CTC AAG ATT CTG CAG GCA GCC     2822
Thr Ala Ser Ser Ala Gln Ala Ser Val Leu Lys Ile Leu Gln Ala Ala
        865                 870                 875

CGC GAC ATG GTG ACC ACG GCG GGC GTA AGC AAC TCC CTG GAC CGC GCC     2870
Arg Asp Met Val Thr Thr Ala Gly Val Ser Asn Ser Leu Asp Arg Ala
    880                 885                 890

ACT CGC ACC ATC GAG AAT TGG GGT GGC GGC CGC CGT GCG CCC CCA CCG     2918
Thr Arg Thr Ile Glu Asn Trp Gly Gly Gly Arg Arg Ala Pro Pro Pro
895                 900                 905                 910

TCC CCC TGC CCG ACC CCG CGG TCT GGC CCC AGC CCA TGC CTG CCC ACC     2966
Ser Pro Cys Pro Thr Pro Arg Ser Gly Pro Ser Pro Cys Leu Pro Thr
                915                 920                 925

CCC GAC CCG CCC CCA GAG CCG AGC CCC ACG GGC TGG GGA CCG CCA GAC     3014
Pro Asp Pro Pro Pro Glu Pro Ser Pro Thr Gly Trp Gly Pro Pro Asp
            930                 935                 940

GGG GGT CGC GCG GCG CTT GTG CGC AGG GCT CCG CAG CCC CCG GGC CGC     3062
Gly Gly Arg Ala Ala Leu Val Arg Arg Ala Pro Gln Pro Pro Gly Arg
        945                 950                 955

CCC CCG ACG CCG GGG CCG CCC CTG TCC GAC GTC TCC CGA GTG TCG CGC     3110
Pro Pro Thr Pro Gly Pro Pro Leu Ser Asp Val Ser Arg Val Ser Arg
    960                 965                 970

CGC CCA GCC TGG GAG GCG CGG TGG CCG GTG CGG ACC GGG CAC TGC GGG     3158
Arg Pro Ala Trp Glu Ala Arg Trp Pro Val Arg Thr Gly His Cys Gly
```

-continued

```
975                 980                 985                 990

AGG CAC CTC TCG GCC TCC GAG CGG CCC CTG TCG CCC GCG CGC TGT CAC      3206
Arg His Leu Ser Ala Ser Glu Arg Pro Leu Ser Pro Ala Arg Cys His
                995                1000                1005

TAC AGC TCC TTT CCT CGA GCC GAC CGA TCC GGC CGC CCC TTC CTC CCG      3254
Tyr Ser Ser Phe Pro Arg Ala Asp Arg Ser Gly Arg Pro Phe Leu Pro
            1010                1015                1020

CTC TTC CCG GAG CCC CCG GAG CTG GAG GAC CTG CCG CTG CTC GGT CCG      3302
Leu Phe Pro Glu Pro Pro Glu Leu Glu Asp Leu Pro Leu Leu Gly Pro
        1025                1030                1035

GAG CAG CTG GCC CGG CGG GAG GCC CTG CTG AAC GCG GCC TGG GCC CGG      3350
Glu Gln Leu Ala Arg Arg Glu Ala Leu Leu Asn Ala Ala Trp Ala Arg
    1040                1045                1050

GGC TCG CGC CCG AGT CAC GCT TCC CTG CCC AGC TCC GTG GCC GAG GCC      3398
Gly Ser Arg Pro Ser His Ala Ser Leu Pro Ser Ser Val Ala Glu Ala
1055                1060                1065                1070

TTC GCT CGG CCC AGC TCG CTG CCC GCT GGG TGC ACC GGC CCC GCC TGC      3446
Phe Ala Arg Pro Ser Ser Leu Pro Ala Gly Cys Thr Gly Pro Ala Cys
                1075                1080                1085

GCC CGC CCC GAC GGC CAC TCG GCC TGC AGG CGC TTG GCG CAG GCG CAG      3494
Ala Arg Pro Asp Gly His Ser Ala Cys Arg Arg Leu Ala Gln Ala Gln
            1090                1095                1100

TCG ATG TGC TTG CCG ATC TAC CGG GAG GCC TGC CAG GAG GGC GAG CAG      3542
Ser Met Cys Leu Pro Ile Tyr Arg Glu Ala Cys Gln Glu Gly Glu Gln
        1105                1110                1115

GCA GGG GCC CCC GCC TGG CAG CAC AGA CAG CAC GTC TGC CTG CAC GCC      3590
Ala Gly Ala Pro Ala Trp Gln His Arg Gln His Val Cys Leu His Ala
    1120                1125                1130

CAC GCC CAC CTG CCA TTG TGC TGG GGG GCT GTC TGT CCT CAC CTT CCA      3638
His Ala His Leu Pro Leu Cys Trp Gly Ala Val Cys Pro His Leu Pro
1135                1140                1145                1150

CCC TGT GAC AGC CAC GGC TCC TGG CTC TCC GGC GCC TGG GGG CCT CTG      3686
Pro Cys Asp Ser His Gly Ser Trp Leu Ser Gly Ala Trp Gly Pro Leu
                1155                1160                1165

GGG CAC AGC GGC AGG ACT CTG GGG CTG GGC ACA GGC TAC AGA GAC AGT      3734
Gly His Ser Gly Arg Thr Leu Gly Leu Gly Thr Gly Tyr Arg Asp Ser
            1170                1175                1180

GGG GGA CTG GAC GAG ATC AGC AGT GTA GCC CGT GGG ACG CAA GGC TTC      3782
Gly Gly Leu Asp Glu Ile Ser Ser Val Ala Arg Gly Thr Gln Gly Phe
        1185                1190                1195

CCG GGA CCC TGC ACC TGG AGA CGG ATC TCC AGT CTG GAG TCA GAA GTG      3830
Pro Gly Pro Cys Thr Trp Arg Arg Ile Ser Ser Leu Glu Ser Glu Val
    1200                1205                1210

TGAGTTATCA GCCACTCAGG CTCCGAGCCA GCTGGATTCT CTGCCTGCCA CTGTCAGGGT   3890

TAAGCGGCAG GCAGGATTGG CCCTTCTCTG GCTTCTACCA TGAAATCCTG GCCATGGCAC   3950

CCCAGTGACA GATGATGTCT TCCATGGTCA TCAGTGACCT CAGCTAGCCT CA           4002
```

(2) INFORMATION FOR SEQ ID NO:54:

(i) SEQUENCE CHARACTERISTICS:
(A) LENGTH: 1214 amino acids
(B) TYPE: amino acid
(D) TOPOLOGY: linear (ii) MOLECULE TYPE: protein (xi) SEQUENCE DESCRIPTION: SEQ ID NO:54:

```
Met Gly Gly Ala Leu Gly Pro Ala Leu Leu Leu Thr Ser Leu Phe Gly
  1               5                  10                  15
```

-continued

Ala Trp Ala Gly Leu Gly Pro Gly Gln Gly Glu Gln Gly Met Thr Val
20 25 30

Ala Val Val Phe Ser Ser Ser Gly Pro Pro Gln Ala Gln Phe Arg Val
35 40 45

Arg Leu Thr Pro Gln Ser Phe Leu Asp Leu Pro Leu Glu Ile Gln Pro
50 55 60

Leu Thr Val Gly Val Asn Thr Thr Asn Pro Ser Ser Leu Leu Thr Gln
65 70 75 80

Ile Cys Gly Leu Leu Gly Ala Ala His Val His Gly Ile Val Phe Glu
85 90 95

Asp Asn Val Asp Thr Glu Ala Val Ala Gln Ile Leu Asp Phe Ile Ser
100 105 110

Ser Gln Thr His Val Pro Ile Leu Ser Ile Ser Gly Gly Ser Ala Val
115 120 125

Val Leu Thr Pro Lys Glu Pro Gly Ser Ala Phe Leu Gln Leu Gly Val
130 135 140

Ser Leu Glu Gln Gln Leu Gln Val Leu Phe Lys Val Leu Glu Glu Tyr
145 150 155 160

Asp Trp Ser Ala Phe Ala Val Ile Thr Ser Leu His Pro Gly His Ala
165 170 175

Leu Phe Leu Glu Gly Val Arg Ala Val Ala Asp Ala Ser His Val Ser
180 185 190

Trp Arg Leu Leu Asp Val Val Thr Leu Glu Leu Asp Pro Gly Gly Pro
195 200 205

Arg Ala Arg Thr Gln Arg Leu Leu Arg Gln Leu Asp Ala Pro Val Phe
210 215 220

Val Ala Tyr Cys Ser Arg Glu Glu Ala Glu Val Leu Phe Ala Glu Ala
225 230 235 240

Ala Gln Ala Gly Leu Val Gly Pro Gly His Val Trp Leu Val Pro Asn
245 250 255

Leu Ala Leu Gly Ser Thr Asp Ala Pro Pro Ala Thr Phe Pro Val Gly
260 265 270

Leu Ile Ser Val Val Thr Glu Ser Trp Arg Leu Ser Leu Arg Gln Lys
275 280 285

Val Arg Asp Gly Val Ala Ile Leu Ala Leu Gly Ala His Ser Tyr Trp
290 295 300

Arg Gln His Gly Thr Leu Pro Ala Pro Ala Gly Asp Cys Arg Val His
305 310 315 320

Pro Gly Pro Val Ser Pro Ala Arg Glu Ala Phe Tyr Arg His Leu Leu
325 330 335

Asn Val Thr Trp Glu Gly Arg Asp Phe Ser Phe Ser Pro Gly Gly Tyr
340 345 350

Leu Val Gln Pro Thr Met Val Val Ile Ala Leu Asn Arg His Arg Leu
355 360 365

Trp Glu Met Val Gly Arg Trp Glu His Gly Val Leu Tyr Met Lys Tyr
370 375 380

Pro Val Trp Pro Arg Tyr Ser Ala Ser Leu Gln Pro Val Val Asp Ser
385 390 395 400

Arg His Leu Thr Val Ala Thr Leu Glu Glu Arg Pro Phe Val Ile Val
405 410 415

Glu Ser Pro Asp Pro Gly Thr Gly Gly Cys Val Pro Asn Thr Val Pro
420 425 430

Cys Arg Arg Gln Ser Asn His Thr Phe Ser Ser Gly Asp Val Ala Pro

-continued

```
        435                 440                 445

Tyr Thr Lys Leu Cys Cys Lys Gly Phe Cys Ile Asp Ile Leu Lys Lys
    450                 455                 460

Leu Ala Arg Val Val Lys Phe Ser Tyr Asp Leu Tyr Leu Val Thr Asn
465                 470                 475                 480

Gly Lys His Gly Lys Arg Val Arg Gly Val Trp Asn Gly Met Ile Gly
                485                 490                 495

Glu Val Tyr Tyr Lys Arg Ala Asp Met Ala Ile Gly Ser Leu Thr Ile
            500                 505                 510

Asn Glu Glu Arg Ser Glu Ile Val Asp Phe Ser Val Pro Phe Val Glu
        515                 520                 525

Thr Gly Ile Ser Val Met Val Ala Arg Ser Asn Gly Thr Val Ser Pro
    530                 535                 540

Ser Ala Phe Leu Glu Pro Tyr Ser Pro Ala Val Trp Val Met Met Phe
545                 550                 555                 560

Val Met Cys Leu Thr Val Val Ala Ile Thr Val Phe Met Phe Glu Tyr
                565                 570                 575

Phe Ser Pro Val Ser Tyr Asn Gln Asn Leu Thr Arg Gly Lys Thr Phe
            580                 585                 590

Thr Ile Gly Lys Ser Val Trp Leu Leu Trp Ala Leu Val Phe Asn Asn
        595                 600                 605

Ser Val Pro Ile Glu Asn Pro Arg Gly Thr Thr Ser Lys Ile Met Val
    610                 615                 620

Leu Val Trp Ala Phe Phe Ala Val Ile Phe Leu Ala Arg Tyr Thr Ala
625                 630                 635                 640

Asn Leu Ala Ala Phe Met Ile Gln Glu Gln Tyr Ile Asp Thr Val Ser
                645                 650                 655

Gly Leu Ser Asp Lys Lys Phe Gln Arg Pro Gln Asp Gln Tyr Pro Pro
            660                 665                 670

Phe Arg Phe Gly Thr Val Pro Asn Gly Ser Thr Glu Arg Asn Ile Arg
        675                 680                 685

Ser Asn Tyr Arg Asp Met His Thr His Met Val Lys Phe Asn Gln Arg
    690                 695                 700

Ser Val Glu Asp Ala Leu Thr Ser Leu Lys Met Gly Lys Asp Glu Gly
705                 710                 715                 720

Cys Lys Leu Val Thr Ile Gly Ser Gly Lys Val Phe Ala Thr Thr Gly
                725                 730                 735

Tyr Gly Ile Ala Met Gln Lys Asp Ser His Trp Lys Arg Ala Ile Asp
            740                 745                 750

Leu Ala Leu Leu Gln Phe Leu Gly Asp Gly Glu Thr Gln Lys Leu Glu
        755                 760                 765

Thr Val Trp Leu Ser Gly Ile Cys Gln Asn Glu Lys Asn Glu Val Met
    770                 775                 780

Ser Ser Lys Leu Asp Ile Asp Asn Met Gly Gly Val Phe Tyr Met Leu
785                 790                 795                 800

Leu Val Ala Met Gly Leu Ala Leu Leu Val Phe Ala Trp Glu His Leu
                805                 810                 815

Val Tyr Trp Lys Leu Arg His Ser Val Pro Asn Ser Ser Gln Leu Asp
            820                 825                 830

Phe Leu Leu Ala Phe Ser Arg Gly Ile Tyr Ser Cys Phe Ser Gly Val
        835                 840                 845

Gln Ser Leu Ala Ser Pro Pro Arg Gln Ala Ser Pro Asp Leu Thr Ala
    850                 855                 860
```

-continued

```
Ser Ser Ala Gln Ala Ser Val Leu Lys Ile Leu Gln Ala Ala Arg Asp
865                 870                 875                 880

Met Val Thr Thr Ala Gly Val Ser Asn Ser Leu Asp Arg Ala Thr Arg
                885                 890                 895

Thr Ile Glu Asn Trp Gly Gly Gly Arg Arg Ala Pro Pro Pro Ser Pro
            900                 905                 910

Cys Pro Thr Pro Arg Ser Gly Pro Ser Pro Cys Leu Pro Thr Pro Asp
        915                 920                 925

Pro Pro Pro Glu Pro Ser Pro Thr Gly Trp Gly Pro Pro Asp Gly Gly
    930                 935                 940

Arg Ala Ala Leu Val Arg Arg Ala Pro Gln Pro Pro Gly Arg Pro Pro
945                 950                 955                 960

Thr Pro Gly Pro Pro Leu Ser Asp Val Ser Arg Val Ser Arg Arg Pro
                965                 970                 975

Ala Trp Glu Ala Arg Trp Pro Val Arg Thr Gly His Cys Gly Arg His
            980                 985                 990

Leu Ser Ala Ser Glu Arg Pro Leu Ser Pro Ala Arg Cys His Tyr Ser
        995                 1000                1005

Ser Phe Pro Arg Ala Asp Arg Ser Gly Arg Pro Phe Leu Pro Leu Phe
    1010                1015                1020

Pro Glu Pro Pro Glu Leu Glu Asp Leu Pro Leu Leu Gly Pro Glu Gln
1025                1030                1035                1040

Leu Ala Arg Arg Glu Ala Leu Leu Asn Ala Ala Trp Ala Arg Gly Ser
                1045                1050                1055

Arg Pro Ser His Ala Ser Leu Pro Ser Ser Val Ala Glu Ala Phe Ala
            1060                1065                1070

Arg Pro Ser Ser Leu Pro Ala Gly Cys Thr Gly Pro Ala Cys Ala Arg
        1075                1080                1085

Pro Asp Gly His Ser Ala Cys Arg Arg Leu Ala Gln Ala Gln Ser Met
    1090                1095                1100

Cys Leu Pro Ile Tyr Arg Glu Ala Cys Gln Glu Gly Glu Gln Ala Gly
1105                1110                1115                1120

Ala Pro Ala Trp Gln His Arg Gln His Val Cys Leu His Ala His Ala
                1125                1130                1135

His Leu Pro Leu Cys Trp Gly Ala Val Cys Pro His Leu Pro Pro Cys
            1140                1145                1150

Asp Ser His Gly Ser Trp Leu Ser Gly Ala Trp Gly Pro Leu Gly His
        1155                1160                1165

Ser Gly Arg Thr Leu Gly Leu Gly Thr Gly Tyr Arg Asp Ser Gly Gly
    1170                1175                1180

Leu Asp Glu Ile Ser Ser Val Ala Arg Gly Thr Gln Gly Phe Pro Gly
1185                1190                1195                1200

Pro Cys Thr Trp Arg Arg Ile Ser Ser Leu Glu Ser Glu Val
                1205                1210
```